(12) United States Patent
Christianson et al.

(10) Patent No.: US 12,310,850 B2
(45) Date of Patent: *May 27, 2025

(54) TRANSCATHETER DELIVERABLE PROSTHETIC HEART VALVES AND METHODS OF DELIVERY

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US)

(73) Assignee: VDyne, Inc., Maple Grove, MN (US)

( * ) Notice: Subject to any disclaimer, the term of this patent is extended or adjusted under 35 U.S.C. 154(b) by 607 days.

This patent is subject to a terminal disclaimer.

(21) Appl. No.: 17/682,875

(22) Filed: Feb. 28, 2022

(65) Prior Publication Data

US 2022/0409369 A1    Dec. 29, 2022

Related U.S. Application Data

(63) Continuation-in-part of application No. 16/443,862, filed on Jun. 17, 2019, now Pat. No. 11,273,033, (Continued)

(51) Int. Cl.
*A61F 2/24* (2006.01)
*A61F 2/95* (2013.01)

(52) U.S. Cl.
CPC .......... *A61F 2/2427* (2013.01); *A61F 2/2409* (2013.01); *A61F 2/2412* (2013.01); (Continued)

(58) Field of Classification Search
CPC ...... A61F 2/2427; A61F 2/243; A61F 2/2436; A61F 2/2439; A61F 2/2409; A61F 2/2418; A61F 2/95
See application file for complete search history.

(56) References Cited

U.S. PATENT DOCUMENTS

| 3,744,060 A | 7/1973 | Bellhouse et al. |
| 4,079,468 A | 3/1978 | Liotta et al. |

(Continued)

FOREIGN PATENT DOCUMENTS

| CN | 107249482 A | 10/2017 |
| CN | 107920862 A | 4/2018 |

(Continued)

OTHER PUBLICATIONS

International Search Report and Written Opinion for International Application No. PCT/US2023/076845 dated Mar. 4, 2024, 10 pages.

(Continued)

*Primary Examiner* — Diane D Yabut
(74) *Attorney, Agent, or Firm* — COOLEY LLP

(57) ABSTRACT

A prosthetic valve includes a frame and a flow control component. The frame has an aperture extending through the frame about a central axis. The flow control component is mounted within the aperture and is configured to permit blood flow in a first direction approximately parallel to the vertical axis from an inflow end to an outflow end of the flow control component and to block blood flow in a second direction, opposite the first direction. The frame has an expanded configuration with a first height along the central axis, a first lateral width along a lateral axis perpendicular to the central axis, and a first longitudinal length along a longitudinal axis perpendicular to the central axis and the lateral axis. The frame has a compressed configuration with a second height less than the first height and a second lateral width less than the first lateral width.

19 Claims, 94 Drawing Sheets

Related U.S. Application Data which is a continuation of application No. 16/155,890, filed on Oct. 10, 2018, now Pat. No. 10,321,995, application No. 17/682,875 is a continuation-in-part of application No. 16/449,420, filed on Jun. 23, 2019, now Pat. No. 11,278,437, and a continuation of application No. 17/167,983, filed on Feb. 4, 2021, now Pat. No. 11,344,413, which is a continuation of application No. PCT/US2019/051957, filed on Sep. 19, 2019, which is a continuation-in-part of application No. 16/163,577, filed on Oct. 18, 2018, now Pat. No. 11,071,627.

(60) Provisional application No. 62/766,611, filed on Sep. 20, 2018, provisional application No. 62/737,343, filed on Sep. 27, 2018, provisional application No. 62/749,121, filed on Oct. 22, 2018, provisional application No. 62/777,070, filed on Dec. 8, 2018.

(52) U.S. Cl.
CPC .......... *A61F 2/2418* (2013.01); *A61F 2/2433* (2013.01); *A61F 2/95* (2013.01); *A61F 2210/0014* (2013.01); *A61F 2220/0008* (2013.01); *A61F 2220/0016* (2013.01); *A61F 2220/0075* (2013.01); *A61F 2230/0006* (2013.01); *A61F 2230/001* (2013.01); *A61F 2230/0069* (2013.01); *A61F 2250/0039* (2013.01)

(56) References Cited

U.S. PATENT DOCUMENTS

| | | | |
|---|---|---|---|
| 5,509,428 | A | 4/1996 | Dunlop |
| 5,554,185 | A | 9/1996 | Block et al. |
| 5,800,531 | A | 9/1998 | Cosgrove et al. |
| 5,906,642 | A | 5/1999 | Caudillo et al. |
| 6,006,134 | A | 12/1999 | Hill et al. |
| 6,290,719 | B1 | 9/2001 | Garberoglio |
| 6,312,464 | B1 | 11/2001 | Navia |
| 6,449,507 | B1 | 9/2002 | Hill et al. |
| 6,458,153 | B1 | 10/2002 | Bailey et al. |
| 6,532,388 | B1 | 3/2003 | Hill et al. |
| 6,628,987 | B1 | 9/2003 | Hill et al. |
| 6,669,724 | B2 | 12/2003 | Park et al. |
| 6,718,208 | B2 | 4/2004 | Hill et al. |
| 6,769,434 | B2 | 8/2004 | Liddicoat et al. |
| 6,890,330 | B2 | 5/2005 | Streeter et al. |
| 6,896,690 | B1 | 5/2005 | Lambrecht et al. |
| 6,904,318 | B2 | 6/2005 | Hill et al. |
| 6,929,653 | B2 | 8/2005 | Strecter |
| 7,175,660 | B2 | 2/2007 | Cartledge et al. |
| 7,201,761 | B2 | 4/2007 | Woolfson et al. |
| 7,225,019 | B2 | 5/2007 | Jahns et al. |
| 7,269,457 | B2 | 9/2007 | Shafer et al. |
| 7,361,189 | B2 | 4/2008 | Case et al. |
| 7,442,204 | B2 | 10/2008 | Schwammenthal et al. |
| 7,621,948 | B2 | 11/2009 | Herrmann et al. |
| 7,648,527 | B2 | 1/2010 | Agnew |
| 7,749,245 | B2 | 7/2010 | Cohn et al. |
| 7,753,949 | B2 | 7/2010 | Lamphere et al. |
| 7,811,316 | B2 | 10/2010 | Kalmann et al. |
| 8,628,571 | B1 | 1/2014 | Hacohen et al. |
| 8,900,295 | B2 | 12/2014 | Migliazza et al. |
| 8,926,694 | B2 | 1/2015 | Costello |
| 8,986,370 | B2 | 3/2015 | Annest |
| 8,998,982 | B2 | 4/2015 | Richter et al. |
| 9,232,995 | B2 | 1/2016 | Kovalsky et al. |
| 9,308,086 | B2 | 4/2016 | Ho |
| 9,402,720 | B2 | 8/2016 | Richter et al. |
| 9,414,915 | B2 | 8/2016 | Lombardi et al. |
| 9,468,525 | B2 | 10/2016 | Kovalsky |
| 9,504,562 | B2 | 11/2016 | Richter et al. |
| 9,526,613 | B2 | 12/2016 | Gross et al. |
| 9,597,181 | B2 | 3/2017 | Christianson et al. |
| 9,662,202 | B2 | 5/2017 | Quill et al. |
| 9,788,946 | B2 | 10/2017 | Bobo, Jr. et al. |
| 9,895,219 | B2 | 2/2018 | Costello |
| 10,085,834 | B2 | 10/2018 | Benson et al. |
| 10,321,995 | B1* | 6/2019 | Christianson ......... A61F 2/2409 |
| 10,327,895 | B2 | 6/2019 | Lozonschi et al. |
| 10,463,489 | B2 | 11/2019 | Christianson et al. |
| 10,485,662 | B2 | 11/2019 | Alkhatib |
| 10,485,976 | B2 | 11/2019 | Streeter et al. |
| 10,517,718 | B2 | 12/2019 | Richter et al. |
| 10,537,425 | B2 | 1/2020 | Richter et al. |
| 10,595,994 | B1* | 3/2020 | Christianson ......... A61L 31/129 |
| 10,631,983 | B1 | 4/2020 | Christianson et al. |
| 10,653,522 | B1 | 5/2020 | Vidlund et al. |
| 10,653,523 | B2 | 5/2020 | Chambers et al. |
| 10,758,346 | B1 | 9/2020 | Christianson et al. |
| 10,761,511 | B2 | 9/2020 | Chen et al. |
| 10,779,937 | B2 | 9/2020 | Vidlund et al. |
| 11,071,627 | B2 | 7/2021 | Saikrishnan et al. |
| 11,076,956 | B2* | 8/2021 | Christianson ......... A61F 2/2418 |
| 11,109,969 | B2* | 9/2021 | Vidlund ............... A61F 2/2466 |
| 11,166,814 | B2 | 11/2021 | Vidlund, I et al. |
| 11,173,027 | B2 | 11/2021 | Christianson et al. |
| 11,179,239 | B2 | 11/2021 | Vidlund et al. |
| 11,185,409 | B2 | 11/2021 | Christianson et al. |
| 11,202,706 | B2 | 12/2021 | Christianson et al. |
| 11,234,812 | B2 | 2/2022 | Green et al. |
| 11,234,813 | B2 | 2/2022 | Perrin |
| 11,253,359 | B2 | 2/2022 | Vidlund et al. |
| 11,273,032 | B2 | 3/2022 | Christianson et al. |
| 11,273,033 | B2* | 3/2022 | Christianson ......... A61F 2/2427 |
| 11,278,437 | B2* | 3/2022 | Christianson ............ A61F 2/95 |
| 11,298,227 | B2 | 4/2022 | Vidlund et al. |
| 11,331,186 | B2 | 5/2022 | Christianson et al. |
| 11,337,807 | B2 | 5/2022 | Christianson et al. |
| 11,344,412 | B2 | 5/2022 | Vidlund et al. |
| 11,344,413 | B2* | 5/2022 | Christianson ......... A61F 2/2436 |
| 11,712,335 | B2 | 8/2023 | Christianson et al. |
| 11,717,399 | B2 | 8/2023 | Armer et al. |
| 11,786,366 | B2 | 10/2023 | Vidlund et al. |
| 12,138,158 | B2 | 11/2024 | Vidlund et al. |
| 12,144,731 | B2 | 11/2024 | Vidlund et al. |
| 12,150,852 | B2 | 11/2024 | Vidlund et al. |
| 2002/0138138 | A1 | 9/2002 | Yang |
| 2002/0183827 | A1 | 12/2002 | Derus et al. |
| 2003/0040808 | A1 | 2/2003 | Stack et al. |
| 2003/0055495 | A1 | 3/2003 | Pease et al. |
| 2004/0049207 | A1 | 3/2004 | Goldfarb et al. |
| 2004/0088047 | A1 | 5/2004 | Spence et al. |
| 2004/0093060 | A1 | 5/2004 | Seguin et al. |
| 2004/0116996 | A1 | 6/2004 | Freitag |
| 2004/0117009 | A1 | 6/2004 | Cali et al. |
| 2004/0167619 | A1 | 8/2004 | Case et al. |
| 2004/0199209 | A1 | 10/2004 | Hill et al. |
| 2004/0225352 | A1 | 11/2004 | Osborne et al. |
| 2005/0010246 | A1 | 1/2005 | Streeter et al. |
| 2005/0075659 | A1 | 4/2005 | Realyvasquez et al. |
| 2005/0075725 | A1 | 4/2005 | Rowe |
| 2005/0107811 | A1 | 5/2005 | Starksen et al. |
| 2005/0137686 | A1 | 6/2005 | Salahieh et al. |
| 2005/0203614 | A1 | 9/2005 | Forster et al. |
| 2005/0228472 | A1 | 10/2005 | Case et al. |
| 2005/0228495 | A1 | 10/2005 | Macoviak |
| 2006/0173524 | A1 | 8/2006 | Salahieh et al. |
| 2006/0190075 | A1 | 8/2006 | Jordan et al. |
| 2006/0195180 | A1 | 8/2006 | Kheradvar et al. |
| 2006/0195183 | A1 | 8/2006 | Navia et al. |
| 2006/0229708 | A1 | 10/2006 | Powell et al. |
| 2006/0241745 | A1 | 10/2006 | Solem |
| 2006/0276887 | A1 | 12/2006 | Brady et al. |
| 2007/0016286 | A1 | 1/2007 | Herrmann et al. |
| 2007/0073387 | A1 | 3/2007 | Forster et al. |
| 2007/0100427 | A1 | 5/2007 | Perouse |
| 2007/0239271 | A1 | 10/2007 | Nguyen |
| 2008/0065204 | A1 | 3/2008 | Macoviak et al. |
| 2008/0071287 | A1 | 3/2008 | Goto |
| 2008/0140181 | A1 | 6/2008 | Reynolds et al. |

(56) References Cited

U.S. PATENT DOCUMENTS

| | | |
|---|---|---|
| 2008/0154355 A1 | 6/2008 | Benichou et al. |
| 2008/0183279 A1 | 7/2008 | Bailey et al. |
| 2008/0200980 A1 | 8/2008 | Robin et al. |
| 2008/0221672 A1 | 9/2008 | Lamphere et al. |
| 2008/0262592 A1 | 10/2008 | Jordan et al. |
| 2009/0005863 A1 | 1/2009 | Goetz et al. |
| 2009/0048656 A1 | 2/2009 | Wen |
| 2009/0054976 A1 | 2/2009 | Tuval et al. |
| 2009/0132035 A1 | 5/2009 | Roth et al. |
| 2009/0164003 A1 | 6/2009 | Kheradvar |
| 2009/0192601 A1 | 7/2009 | Rafiee et al. |
| 2010/0016894 A1 | 1/2010 | Houard et al. |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0185275 A1 | 7/2010 | Richter et al. |
| 2010/0280591 A1 | 11/2010 | Shin et al. |
| 2010/0298929 A1 | 11/2010 | Thornton et al. |
| 2011/0004237 A1 | 1/2011 | Schneider et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0137397 A1 | 6/2011 | Chau et al. |
| 2011/0160836 A1 | 6/2011 | Behan |
| 2011/0172784 A1 | 7/2011 | Richter et al. |
| 2011/0224785 A1 | 9/2011 | Hacohen |
| 2011/0245911 A1 | 10/2011 | Quill et al. |
| 2011/0264191 A1 | 10/2011 | Rothstein |
| 2011/0319989 A1 | 12/2011 | Lane et al. |
| 2012/0022605 A1 | 1/2012 | Jahns et al. |
| 2012/0022639 A1 | 1/2012 | Hacohen et al. |
| 2012/0035719 A1 | 2/2012 | Forster et al. |
| 2012/0065723 A1 | 3/2012 | Drasler et al. |
| 2012/0083874 A1 | 4/2012 | Dale et al. |
| 2012/0165928 A1 | 6/2012 | Nitzan et al. |
| 2012/0203336 A1 | 8/2012 | Annest |
| 2012/0310327 A1 | 12/2012 | Mchugo |
| 2012/0310328 A1 | 12/2012 | Olson et al. |
| 2013/0035759 A1 | 2/2013 | Gross et al. |
| 2013/0046373 A1 | 2/2013 | Cartledge et al. |
| 2013/0166017 A1 | 6/2013 | Cartledge et al. |
| 2013/0178931 A1 | 7/2013 | Fargahi |
| 2013/0190861 A1 | 7/2013 | Chau et al. |
| 2013/0238089 A1 | 9/2013 | Lichtenstein et al. |
| 2013/0282110 A1 | 10/2013 | Schweich, Jr. et al. |
| 2013/0304197 A1 | 11/2013 | Buchbinder et al. |
| 2013/0304200 A1 | 11/2013 | McLean et al. |
| 2013/0325110 A1 | 12/2013 | Khalil et al. |
| 2013/0338764 A1 | 12/2013 | Thornton et al. |
| 2014/0005778 A1 | 1/2014 | Buchbinder et al. |
| 2014/0012372 A1 | 1/2014 | Chau et al. |
| 2014/0018915 A1 | 1/2014 | Biadillah et al. |
| 2014/0025164 A1 | 1/2014 | Montorfano et al. |
| 2014/0031924 A1 | 1/2014 | Bruchman et al. |
| 2014/0039611 A1 | 2/2014 | Lane et al. |
| 2014/0052237 A1 | 2/2014 | Lane et al. |
| 2014/0067037 A1 | 3/2014 | Fargahi |
| 2014/0121763 A1 | 5/2014 | Duffy et al. |
| 2014/0135908 A1 | 5/2014 | Glozman et al. |
| 2014/0142695 A1 | 5/2014 | Gross et al. |
| 2014/0172077 A1 | 6/2014 | Bruchman et al. |
| 2014/0172083 A1 | 6/2014 | Bruchman et al. |
| 2014/0194983 A1 | 7/2014 | Kovalsky et al. |
| 2014/0207231 A1 | 7/2014 | Hacohen et al. |
| 2014/0222136 A1 | 8/2014 | Geist et al. |
| 2014/0222142 A1* | 8/2014 | Kovalsky .......... A61F 2/2418 623/2.17 |
| 2014/0249621 A1 | 9/2014 | Eidenschink |
| 2014/0257466 A1 | 9/2014 | Board et al. |
| 2014/0257467 A1 | 9/2014 | Lane et al. |
| 2014/0276971 A1 | 9/2014 | Kovach |
| 2014/0277342 A1 | 9/2014 | Roeder et al. |
| 2014/0277563 A1 | 9/2014 | White |
| 2014/0288480 A1 | 9/2014 | Zimmerman et al. |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0379076 A1 | 12/2014 | Vidlund et al. |
| 2015/0039081 A1 | 2/2015 | Costello |
| 2015/0045880 A1 | 2/2015 | Hacohen |
| 2015/0119978 A1 | 4/2015 | Tegels et al. |
| 2015/0142103 A1 | 5/2015 | Vidlund |
| 2015/0157457 A1 | 6/2015 | Hacohen |
| 2015/0173897 A1 | 6/2015 | Raanani et al. |
| 2015/0173898 A1 | 6/2015 | Drasler et al. |
| 2015/0196390 A1 | 7/2015 | Ma et al. |
| 2015/0216661 A1 | 8/2015 | Hacohen et al. |
| 2015/0257878 A1 | 9/2015 | Lane et al. |
| 2015/0265400 A1 | 9/2015 | Eidenschink et al. |
| 2015/0282922 A1 | 10/2015 | Hingston et al. |
| 2015/0282931 A1 | 10/2015 | Brunnett et al. |
| 2015/0313701 A1 | 11/2015 | Krahbichler |
| 2015/0335424 A1 | 11/2015 | Mclean et al. |
| 2015/0351906 A1 | 12/2015 | Hammer et al. |
| 2015/0351910 A1 | 12/2015 | Gilmore et al. |
| 2016/0008131 A1 | 1/2016 | Christianson et al. |
| 2016/0038280 A1 | 2/2016 | Morriss et al. |
| 2016/0081799 A1 | 3/2016 | Leo et al. |
| 2016/0213470 A1 | 7/2016 | Ahlberg et al. |
| 2016/0213473 A1 | 7/2016 | Hacohen et al. |
| 2016/0220363 A1 | 8/2016 | Peter |
| 2016/0235525 A1 | 8/2016 | Rothstein et al. |
| 2016/0302921 A1 | 10/2016 | Gosal et al. |
| 2016/0310274 A1 | 10/2016 | Gross et al. |
| 2016/0324633 A1 | 11/2016 | Gross et al. |
| 2016/0324639 A1 | 11/2016 | Nguyen et al. |
| 2016/0367360 A1 | 12/2016 | Cartledge et al. |
| 2017/0020670 A1 | 1/2017 | Murray et al. |
| 2017/0035568 A1 | 2/2017 | Lombardi et al. |
| 2017/0056163 A1 | 3/2017 | Tayeb et al. |
| 2017/0056166 A1 | 3/2017 | Ratz et al. |
| 2017/0071733 A1 | 3/2017 | Ghione et al. |
| 2017/0071736 A1 | 3/2017 | Zhu et al. |
| 2017/0100236 A1 | 4/2017 | Robertson et al. |
| 2017/0128208 A1 | 5/2017 | Christianson et al. |
| 2017/0143446 A1 | 5/2017 | Kölbel |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181852 A1 | 6/2017 | Kassas |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0245993 A1 | 8/2017 | Gross et al. |
| 2017/0252163 A1 | 9/2017 | Kheradvar |
| 2017/0273784 A1 | 9/2017 | Racchini et al. |
| 2017/0281341 A1 | 10/2017 | Lim et al. |
| 2017/0319333 A1 | 11/2017 | Tegels et al. |
| 2017/0325943 A1 | 11/2017 | Robin et al. |
| 2017/0325948 A1 | 11/2017 | Wallace et al. |
| 2017/0333240 A1 | 11/2017 | Stangenes et al. |
| 2017/0348099 A1 | 12/2017 | Mendelson et al. |
| 2017/0360557 A1 | 12/2017 | Kheradvar et al. |
| 2017/0360558 A1 | 12/2017 | Ma |
| 2018/0000586 A1 | 1/2018 | Ganesan et al. |
| 2018/0014932 A1 | 1/2018 | Hammer et al. |
| 2018/0021130 A1 | 1/2018 | Danino |
| 2018/0042721 A1 | 2/2018 | Chambers |
| 2018/0098847 A1 | 4/2018 | Tuseth et al. |
| 2018/0116793 A1 | 5/2018 | Salahieh et al. |
| 2018/0147055 A1 | 5/2018 | Vidlund et al. |
| 2018/0153689 A1 | 6/2018 | Maimon et al. |
| 2018/0200049 A1* | 7/2018 | Chambers .......... A61F 2/2439 |
| 2018/0206983 A1 | 7/2018 | Noe et al. |
| 2018/0256322 A1 | 9/2018 | Zhang et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0289474 A1 | 10/2018 | Rajagopal et al. |
| 2018/0289475 A1 | 10/2018 | Chung et al. |

(56) References Cited

U.S. PATENT DOCUMENTS

| | | |
|---|---|---|
| 2018/0296325 A1 | 10/2018 | Mclean |
| 2018/0296341 A1 | 10/2018 | Noe et al. |
| 2018/0303612 A1 | 10/2018 | Pasquino et al. |
| 2018/0311037 A1 | 11/2018 | Morriss et al. |
| 2018/0318071 A1 | 11/2018 | Lozonschi et al. |
| 2018/0333259 A1 | 11/2018 | Dibie |
| 2018/0344456 A1 | 12/2018 | Barash et al. |
| 2018/0353293 A1 | 12/2018 | Colavito et al. |
| 2019/0000619 A1 | 1/2019 | Quijano et al. |
| 2019/0008636 A1 | 1/2019 | Francis et al. |
| 2019/0029819 A1 | 1/2019 | Huber |
| 2019/0060057 A1 | 2/2019 | Cohen et al. |
| 2019/0069995 A1 | 3/2019 | Levi et al. |
| 2019/0105153 A1 | 4/2019 | Barash et al. |
| 2019/0262129 A1 | 8/2019 | Cooper et al. |
| 2019/0321171 A1 | 10/2019 | Morriss et al. |
| 2019/0365538 A1 | 12/2019 | Chambers et al. |
| 2019/0388219 A1 | 12/2019 | Lane et al. |
| 2020/0008941 A1 | 1/2020 | Stappenbeck et al. |
| 2020/0093589 A1 | 3/2020 | Christianson et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154010 A1 | 5/2021 | Schneider et al. |
| 2021/0154011 A1 | 5/2021 | Christianson et al. |
| 2021/0186693 A1 | 6/2021 | Vidlund, I et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |
| 2021/0401572 A1 | 12/2021 | Nasr et al. |
| 2022/0000614 A1 | 1/2022 | Vidlund et al. |
| 2022/0087815 A1 | 3/2022 | Bernshtein et al. |
| 2022/0096226 A1 | 3/2022 | Christianson et al. |
| 2022/0160504 A1 | 5/2022 | Vidlund et al. |
| 2022/0249228 A1 | 8/2022 | Vidlund et al. |
| 2022/0280292 A1 | 9/2022 | Vidlund et al. |
| 2022/0280296 A1 | 9/2022 | Christianson et al. |
| 2022/0296369 A1 | 9/2022 | Kheradvar et al. |
| 2022/0323212 A1 | 10/2022 | Vidlund et al. |
| 2022/0338978 A1 | 10/2022 | Yushtein |
| 2022/0370198 A1 | 11/2022 | Nir et al. |
| 2022/0378410 A1 | 12/2022 | Hacohen et al. |
| 2022/0387174 A1 | 12/2022 | Schwarcz et al. |
| 2022/0395370 A1 | 12/2022 | Vidlund et al. |
| 2023/0157816 A1 | 5/2023 | Perrin |
| 2023/0172710 A1 | 6/2023 | Nir |
| 2023/0190463 A1 | 6/2023 | Nir |
| 2023/0200990 A1 | 6/2023 | Chen et al. |
| 2023/0263630 A1 | 8/2023 | Saar et al. |
| 2023/0338140 A1 | 10/2023 | Cartledge et al. |
| 2024/0074855 A1 | 3/2024 | Atias et al. |
| 2024/0138983 A1 | 5/2024 | Ekvall et al. |
| 2024/0148496 A1 | 5/2024 | Christianson |
| 2024/0148497 A1 | 5/2024 | Bukin et al. |
| 2024/0225828 A1 | 7/2024 | Vidlund et al. |

FOREIGN PATENT DOCUMENTS

| | | |
|---|---|---|
| EP | 3897462 A1 | 10/2021 |
| JP | 2010508093 A | 3/2010 |
| JP | 2013517011 A | 5/2013 |
| JP | 2014528761 A | 10/2014 |
| JP | 2016508858 A | 3/2016 |
| JP | 2016533787 A | 11/2016 |
| JP | 2018515306 A | 6/2018 |
| WO | WO-2008055301 A1 | 5/2008 |
| WO | WO-2010079427 A1 | 7/2010 |
| WO | WO-2012035279 A1 | 3/2012 |
| WO | WO-2016183523 A1 | 11/2016 |
| WO | WO-2017123802 A1 | 7/2017 |
| WO | WO-2018136726 A1 | 7/2018 |
| WO | WO-2019195860 A2 | 10/2019 |
| WO | WO-2020061124 A1 | 3/2020 |
| WO | WO-2020061331 A2 | 3/2020 |
| WO | WO-2020131978 A1 | 6/2020 |
| WO | WO-2020146842 A1 | 7/2020 |
| WO | WO-2020154735 A1 | 7/2020 |
| WO | WO-2020181154 A2 | 9/2020 |
| WO | WO-2020186251 A1 | 9/2020 |
| WO | WO-2020227249 A1 | 11/2020 |
| WO | WO-2021035032 A1 | 2/2021 |
| WO | WO-2021040996 A1 | 3/2021 |
| WO | WO-2021146515 A1 | 7/2021 |
| WO | WO-2022010974 A1 | 1/2022 |
| WO | WO-2023164489 A2 | 8/2023 |
| WO | WO-2024081883 A1 | 4/2024 |

OTHER PUBLICATIONS

Non-Final Office Action for U.S. Appl. No. 17/526,691 dated Mar. 11, 2024, 9 pages.

Office Action and Search report for Chinese Application No. CN201980075586.9 dated Feb. 5, 2024, 15 pages.

Office Action for Canadian Application No. CA3152042 dated Feb. 20, 2024, 5 pages.

Office Action for Canadian Patent Application No. CA20203152632 dated Feb. 19, 2024, 4 pages.

Office Action for Canadian Patent Application No. CA3113429 dated Feb. 13, 2024, 4 pages.

Office Action for European Application No. EP20200801681 dated Dec. 11, 2023, 7 pages.

Office Action for Japanese Application No. JP20210563105 mailed Feb. 26, 2024, 8 pages.

Office Action for Japanese Patent Application No. JP20210555207 dated Jan. 31, 2024, 6 pages.

Office Action for Japanese Patent Application No. JP2021547343 dated Jan. 31, 2024, 6 pages.

Office Action for Australian Application No. 2019342130 mailed May 22, 2024, 3 pages.

Office Action for Chinese Application No. 201980090378.6, with Search Report, mailed Mar. 12, 2024, 28 pages, English translation included.

Office Action for Chinese Application No. 202080074543.1, with Search Report, mailed Mar. 28, 2024, 18 pages, English translation included.

Office Action for Japanese Application No. 2021-516666 mailed Apr. 22, 2024, 6 pages, English translation included.

Office Action for Japanese Application No. 2021-535023 mailed Apr. 22, 2024, 4 pages, English translation included.

Office Action for Japanese Application No. 2021-547343 mailed May 13, 2024, 4 pages, English translation included.

Office Action for Japanese Application No. 2022-511360 mailed Apr. 18, 2024, 6 pages, English translation included.

Office Action for Japanese Application No. 2022-513172 mailed Apr. 18, 2024, 12 pages, English translation included.

Office Action for U.S. Appl. No. 17/707,493 mailed Mar. 29, 2024, 21 pages.

Office Action for U.S. Appl. No. 18/410,230, mailed Jun. 4, 2024, 11 pages.

(56) References Cited

OTHER PUBLICATIONS

Extended European Search Report for European Application No. EP20854535 dated Jun. 23, 2023, 8 pages.
Office Action for U.S. Appl. No. 17/666,086 dated Jul. 5, 2023, 16 pages.
Office Action for European Application No. 19863898.3 dated Mar. 24, 2023, 6 pages.
Invitation to Pay Additional Fees for International Application No. PCT/US2023/63044, mailed Jul. 31, 2023, 2 pages.
Extended European Search Report for European Application No. 19863898.3, mailed Apr. 29, 2022, 13 pages.
Extended European Search Report for European Application No. 19897707.6, mailed Sep. 6, 2022, 7 pages.
Extended European Search Report for European Application No. 20745513.0, mailed Sep. 20, 2022, 9 pages.
Extended European Search Report for European Application No. 20767325.2, mailed on Oct. 25, 2022, 5 pages.
Extended European Search Report for European Application No. 20769769.9, mailed Oct. 17, 2022, 6 pages.
Extended European Search Report for European Application No. 20801681.6, mailed Jan. 18, 2023, 13 pages.
International Search Report and Written Opinion for International Application No. PCT/US2019/028822, mailed Oct. 24, 2019, 14 pages.
International Search Report and Written Opinion for International Application No. PCT/US2019/051615, mailed Mar. 2, 2020, 14 pages.
International Search Report and Written Opinion for International Application No. PCT/US2019/051957, mailed Apr. 30, 2020, 16 pages.
International Search Report and Written Opinion for International Application No. PCT/US2019/067010, mailed Mar. 10, 2020, 17 pages.
International Search Report and Written Opinion for International Application No. PCT/US2020/013240, mailed Jun. 3, 2020, 7 pages.
International Search Report and Written Opinion for International Application No. PCT/US2020/015231, mailed Apr. 23, 2020, 10 pages.
International Search Report and Written Opinion for International Application No. PCT/US2020/021300, mailed Oct. 7, 2020, 6 pages.
International Search Report and Written Opinion for International Application No. PCT/US2020/022828, mailed May 19, 2020, 12 pages.
International Search Report and Written Opinion for International Application No. PCT/US2020/031390, mailed Aug. 3, 2020, 10 pages.
International Search Report and Written Opinion for International Application No. PCT/US2020/045195, mailed Jan. 8, 2021, 18 pages.
International Search Report and Written Opinion for International Application No. PCT/US2020/047162, mailed Dec. 30, 2020, 9 pages.
International Search Report and Written Opinion for International Application No. PCT/US2021/013570, mailed Apr. 1, 2021, 9 pages.
Office Action for U.S. Appl. No. 16/155,890, mailed Feb. 8, 2019, 13 pages.
Office Action for U.S. Appl. No. 16/163,577, mailed Mar. 8, 2021, 10 pages.
Office Action for U.S. Appl. No. 16/435,687, mailed Aug. 7, 2019, 19 pages.
Office Action for U.S. Appl. No. 16/442,504, mailed Jan. 14, 2020, 11 pages.
Office Action for U.S. Appl. No. 16/443,862, mailed Nov. 12, 2021, 9 pages.
Office Action for U.S. Appl. No. 16/445,210, mailed Jan. 28, 2021, 7 pages.
Office Action for U.S. Appl. No. 16/448,108, mailed Jan. 21, 2020, 14 pages.
Office Action for U.S. Appl. No. 16/448,108, mailed Mar. 8, 2021, 8 pages.
Office Action for U.S. Appl. No. 16/448,108, mailed Sep. 1, 2020, 14 pages.
Office Action for U.S. Appl. No. 16/449,420, mailed Sep. 1, 2021, 16 pages.
Office Action for U.S. Appl. No. 16/455,417, mailed Sep. 23, 2019, 11 pages.
Office Action for U.S. Appl. No. 16/455,740, mailed Jul. 24, 2020, 7 pages.
Office Action for U.S. Appl. No. 16/711,415, mailed Jan. 18, 2022, 7 pages.
Office Action for U.S. Appl. No. 17/062,080, mailed Dec. 15, 2022, 14 pages.
Office Action for U.S. Appl. No. 17/154,227, mailed Jun. 18, 2021, 8 pages.
Office Action for U.S. Appl. No. 17/154,227, mailed Mar. 29, 2021, 6 pages.
Office Action for U.S. Appl. No. 17/154,438, mailed May 3, 2021, 16 pages.
Office Action for U.S. Appl. No. 17/167,983, mailed Apr. 13, 2021, 20 pages.
Office Action for U.S. Appl. No. 17/167,988, mailed Sep. 22, 2021, 19 pages.
Office Action for U.S. Appl. No. 17/193,936, mailed May 27, 2021, 6 pages.
Office Action for U.S. Appl. No. 17/221,547, mailed Aug. 4, 2021, 11 pages.
Office Action for U.S. Appl. No. 17/221,547, mailed Oct. 21, 2021, 9 pages.
Office Action for U.S. Appl. No. 17/222,182, mailed Sep. 2, 2021, 23 pages.
Office Action for U.S. Appl. No. 17/222,430, mailed Oct. 7, 2021, 17 pages.
Office Action for U.S. Appl. No. 17/236,219, mailed Aug. 4, 2021, 17 pages.
Office Action for U.S. Appl. No. 17/388,983, mailed Jan. 6, 2022, 11 pages.
Extended European Search Report for European Application No. 23215329.6, mailed on Jul. 5, 2024, 5 pages.
Office Action for European Application No. 20856704.0 mailed Jul. 29, 2024, 4 pages.
Office Action for U.S. Appl. No. 17/707,493 mailed Jul. 8, 2024, 9 pages.
Extended European Search Report for European Application No. EP20856704 dated Aug. 22, 2023, 11 pages.
International Search Report and Written Opinion for PCT Application No. PCT/US2023/063044 dated Oct. 24, 2023, 13 pages.
Office Action European Application No. 19863898.3 mailed Nov. 27, 2023, 4 pages.
Office Action for European Application No. 20769769.9 dated Sep. 8, 2023, 4 pages.
Office Action for Japanese Application No. JP20210516666 dated Aug. 31, 2023, 19 pages.
Office Action for Japanese Application No. JP20210535023 dated Oct. 27, 2023, 17 pages.
Office Action for U.S. Appl. No. 17/207,076 dated Aug. 17, 2023, 6 pages.
International Search Report and Written Opinion for International Application No. PCT/US2024/035388, mailed Dec. 3, 2024, 12 pages.
Invitation to Pay Additional Fees for International Application No. PCT/US2024/035388, mailed Sep. 17, 2024, 3 pages.
Office Action for Australian Application No. 2019406832 mailed Jul. 26, 2024, 4 pages.
Office Action for Australian Application No. 2020231221 mailed Sep. 11, 2024, 4 pages.
Office Action for Australian Application No. 2020239265 mailed Sep. 2, 2024, 3 pages.
Office Action for European Application No. 20801681.6 mailed Jul. 31, 2024, 5 pages.

(56) References Cited

OTHER PUBLICATIONS

Office Action for U.S. Appl. No. 17/372,022 mailed Aug. 1, 2024, 15 pages.
Office Action for U.S. Appl. No. 17/825,551, mailed Aug. 29, 2024, 11 pages.
Office Action for U.S. Appl. No. 18/329,098, mailed Oct. 24, 2024, 12 pages.
Office Action for U.S. Appl. No. 18/410,230, mailed Nov. 5, 2024, 6 pages.

* cited by examiner

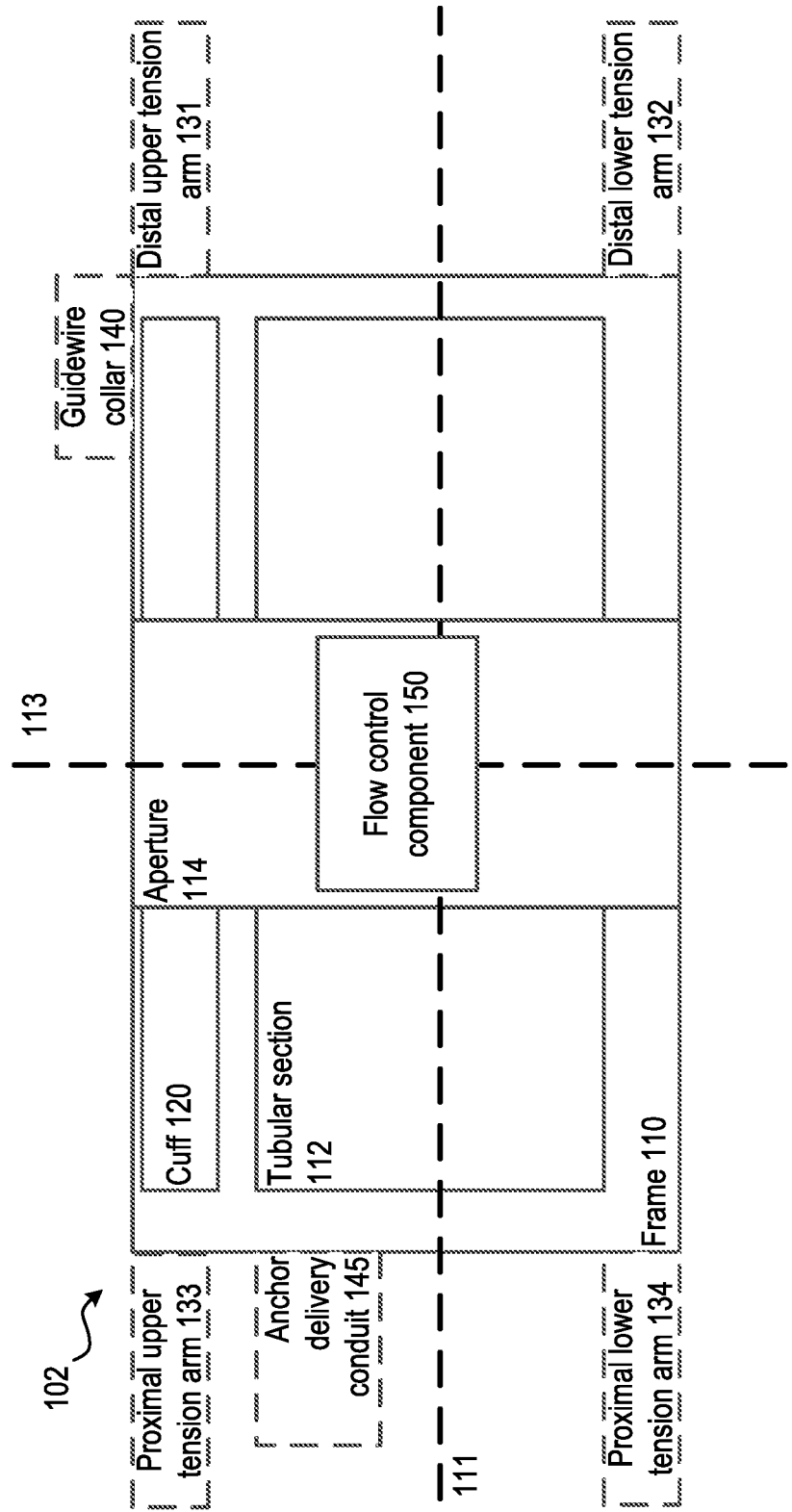

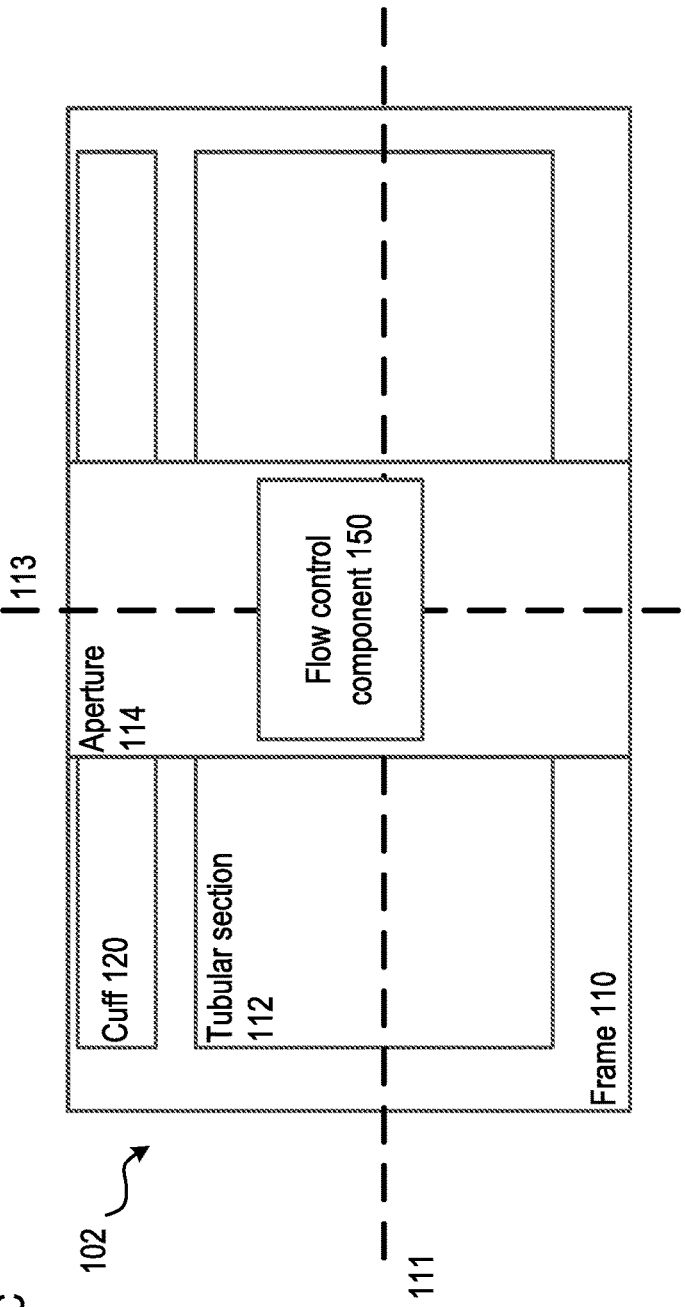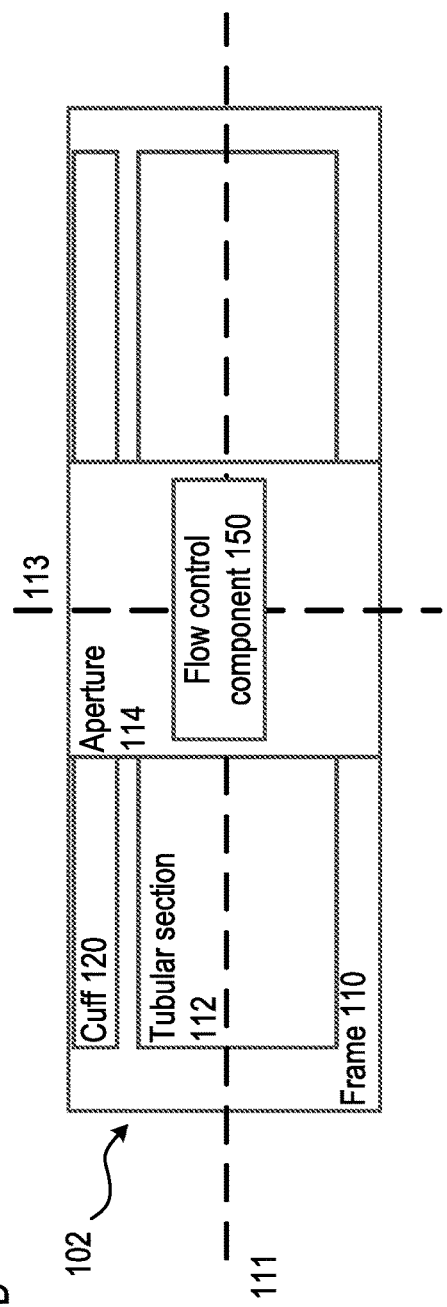

FIG. 25
FIG. 26
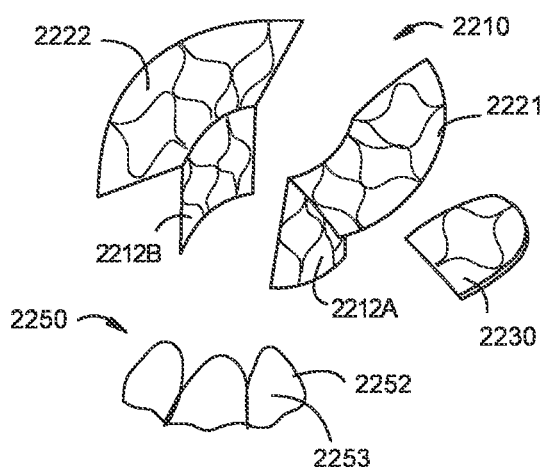
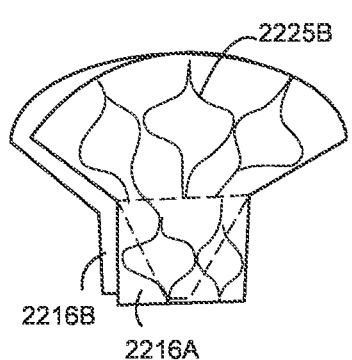
FIG. 27
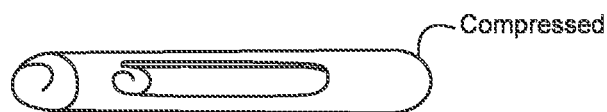

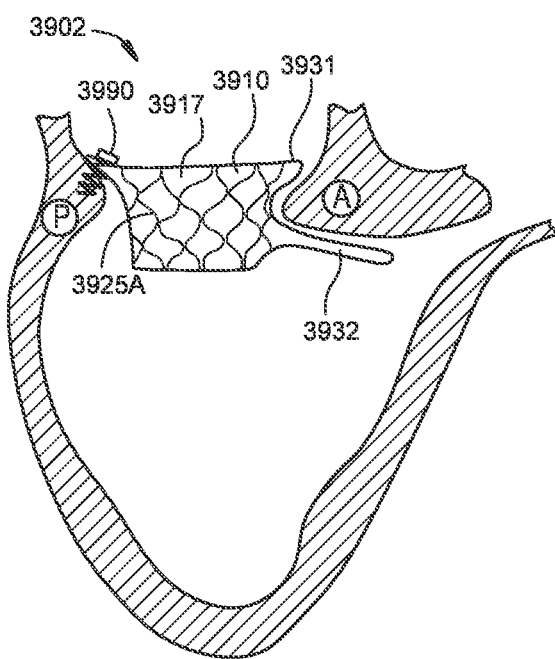

Dispose in atrium of heart a distal portion of delivery catheter containing a frame of a prosthetic valve in a compressed configuration, directed towards the annulus of a native valve of the heart
302

Release a tension arm of the prosthetic valve frame from the delivery catheter
304

Dispose a distal portion of the tension arm on the ventricle side of the annulus of the native valve while the distal end of the delivery catheter remains on the atrium side of the annulus
306

Release the remainder of the prosthetic valve frame from the delivery catheter
308

Hold the prosthetic valve frame at an angle relative to the native valve annulus
310

Allow blood to flow from the atrium to the ventricle partially through the native valve annulus around the prosthetic valve frame, and partially through the prosthetic valve frame
312

Assess valve function
314

Dispose the tubular portion of the frame within the annulus of the native valve
316

Anchor the proximal portion of the frame of the prosthetic valve to tissue surrounding the native valve
318

Deliver to an aperture of the prosthetic valve frame a flow control apparatus
320

```
Provide a compressible and expandable prosthetic valve,
(i) where the valve has a tubular frame with a flow control component
mounted within the tubular frame,
(ii) where the valve or flow control component is configured to permit
blood flow in a first direction through an inflow end of the valve and to
block blood flow in a second direction, opposite the first direction,
through an outflow end of the valve,
(iii) where the valve is compressible and expandable and has a long-axis
oriented at an intersecting angle of between 45-135 degrees to the first
direction, and
(iv) where the long-axis is parallel to a length-wise cylindrical axis of a
delivery catheter used to deliver the valve
8101
```

Advance a delivery catheter to a desired location in the body
8102

Deliver the compressible and expandable prosthetic valve that has a height
of about 5-60mm and a diameter of about 25-80mm
8103

Release the valve from the delivery catheter
8104

Provide a compressible and expandable prosthetic valve,
(i) where the valve has a tubular frame with a flow control component mounted within the tubular frame,
(ii) where the valve or flow control component is configured to permit blood flow in a first direction through an inflow end of the valve and to block blood flow in a second direction, opposite the first direction, through an outflow end of the valve,
(iii) where the valve is compressible and expandable and has a long-axis oriented at an intersecting angle of between 45-135 degrees to the first direction,
(iv) where the long-axis is parallel to a length-wise cylindrical axis of a delivery catheter used to deliver the valve, and
(v) where the valve has a height of about 5-60mm and a diameter of about 25-80mm
8201

Load the compressible and expandable prosthetic valve into a tapering fixture or funnel attached to a delivery catheter, to compress the valve to a compressed configuration for introduction into the body using a delivery catheter for implanting at a desired location in the body
8202

FIG. 103G
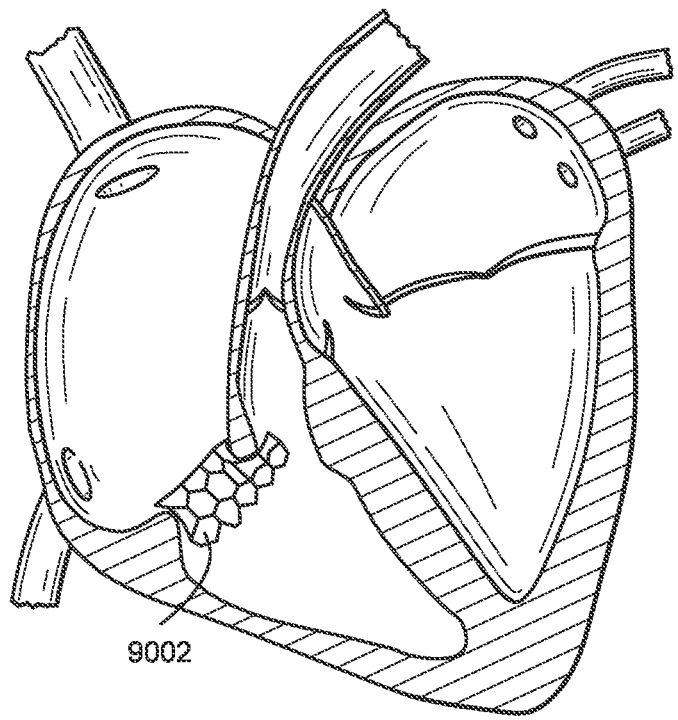
FIG. 104A
FIG. 104B
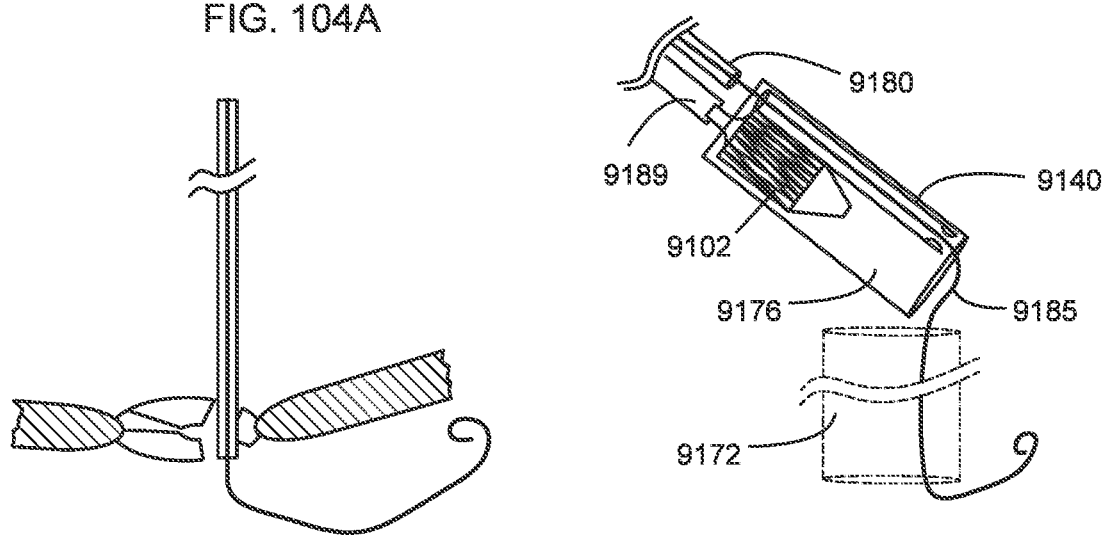

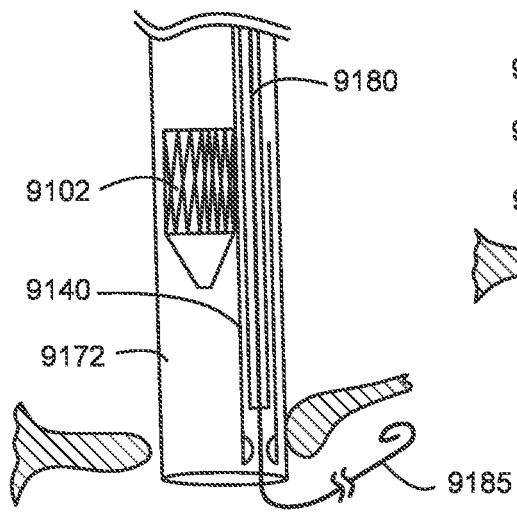
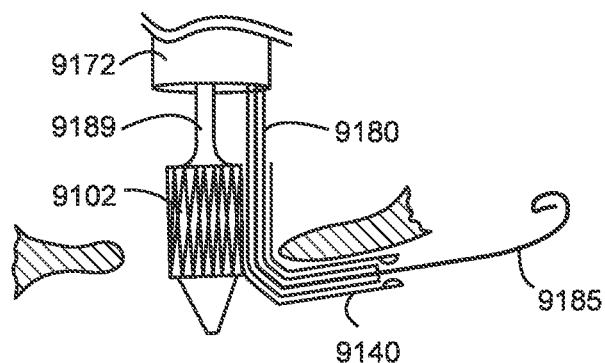
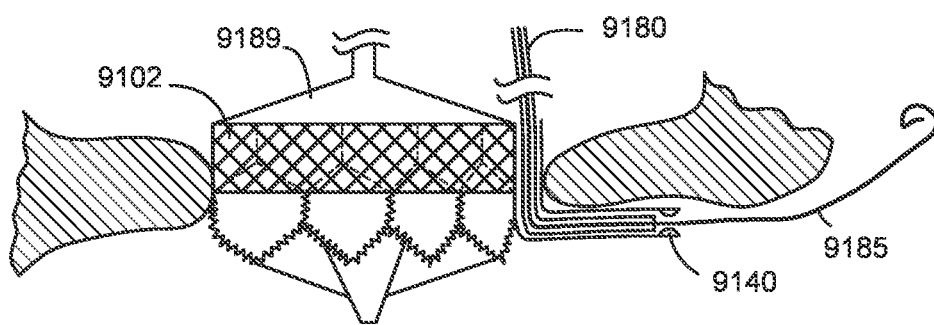
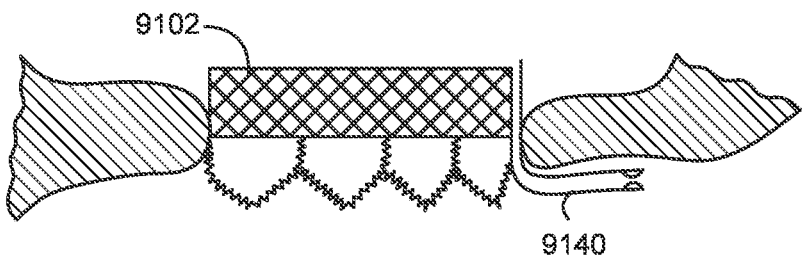

TRANSCATHETER DELIVERABLE PROSTHETIC HEART VALVES AND METHODS OF DELIVERY

CROSS-REFERENCE TO RELATED APPLICATIONS

This application is a continuation-in-part of U.S. patent application Ser. No. 16/443,862, entitled "Side-Delivered Transcatheter Heart Valve Replacement," filed Jun. 17, 2019, (now U.S. Pat. No. 11,273,033), which is a continuation of U.S. patent application Ser. No. 16/155,890, entitled "Side-Delivered Transcatheter Heart Valve Replacement," filed Oct. 10, 2018 (now U.S. Pat. No. 10,321,995), which claims priority to and the benefit of U.S. Provisional Patent Application Ser. No. 62/766,611, entitled "Side-Loading Transcatheter Heart Valve Replacement," filed Sep. 20, 2018, the disclosure of which is incorporated herein by reference in its entirety.

This application is also a continuation-in-part of U.S. patent application Ser. No. 16/449,420, entitled "Compression Capable Annular Frames for Side Delivery of Transcatheter Heart Valve Replacement," filed Jun. 23, 2019, (now U.S. Pat. No. 11,278,437), which claims priority to and the benefit of U.S. Provisional Patent Application Ser. No. 62/777,070, entitled "Compression Capable Annular Frames for Orthogonal Delivery of Transcatheter Heart Valve Replacement," filed Dec. 8, 2018, the disclosure of which is incorporated herein by reference in its entirety.

This application is a continuation of U.S. patent application Ser. No. 17/167,983, entitled "Transcatheter Deliverable Prosthetic Heart Valves and Methods of Delivery," filed Feb. 4, 2021, (now U.S. Pat. No. 11,344,413), which is a continuation of International Patent Application Serial No. PCT/US2019/051957, entitled "Transcatheter Deliverable Prosthetic Heart Valves and Methods of Delivery," filed Sep. 19, 2019, the disclosure of each of which is incorporated herein by reference in its entirety.

International Patent Application Serial No. PCT/US2019/051957 is a continuation-in-part of U.S. patent application Ser. No. 16/163,577, entitled "Orthogonally Delivered Transcatheter Heart Valve Frame for Valve in Valve Prostheses," filed Oct. 18, 2018 (now U.S. Pat. No. 11,071,627), the disclosure of which is incorporated herein by reference in its entirety.

International Patent Application Serial No. PCT/US2019/051957 also claims priority to and the benefit of U.S. Provisional Patent Application Ser. No. 62/766,611, entitled "Side-Loading Transcatheter Heart Valve Replacement," filed Sep. 20, 2018; U.S. Provisional Patent Application Ser. No. 62/737,343, entitled "Side-Loading Transcatheter Heart Valve Replacement," filed Sep. 27, 2018; U.S. Provisional Patent Application Ser. No. 62/749,121, entitled "Guidewire Delivery of Tricuspid Valve," filed Oct. 22, 2018; and U.S. Provisional Patent Application Ser. No. 62/777,070, entitled "Compression Capable Annular Frames for Orthogonal Delivery of Transcatheter Heart Valve Replacement," filed Dec. 8, 2018, the disclosure of each of which is incorporated herein by reference in its entirety.

BACKGROUND

Embodiments are described herein that relate to prosthetic heart valves, and devices and methods for use in the delivery and deployment of such valves.

Prosthetic heart valves can pose challenges for delivery and deployment within a heart, particularly for delivery by catheters through the patient's vasculature rather than through a surgical approach. Traditional valves have a central cylinder axis that is parallel to the lengthwise axis of the delivery catheter and are deployed from the end of the delivery catheter and expanded radially outward from the central annular axis, in a manner akin to pushing a closed spring-loaded umbrella out of a sleeve to make it spring open. Traditional valves can only be expanded as large as what the internal diameter of the delivery catheter will allow. Efforts to increase the expanded diameter of traditional valves have run into the problems of trying to compress too much material and structure into too little space.

A need exists for valves that can be delivered through small diameter delivery catheters, particularly to native valves such as tricuspid valves.

SUMMARY

The embodiments described herein relate generally to transcatheter prosthetic valves and methods for delivering transcatheter prosthetic valves. In some embodiments, a prosthetic valve includes a frame and a flow control component. The frame has an aperture extending through the frame about a central axis. The flow control component is mounted within the aperture and is configured to permit blood flow in a first direction approximately parallel to the central axis from an inflow end to an outflow end of the flow control component and to block blood flow in a second direction, opposite the first direction. The frame has an expanded configuration with a first height along the central axis, a first lateral width along a lateral axis perpendicular to the central axis, and a first longitudinal length along a longitudinal axis perpendicular to the central axis and the lateral axis. The frame has a compressed configuration with a second height, less than the first height, along the central axis and a second lateral width, less than the first lateral width, along the lateral axis.

BRIEF DESCRIPTION OF THE FIGURES

FIGS. 1A-1F are schematic illustrations of a transcatheter prosthetic valve according to an embodiment.

FIGS. 2-4A illustrate a transcatheter prosthetic valve according to an embodiment and being delivered within a delivery catheter to a target tissue, being inserted into a native annulus of the target tissue and being deployed in the native annulus of the target tissue, respectively.

FIG. 25 is an exploded view of a two-panel transcatheter prosthetic valve according to an embodiment.

FIG. 26 is a side view of the two-panel transcatheter prosthetic valve of FIG. 25.

FIG. 27 is a side view of the two-panel transcatheter prosthetic valve of FIG. 25 in a compressed configuration.

FIG. 50 is side view of a transcatheter prosthetic valve deployed in and anchored to a native annulus of a heart.

FIG. 72D is a flowchart describing a method for delivering a transcatheter prosthetic valve according to an embodiment.

FIG. 94 is a flowchart describing a method for delivering a transcatheter prosthetic valve according to an embodiment.

FIG. 95 is a flowchart describing a method for loading a transcatheter prosthetic valve into a delivery catheter according to an embodiment.

FIGS. 103A-103G illustrate a process of deploying a transcatheter prosthetic valve into a native annulus of a human heart according to an embodiment.

FIGS. 104A-104F illustrate a process of deploying a transcatheter prosthetic valve into a native annulus of a human heart according to an embodiment.

DETAILED DESCRIPTION

Figure 1B:
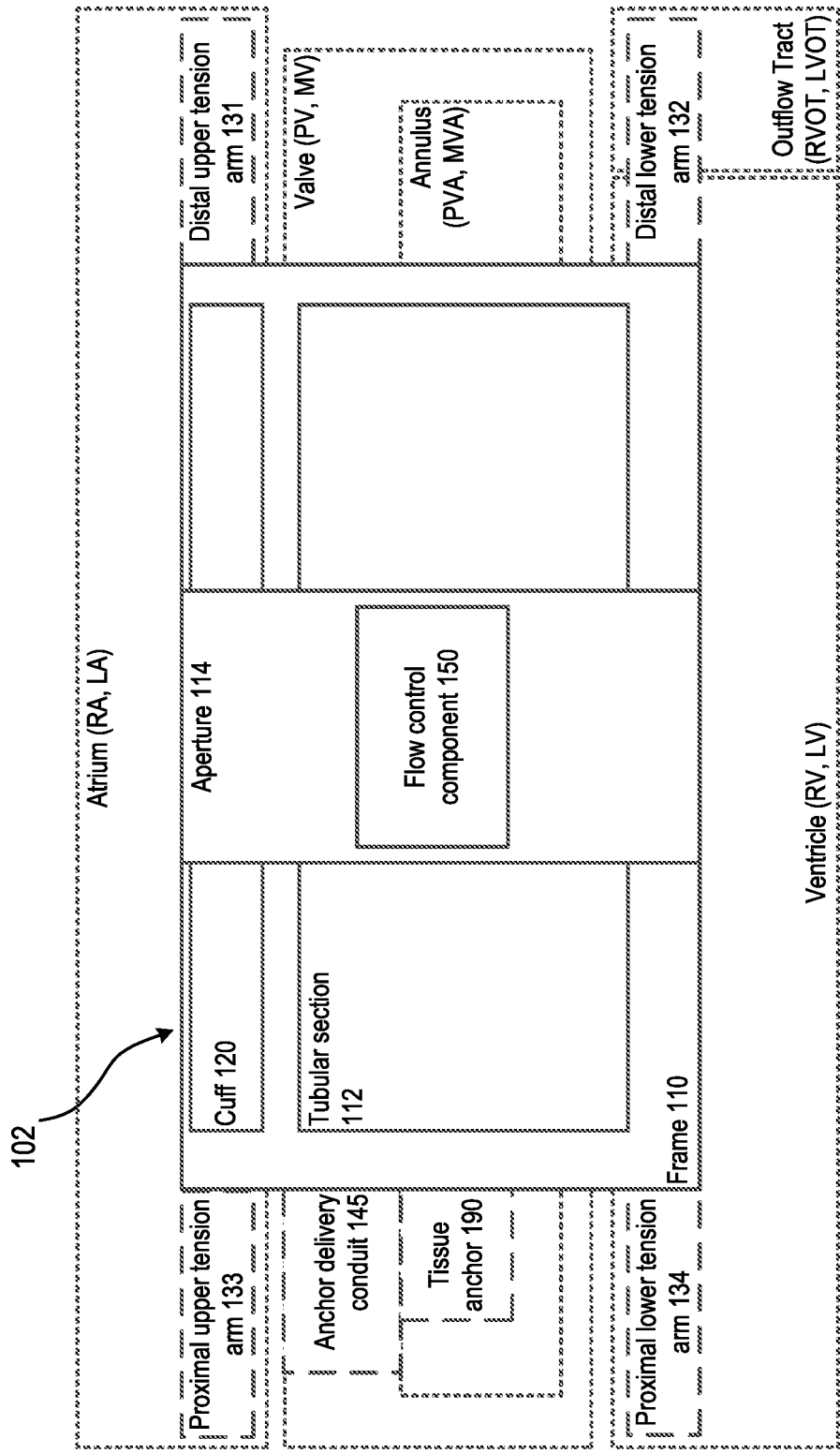

Disclosed embodiments are directed to an orthogonally delivered transcatheter prosthetic valves and/or components thereof, and methods of manufacturing, loading, delivering, and deploying the transcatheter prosthetic valves and/or components thereof. The transcatheter prosthetic valves have a tubular frame and a flow control component mounted within a central lumen of the tubular frame. The flow control component is configured to permit blood flow in a first direction through an inflow end of the valve and block blood flow in a second direction, opposite the first direction, through an outflow end of the valve. The valve is compressible and expandable along a long-axis substantially parallel to a lengthwise cylindrical axis of a delivery catheter. The valve is configured to transition between a compressed configuration for introduction into the body using the delivery catheter, and an expanded configuration for implanting at a desired location in the body. The valve is configured to permit blood flow in a first direction through an inflow end of the valve and to block blood flow in a second direction, opposite the first direction, through an outflow end of the valve.

In some embodiments, the transcatheter prosthetic valve has the compressible configuration in a lengthwise or orthogonal direction relative to the central axis of the flow control component can allow a large diameter valve (e.g., having a height of about 5-60 mm and a diameter of about 20-80 mm) to be delivered and deployed from the inferior vena cava directly into the mitral or tricuspid valve using, for example, a 24-36 Fr delivery catheter and without delivery and deployment from the delivery catheter at an acute angle of approach.

In some embodiments, the transcatheter prosthetic valve has a central axis when in the compressed configuration that is co-axial or at least substantially parallel with the first direction (e.g., the blood flow direction). In some embodiments, the compressed configuration of the valve is orthogonal to the first direction. In some embodiments, the long-axis is oriented at an intersecting angle of between 45-135 degrees to the first direction when in the compressed configuration and/or the expanded configuration.

In some embodiments, the transcatheter prosthetic valve includes a tension arm extending from a distal side of the tubular frame, which can be used, for example, as a Right Ventricular Outflow Tract ("RVOT") tab. The tension arm can include a wire loop or wire frame, integrated frame section, or stent, extending from about 10-40 mm away from the tubular frame.

In some embodiments, the transcatheter prosthetic valve includes (i) an upper tension arm attached to a distal upper edge of the tubular frame, the upper tension arm comprised of wire loop or wire frame extending from about 2-20 mm away from the tubular frame, and (ii) a lower tension arm (e.g., used as a RVOT tab) extending from a distal side of the tubular frame, the lower tension arm comprised of wire loop or wire frame extending from about 10-40 mm away from the tubular frame.

In some embodiments, the transcatheter prosthetic valve includes at least one tissue anchor connected to the tubular frame for engaging annular tissue.

In some embodiments, the transcatheter prosthetic valve is one of a balloon-inflated valve or a self-expanding valve.

In some embodiments, the tubular frame forms a two-part framework. A first part includes a flared atrial cuff joined to a second part that comprises cylindrical member/segment. The cuff is joined to the cylindrical member/segment around the circumference of a top edge of the cylindrical member/segment.

In some embodiments, the tubular frame has a side profile of a flat cone shape having a diameter R of 40-80 mm, a diameter r of 20-60 mm, and a height of 5-60 mm. In some embodiments, the tubular frame has a side profile of an hourglass flat conical shape having a top diameter R1 of 40-80 mm, a bottom diameter R2 of 50-70 mm, an internal diameter r of 20-30 mm, and a height of 5-60 mm. In some embodiments, the tubular frame has an outer diameter of 20-80 mm and an inner diameter of 21-79 mm.

In some embodiments, the tubular frame is formed of a braided wire, laser-cut wire, photolithography produced wire cells, 3D printed wire cells, wire cells formed from intermittently connected single strand wires in a wave shape, a zigzag shape, or spiral shape, and/or combinations thereof, and is covered with a biocompatible material. In some embodiments, the tubular frame is formed of a plurality of compressible wire cells having an orientation and cell geometry substantially orthogonal to a central vertical axis of the valve to minimize wire cell strain when the tubular frame is configured in a vertical compressed configuration, a rolled compressed configuration, or a folded compressed configuration.

In some embodiments, the tubular frame has a central channel and an outer perimeter wall circumscribing a central vertical axis in an expanded configuration. The perimeter wall has a front wall portion and a back wall portion connected along a proximal side to a proximal fold area and connected along a distal side to a distal fold area. The front wall portion has a front upper collar portion and a front lower body portion. The back wall portion has a back upper collar portion and a back lower body portion. In some embodiments, the front lower body portion and the back lower body portion in an expanded configuration form a shape selected from a funnel, cylinder, flat cone, or circular hyperboloid. In some embodiments, the proximal fold area and the distal fold area each comprise a sewn seam, a fabric panel, or a rigid hinge. In some embodiments, the proximal fold area and the distal fold area each comprise a flexible fabric span without any wire cells.

In some embodiments, the tubular frame has an inner surface covered with a biocompatible material comprising pericardial tissue, and an outer surface covered with a biocompatible material comprising a woven synthetic polyester material.

In some embodiments, the flow control component has an internal diameter of 20-35 mm and a height of 5-40 mm, and a plurality of leaflets of pericardial material joined to form a rounded cylinder at an inflow end and having a flat closable aperture at an outflow end. For example, a flow control component can include 2-4 leaflets of pericardial material.

In some embodiments, the flow control component is supported with one or more longitudinal supports integrated into or mounted upon the flow control component. The one or more longitudinal supports selected from rigid or semi-rigid posts, rigid or semi-rigid ribs, rigid or semi-rigid battens, rigid or semi-rigid panels, and combination thereof.

In some embodiments, a delivery system for deployment of the transcatheter prosthetic valve includes (i) a delivery catheter comprising an elongated tube with a central lumen; (ii) a hypotube sheathed guidewire assembly having an outer sheath and an inner guidewire shaft configured to push against a guidewire collar on a tension arm of a compressed transcatheter prosthetic valve to deliver the valve; (ii) the transcatheter prosthetic valve having a tension arm extending from a distal side of the tubular frame. The tension arm is comprised of wire loop or wire frame, integrated frame section, or stent, extending about 10-40 mm away from the tubular frame. The tension arm having a guidewire collar element attached the tension arm, wherein the guidewire collar element is sized and configured with a guidewire aperture to allow the inner guidewire shaft of the hypotube sheathed guidewire assembly to pass through the guide aperture, and to block passage of the outer sheath of the guidewire assembly through the guidewire aperture.

In some embodiments, a method for manufacturing the transcatheter prosthetic valve includes (i) using additive or subtractive metal or metal-alloy manufacturing to produce the tubular frame, wherein the additive metal or metal-alloy manufacturing is 3D printing or direct metal laser sintering (powder melt), and wherein the subtractive metal or metal-alloy manufacturing is photolithography, laser sintering/cutting, CNC machining, or electrical discharge machining; (ii) mounting a flow control component within the tubular frame; (iii) covering an outer surface of the tubular frame with a pericardium material or similar biocompatible material.

In some embodiments, a method for orthogonal delivery of the transcatheter prosthetic valve to a desired location in the body includes (i) advancing a delivery catheter to the desired location in the body and (ii) delivering the transcatheter prosthetic valve to the desired location in the body by releasing the valve from the delivery catheter. The valve being in the compressed configuration when in the delivery catheter. The valve transitioning to the expanded configuration when released from the delivery catheter.

In some embodiments, the method further includes attaching a pulling wire (e.g., a rigid elongated pulling/pushing rod or draw wire) to a sidewall of the transcatheter prosthetic valve and pulling the valve into a tapering fixture or funnel (e.g., attached to a proximal end of the delivery catheter) such that the tapering fixture or funnel compresses or spirals the valve to the compressed configuration for loading into the delivery catheter.

In some embodiments, the method includes releasing the valve from the delivery catheter by (i) pulling the valve out of the delivery catheter using the pulling wire that is releasably connected to the distal side of the valve, wherein advancing the pushing rod away from the delivery catheter pulls the compressed valve out of the delivery catheter, or (ii) pushing the valve out of the delivery catheter using the pulling wire that is releasably connected to the proximal side of the valve, wherein advancing the pushing rod out of from the delivery catheter pushes the compressed valve out of the delivery catheter.

In some embodiments, the method includes releasing the valve from the delivery catheter while increasing blood flow during deployment of the valve by (i) partially releasing the valve from the delivery catheter to establish blood flow around the partially released valve and blood flow through the flow control component; (ii) completely releasing the valve from the delivery catheter while maintaining attachment to the valve with a positioning catheter or the pulling wire to transition to a state with increased blood flow through the flow control component and decreased blood flow around the valve; (iii) deploying the valve into a final mounted position to transition to a state with complete blood flow through the flow control component and minimal or no blood flow around the valve; and (iv) disconnecting and withdrawing the positioning catheter or pulling wire from the valve.

In some embodiments, the method further includes inserting a tension arm (e.g., a RVOT tab) in the RVOT during the transition from partial release of the valve to complete release of the valve.

In some embodiments, the method further includes rotating the transcatheter prosthetic valve using a steerable catheter along an axis parallel to the plane of the valve annulus such that (i) the upper tension arm is conformationally pressure locked against supra-annular tissue and (ii) the lower tension arm is conformationally pressure locked against sub-annular tissue.

In some embodiments, the method further includes anchoring one or more tissue anchors attached to the valve into annular tissue.

In some embodiments, a method for orthogonal delivery of the transcatheter prosthetic valve to the desired location in the body includes (i) advancing a first delivery catheter to the desired location in the body, (ii) delivering the tubular frame to the desired location in the body by releasing the tubular frame from the delivery catheter, (iii) advancing a second delivery catheter to the desired location in the body, and (iv) delivering the flow control component into the central lumen of the tubular frame. The tubular frame being in the compressed configuration when in the first delivery catheter and the flow control component being in the compressed configuration when in the second delivery catheter. The tubular frame transitioning to the expanded configuration when released from the first delivery catheter and the flow control component transitioning to the expanded configuration when released from the second delivery catheter to mount into the tubular frame.

In some embodiments, a method for compressing the transcatheter prosthetic valve for lengthwise orthogonal release from a delivery catheter includes (i) flattening, rolling or folding the valve into a compressed configuration wherein the long-axis of the valve is substantially parallel to a lengthwise cylindrical axis of the delivery catheter. In some embodiments, the method includes one of (i) unilaterally rolling the valve into the compressed configuration from one side of the tubular frame; (ii) bilaterally rolling the valve into the compressed configuration from two opposing sides of the tubular frame; (iii) flattening the tubular frame into two parallel panels that are substantially parallel to the long-axis, and then rolling the flattened tubular frame into the compressed configuration; or (iv) flattening the tubular frame along a vertical axis to reduce a vertical dimension of the valve from top to bottom.

In some embodiments, a method for orthogonal delivery of the transcatheter prosthetic valve to a desired location in the body includes (i) advancing a guidewire to a desired location within a body, said guidewire having an outer sheath and an inner shaft; (ii) advancing a delivery catheter over the guidewire to the desired location; (iii) mounting a valve capsule onto a proximal end of the guidewire, said valve capsule containing a compressed valve having a threaded guidewire collar having an aperture sized to permit the inner shaft of the guidewire to extend through the aperture and to block the outer sheath of the guidewire from extending through the aperture; (iv) loading the valve capsule into a proximal end of the delivery catheter; (v) advancing the compressed valve from the valve capsule into and through a lumen of the delivery catheter to the desired location in the body by advancing the outer sheath over the inner shaft to deploy the valve at the desired location.

In some embodiments, a method for orthogonal delivery of the transcatheter prosthetic valve to a native annulus of a human heart can include at least one of (i) advancing the delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach, e.g., fossa ovalis or lower, via the IVC-femoral or the SVC jugular approach; and (iv) delivering transcatheter prosthetic valve to the native annulus by releasing the valve from the delivery catheter.

In some embodiments, the method further includes positioning a tension arm of the transcatheter prosthetic valve into a RVOT of a right ventricle of a human heart. For example, the method can further include (i) positioning a lower tension arm of the valve into the RVOT of the right ventricle and (ii) positioning an upper tension arm—connected to the lower tension arm—into a supra-annular position such that the upper tension arm provides a supra-annular downward force in the direction of the right ventricle and the lower tension arm provides a sub-annular upward force in the direction of the right atrium.

In some embodiments, a prosthetic valve includes a tubular frame, a distal subannular anchoring tension arm, and a flow control component. The tubular frame has a sidewall and an atrial collar attached around a top edge of the sidewall. The distal subannular anchoring tension arm is attached to and extends away from a lower distal sidewall of the tubular frame. The flow control component is mounted within the tubular frame and configured to permit blood flow in a first direction through an inflow end of the prosthetic valve and block blood flow in a second direction, opposite the first direction, through an outflow end of the prosthetic valve. The prosthetic valve is compressible to a compressed configuration for introduction into the body using a delivery catheter for implanting at a desired location in the body. The prosthetic valve, in the compressed configuration, has a long-axis oriented at an intersecting angle of between 45-135 degrees to the first direction and substantially parallel to a lengthwise cylindrical axis of the lumen of the delivery catheter. The prosthetic valve is expandable to an expanded configuration having a long-axis oriented at an intersecting angle of between 45-135 degrees to the first direction.

In some embodiments, a prosthetic valve includes a valve frame and a flow control component. The valve frame has an aperture extending through the valve frame along a central axis. The flow control component is mounted within the aperture and is configured to permit blood flow in a first direction approximately parallel to the central axis from an inflow end to an outflow end of the flow control component and to block blood flow in a second direction, opposite the first direction. The valve frame has an expanded configuration with a first height along the central axis, a first lateral width along a lateral axis perpendicular to the central axis, and a first longitudinal length along a longitudinal axis perpendicular to the central axis and the lateral axis. The valve frame has a compressed configuration with a second height, less than the first height, along the central axis and a second lateral width, less than the first lateral width, along the lateral axis.

In some embodiments, a frame for a prosthetic valve includes a tubular frame having a central lumen defined by an inner circumferential surface of the tubular frame and defining a vertical axis of the tubular frame. The tubular frame has an outer circumferential surface engageable with native annular tissue. The tubular frame is compressible to a compressed configuration for introduction into the body using a delivery catheter for implanting at a desired location in the body. The valve, in compressed configuration, has a horizontal long-axis oriented at an intersecting angle between 45-135 degrees relative to the vertical axis of the tubular frame and substantially parallel to a lengthwise cylindrical axis of a lumen of the delivery catheter when disposed therein. The valve is expandable to an expanded configuration having a horizontal long-axis oriented at an intersecting angle between 45-135 degrees relative to the vertical axis of the tubular frame.

In some embodiments, a method for delivering a prosthetic valve to a native valve between a ventricle and an atrium of a heart includes advancing to the atrium of the heart a delivery catheter containing a prosthetic valve. The prosthetic valve includes a tubular frame having a side wall and an atrial collar attached around a top edge of the side wall, a distal subannular anchoring tension arm attached and extending distally away from a lower distal side wall of the tubular frame, and a flow control component mounted within the tubular frame. The flow control component configured to permit blood flow in a first direction through an inflow end of the prosthetic valve and block blood flow in a second direction, opposite the first direction, through an outflow end of the prosthetic valve. The prosthetic valve is disposed in the delivery catheter in a compressed configuration having a long-axis oriented at an intersecting angle of between 45-135 degrees to the first direction and substantially parallel to a length-wise cylindrical axis of the delivery catheter, and expandable to an expanded configuration having a long-axis oriented at an intersecting angle of between 45-135 degrees to the first direction. The method includes releasing the distal subannular anchoring tension arm of the prosthetic valve from the delivery catheter by pulling the tension arm out of the delivery catheter by pushing away from the delivery catheter a rigid elongated pushing rod that is releasably connected to the tension arm. The distal subannular anchoring tension arm is delivered to the ventricle side of the annulus of the native valve. The remainder of the prosthetic valve is then released from the delivery catheter to an expanded configuration so that the tubular frame is disposed within the annulus of the native valve.

In some embodiments, a method of delivering a prosthetic valve to an annulus of a native valve between a ventricle and an atrium of a heart includes disposing in the atrium of the heart a distal portion of a delivery catheter having a lumen and a longitudinal axis, with a distal end of the delivery catheter directed towards the annulus of the native valve. The prosthetic valve being disposed within the distal portion of the delivery catheter in a compressed configuration. The prosthetic valve having a tubular frame with a tension arm coupled thereto and a flow control component mounted within the tubular frame and having an expanded configuration in which the prosthetic valve is configured to permit blood flow in a first direction through an inflow end of the prosthetic valve and block blood flow in a second direction, opposite the first direction, through an outflow end of the prosthetic valve. The tension arm extends laterally from the tubular frame and is disposed on the ventricle side of the annulus of the native valve when the tubular frame is disposed within the annulus. The prosthetic valve, when in the expanded configuration, has an extent in any direction lateral to the first direction that is larger than a diameter of the lumen of the distal portion of the delivery catheter. The prosthetic valve, when in the compressed configuration, is disposed within the distal portion of the delivery catheter and is elongated in a longitudinal direction and compressed in a lateral direction relative to the dimensions of the prosthetic valve in the expanded configuration. The prosthetic valve has a long axis in the longitudinal direction that is parallel to the longitudinal axis of the delivery catheter and oriented at an intersecting angle of between 45 and 135 degrees to the first direction, with the tension arm disposed distally in the longitudinal direction, towards the distal end of the delivery catheter. The method further includes releasing the tension arm from the lumen of the catheter. At least a distal portion of the tension arm is disposed on the ventricle side of the annulus of the native valve while the distal end of the delivery catheter remains on the atrium side of the annulus. The remainder of the prosthetic valve is released from the lumen of the delivery catheter so that the tubular frame is disposed within the annulus of the native valve.

In some embodiments, a method of delivering a prosthetic valve to an annulus of a native valve between a ventricle and an atrium of a heart includes disposing in the atrium of the heart a distal portion of a delivery catheter having a lumen and a longitudinal axis, with a distal end of the delivery catheter directed towards the annulus of the native valve. The prosthetic valve being disposed within the distal portion of the delivery catheter in a compressed configuration. The prosthetic valve having a tubular frame with a tension arm coupled thereto and a flow control component mounted within the tubular frame and having an expanded configuration in which the prosthetic valve is configured to permit blood flow in a first direction through an inflow end of the prosthetic valve and block blood flow in a second direction, opposite the first direction, through an outflow end of the prosthetic valve. The tension arm extends laterally from the tubular frame and is disposed on the ventricle side of the annulus of the native valve when the tubular frame is disposed within the annulus. The tubular frame is disposed within the lumen of the delivery catheter with the tension arm disposed towards the distal end of the delivery catheter. The method further includes releasing the tension arm from the lumen of the delivery catheter. At least a distal portion of the tension arm is disposed on the ventricle side of the annulus of the native valve while the distal end of the delivery catheter remains on the atrium side of the annulus. The remainder of the prosthetic valve is released from the lumen of the delivery catheter. The prosthetic valve is held at an oblique angle relative to the annulus of the native valve and blood is allowed to flow from the atrium to the ventricle both through the native valve and through the prosthetic valve to allow assessment of the function of the native valve and the prosthetic valve.

In some embodiments, a method for delivering a prosthetic valve includes advancing, over a guidewire having a diameter, a delivery catheter to dispose a distal end of the delivery catheter at a desired location within a body. A proximal end of the guidewire is mounted onto a valve capsule containing a prosthetic valve in a compressed configuration. The prosthetic valve has a guidewire collar with an aperture therethrough having an internal diameter larger than the diameter of the guidewire. The guidewire is disposed through the aperture of the guidewire collar. The valve capsule is loaded into a proximal end of the delivery catheter. A pusher is disposed over the guidewire proximal to the prosthetic valve. The pusher has an outside diameter larger than the internal diameter of the aperture in the guidewire collar. The prosthetic valve is advanced from the valve capsule into and through a lumen of the delivery catheter to the distal end thereof by advancing the pusher over the guidewire and the prosthetic valve is deployed from the distal end of the delivery catheter to the desired location.

In some embodiments, a method of delivering a prosthetic valve to an annulus of a native valve between a ventricle and an atrium of a heart includes disposing in the atrium of the heart a distal portion of a delivery catheter having a lumen and a longitudinal axis, with a distal end of the delivery catheter directed towards the annulus of the native valve. A tubular frame for the prosthetic valve being disposed within the lumen of the delivery catheter in a compressed configuration. The tubular frame defines a central lumen having a central axis and a tension arm coupled thereto. The tubular frame has an expanded configuration in which the tubular frame. The tubular frame, when in the expanded configuration, has an extent in any direction lateral to the central axis that is larger than a diameter of the lumen of the distal portion of the delivery catheter. The tubular frame, when in the compressed configuration, is disposed within the distal portion of the delivery catheter and is elongated in a longitudinal direction and compressed in a lateral direction relative to the dimensions of the tubular frame in the expanded configuration. The tubular frame has a long-axis in the longitudinal direction that is parallel to the longitudinal axis of the delivery catheter and oriented at an intersecting angle between 45 and 135 degrees relative to the central axis with the tension arm disposed distally in the longitudinal direction, towards the distal end of the delivery catheter. The method further includes releasing the tension arm from the lumen of the catheter. At least a distal portion of the tension arm is disposed on the ventricle side of the annulus of the native valve while the distal end of the delivery catheter remains on the atrium side of the annulus and the remainder of the tubular frame is released from the lumen of the delivery catheter so that the tubular frame is disposed within the annulus of the native valve.

In some embodiments, a prosthetic valve has an annular valve frame defining a central axis and has an expanded configuration with a vertical height along the central axis, a lateral width along a lateral axis perpendicular to the central axis, and a longitudinal length along a longitudinal axis perpendicular to the central axis and the lateral axis. A method for preparing the prosthetic valve for delivery to a patient by a delivery catheter having a lumen with a lumen diameter includes compressing the annular support frame vertically by reducing the dimension of the annular support frame along the central axis from the expanded configuration to a dimension less than the lumen diameter. The annular support frame is compressed laterally by reducing the dimension of the annular support frame along the lateral axis from the expanded configuration to a dimension less than the lumen diameter. The compressing of the annular support frame vertically and the compressing of the annular support frame laterally collectively disposing the annular support frame in a compressed configuration. The annular support frame, when in the compressed configuration, is inserted into the lumen of the delivery catheter.

In some embodiments, a method of delivering a prosthetic valve to an annulus of a native valve between a ventricle and an atrium of a heart includes disposing in the atrium of the heart a distal portion of a delivery catheter having a lumen and a longitudinal axis, with a distal end of the delivery catheter directed towards the annulus of the native valve. The prosthetic valve is disposed within the distal portion of the delivery catheter in a compressed configuration. The prosthetic valve has a tubular frame with a distal lower tension arm and a distal upper tension arm coupled to a distal sidewall thereof and a flow control component mounted within the tubular frame. The prosthetic valve has an expanded configuration in which the flow control component permits blood flow through the prosthetic valve in a first direction and blocks blood flow through the prosthetic valve in a second direction, opposite the first direction. The prosthetic valve is disposed within the lumen of the delivery catheter with the distal lower tension arm and the distal upper tension arm disposed towards the distal end of the delivery catheter. The method further includes releasing the distal lower tension arm from the lumen of the delivery catheter and releasing the distal upper tension arm from the lumen of the delivery catheter. A portion of the distal lower tension arm is placed on the ventricle side of the annulus of the native valve while the distal upper tension arm remains on the atrium side of the annulus. After releasing the distal lower tension arm and releasing the distal upper tension arm, the remainder of the prosthetic valve is released from the lumen of the delivery catheter and the prosthetic valve is deployed into and secured to the annulus of the native valve while the distal upper tension arm is in contact with supra-annular tissue on the atrium side of the annulus and the distal lower tension arm is in contact with subannular tissue on the ventricle side of the annulus during the deploying.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. Rather, these embodiments are provided so that this disclosure will be thorough and complete, and will fully convey the scope of the inventive concepts to those skilled in the art. Like numbers refer to like elements throughout.

The terminology used herein is for the purpose of describing particular embodiments only and is not intended to limit the full scope of the claims. As used herein, the singular forms "a," "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used in this document, the term "comprising" means "including, but not limited to."

As used herein the term "and/or" includes any and all combinations of one or more of the associated listed items.

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

The term "valve prosthesis" or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

The disclosed valves include a member (e.g., a frame) that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves, including ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

In some embodiments, the frame and the flow control component can be separate structures and delivered together or separately. The term "valve frame" or "prosthetic valve frame" or "valve-in-valve" can refer to a three-dimensional structural component, usually tubular, cylindrical, or oval or ring-shaped, and that can be seated within a native valve annulus and used as a mounting element for a commercially available valve such as a Sapien, Sapien 3, or Sapien XT from Edwards Lifesciences, the Inspiris Resilia aortic valve from Edwards Lifesciences, the Masters HP 15 mm valve from Abbott, Lotus Edge valve from Boston Scientific, the Crown PRT leaflet structure from Livanova/Sorin, the Carbomedics family of valves from Sorin, or other flow control component, or a flexible reciprocating sleeve or sleeve-valve.

The term "expandable" as used herein may refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

The terms "side-delivered," "side-delivery," "orthogonal," "orthogonally delivered" and so forth are used to describe that the valves are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Mathematically, the term "orthogonal" refers to an intersecting angle of 90 degrees between two lines or planes. As used herein, the term "substantially orthogonal" refers to an intersecting angle or 90 degrees plus or minus a suitable tolerance. For example, "substantially orthogonal" can refer to an intersecting angle ranging from 75 to 105 degrees.

The disclosed valve embodiments may be delivered by a transcatheter approach. The term "transcatheter" is used to define the process of accessing, controlling, and delivering a medical device or instrument within the lumen of a catheter that is deployed into a heart chamber (or other desired location in the body), as well as an item that has been delivered or controlled by such as process. Transcatheter access is known to include via femoral artery and femoral vein, via brachial artery and vein, via carotid and jugular, via intercostal (rib) space, and via sub-xiphoid. Transcatheter can be synonymous with transluminal and is functionally related to the term "percutaneous" as it relates to delivery of heart valves.

In some of the disclosed embodiments, the prosthetic valve is secured in part to native tissue by a tissue anchor. The term "tissue anchor" or "plication tissue anchor" or "secondary tissue anchor," or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Some disclosed embodiments include a support post. The term "support post" refers to a rigid or semi-rigid length of material such as Nickel-Titanium alloy (Nitino™) or polyetheretherketone (PEEK), that may be mounted on a spoked frame and that runs axially, or down the center of, or within a sewn seam of, the flexible sleeve. The sleeve may be unattached to the support post, or the sleeve may be directly or indirectly attached to the support post.

The term "body channel" may be used to define a blood conduit or vessel within the body, the particular application of the disclosed embodiments of prosthetic valves determines the body channel at issue. An aortic valve replacement, for example, would be implanted in, or adjacent to, the aortic annulus. Likewise, a tricuspid or mitral valve replacement would be implanted at the tricuspid or mitral annulus. Certain features are particularly advantageous for one implantation site or the other. However, unless the combination is structurally impossible, or excluded by claim language, any of the valve embodiments described herein could be implanted in any body channel.

As used herein, the term "lumen" can refer to the inside of a cylinder or tube. The term "bore" can refer to the inner diameter of the lumen.

In some embodiments, components may be fabricated from a synthetic material such a polyurethane or polytetrafluoroethylene. Where a thin, durable synthetic material is contemplated, e.g., for a covering, synthetic polymer materials such expanded polytetrafluoroethylene (PTFE) or polyester may optionally be used. Other suitable materials may optionally include thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene, high-density polyethylene, and ultra-high molecular weight polyethylene. Additional biocompatible polymers may optionally include elastomers, polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, polyurethanes, siloxane polymers and/or oligomers, and/or polylactones, and block co-polymers using the same.

The annular support frame is optionally internally or externally covered, partially or completely, with a biocompatible material such as pericardium. The annular or tubular frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

In some embodiments, frame components may include drug-eluting wire frames. Drug-eluting wire frames may consist of three parts: wire frame platform, coating, and drug. Some of the examples for polymer-free coated frames are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel, which elutes over a period of about 90 days. Endeavour (Medtronic) uses a cobalt chrome driver wire frame for carrying Zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug Novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

FIGS. 1A-1F are various schematic illustrations of a transcatheter prosthetic valve 102 according to an embodiment. The transcatheter prosthetic valve 102 is configured to deployed in a desired location within a body (e.g., of a human patient) and to permit blood flow in a first direction through an inflow end of the transcatheter prosthetic valve 102 and to block blood flow in a second direction, opposite the first direction, through an outflow end of the transcatheter prosthetic valve 102. For example, the transcatheter prosthetic valve 102 can be a transcatheter prosthetic heart valve configured to be deployed within the annulus of a native tricuspid valve or native mitral valve of a human heart to supplement and/or replace the functioning of the native valve.

The transcatheter prosthetic valve 102 (also referred to herein as "valve") is compressible and expandable in at least one direction perpendicular to a long-axis 111 of the valve 102 (also referred to herein as "horizontal axis," "longitudinal axis," or "lengthwise axis"). The valve 102 is configured to compressible and expandable between an expanded configuration (FIGS. 1A, 1B, 1C, and 1E) for implanting at a desired location in a body (e.g., a human heart) and a compressed configuration (FIGS. 1D and 1F) for introduction into the body using a delivery catheter (not shown).

In some embodiments, the valve 102 can be centric, or radially symmetrical. In other embodiments, the valve 102 can be eccentric, or radially (y-axis) asymmetrical. In some eccentric embodiments, the valve 102 (or an outer frame thereof) may have a D-shape (viewed from the top) so the flat portion can be matched to the anatomy in which the valve 102 will be deployed. For example, in some instances, the valve 102 may be deployed in the tricuspid annulus and may have a complex shape determined by the anatomical structures where the valve 102 is being mounted. In the tricuspid annulus, the circumference of the tricuspid valve may be a rounded ellipse, the septal wall is known to be substantially vertical, and the tricuspid is known to enlarge in disease states along the anterior-posterior line. In other instances, the valve 102 may be deployed in the mitral annulus (e.g., near the anterior leaflet) and may have a complex shape determined by the anatomical structures where the valve 102 is being mounted. For example, in the mitral annulus, the circumference of the mitral valve may be a rounded ellipse, the septal wall is known to be substantially vertical, and the mitral is known to enlarge in disease states.

As shown, the valve 102 generally includes an annular support frame 110 and a flow control component 150. In addition, the valve 102 and/or at least the annular support frame 110 of the valve 102 optionally can include one or more of a distal upper tension arm 131, a distal lower tension arm 132, a proximal upper tension arm 133, a proximal lower tension arm 134, a guidewire collar 140, and/or an anchor delivery conduit 145.

The annular support frame 110 (also referred to herein as "tubular frame," "valve frame," "wire frame," or "fame") can have or can define an aperture 114 that extends along a central axis 113. The aperture 114 (e.g., a central axial lumen) can be sized and configured to receive the flow control component 150 across a diameter of the aperture 114. The frame 110 may have an outer circumferential surface for engaging native annular tissue that may be tensioned against an inner aspect of the native annulus to provide structural patency to a weakened native annular ring.

The frame 110 includes a cuff or collar 120 and a tubular section 112. The cuff or collar 120 (referred to herein as "cuff") can be attached to and/or can form an upper edge of the frame 110. When the valve 102 is deployed within a human heart, the cuff 120 can be an atrial cuff or collar. The atrial collar 120 can be shaped to conform to the native deployment location. In a mitral replacement, for example, the atrial collar 120 will be configured with varying portions to conform to the native valve. In one embodiment, the collar 120 will have a distal and proximal upper collar portion. The distal collar portion can be larger than the proximal upper collar portion to account for annular or subannular geometries.

The frame 110 may optionally have a separate atrial collar attached to the upper (atrial) edge of the frame 110, for deploying on the atrial floor that is used to direct blood from the atrium into the flow control component 150 and to seal against blood leakage (perivalvular leakage) around the frame 110. The frame 110 may also optionally have a separate ventricular collar attached to the lower (ventricular) edge of the frame 110, for deploying in the ventricle immediately below the native annulus that is used to prevent regurgitant leakage during systole, to prevent dislodging of the valve 102 during systole, to sandwich or compress the native annulus or adjacent tissue against the atrial collar or cuff 120, and/or optionally to attach to and support the flow control component 150. Some embodiments may have both an atrial collar and a ventricular collar, whereas other embodiments either include a single atrial collar, a single ventricular collar, or have no additional collar structure.

In some embodiments, the frame 110 can have an outer perimeter wall circumscribing the aperture 114 and the central axis 113 in the expanded configuration. The perimeter wall can encompass both the collar 120 and the tubular section 112. In some embodiments, the perimeter wall can be further defined as having a front wall portion and a back wall portion, which are connected along a near side (e.g., relative to the inferior vena cava ("IVC")) or proximal side to a proximal fold area, and connected along a far or distal side to a distal fold area. The front wall portion can be further defined as having a front upper collar portion and a front lower body portion, and the back wall portion can be further defined as having a back upper collar portion and a back lower body portion. The front upper collar portion and the back upper collar portion can collectively form the collar or cuff 120. The front lower body portion and the back lower body portion can collectively form the tubular section 112.

The frame 110 can be a ring, or cylindrical or conical tube, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both.

The frame 110 may have a height in the range of about 5-60 mm, may have an outer diameter dimension, R, in the range of about 20-80 mm, and may have an inner diameter dimension in the range of about 21-79 mm, accounting for the thickness of the frame 110 (e.g., a wire material forming the frame 110).

The frame 110 design is preferably compressible and when released has the stated property that it returns to its original (uncompressed) shape. The frame 110 may be compressed for transcatheter delivery and may be expandable using a transcatheter expansion balloon or as a self-expandable shape-memory element. In some instances, suitable shape-memory materials can include metals and plastics that are durable and biocompatible. For example, the frame 110 can be made from super elastic metal wire, such as a Nitinol wire or other similarly functioning material. Nitinol can be desirable useful since it can be processed to be austenitic, martensitic or super elastic. Martensitic and super elastic alloys can be processed to demonstrate the desired compression. The material may be used for the frame 110 or any portion thereof. It is contemplated to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers.

The frame 110 may be constructed as a braid, wire, or laser cut wire frame. Such materials are available from any number of commercial manufacturers, such as Pulse Systems. One possible construction of the wire frame 110 envisions the laser cutting of a thin, isodiametric Nitinol tube. The laser cuts form regular cutouts in the thin Nitinol tube. In one embodiment, the Nitinol tube is expanded to form a three-dimensional structure formed from diamond-shaped cells. The structure may also have additional functional elements, e.g., loops, anchors, etc. for attaching accessory components such as biocompatible covers, tissue anchors, releasable deployment and retrieval control guides, knobs, attachments, rigging, and so forth. Secondarily the frame 110 can be placed on a mold of the desired shape, heated to a corresponding martensitic temperature, and quenched. The treatment of the wire frame in this manner will form a frame 110 that has shape memory properties and will readily revert to the memory shape at the calibrated temperature. Laser cut wire frames are preferably made from Nitinol, but also without limitation made from stainless steel, cobalt chromium, titanium, and other functionally equivalent metals and alloys.

Alternatively, the frame 110 can be constructed utilizing simple braiding techniques. Using a Nitinol wire—for example, a 0.012" wire—and a simple braiding fixture, the wire can be wound on the braiding fixture in a simple over/under braiding pattern until an isodiametric tube is formed from a single wire (e.g., the frame 110). The two loose ends of the wire are coupled using a stainless steel or Nitinol coupling tube into which the loose ends are placed and crimped. In some embodiments, angular braids of approximately 60 degrees can be desirable. Secondarily, the braided wire frame 110 is placed on a shaping fixture and placed in a muffle furnace at a specified temperature to set the wire frame 110 to the desired shape and to develop the martensitic or super elastic properties desired.

Since the frame 110 is made of super elastic metal or alloy such as Nitinol, the frame 110 is compressible. Preferably, the frame 110 is constructed of a plurality of compressible wire cells having an orientation and cell geometry substantially orthogonal to the central axis 113 to minimize wire cell strain in the frame 110 when configured in a vertical compressed configuration, a rolled compressed configuration, or a folded compressed configuration.

In a particular embodiment, the frame 110 (e.g., of a prosthetic heart valve) may start in a roughly tubular configuration, and be heat-shaped to provide an upper atrial cuff or flange (e.g., the cuff 120) for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

The flow control component 150 can refer in a non-limiting sense to a device for controlling fluid flow therethrough. In some embodiments, the flow control component 150 can be a leaflet structure having 2-, 3-, 4-leaflets, or more, made of flexible biocompatible material such a treated or untreated pericardium. The leaflets can be sewn or joined to a support structure and/or can be sewn or joined to the frame 110. The flow control component 150 can be mounted within the frame 110 and configured to permit blood flow in a first direction through an inflow end of the valve and block blood flow in a second direction, opposite the first direction, through an outflow end of the valve. For example, the flow control component 150 can be configured such that the valve 102 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating." The flow control component 150 is contemplated to include a wide variety of (bio)prosthetic artificial valves, including ball valves (e.g., Starr-Edwards), bileaflet valves (St. Jude), tilting disc valves (e.g., Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

The arrangement of the valve 102 can be such that a commercially available valve (flow control component 150) can be received or accepted by and/or otherwise mounted in the frame 110. Commercially available valves (flow control components 150) may include, for example, a Sapien, Sapien 3, or Sapien XT from Edwards Lifesciences, an Inspiris Resilia aortic valve from Edwards Lifesciences, a Masters HP 15 mm valve from Abbott, a Lotus Edge valve from Boston Scientific, a Crown PRT leaflet structure from Livanova/Sorin, a valve from the Carbomedics family of valves from Sorin, or other flow control component(s), or a flexible reciprocating sleeve or sleeve-valve.

As described above, the valve 102 and/or at least the frame 110 of the valve 102 can optionally include one or more of the distal upper tension arm 131, the distal lower tension arm 132, the proximal upper tension arm 133, the proximal lower tension arm 134, the guidewire collar 140, and/or the anchor delivery conduit 145. The tension arms 131, 132, 133, and 134 can be configured to engage a portion of the annular tissue to mount the frame 110 to the annulus of the native valve in which the valve 102 is deployed. The tension arms 131, 132, 133, and/or 134 can be any suitable configuration such as those described below with respect to specific embodiments. The anchor delivery conduit 145 can be attached to the frame 110 and configured to receive a tissue anchor 190 (FIG. 1B) therethrough. The tissue anchor 190, in turn, can anchor the valve 102 and/or at least the frame 110 to the annular tissue.

The valve 102 can be delivered to the desired location in the body via a procedure generally including advancing a delivery catheter over a guide wire (not shown in FIGS. 1A-1F) to place a distal end of the delivery catheter at or near the desired location. The guidewire, therefore, may be disposed within the lumen of the delivery catheter. The valve 102 can be disposed within the lumen of the delivery catheter (e.g., in the compressed configuration) and advanced over the guidewire through the delivery catheter. More particularly, in embodiments including the guidewire collar 140, the guidewire can extend through an aperture of the guidewire collar 140, thereby allowing the valve 102 to be advanced over or along the guidewire. The guidewire collar 140 can be attached to the frame 110 and/or to at least one of the tension arms 131, 132, 133, and/or 134. The guidewire collar 140 can be configured to selectively engage a portion of the guidewire or a portion of a guidewire assembly and/or can have any suitable configuration as described below with respect to specific embodiments.

The valve 102 is compressible and expandable between the expanded configuration and the compressed configuration. The valve 102 is in the expanded configuration when deployed or implanted (or ready to be deployed or implanted) at the desired location in the body (e.g., the annulus of a native valve). The valve 102, when in the expanded configuration shown in FIG. 1C, has an extent in any direction along or lateral to the central axis 113 that is larger than a diameter of a lumen of the delivery catheter used to deliver the valve 102 to the desired location in the body. Said another way, the valve 102 has an extent in any direction perpendicular to the longitudinal axis of the valve 111 that is larger than the diameter of the lumen of the delivery catheter.

The valve 102 is in the compressed configuration when being delivered to the desired location in the body via the delivery catheter. When in the compressed configuration shown in FIG. 1D, the valve 102 can be disposed within the delivery catheter and can be compressed in a lateral direction relative to the dimensions of the valve 102 in the expanded configuration and can be elongated in a longitudinal direction along the longitudinal axis 111. The longitudinal axis 111 can be parallel to a longitudinal axis of the delivery catheter and can be oriented at an intersecting angle between 45 and 135 degrees relative to the central axis 113 (e.g., perpendicular or at about 90 degrees). In some embodiments, the horizontal x-axis (e.g., the longitudinal axis 111) of the valve 102 is orthogonal to (90 degrees), or substantially orthogonal to (75-105 degrees), or substantially oblique to (45-135 degrees) to the central vertical y-axis (e.g., the central axis 113) when in an expanded configuration. In some embodiments, the horizontal x-axis (e.g., the longitudinal axis 111) of the valve 102 in the compressed configuration is substantially parallel to a lengthwise cylindrical axis of the delivery catheter.

As used herein, the terms "intersecting angle" and/or "orthogonal angle" can refer to both (i) the relationship between the lengthwise cylindrical axis of the delivery catheter and the long-axis 111 of the compressed valve 102, where the long-axis 111 is perpendicular to the central axis 113 of traditional valves, and (ii) the relationship between the long-axis 111 of the compressed or expanded valve 102 and the axis defined by the blood flow through the prosthetic valve 102 where the blood is flowing, e.g., from one part of the body or chamber of the heart to another downstream part of the body or chamber of the heart, such as from an atrium to a ventricle through a native annulus.

As shown in FIGS. 1C and 1D, the valve 102 can have a first height or size along the central axis 113 when in the expanded configuration and can have a second height or size, less than the first height or size, along the central axis 113 when in the compressed configuration. The second height or size of the valve 102 when in the compressed configuration is smaller than the diameter of the lumen of the delivery catheter, allowing the valve 102 to be delivered therethrough.

Figure 1E:
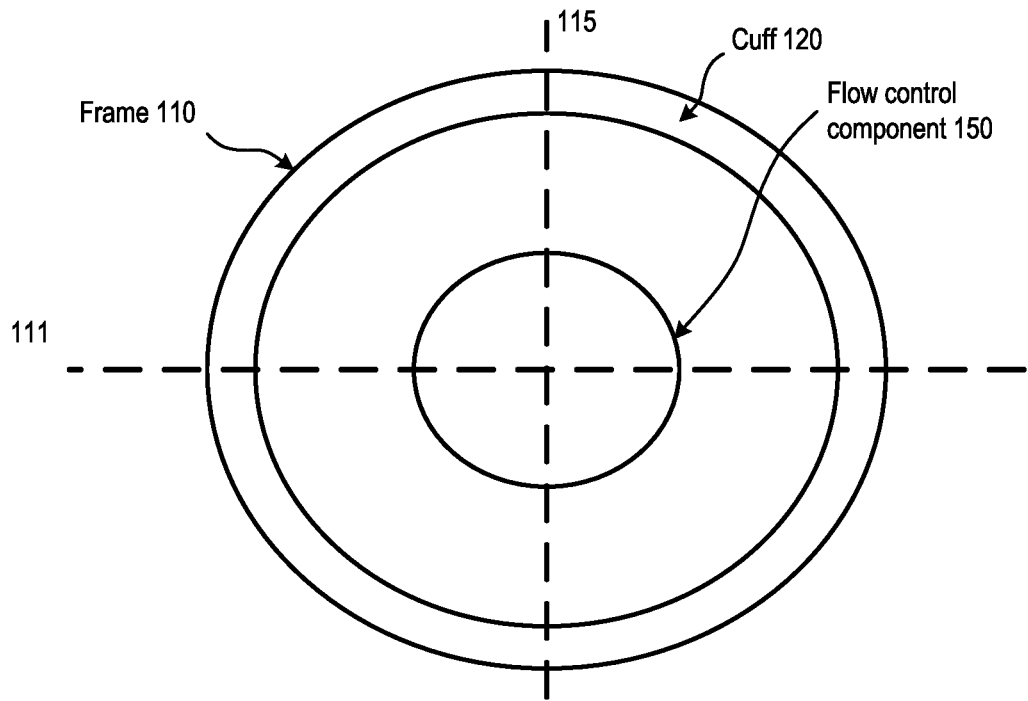
Figure 1F:
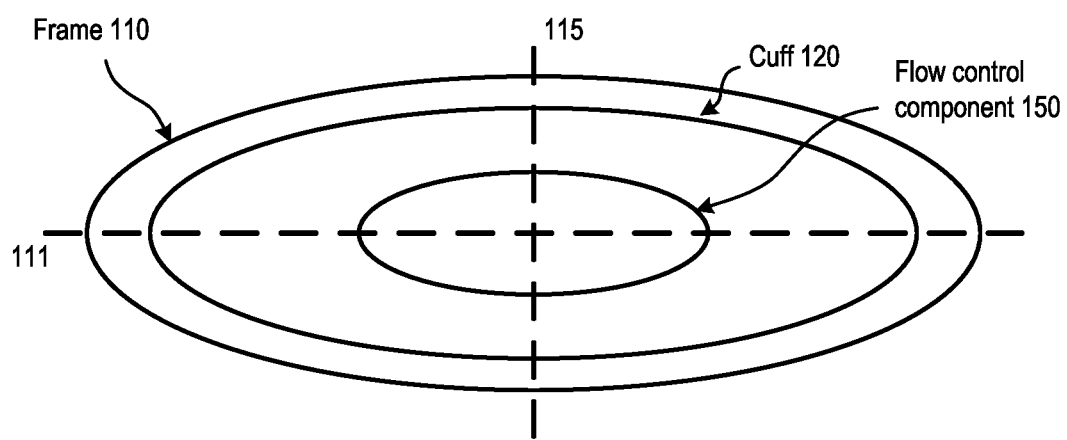

The valve 102 can also be compressed in additional directions. For example, FIGS. 1E and 1F are top views of the valve 102 in the expanded configuration and the compressed configuration, respectively. The valve 102 has a lateral axis 115 that is perpendicular to the longitudinal axis 111 and the central axis 113. The valve 102, when in the expanded configuration, has an extent in any direction along or lateral to the lateral axis 115 that is larger than a diameter of the lumen of the delivery catheter used to deliver the valve 102. In other words, the valve 102 can have a first width or size along the lateral axis 115 when in the expanded configuration shown in FIG. 1E and can have a second width or size, less than the first width or size, along the lateral axis 115 when in the compressed configuration shown in FIG. 1F.

The valve 102 may be compressed (as described above) and delivered in a sideways or orthogonal manner such that the longitudinal axis 111 is substantially parallel to a delivery axis (e.g., a lengthwise axis of a delivery catheter). The shape of the expanded valve 102 can be that of a large diameter shortened cylinder with an extended collar or cuff (e.g., the cuff 120). The valve 120 can be compressed, in some embodiments, where the central axis 113 of the valve 102 is roughly perpendicular to (orthogonal to) the lengthwise axis of the delivery catheter. In some embodiments, the valve 102 can be compressed vertically (e.g., along the central axis 113), similar to collapsing the height of a cylinder accordion-style from taller to shorter. In addition, or as an alternative, the valve 102 can be compressed laterally (e.g., along the lateral axis 115) similar to folding or compressing a front panel against a back panel. In other embodiments, the valve 102 can be compressed by rolling. In other embodiments, the valve 102 can be compressed using a combination of compressing, folding, and/or rolling. The compression along the central axis 113 (e.g., compression in a vertical direction) and compression along the lateral axis 115 (e.g., compression in a lateral or width-wise direction) is in contrast to the compression of traditional co-axially delivered prosthetic valves, which are generally compressed along the lateral axis (e.g., the lateral axis 115) and the longitudinal axis (e.g., the longitudinal axis 111) and elongated along the central axis (e.g., the central axis 113).

In some embodiments, the valve 102 can have an expanded height (y-axis) of 5-60 mm. In some embodiments, the valve 102 can have an expanded diameter length and width of 20-80 mm, preferably 40-80 mm, and in certain embodiments length and/or width may vary and include lengths of 20 mm, 25 mm, 30 mm, 35 mm, 40 mm, 45 mm, 50 mm, 55 mm, 60 mm, 65 mm, 70 mm, 75 mm, and 80 mm, in combination with widths that are the same or different as the length.

In some embodiments, the valve 102 can have a compressed height (y-axis) and/or width (z-axis) of 6-15 mm, preferably 8-12 mm, and more preferably 9-10 mm, and an expanded deployed height of about 5-60 mm, preferably about 5-30 mm, and more preferably about 5-20 mm or even 8-12 mm or 8-10 mm. In some embodiments, the length of the valve 102 (x-axis) does not require compression since it can extend along the length of the central cylindrical axis of the delivery catheter when disposed therein.

In some embodiments, the valve 102 can be arranged such that an inner frame or structure of the flow control component 150 that holds, for example, leaflet tissue is 25-29 mm in diameter, the frame 110 or a portion thereof is 50-70 mm in diameter, and the collar structure (cuff 120) of the frame 110 extends beyond the top edge of the frame 110 by 10-30 mm to provide a seal on the atrial floor against perivalvular leaks (PVLs).

Referring back to FIG. 1B, the valve 102 can be disposed within an annulus of a native valve in the human heart such as, for example, the pulmonary valve (PV) or the mitral valve (MV)— or the aortic valve or tricuspid valve, not shown in FIG. 1B). As described above, the valve 102 can be in the compressed configuration and delivered to the annulus via the delivery catheter. The valve 102 can be released from the delivery catheter and allowed to expand to the expanded configuration shown in FIG. 1B. The deployment of the valve 102 can include placing the distal lower tension arm 132 in the ventricle below the annulus while the remaining portions of the valve 102 is in the atrium. The valve 102 can be placed in the annulus of the native valve (PV or MV) and at least a portion of the distal lower tension arm 132 can be positioned in an outflow tract of the ventricle (e.g., the RVOT, as shown in FIG. 1B). In embodiments in which the valve 102 includes additional tension arms, the distal upper tension arm 131 and the proximal upper tension arm 133 can be disposed in the atrium above the native valve and the proximal lower tension arm 134 can be disposed in the ventricle below the native valve. As such, the one or more optional tension arms 131, 132, 133, 134 included in the valve 102 can exert a force on the native valve structure or tissue to mount the valve 102 within the annulus of the native valve. For example, the upper tension arms 131 and/or 133 can exert a supra-annular downward force in the direction of the right ventricle and the lower tension arms 132 and/or 134 can exert a sub-annular upward force in the direction of the right atrium.

The mounting of the valve 102 in the annulus optionally can include anchoring the valve 102 to the native valve via the tissue anchor 190. The tissue anchor 190 can be, for example, tines or barbs that are located to provide attachment to tissue adjacent the annulus. The tissue anchor 190 can be forced into the annular tissue by mechanical means such as using a balloon catheter. In one non-limiting embodiment, the tissue anchor 190 may optionally be semi-circular hooks that upon expansion of the frame 110 (or valve 102), pierce, rotate into, and hold annular tissue securely. The tissue anchors 190 can be deployed by over-wire delivery through a delivery catheter (e.g., via the anchor delivery conduit 145). The delivery catheter may have multiple axial lumens for delivery of a variety of anchoring tools, including anchor setting tools, force application tools, hooks, snaring tools, cutting tools, radio frequency and radiological visualization tools and markers, and suture/thread manipulation tools. Once the tissue anchor(s) 190 are attached to the valve, tensioning tools may be used to adjust the length of one or more tethers or the like that connect to the implanted valve 102 to adjust and secure the implanted valve 102 as necessary for proper functioning. It is also contemplated that the tissue anchor(s) 190 may be spring-loaded and may have tether-attachment or tether-capture mechanisms built into the tethering face of the anchor(s) 190. The anchors 190 or tether may pass through the anchor delivery conduit 145 of the valve 102 or frame 110. The anchors 190 may also have in-growth material, such as polyester fibers, to promote in-growth of the anchors into the heart tissue. In one embodiment, where the valve 102 may or may not include a ventricular collar, the anchor 190 (e.g., a dart, tine, or barb) is not attached to a lower ventricular collar but is attached directly into annular tissue or other tissue useful for anchoring.

In some embodiments, the frame 110 and the flow control component 150 can be separate structures and delivered to a desired location in the body either together or separately. For example, the flow control component 150 can be positioned within the aperture 114 of the frame 110 to form the complete valve 102, and the valve 102 can be compressed and delivered to the desired location in the body via the delivery catheter as described in detail above. In other embodiments, the frame 110 and the flow control component 150 can be delivered to the desired location in the body separately. For example, the frame 110 can be compressed and delivered to the desired location in the body via the delivery catheter. The frame 110 can be released from the delivery catheter and deployed, for example, in the annulus of the native valve. The frame 110 is in the expanded configuration once released from the delivery catheter, and thus, is deployed in the annulus of the native valve in the expanded configuration. The flow control component 150 can then be delivered separately (e.g., via the delivery catheter) and mounted into the deployed frame 110.

Provided below is a discussion of certain aspects or embodiments of transcatheter prosthetic valves. The transcatheter prosthetic valves (or aspects or portions thereof) described below with respect to specific embodiments can be substantially similar in at least form and/or function to the valve 102 and/or corresponding aspects of the valve 102 described above with reference to FIGS. 1A-1F. Thus, certain aspects of the specific embodiments are not described in further detail herein.

Figure 2:
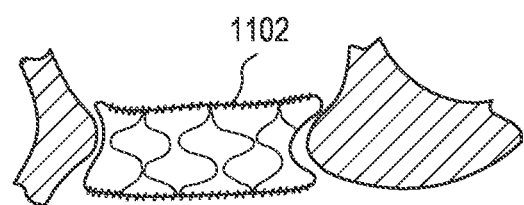

FIG. 2 is an illustration of a low profile, e.g., 8-20 mm, side-loaded prosthetic valve 1102 according to an embodiment. The valve 1102 can be substantially similar to the valve 102 shown in FIGS. 1A-1F. FIG. 2 shows the valve 1102 in an expanded configuration and deployed into the native annulus.

Figure 3:
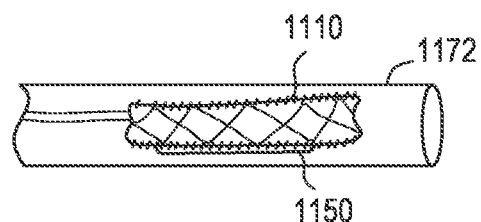

FIG. 3 is an illustration of the valve 1102 having a frame 1110 and a flow control component 1150 shown compressed or housed within a delivery catheter 1172.

Figure 4A:
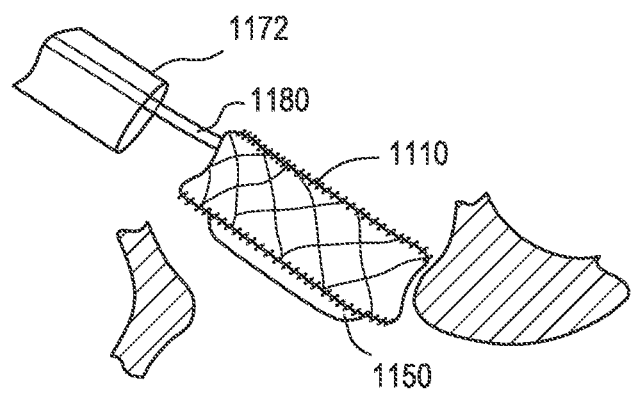

FIG. 4A is an illustration of the valve 1102 shown ejected from the delivery catheter 1172 and positioned against the anterior side of the native annulus. While the valve 1102 is held at this oblique angle by a secondary catheter 1180, valve function and patient condition are assessed, (as described in more detail below) and if appropriate, the valve is completely deployed within the native annulus, and anchored using traditional anchoring elements (e.g., such as the tissue anchor 190).

Figure 4B:
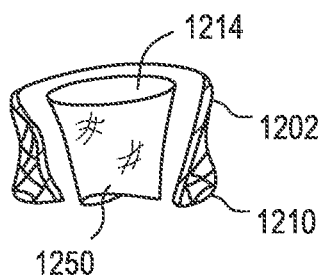
FIG. 4B is a partial cut-away view of a transcatheter prosthetic valve showing an inner valve sleeve thereof according to an embodiment.

FIG. 4B is an illustration of an open cross-section view of a low profile, side-loaded prosthetic valve 1202 according to an embodiment. The valve 1202 includes an inner valve sleeve or flow control component 1250 and a frame 1210. The valve 1202 can be similar to the valve 1102.

Figure 5:
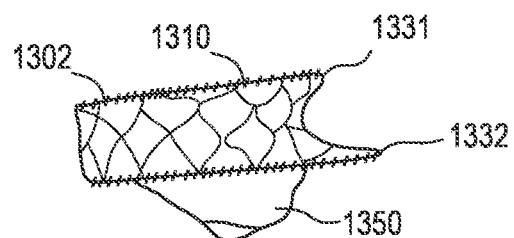
FIG. 5 is a side view of a transcatheter prosthetic valve according to an embodiment.

FIG. 5 is an illustration of a low profile, side-loaded heart prosthetic valve 1302 according to an embodiment. The valve 1302 has a braid or laser-cut construction for a tubular frame 1310, with a valve sleeve or flow control component 1350 that extends beyond the bottom of the tubular frame 1310. FIG. 5 shows a longer lower tension arm 1332 for extending sub-annularly towards the RVOT, and a shorter upper tension arm 1331 for extending over the atrial floor.

Figure 6:
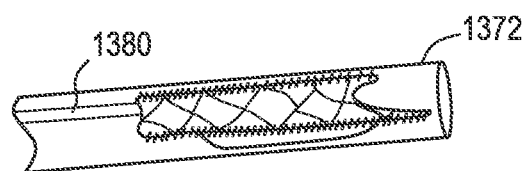
FIGS. 6-9 illustrate a process of delivering the transcatheter prosthetic valve of FIG. 5 to a native annulus of a target tissue.

FIG. 6 is an illustration of the valve 1302 being in a compressed configuration within a delivery catheter 1372. FIG. 6 shows the valve 1302 attached to a secondary steerable catheter 1380 for ejecting, positioning, and anchoring the valve 1302. The secondary catheter 1380 can also be used to retrieve a failed deployment of the valve 1302.

Figure 7:
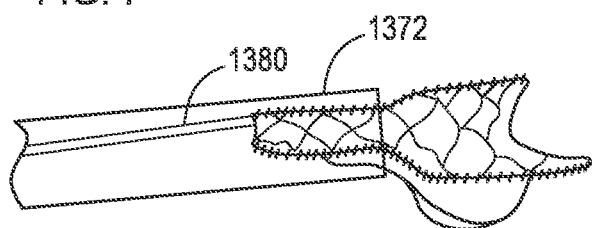

FIG. 7 is an illustration of the valve 1302 shown in a partially compressed configuration, partially within the delivery catheter 1372 and partially ejected from the delivery catheter 1372. FIG. 7 shows that while the valve 1302 is still compressed the lower tension arm 1332 can be manipulated through the leaflets and chordae tendineae of the native valve to find a stable anterior-side lodgment for the distal side of the valve 1302.

Figure 8:
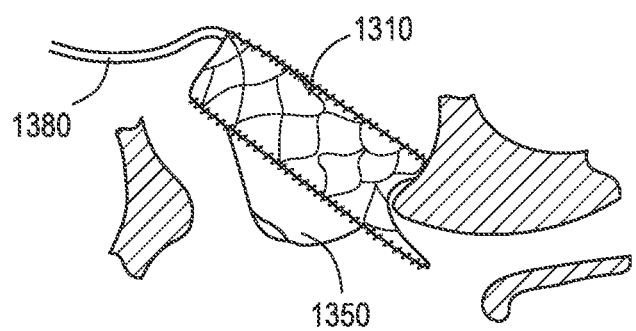

FIG. 8 is an illustration of the valve 1302 engaging the tissue on the anterior side of the annulus of a native valve with the curved distal sidewall of the tubular frame 1310 sealing around the native annulus. FIG. 8 shows the valve 1302 held by the steerable secondary catheter 1380 at an oblique angle in which valve function can be assessed.

Figure 9:
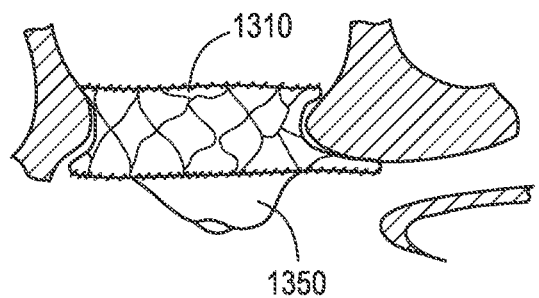

FIG. 9 is an illustration of valve 1302 fully deployed into the annulus of the native valve. The distal side of the valve 1350 is shown engaging the tissue on the anterior side of the native annulus with the curved distal sidewall of the tubular frame 1310 sealing around the native annulus, and with the proximal sidewall tension-mounted into the posterior side of the native annulus.

Figure 10:
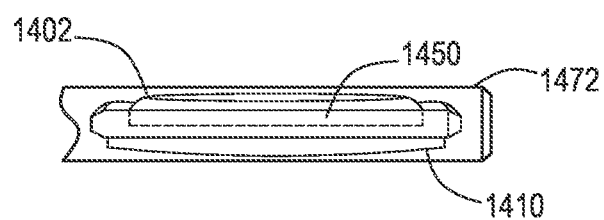
FIGS. 10-12 are various views of a transcatheter prosthetic valve in a compressed configuration within a delivery catheter according to an embodiment.

FIG. 10 is an illustration of a plan view of an embodiment of a prosthetic valve 1402 shown in a compressed configuration within a delivery catheter 1472. FIG. 10 shows a tubular frame 1410 rolled-over, outwardly, resulting in a 50% reduction in height of the catheter-housed valve 1402. The low profile, side-loaded valve 1402 does not require the aggressive, strut-breaking, tissue-tearing, stitch-pulling forces that traditional transcatheter valves are engineered to mitigate.

Figure 11:
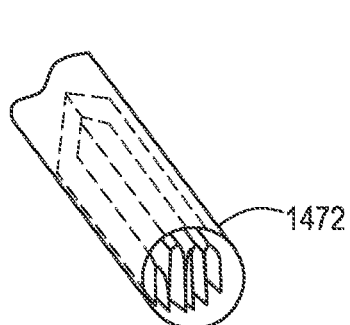

FIG. 11 is an illustration of a cross-sectional view of the compressed valve 1402 within the delivery catheter 1472. This cross-sectional end view shows one embodiment of a single-fold compression configuration where the tubular frame 1402 and attached two-panel sleeve or flow control component 1450 are folded-over, outwardly, five times, resulting in a 50% reduction in height, and providing the ability to fit within the inner diameter of the 1 cm (10 mm) delivery catheter 1472.

Figure 12:
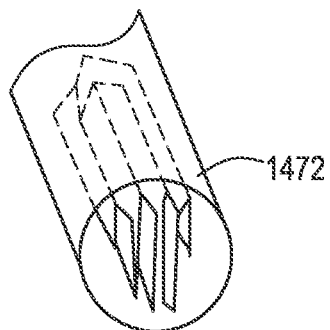

FIG. 12 is an illustration of a cross-sectional view of another embodiment of the compressed valve 1402 folded within the delivery catheter 1472. This cross-sectional end view shows another embodiment of a single-fold compression configuration where the tubular frame 1410 and attached two-panel sleeve or flow control component 1450 are folded-over, outwardly, four times, resulting in a 50% reduction in height, and providing the ability to fit within the inner diameter of the 1 cm (10 mm) delivery catheter 1472.

Figure 13:
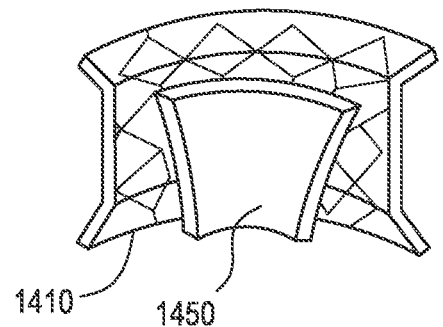
FIG. 13 is a partial cross-sectional view of the transcatheter prosthetic valve of FIG. 10.

FIG. 13 is an illustration of a cross-sectional view of the valve 1402 to further illustrate how the folding and rolling configurations can be effectuated due to the minimal material requirement of the low profile, side-loaded valve 1402.

Figure 14A:
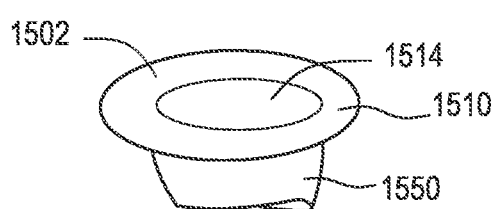
FIGS. 14A-14C illustrate a transcatheter prosthetic valve being transitioned from an expanded configuration (FIG. 14A) to a compressed configuration (FIG. 14C) according to an embodiment.
Figure 14B:
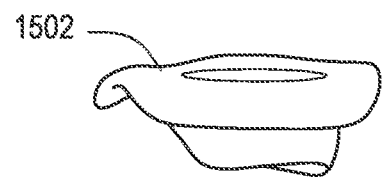
Figure 14C:
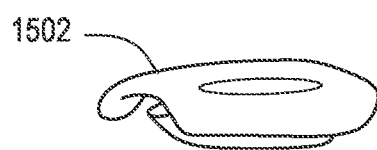

FIG. 14A-14C illustrate a sequence of a low profile valve 1502 being rolled into a compressed configuration for placement within a delivery catheter 1572. The valve 1502 includes a tubular frame 1510 having an aperture 1514 and supporting a sleeve or flow control component 1550.

Figure 15:
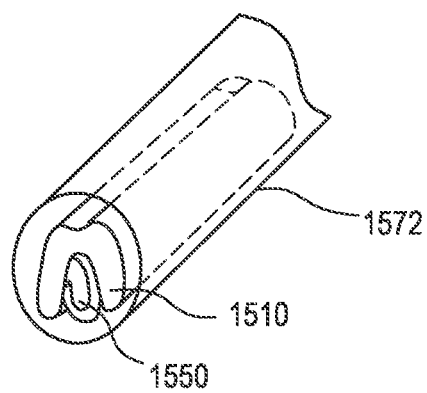
FIG. 15 is a perspective view of the transcatheter prosthetic valve of FIG. 14A in the compressed configuration within a delivery catheter.

FIG. 15 is an illustration of an end view that shows the valve 1502 having been longitudinally rolled and loaded within the delivery catheter 1572 and shows the frame 1510 and sleeve flow control component 1550.

FIGS. 16A to 16D illustrate one embodiment showing a four step process for compressing a prosthetic valve 1602 to provide a long-axis (e.g., similar to the long-axis 111 shown in FIGS. 1A-1F) that is co-planar or parallel with the lengthwise axis of a delivery catheter (not shown). These figures show that the valve 1602, having a tubular frame 1610 made of a cuff and a trans-annular tubular section, having a flow control component 1610 mounted within the tubular frame 1610 and configured to permit blood flow in a first direction through an inflow end of the valve and block blood flow in a second direction, opposite the first direction, through an outflow end of the valve 1602, is compressible about a long-axis that is parallel to a lengthwise axis of a delivery catheter. These figures show that the valve 1602 is compressible to a compressed configuration for introduction into the body using a delivery catheter where the compressed configuration has a long-axis that is perpendicular to the blood flow direction axis (e.g., oriented at an intersecting (orthogonal) angle of between 45-135 degrees (e.g., 90 degrees) to the first (blood flow) direction), and where the long-axis of the compressed configuration of the valve 1602 is substantially parallel to a lengthwise axis of the delivery catheter, wherein the valve 1602 has a height of about 5-60 mm and a diameter of about 25-80 mm.

Figure 16A:
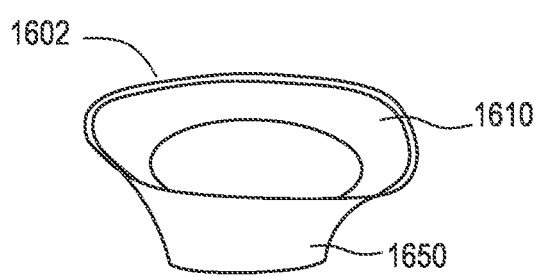
FIGS. 16A-16D illustrate a transcatheter prosthetic valve being transitioned from an expanded configuration (FIG. 16A) to a compressed configuration (FIG. 16D) according to an embodiment.
Figure 16B:
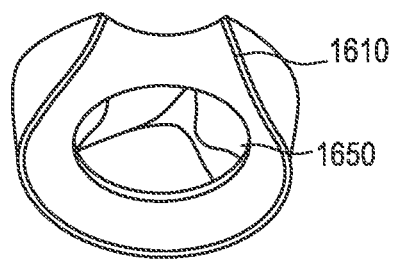
Figure 16C:
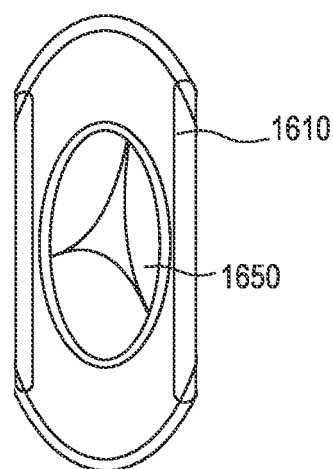
Figure 16D:
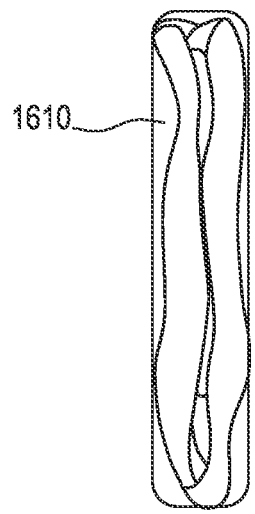

FIG. 16A shows an illustration of the valve 1602 in an uncompressed configuration. FIG. 16B shows an illustration of an initial rolling or folding of the cuff of the frame 1610. The folding or rolling can be inwards as shown here, or may be outwardly rolled, or may also be flattened together for rolling the entire valve 1602 up from bottom to top. FIG. 16C shows an illustration of the valve 1602 that has been rolled or folded, using multiple folds or rolls, along a long-axis into a tube-shape. FIG. 16D shows an illustration of the completely compressed valve 1602, that has been folded or rolled, e.g., using a compression accessory, into a compressed configuration, and which can be then loaded into a delivery catheter (not shown). The compressed valve 1602 may be self-expanding when released from the delivery catheter using shape-memory alloys, or the valve 1602 may be balloon expanded in a secondary process once the valve 1602 is released from the delivery catheter.

Figure 17A:
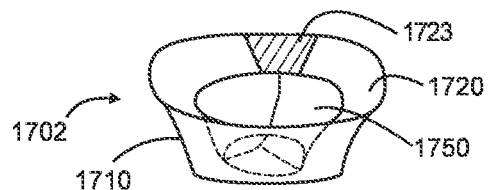
FIGS. 17A-17E illustrate a transcatheter prosthetic valve being transitioned from an expanded configuration (FIG. 17A) to a compressed configuration (FIG. 17E) according to an embodiment.

FIG. 17A is an illustration of a side perspective view of a side deliverable transcatheter prosthetic valve 1702 with at least one fold area according to an embodiment, in an expanded configuration. FIG. 17A shows a distal fold area 1723A in a collar portion 1720 of an annular frame 1710 that permits compression of the valve 1702 without subjecting the annular frame 1710 or an inner flow control component 1750 to damaging compression forces.

Figure 17B:

FIG. 17B is an illustration of a side perspective view of the valve 1702 showing an anterior side 1721 of the collar portion 1720 of the valve 1702 commence a unilateral rolling process, indicated by the arrow 1763. FIG. 17B shows two fold areas, a proximal (near) fold area 1723A and distal (far) area 1723B. The fold areas 1723A and 1723B may be devoid of wire cells (wire frame portions) or may consist of cells that are large or oriented to minimize the folding or rolling damage from the compression process. Leaflets 1753 of the flow control component 1750 are visible from this angle.

Figure 17C:
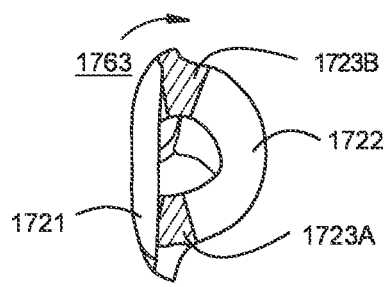

FIG. 17C is an illustration of a side perspective view of the valve 1702 showing a second rolling step of the unilateral rolling process 1763. The anterior collar 1721 is rolled over to the central distal fold area 1723B and the proximal fold area 1723A with a posterior-septal collar 1722 in an unrolled expanded configuration.

Figure 17D:
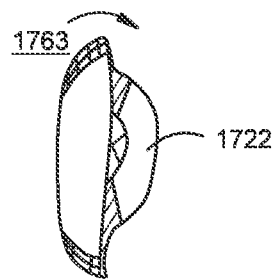

FIG. 17D is an illustration of a side perspective view of the valve 1702 showing a third rolling step of the unilateral rolling process 1763. The valve 1702 continues to be roll compressed towards the posterior-septal collar 1722.

Figure 17E:
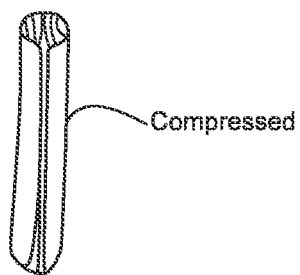

FIG. 17E is an illustration of a side perspective view of the valve 1702 showing a completion of the unilateral rolling process 1763 to achieve a compressed configuration.

Figure 18A:
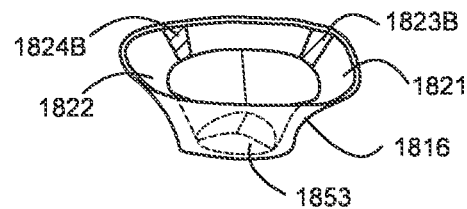
FIGS. 18A-18D illustrate a transcatheter prosthetic valve being transitioned from an expanded configuration (FIG. 18A) to a compressed configuration (FIG. 18D) according to an embodiment.

FIG. 18A is an illustration of a side perspective view of a valve 1802 in an expanded configuration, showing two sides of the valve 1802 commence a bilateral rolling process 1864, with two of four (shown) fold areas, distal fold area 1823B and second distal fold are 1824B. An anterior collar 1821 of a frame 1810 of the valve 1802 and a posterior-septal collar 1822 of the frame 1810 are shown with outer frame wall 1816 and leaflets 1853 in dashed line for reference.

Figure 18B:
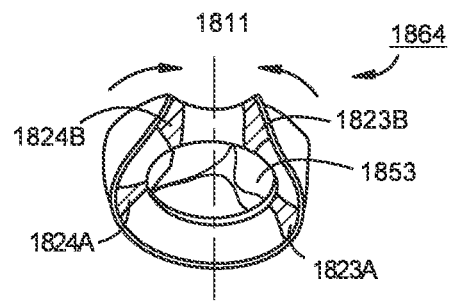

FIG. 18B is an illustration of a side perspective view of the valve 1802 showing a second rolling step of the bilateral rolling process 1864. A rim of the annular support frame 1810 is shown rolling inward towards a central axis 1811. The distal fold 1823B and the second distal fold 124B are shown opposite from a proximal fold area 1823A and second proximal fold area 1824A, respectively. Flow control leaflets 1853 of a flow control component 1850 of the valve 1802 are shown for reference.

Figure 18C:
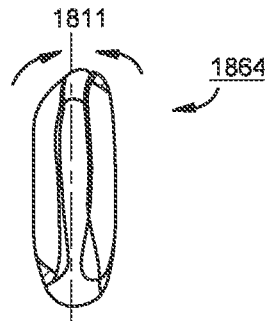

FIG. 18C is an illustration of a side perspective view of the valve 1802 showing a third rolling step of the bilateral rolling process 1864. Here, the rolled rim is further rolled inward towards the central axis 1811.

Figure 18D:
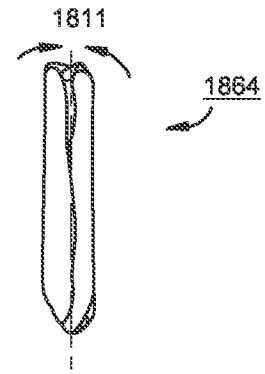

FIG. 18D is an illustration of a side perspective view of the valve 1802 showing a completion of the bilateral rolling compression process 1864 shown rolled inward towards the central axis 1811. FIG. 18D shows the valve 1802 as it would appear in a compressed configuration within a delivery catheter (not shown).

Figure 19A:
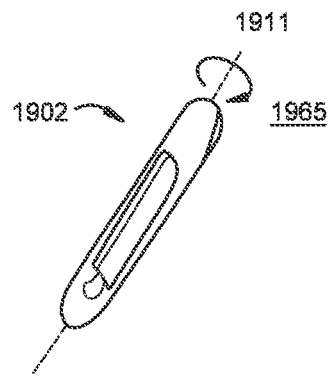
FIGS. 19A-19D illustrate a transcatheter prosthetic valve being transitioned from a compressed configuration (FIG. 19A) to an expanded configuration (FIG. 19D) according to an embodiment.

FIG. 19A is an illustration of a side perspective view of a valve 1902 in a compressed configuration, that has been compressed using a rolling and folding process 1965. A lower portion of the valve 1902 is rolled, and an upper collar portion of the valve 1902 is folded lengthwise around a central long-axis 1911.

Figure 19B:
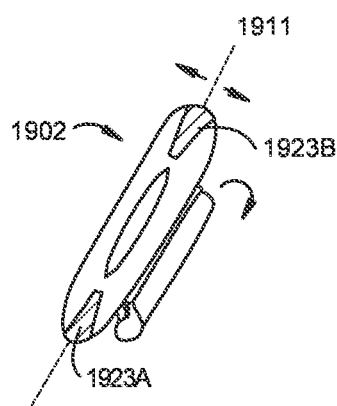

FIG. 19B is an illustration of a side perspective view of the valve 1902, partially uncompressed, showing unrolling of the lower body portion and unfolding of the flattened upper collar portion. FIG. 19B shows fold areas 1923A and 1923B in the collar portion.

Figure 19C:
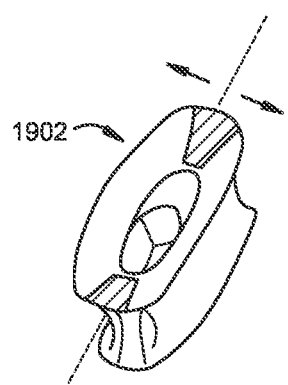

FIG. 19C is an illustration of a side perspective view of the valve 1902, further uncompressed, showing the unrolled lower body portion and the unfolded upper collar portion. The fold areas in the collar are wider as the valve 1902 assumes its expanded configuration.

Figure 19D:
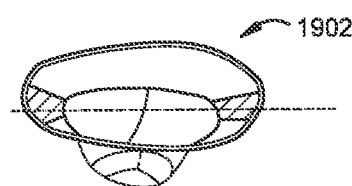

FIG. 19D is an illustration of a side perspective view of the valve 1902 in an expanded configuration, showing a different side/orientation, which is 90 degrees from the prior views.

Figure 20:
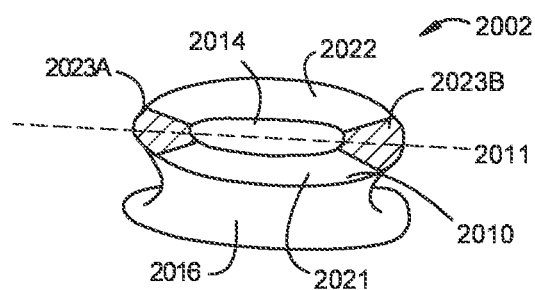
FIG. 20 is a side perspective view of a transcatheter prosthetic valve according to an embodiment.

FIG. 20 is an illustration of a side perspective view of a valve 2002 having a circular hyperboloid (hourglass) shape. Wire frame details are not shown since in practice the external surface would preferably be covered, such as with Dacron polyester to facilitate in-growth. A proximal fold area 2023A and a distal fold area 2023B are shown on opposite ends of an anterior collar 2021 and a posterior-septal collar 2022 of the frame 2010 along a horizontal axis 2011 with a front anterior wall 2016 and central channel or aperture 2014 shown, according to an embodiment.

Figure 21:
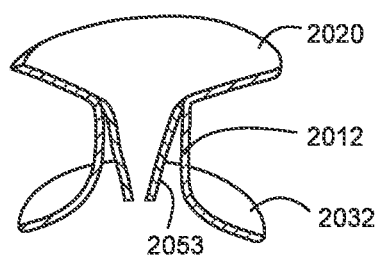
FIG. 21 is partial cross-sectional view of the transcatheter prosthetic valve of FIG. 20.

FIG. 21 is an illustration of a cut away view of the valve 2002. FIG. 21 shows that inner leaflet 2053 and inner frame of the flow control component are attached to the inner surface of the annular frame 2010, with a collar portion 2020 attached to a subannular anchor portion 2032 via a wall portion 2012. Here, the flow control component is only attached at a top edge of the frame 2010 although other non-limiting attachments are contemplated (e.g., mid-wall, multiple attachment points, etc.).

Figure 22:
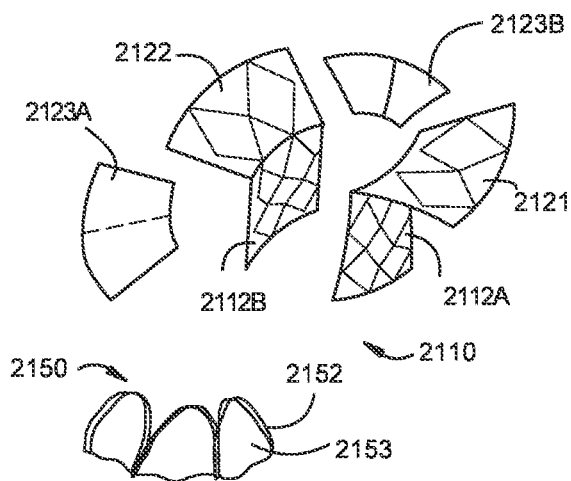
FIG. 22 is an exploded view of a two-panel transcatheter prosthetic valve according to an embodiment.

FIG. 22 is an illustration of an exploded view of a valve or valve frame 2110 according to an embodiment, having a funnel anterior collar 2121, funnel posterior-septal collar 2122, anterior cylinder body portion 2112A, and posterior-septal cylinder body portion 2112B. FIG. 22 shows one variation where the valve frame 2110 includes wire cells used to create opposing panels, which are joined using fabric strain-minimizing panels at a proximal fold area 2123A and a distal flow area 2123B. FIG. 22 also shows a flow control component 2150 having a three-leaflet valve 2153 mounted on an inner U-shaped wire frame 2152.

Figure 23:
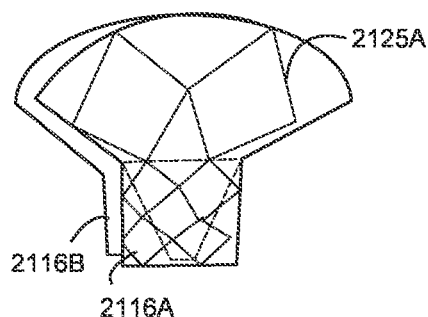
FIG. 23 is a side view of the two-panel transcatheter prosthetic valve of FIG. 22.

FIG. 23 is an illustration of a side view of the valve or valve frame 2110 showing two (2) panels or walls 2116A and 2116B of the valve frame 2110. The panel or wall 2116A can include the anterior collar portion 2121 and the anterior cylinder body portion 2112A and the panel or wall 2116B can include the posterior-septal collar portion 2122 and the posterior-septal cylinder body portion 2112B. FIG. 23 shows that diamond wire cells 2125A of the frame 2110 for the collar portion 2121 may be one large diamond in height, while the lower body portion 2112A may be constructed using two smaller diamond wire cells in height. Dashed lines illustrate where the inner flow control component is attached but not shown.

Figure 24:
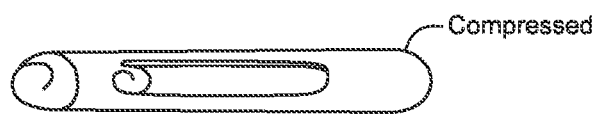
FIG. 24 is a side view of the two-panel transcatheter prosthetic valve of FIG. 22 in a compressed configuration.

FIG. 24 is an illustration of a side view of the two-panel embodiment of the valve or valve frame 2110 in a compressed configuration.

FIG. 25 is an illustration of an exploded view of a valve or valve frame 2110 according to an embodiment, having a funnel anterior collar 2221, funnel posterior-septal collar 2222, anterior cylinder body portion 2212A, and posterior-septal cylinder body portion 2212B. FIG. 25 shows one variation where the valve frame 2210 includes wire cells used to create the entire opposing panels. FIG. 25 also shows a flow control component 2250 having a three-leaflet valve 2253 mounted on an inner U-shaped wire frame 2252. FIG. 25 also shows a subannular tab 2230 that can be used for anchoring the frame 2210 in an annulus of a native valve.

FIG. 26 is an illustration of a side view of the valve or valve frame 2210 showing two (2) panels or walls 2216A and 2216B of the valve frame 2210. FIG. 26 shows that wave wire cells 2225B of the frame 2210 for the collar portion 2221 may be one large wave cell in height, while the lower body portion 2212A may be constructed using one or two smaller wave wire cells in height. Dashed line illustrates where the inner flow control component is attached but not shown.

FIG. 27 is an illustration of a side view of the two-panel embodiment of the valve or valve frame 2210 in a compressed configuration.

Figure 28:
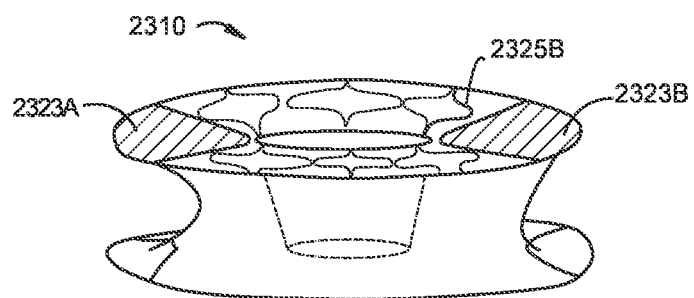
FIGS. 28 and 29 are a side perspective view and a top view, respectively, of a transcatheter prosthetic valve according to an embodiment.

FIG. 28 is an illustration of a side perspective view of a frame 2310 of a prosthetic valve formed by wave wire cells 2325B. The frame 2310 has a proximal folding area 2323A and a distal folding area 2323B in the wave wire cells 2325B. Dashed lines illustrate where an inner flow control component is attached but not shown.

Figure 29:
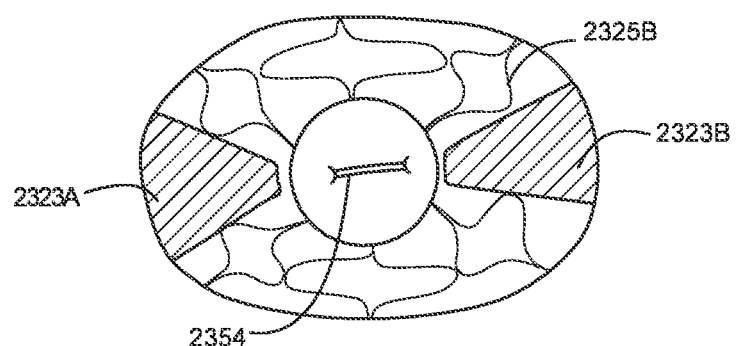

FIG. 29 is an illustration of a top view of the valve frame 2310 showing the proximal folding area or gap 2323A and the distal folding area or gap 2323B in the wave wire cells 2325B. A central flow control component opening is shown as a horizontal linear gap 2354.

Figure 30:
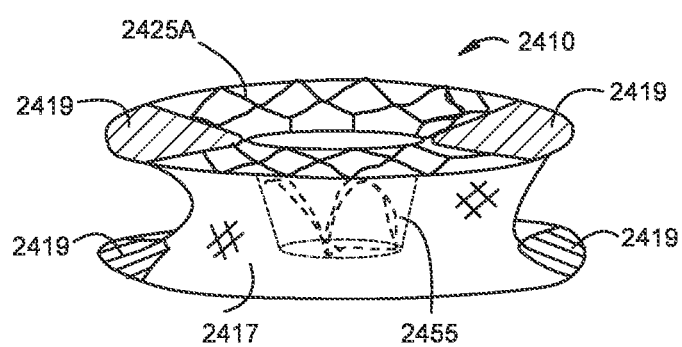
FIGS. 30 and 31 are a side perspective view and a top view, respectively, of a transcatheter prosthetic valve according to an embodiment.

FIG. 30 is an illustration of a side perspective view of a frame 2410 of a prosthetic valve formed by diamond wire cells 2425A. The frame 2310 has a set of folding areas or gaps 2419 in the diamond wire cells 2425A. Dashed lines illustrate where an inner flow control component is attached but not shown. Wire frame details are not shown since in practice the external surface would preferably be covered, such as with Dacron polyester cover 2417 to facilitate in-growth.

Figure 31:
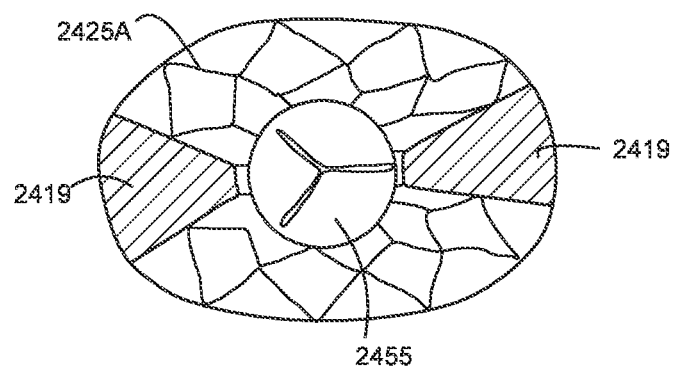

FIG. 31 is an illustration of a top view of the valve showing the folding areas or gaps 2419 in the generic annular support wire frame having diamond wire cells 2425A. A central flow control component opening is shown as a three-leaflet structure 2455.

Figure 32A:
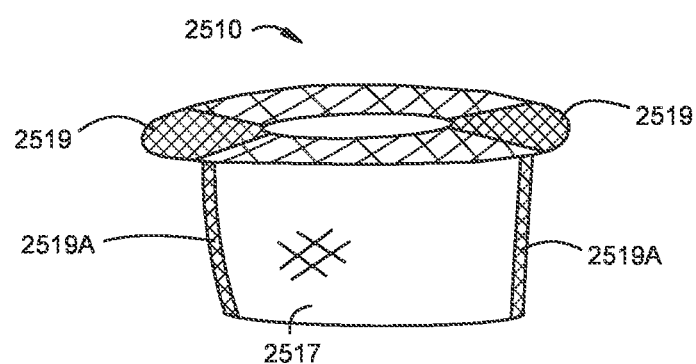
FIGS. 32A and 32B are side perspective views of a transcatheter prosthetic valve according to an embodiment in an expanded configuration and a collapsed configuration, respectively.

FIG. 32A is an illustration of a side perspective view of a frame 2510 of a prosthetic valve according to an embodiment. The frame 2510 has a set of folding areas or gaps 2519 in a generic wire cell structure where the folding gaps 2519 are covered with a fabric mesh spanning the gaps 2519. Fabric folding panels 2519A are illustrated on the proximal and distal sides of a lower body portion of the frame 2510. A polyester cover 2517 for the lower body portion of the frame 2510 is also shown.

Figure 32B:
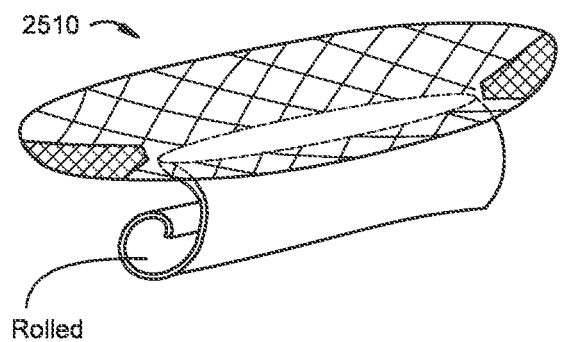

FIG. 32B is an illustration of a side view of frame 2510 showing the lower body portion in a partially rolled configuration. FIG. 32B shows that the lower body portion is unfurled towards the septal leaflet of the native valve.

Figure 33A:
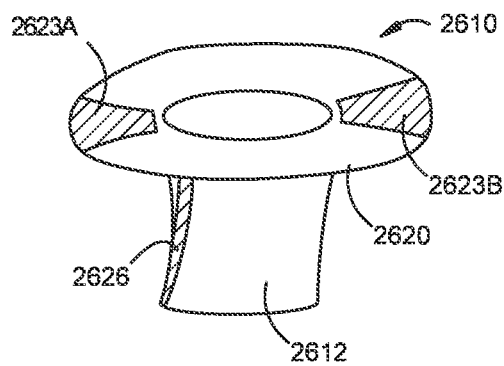
FIGS. 33A-33E illustrate a transcatheter prosthetic valve being transitioned from an expanded configuration (FIG. 33A) to a compressed configuration (FIG. 33E) according to an embodiment.

FIG. 33A is an illustration of a side perspective view of a frame 2610 of a prosthetic valve according to an embodiment. The valve 2610 has a flat collar portion 2620 and cylinder body portion 2612. FIG. 33A shows a proximal fold area 2623A and a distal fold area 2623B in the collar portion 2620 and a fold area 2626 in the lower body portion 2612 of the frame 2610.

Figure 33B:
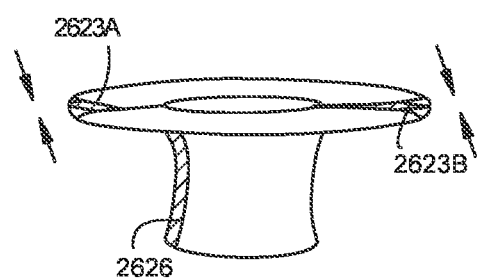

FIG. 33B is an illustration of a side perspective view of the frame 2610 shown flattened and partially compressed. FIG. 33B shows the two sides of the collar slide 2620 inward, compressing the fold areas 2623A, 2623B, to collapse the central axial opening or aperture, while flattening the lower body portion 2612 along the fold area or seam 2626.

Figure 33C:
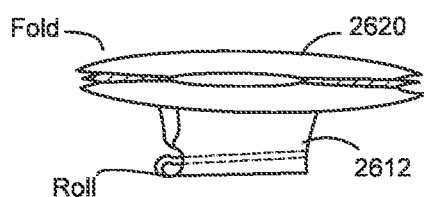

FIG. 33C is an illustration of a side perspective view of the frame 2610 shown with the collar portion 2620 folded to be flattened and partially compressed and with the lower body portion 2612 rolled to be flattened and partially compressed.

Figure 33D:
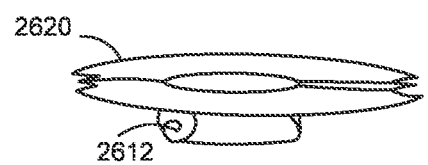

FIG. 33D is an illustration of a side perspective view of the frame 2610 shown with the collar portion 2620 folded to be flattened and partially compressed and with the lower body portion 2612 being completely compressed by rolling up to the collar portion 2620.

Figure 33E:

FIG. 33E is an illustration of a side perspective view of the flattened, compressed valve frame 2610 in its compressed configuration, with the lower body portion 2612 compressed by rolling and folded onto the flattened upper collar portion 2620.

Figure 34A:
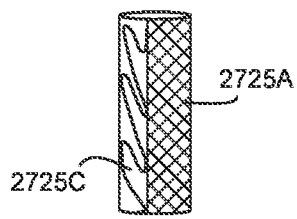
FIGS. 34A and 34B illustrate a transcatheter prosthetic valve according to an embodiment in a collapsed configuration and an expanded configuration, respectively.

FIG. 34A is an illustration of a side perspective view of a composite laser-cut workpiece prior to expansion into a valve frame 2710. FIG. 34A shows that a wire loop portion 2725C in combination with a wire mesh or wire braid portion 2725A can be combined in a single wire frame structure.

Figure 34B:
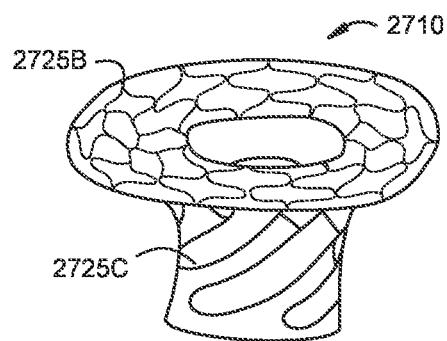

FIG. 34B is an illustration of a side perspective view of the valve 2710 showing the composite laser-cut workpiece after expansion into the valve wireframe in an expanded configuration. FIG. 34B shows a collar portion of the frame 2710 having the braid or laser-cut wire cell structure 2725B, and a lower body portion having the wire loop structure 2725C.

Figure 35A:
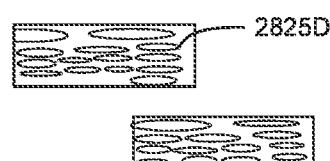
FIGS. 35A and 35B illustrate a transcatheter prosthetic valve according to an embodiment.

FIG. 35A is an illustration of a side perspective view of a laser-cut orthogonal cell workpiece prior to expansion into a set of valve frame panels or walls 2816A and 2816B. FIG. 35A illustrates asymmetric irregular rounded wire cells 2825D.

Figure 35B:
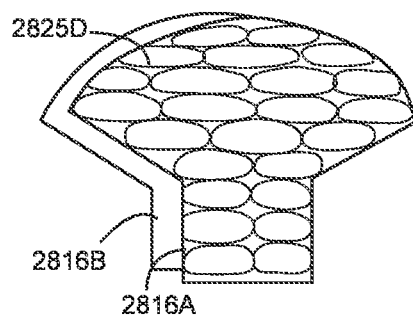

FIG. 35B is an illustration of a side perspective view of the laser-cut orthogonal workpiece after expansion into the valve wireframe panels or walls 2816A and 2816B prior to assembly of the frame. FIG. 35B shows rounded, horizontally oriented wire cells 2825D for minimizing wire strain during folding, rolling, and compression of the assembled frame.

Figure 36A:
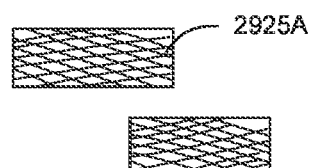
FIGS. 36A and 36B illustrate a transcatheter prosthetic valve according to an embodiment.

FIG. 36A is an illustration of a side perspective view of a laser-cut orthogonal cell workpiece with zig-zag/diamond shape cells 2925A prior to expansion into a valve frame panels or walls 2916A and 2916B.

Figure 36B:
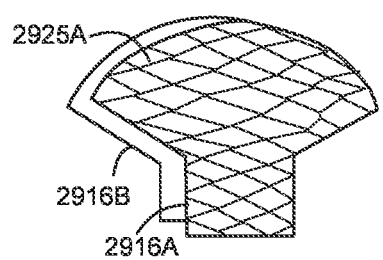

FIG. 36B is an illustration of a side perspective view of the laser-cut orthogonal workpiece with zig-zag/diamond shape cells 298 after expansion into the valve wireframe panels 280, 282, prior to assembly. FIG. 36B illustrates diamond-shaped, horizontally oriented wire cells 298 for minimizing wire strain during folding, rolling and compression.

Figure 37A:
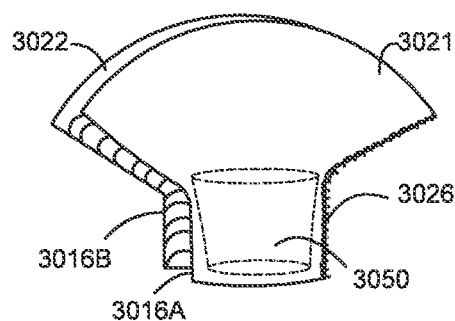
FIGS. 37A and 37B are a side perspective view and a top perspective view, respectively, of a transcatheter prosthetic valve according to an embodiment.

FIG. 37A is an illustration of a side perspective view of valve wireframe panels or walls 3016A and 3016B that are stitched along the side edges 3026A to form a three-dimensional valve frame 3010 having an arc-shape collar portion 3021, 3022 and a cylinder body portion with an internal flow control component 3050 mounted within the cylinder body portion, and shown in a collapsed or folded configuration.

Figure 37B:
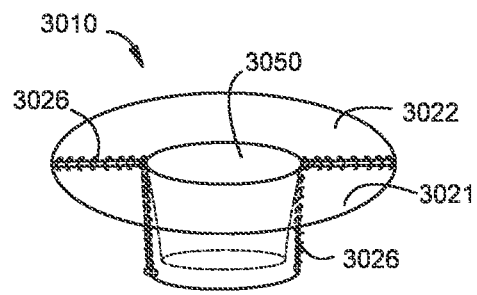

FIG. 37B is an illustration of a top perspective view of the valve wireframe panels or walls 3016A and 3016B that are stitched along the side edges 3026A to form the three-dimensional valve frame 3010 having the arc-shape collar portion 3021, 3022 and the cylinder body portion with the internal flow control component 3050 mounted within the cylinder body portion, and shown in an expanded configuration.

Figure 37C:
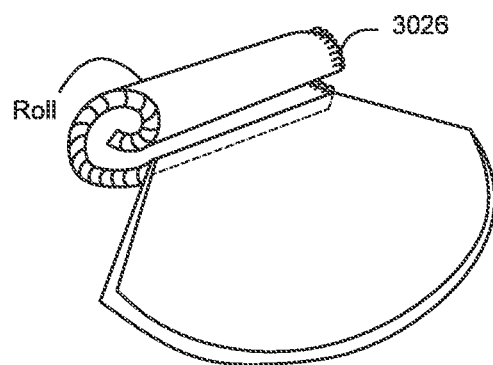
FIGS. 37C and 37D are perspective views of the transcatheter prosthetic valve of FIG. 37A being transitioned to a collapsed configuration.

FIG. 37C is an illustration of a side perspective view of the two-panel valve frame 3010 being compressed by rolling. FIG. 37C shows two panels, sewn along the joining (stitched, joined) edges 3026.

Figure 37D:
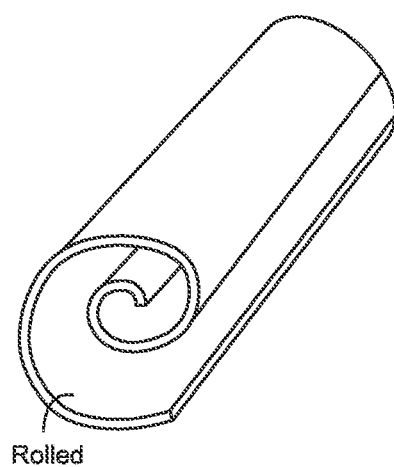

FIG. 37D is an illustration of a side perspective view of the two-panel valve frame 3010 in a rolled, compressed configuration with at least 1 turn, and up to 1.5 turns—or at least 360 degrees, and up to at least 540 degrees.

Figure 38A:
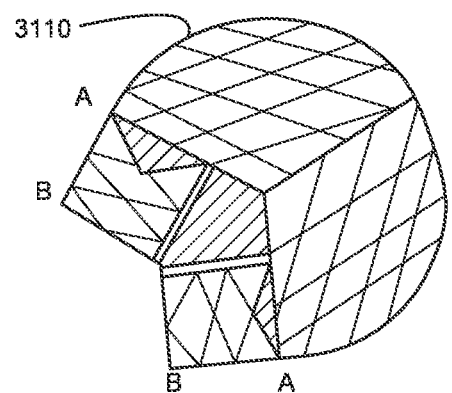
FIGS. 38A-38C are various views of a transcatheter prosthetic valve according to an embodiment.

FIG. 38A is an illustration of a top view of a single sheet of metal or metal alloy with compressible cells cut or formed into a first and second collar panel and a first and second body portion to form a wire valve frame 3110. FIG. 38A shows a cut and fold design. FIG. 38A shows where the collar can be folded so that the two points A on the collar are brought together, and the lower portion can be folded so that the two points B on the lower portion are brought together to form the three-dimensional valve frame structure 3110 with partial folding to minimize the requirement for extensive sewing.

Figure 38B:
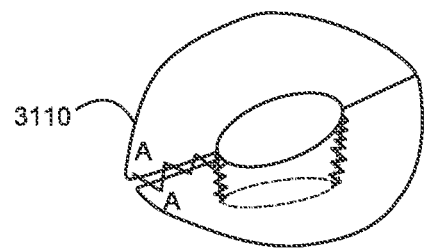

FIG. 38B is an illustration of a top perspective view of the single sheet valve frame 3110 after folding, assembly, and attachment along the open seams.

Figure 38C:
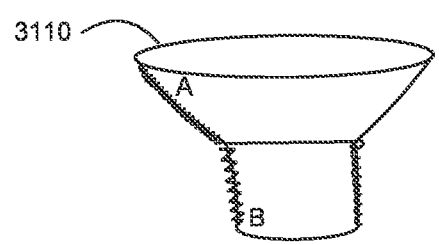

FIG. 38C is an illustration of a side perspective view of the single sheet valve frame 3110 after folding, assembly, and attachment along the open seams, in its expanded configuration.

Figure 39:
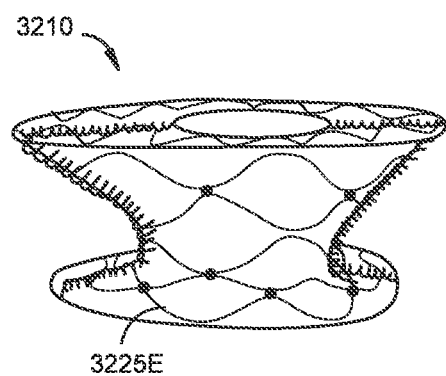
FIGS. 39 and 40 are side perspective views of a transcatheter prosthetic valve each according to a different embodiment.

FIG. 39 is an illustration of a side perspective view of a valve frame 3210 formed from a series of horizontal wave-shaped wires 3225E connected at connection points, with an upper collar portion, and an hourglass shape for the lower body portion, in its expanded configuration. Sewing features are shown along the joining edges.

Figure 40:
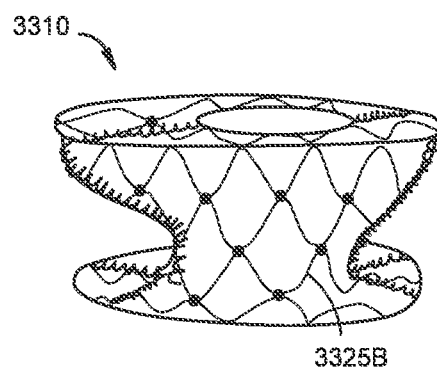

FIG. 40 is an illustration of a side perspective view of a valve frame 3310 formed from a series of (vertical) zigzag-shaped wires 3325B connected at connection points, with an upper collar portion, and an hourglass shape for the body portion, in its expanded configuration. Sewing features are shown along the joining edges.

Figure 41A:
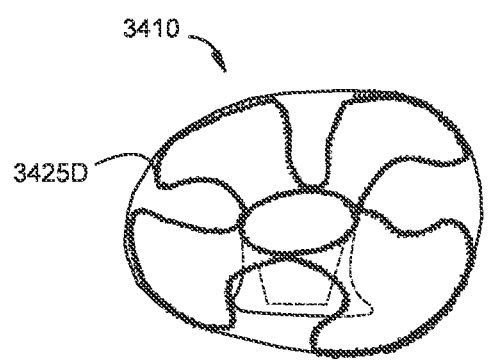
FIGS. 41A-41G are various views of one or more portions of a transcatheter prosthetic valve according to embodiments.

FIG. 41A is an illustration of a top perspective view of a valve frame 3410, in its expanded configuration, according to an embodiment. The valve frame 3410 has an upper collar portion formed from a series of fan-shaped asymmetric, irregular rounded cells/wires 3425D connected circumferentially to the top peripheral edge of a lower body portion of the frame 3410.

Figure 41B:
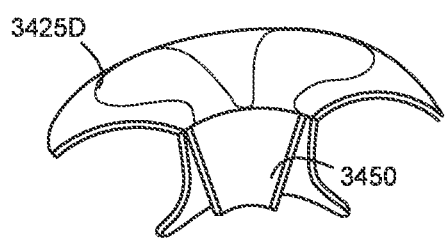

FIG. 41B is an illustration of a cut away view of the valve frame 3410 showing the upper collar portion formed from a series of fan-shaped asymmetric, irregular rounded cells/wires 3425D connected circumferentially to the top peripheral edge of the lower body portion, and showing half of a flow control component 3450 mounted with the lower body portion.

Figure 41C:
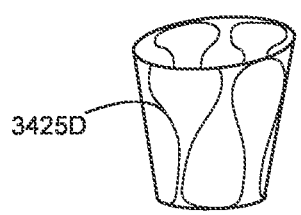

FIG. 41C is an illustration of a side perspective view of the upper cuff or collar portion of the frame 3410 in a partially expanded configuration, showing how the elongated fan-shape asymmetric, irregular rounded cells/wires 3425D permit elongation and radial compression.

Figure 41D:

FIG. 41D is an illustration of a side perspective view of a two-panel embodiment of the flow control component 3450.

Figure 41E:
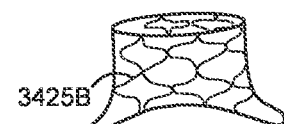

FIG. 41E is an illustration of a side perspective view of an embodiment of the lower body portion of the frame 3410 having a braided wire cell construction 3425B.

Figure 41F:
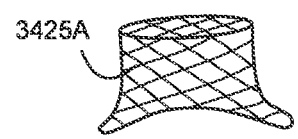

FIG. 41F is an illustration of a side perspective view of an embodiment of the lower body portion of the frame 3410 having a diamond laser-cut wire cell construction 3425A.

Figure 41G:
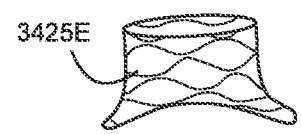

FIG. 41G is an illustration of a side perspective view of an embodiment of a lower body portion of the frame 3410 having a connected-wave wire cell construction 3425E.

Figure 42:
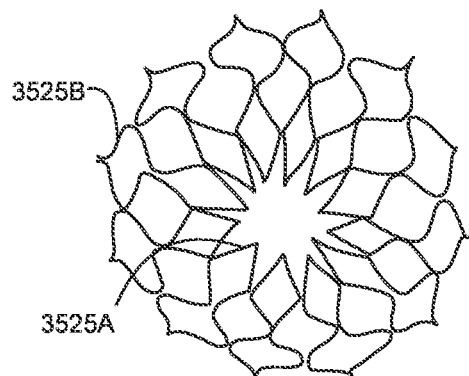
FIGS. 42-46 are various views of one or more portions of a wire frame of a transcatheter prosthetic valve according to embodiments.

FIG. 42 is an illustration of a top view of flat wire frame of metal or metal alloy having compressible wire cells configured in a strain minimizing orientation to facilitate orthogonal loading and delivery of a prosthetic valve. The arrangement and/or formation of the compressible wire cells allows the cells to compress, deform, or reconfigure when the prosthetic valve is compressed to the compressed configuration while minimizing strain within the wire valve frame. FIG. 42 shows outer wave cells 3525B used for a collar portion of a wire frame with inner diamond cells 3525A used for a lower body portion of the wire frame.

Figure 43:
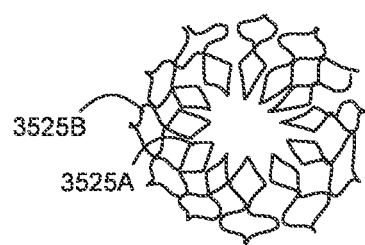

FIG. 43 is an illustration of a top view of a smaller sized flat wire frame of metal or metal alloy having compressible wire cells configured in a strain minimizing orientation to facilitate orthogonal loading and delivery of a prosthetic valve. FIG. 43 shows outer wave cells 3525B used for the collar portion of the wire frame with inner diamond cells 3525A used for the lower body portion of the wire frame.

Figure 44:
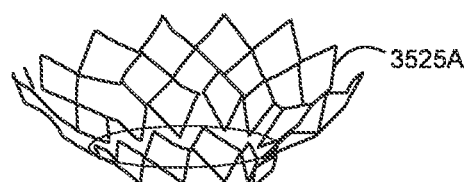

FIG. 44 is an illustration of a side perspective view of a portion of a wire frame in a funnel configuration (heat set) showing compressible wire cells configured in a strain minimizing orientation to facilitate orthogonal loading and delivery of a prosthetic tricuspid valve. FIG. 44 shows outer diamond cells 3525A used for a collar portion of the wire frame and inner diamond cells 3525A used for the lower body portion of the wire frame.

Figure 45:
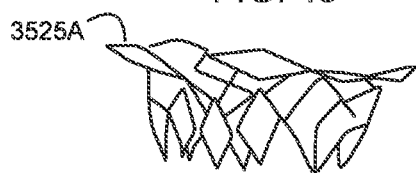

FIG. 45 is an illustration of a side perspective view of a portion of a wire frame in a funnel configuration (heat set) showing compressible wire cells configured in a strain minimizing orientation to facilitate orthogonal loading and delivery of a prosthetic tricuspid valve. FIG. 45 shows outer diamond cells 3525A used for a collar portion of the wire frame and inner diamond cells 3525A used for the lower body portion of the wire frame.

Figure 46:
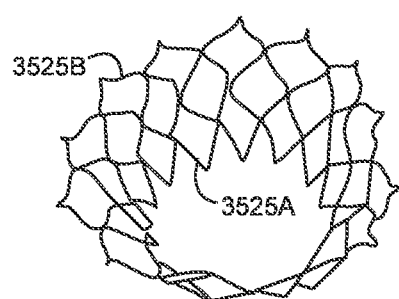

FIG. 46 is an illustration of a top view down the central axis of the wire frame in a funnel configuration (heat set) showing compressible wire cells configured in a strain minimizing orientation to facilitate orthogonal loading and delivery of a prosthetic tricuspid valve. FIG. 46 shows outer wave cells 3525B used for the collar portion of the wire frame and inner diamond cells 3525A used for the lower body portion of the wire frame.

Figure 47A:
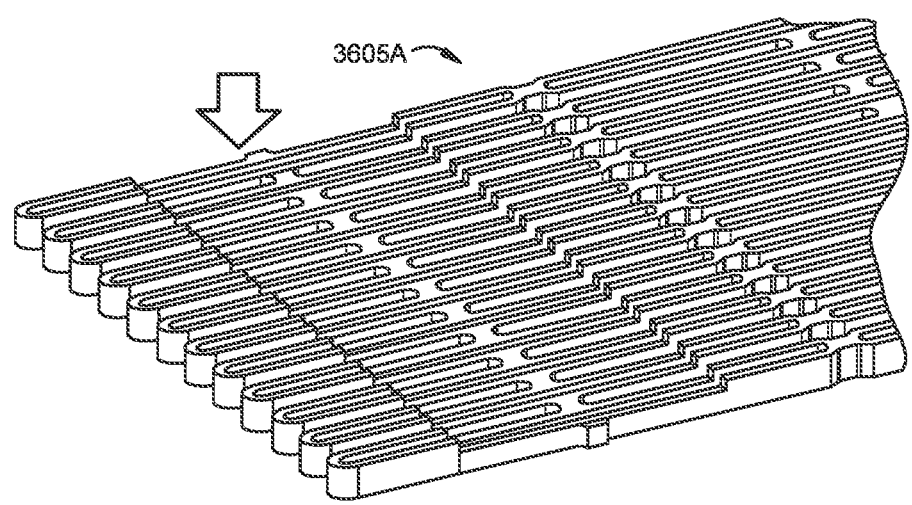
FIGS. 47A and 47B are side perspective views of an etched metal alloy sheet used to form a frame of a transcatheter prosthetic valve each according to a different embodiment.

One benefit of the two (or more) panel valve frame construction described in connection with several embodiments above is that each frame panel can be formed as a flat sheet, rather than as a braid, laser-cut tube, etc. The manufacturing process for such flat sheet components can be substantially less expensive than other techniques. For example, rather than using a laser to cut apertures in the sheet to form the wire frame structure, the sheet can be etched using, for example, photolithography and resistive masks. This technique also enables the sheet to be selectively etched to different thicknesses in different areas of the sheet, providing more design control over the mechanical or structural characteristics of different sections of the sheet (and thus of the valve frame formed from the sheet). FIG. 47A is an illustration of a side perspective view of a metal alloy sheet 3605A that has been etched partially on a single side using photolithography and resistive masks. The metal alloy sheet 3605A can be used to form a wire valve frame.

Figure 47B:
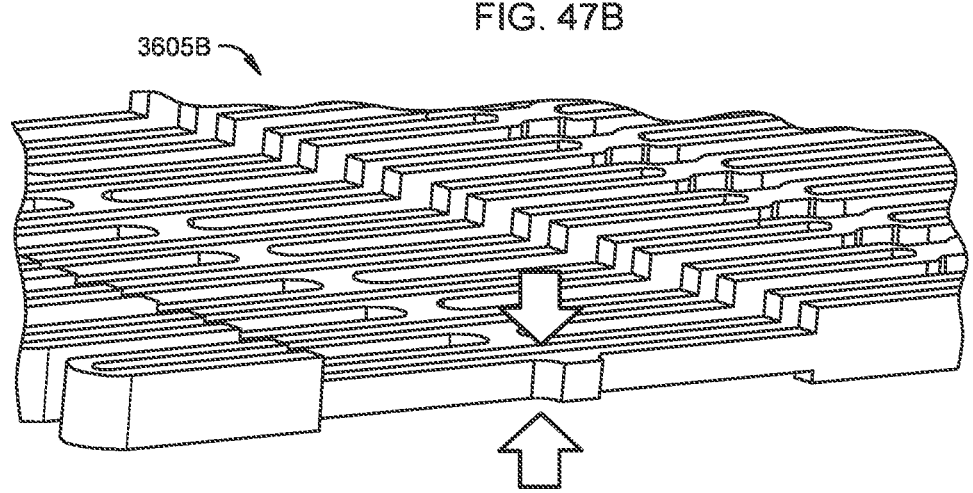

FIG. 47B is an illustration of a side perspective view of a metal alloy sheet 3605B that has been etched partially in a two-sided configuration using photolithography and resistive masks. The metal alloy sheet 3605B can be used to form a wire valve frame.

As described above with reference to FIGS. 1A and 1B, a valve and/or valve frame can include any number of tension arms and/or anchoring members configured to mount, secure, or anchor the valve and/or valve frame within the annulus of a native valve. The tension arms can, for example, extend from the valve frame and can engage supra-annular tissue or subannular tissue. Tension arms included in the valve and/or valve frames described herein can be substantially similar in at least form and/or function to at least one of the tensions arms 131, 132, 133, and/or 134 described above with reference to FIGS. 1A and 1B. A valve and/or valve frame can include and/or can be coupled to an anchoring member that can be used to mount or anchor the valve or valve frame in the annulus of the native valve. Anchoring members included in and/or used with the valves and/or valve members described herein can be substantially similar in at least form and/or function to the tissue anchor 190 described above with reference to FIGS. 1A and 1B.

Figure 48:
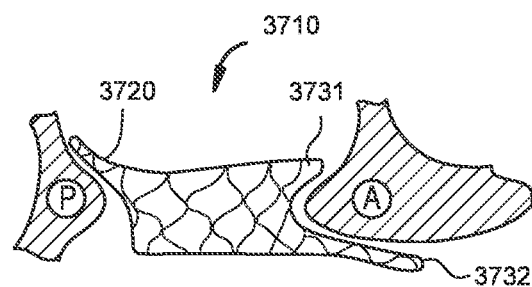
FIGS. 48 and 49 are side views of a transcatheter prosthetic valve deployed in a native annulus of a target tissue each according to a different embodiment.

FIG. 48 is an illustration of a plan view of an embodiment of a prosthetic valve with a valve frame 3710 having a distal upper tension arm 3731 and a distal lower tension arm 3732 mounted on, and anchored to, an anterior leaflet side of a native annulus. The frame 3710 includes a mechanical anchor element such as, for example, a proximal sealing cuff 3720 for anchoring on the posterior-septal side of the native annulus. The sealing cuff 3720 may be a short tab on the posterior side of the valve frame 3710 or may be a semi-circular or circular collar or cuff (e.g., similar to the cuff 120 described above with reference to FIGS. 1A-1F) that engages the atrial floor to seal the annulus from perivalvular leaks. The deployment of the valve can include placing the valve frame 3710 at or near an annulus of a native valve and positioning the distal lower tension arm 3732 in a subannular position such as, for example, the RVOT. The distal upper tension arm 3731 can be placed in a supra-annular position such as, for example, in the atrium of the heart. As such, the distal upper tension arm 3731 can exert a supra-annular downward force on the annular tissue and the distal lower tension arm 132 can exert an opposing subannular upward force on an opposite side of the annular tissue. The forces act to mount or secure the valve frame 3710 within the annulus of the native valve.

Figure 49:
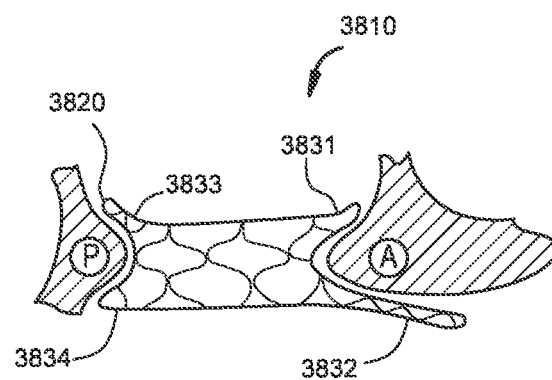

FIG. 49 is an illustration of a plan view of an embodiment of a prosthetic valve with a valve frame 3810 having a distal upper tension arm 3831 and a distal lower tension arm 3832 mounted on, and anchored to, the anterior leaflet side of the native annulus. The frame 3810 includes a mechanical anchor element such as, for example, an hourglass annular seal 3820, for anchoring on the posterior-septal side of the native annulus. The hourglass, or concave, sealing cuff 3820 may be only a short segment on the posterior side of the valve or may be a semi-circular or circular combined upper and lower collar or cuff that engages the atrial floor and the ventricular ceiling to seal the annulus from perivalvular leaks. The hourglass, or concave, sealing cuff 3820 can be formed by, for example, a proximal upper tension arm 3833 and a proximal lower tension arm 3834. The proximal upper tension arm 3833 and the proximal lower tension arm 3834 can exert opposing forces on the annular tissue as described with the distal tension arms 3831 and 3832. This embodiment may also include embodiments having a partial collar. This embodiment may be used in conjunction with other anchoring elements described herein such as a tissue anchor.

FIG. 50 is an illustration of a plan view of a prosthetic valve 3902 according to an embodiment. The valve 3902 includes a valve frame 3910 having a distal upper tension arm 3931 and a distal lower tension arm 3932 mounted on and anchoring to the annulus. FIG. 50 shows distal lower tension arm 3932 extending into the RVOT. The lateral, or side-loaded, delivery of the valve 3902 through the inferior vena cava provides for direct access to the native valve annulus without the need to deliver a compressed valve around a right angle turn, as is done for IVC delivery of axially, or vertically loaded, traditional transcatheter prosthetic valves. FIG. 50 shows one embodiment where a tissue anchor 3990 such as a screw or other anchor device is used in conjunction with the tension-mounting method described herein where the distal upper and lower tension arms 3931 and 3932 on the anterior leaflet side anchor the valve 3902 in place, and a secondary anchor element (e.g., the tissue anchor 3990) completes the securement of the valve 3902 in the annular site.

FIG. 50 shows polyester mesh cover 3917 that covers the valve frame 3910 and encircles a collapsible flow control sleeve of flow control component (not shown). FIG. 50 also shows the frame 3910 having Nitinol wire frame in diamond shape cells 3925A within or covered by the biocompatible covering 3917. In one embodiment, the frame may have a pericardial material on top and a polyester material, e.g., surgical Dacron, underneath to be in contact with the native annulus and promote ingrowth.

Figure 51A:
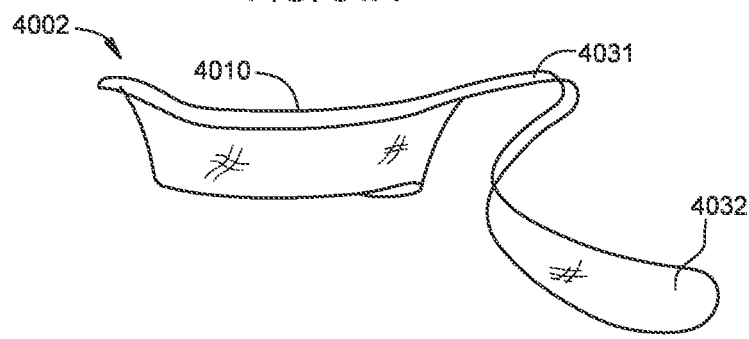
FIGS. 51A-51C are various views of a transcatheter prosthetic valve according to an embodiment.

FIG. 51A is an illustration of a plan view of a low profile, e.g., 10 mm in height, prosthetic valve 4002 according to an embodiment, in an expanded configuration. The valve 4002 includes a frame 4010 that has and/or that forms a wire annulus support loop. The frame 4010 includes and/or forms (or the wire loop includes and/or forms) a distal upper tension arm 4031 and a distal lower tension arm 4032 that can be formed as a unitary or integral part and covered with a biocompatible material. This embodiment shows how the low profile, side-loaded valve 4002 can having a very large diameter, 40-80 mm, without having to deliver the valve 4002 with an undesirably large delivery catheter, as would be otherwise used to deliver a large diameter valve that is delivered using the traditional, vertical or axial, orientation.

Figure 51B:
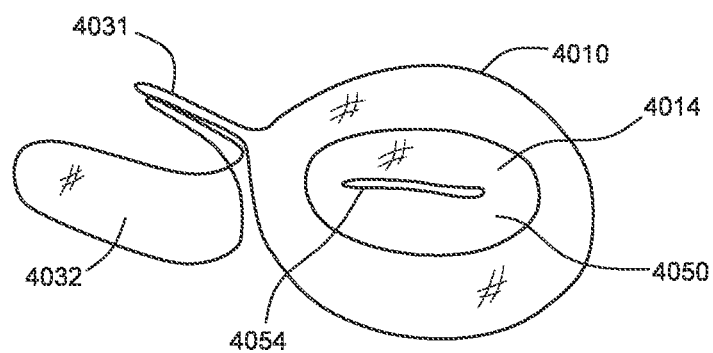

FIG. 51B is an illustration of a top view of the valve 4002 that shows the inner two-panel sleeve or flow control component 4050 and the reciprocating collapsible aperture 4054 at the lower end for delivering blood to the ventricle.

Figure 51C:
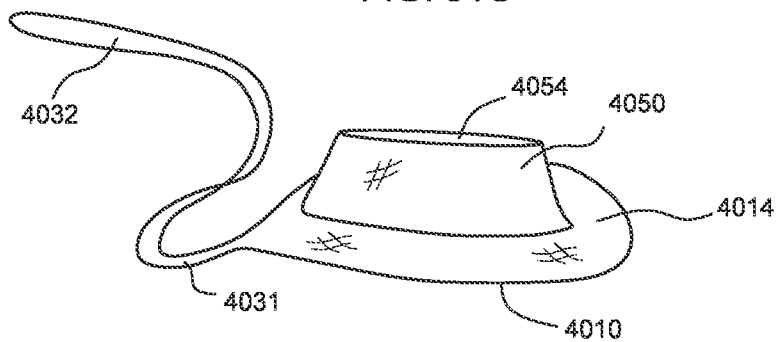

FIG. 51C is an illustration of a bottom-side view of the valve 4002 that shows a plan view of the inner two-panel sleeve or flow control component 4050 and the collapsible terminal aperture 4054 at the ventricular side.

Figure 51D:
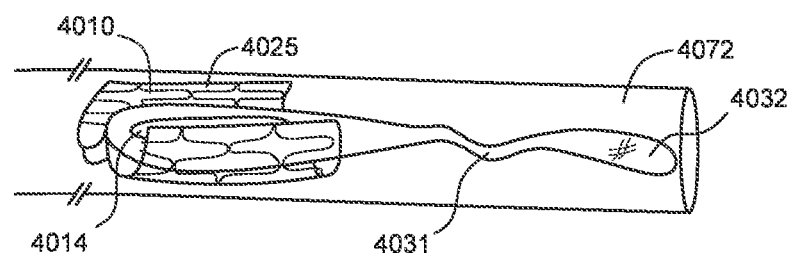
FIGS. 51D and 51E illustrate the transcatheter prosthetic valve of FIG. 51A at least partially disposed within a delivery catheter.

FIG. 51D is an illustration of the valve 4002 in a compressed configuration and disposed within a delivery catheter 4072. FIG. 51D illustrates how a large diameter valve 4002, using side loading, can be delivered via the delivery catheter 4072.

Figure 51E:
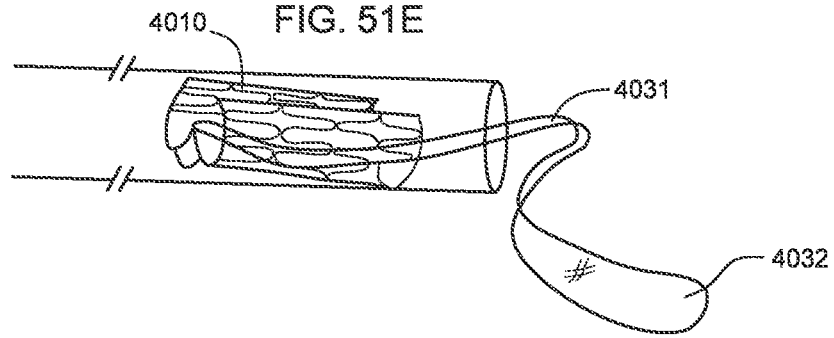

FIG. 51E is an illustration of the valve 4002 in a compressed configuration being partially ejected, and partially disposed within, the delivery catheter 4072. FIG. 51E shows how the valve 4002 can be partially delivered for positioning in the annulus. The distal lower tension arm 4034 can be used to navigate through the native tricuspid leaflets and chordae tendineae while the valve body, the tubular frame, 4010 is still within the steerable delivery catheter 4072.

Figure 52A:
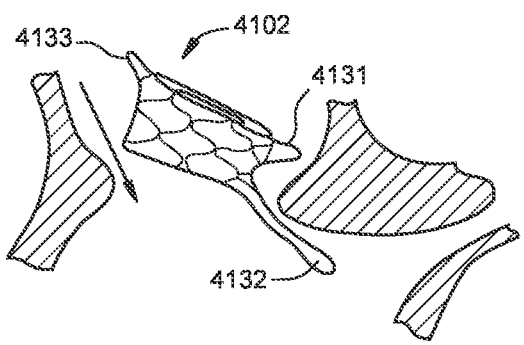
FIGS. 52A and 52B illustrate a transcatheter prosthetic valve partially deployed and fully deployed, respectively, in a native annulus of a target tissue.

FIG. 52A is an illustration of a plan view of a prosthetic valve 4102 partially mounted within a native valve annulus. By using the side-loaded valve 4102 of the disclosed embodiments, the distal upper tension arm 4133 and the distal lower tension arm 4132 can be mounted against an anterior aspect of the native annulus, and valve function can be assessed before completely seating the valve 4102. By allowing two pathways for blood flow, the first through the native valve near the posterior leaflet, and the second through the central aperture of the prosthetic valve 4102, a practitioner can determine if the heart is decompensating or if valve function is less than optimal. FIG. 52A also shows a proximal upper tension arm 4133 which can work in conjunction with the distal tension arms 4131 and 4132 to mount, seat, and/or anchor the valve 4102 in the native annulus.

Figure 52B:
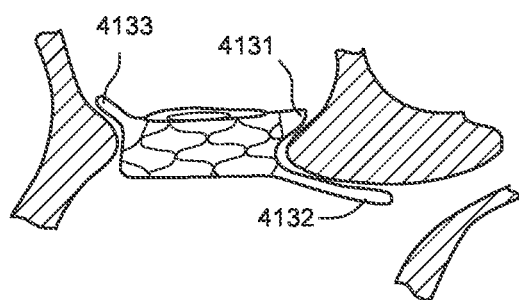

FIG. 52B is an illustration of a plan view of the prosthetic valve 4102 completely seated within the valve annulus. FIG. 52B shows that the valve 4102 can be secured in place once the valve function assessment shows that the deployment is successful. Importantly, since the valve 4102 is a low profile valve, and fits easily within a standard, e.g., 8-12 mm, delivery catheter without requiring the forceful loading of typical transcatheter valves, the side-loading valve 4102 can be easily retrieved using the same delivery catheter that is used to deploy the valve.

Figure 53A:
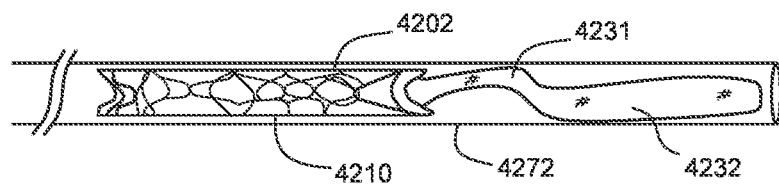
FIGS. 53A-53F are various views of a transcatheter prosthetic valve according to an embodiment.

FIG. 53A is an illustration of a prosthetic valve 4202 according to an embodiment in a compressed configuration within a delivery catheter 4272. The valve 4202 includes a frame 4210 that has and/or that forms a wire annulus support loop. The frame 4210 includes and/or forms (or the wire loop includes and/or forms) a distal upper tension arm 4231 and a distal lower tension arm 4232 that can be formed as a unitary or integral part and covered with a biocompatible material. The lower and upper tension arms 4231 and 4232 are elongated to the right and the prosthetic valve 4202 is shown laterally compressed in the delivery catheter 4272. The lateral compression is a function of the use of minimal structural materials, e.g., a minimal inner valve sleeve of flow control component 4250 (FIG. 53C), and the relatively short height of the frame 4210. This lateral delivery provides for a relatively large, e.g., up to 80 mm or more, prosthetic valve. The lateral delivery also avoids the need to perform a 90-degree right turn when delivering the valve 4202 using the IVC femoral route. This sharp delivery angle when delivering traditional valves has also limited the size and make up of prior valve prostheses and the side-delivery of the valve 4202 avoids such limitations.

Figure 53B:
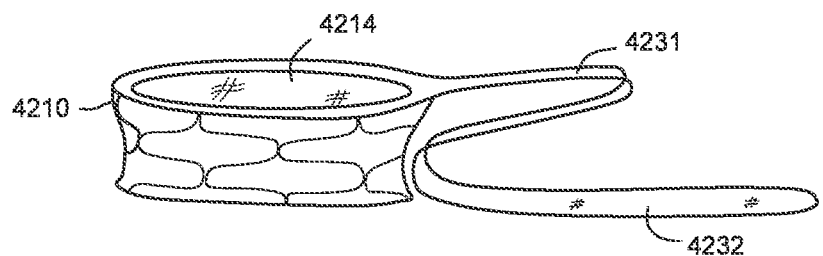

FIG. 53B is an illustration of a profile, or plan, view of the wire-frame 4210 of the valve 4202 in an expanded configuration. FIG. 53B shows the distal upper tension arm 4231 is attached to the tubular frame 4210 while the distal lower tension arm 4232 is shaped in an S-shape and is connected only to the distal upper tension arm 4231.

Figure 53C:
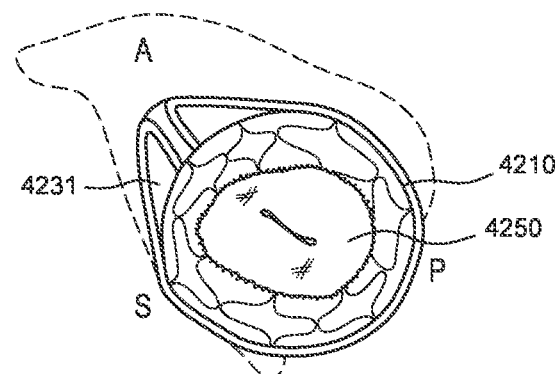

FIG. 53C is an illustration of a top view of the valve 4202 disposed in a native tricuspid valve. FIG. 53C shows the tubular frame 4210 and the inner sleeve or flow control component 4250 sewn into a central aperture 4214 of the frame 4210, with the two (2) panels extending downward (into the page) in a ventricular direction. FIG. 53C shows the distal upper tension arms 4231 oriented towards the anterior leaflet side of the atrial floor around the native tricuspid valve, which is shown in dashed outline.

Figure 53D:
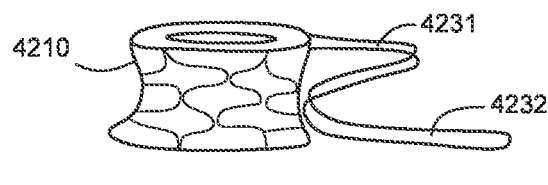
Figure 53E:
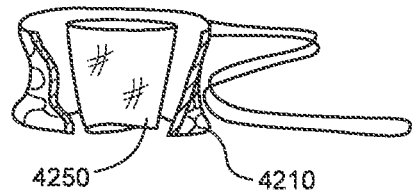

FIG. 53D is an illustration of a plan view and FIG. 53E is an illustration of a cut away plan view of the valve 4202. FIG. 53E shows the inner panel valve sleeve or flow control component 4250 mounted within the inner space or aperture 4214 defined by the tubular frame 4210. FIG. 53E shows an elongated two-panel valve sleeve or flow control component 4250 that extends into the sub-annular leaflet space. The tubular frame 4210 shown in FIG. 53E is about 10 mm in height and the valve sleeve or flow control component 4250 extends about 10 mm below the bottom of the tubular frame 4210, resulting in a valve 4202 having a total height of 20 mm.

Figure 53F:
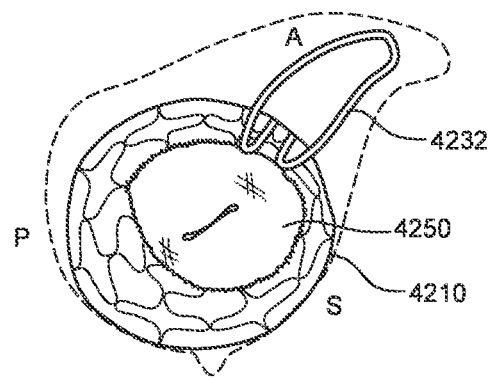

FIG. 53F is an illustration of a bottom view of the valve 4202 that shows the tubular frame 4210 having an inner sleeve or flow control component 4250 sewn into the central aperture 4214, with the two panels extending upward (out of the page) in a ventricular direction. FIG. 53F shows the distal lower tension arm 4242 oriented towards the anterior leaflet side of the ventricular ceiling of the native tricuspid valve, which is shown in dashed outline.

Figure 54A:
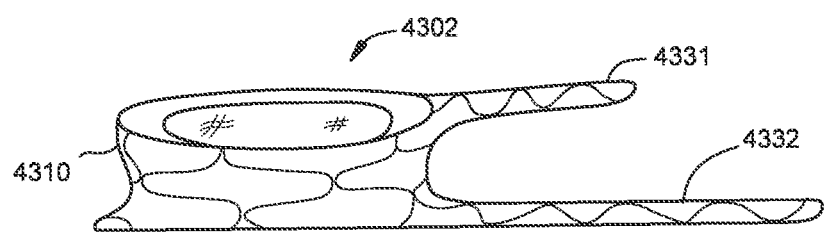
FIGS. 54A-54E are various views of a transcatheter prosthetic valve according to an embodiment.

FIG. 54A is an illustration of a profile, or plan, view of a prosthetic valve 4302 according to an embodiment in an expanded configuration. The valve 4302 has a braid or laser-cut frame 4310. FIG. 54A shows a distal upper tension arm 4331 attached to an upper edge of the tubular frame 4310, and a distal lower tension arm 4332 attached to a lower edge of the tubular frame 4310.

Figure 54B:
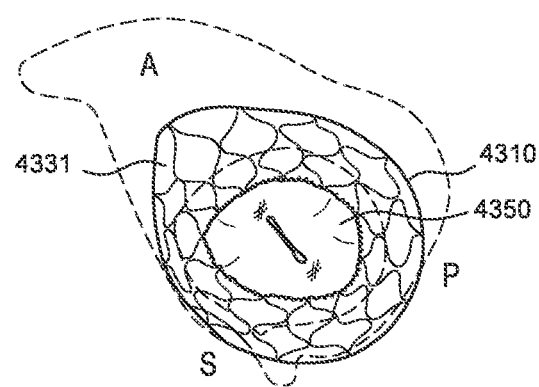

FIG. 54B is an illustration of a top view of the valve 4302 disposed in a native tricuspid valve. FIG. 54B shows the tubular frame 4310 having an inner sleeve or flow control component 4350 sewn into a central aperture of the frame 4310, with the two panels extending downward (into the page) in a ventricular direction. FIG. 54B shows the distal upper tension arm 4331 oriented towards the anterior leaflet side of the atrial floor of the native tricuspid valve, which is shown in dashed outline.

Figure 54C:
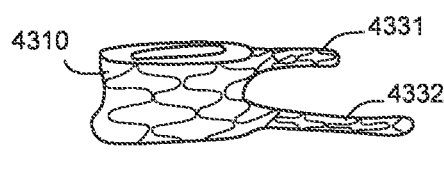
Figure 54D:
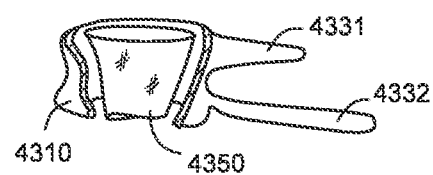

FIG. 54C is an illustration of a plan view and FIG. 54D is an illustration of a cut away plan view of the valve 4302. FIG. 54D shows the inner panel valve sleeve or flow control component 4350 mounted within the inner space or central aperture defined by the tubular frame 4310.

Figure 54E:
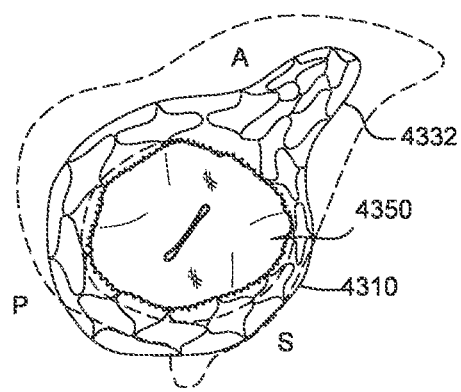

FIG. 54E is an illustration of a bottom view of the valve 4302 that shows the tubular frame 4210 having the inner sleeve or flow control component 4350 sewn into the central aperture, with the two (2) panels extending upward (out of the page) in a ventricular direction. FIG. 54E shows the distal lower tension arm 4334 oriented towards the anterior leaflet side of the ventricular ceiling, which is shown in dashed outline.

Figure 55A:
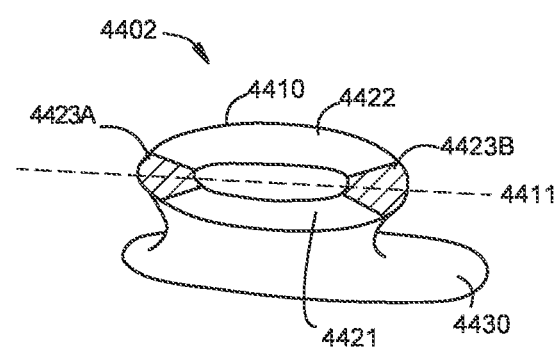
FIG. 55A is a side perspective view of a transcatheter prosthetic valve according to an embodiment.

FIG. 55A is an illustration of a side perspective view of a valve 4402 according to an embodiment having a circular hyperboloid (hourglass) shape, in an expanded configuration. The valve 4402 includes a frame 4410 having an extended RVOT tab 4430. The RVOT tab 4430 can be similar to the distal lower tension arms described herein. The wire frame details are not shown since in practice the external surface would preferably be covered, such as with Dacron polyester to facilitate in-growth. The frame 4410 includes a proximal fold area 4423A and a distal fold area 4423B that are shown on opposite ends of an anterior collar 4421 and posterior-septal collar 4422 along a horizontal long-axis 4411. The frame 4410 defines a central channel or aperture that accepts a flow control component.

Figure 55B:
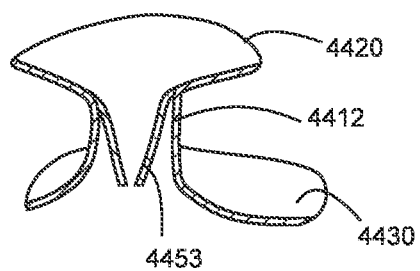
FIG. 55B is a cross-sectional view of the transcatheter prosthetic valve of FIG. 55A.

FIG. 55B is an illustration of a cut away view of the valve 4402 showing circular hyperboloid (hourglass) shape thereof and the RVOT tab 4430 (e.g., the distal lower tension arm). FIG. 55B shows that an inner leaflet 4453 and flow control component inner frame (not visible) are attached to an inner surface of the annular frame 4410, with collar portion 4420 attached to the RVOT tab or subannular anchor portion 4430 via a wall portion 4412. Here, the flow control component is only attached at the top edge although other non-limiting attachments are contemplated, e.g., mid-wall, multiple attachment points, etc.

Figure 56A:
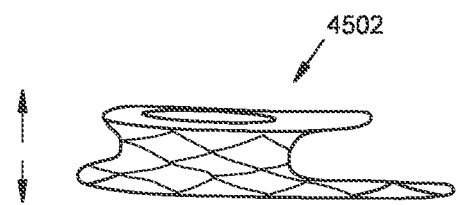
FIGS. 56A and 56B are side views of a transcatheter prosthetic valve according to an embodiment in an expanded configuration and a collapsed configuration, respectively.

FIG. 56A is an illustration of a side view of a vertically compressible valve 4502 with an internal non-extending set of leaflets (e.g., a flow control component) and compressible orthogonal (wide) wire cells and shown in an expanded configuration for implanting in a desired location in the body.

Figure 56B:
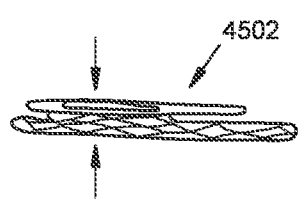

FIG. 56B is an illustration of a side view of the vertically compressible valve 4502 shown in a compressed configuration for delivery of the compressed valve 4502 to the desired location in the body.

Figure 57A:
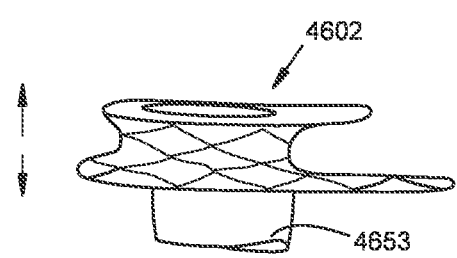
FIGS. 57A and 57B are side views of a transcatheter prosthetic valve according to an embodiment in an expanded configuration and a collapsed configuration, respectively.

FIG. 57A is an illustration of a side view of a vertically compressible valve 4602 with extended leaflets 4653 (e.g., a flow control component) and compressible orthogonal (wide) wire cells and shown in an expanded configuration for implanting in a desired location in the body.

Figure 57B:
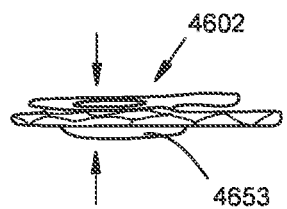

FIG. 57B is an illustration of a side view of the vertically compressible valve 4602 shown in a compressed configuration for delivery of the compressed valve 4602, where the wire frame is reduced in height (vertically compressed) and the extended leaflets are rolled up.

Figure 58A:
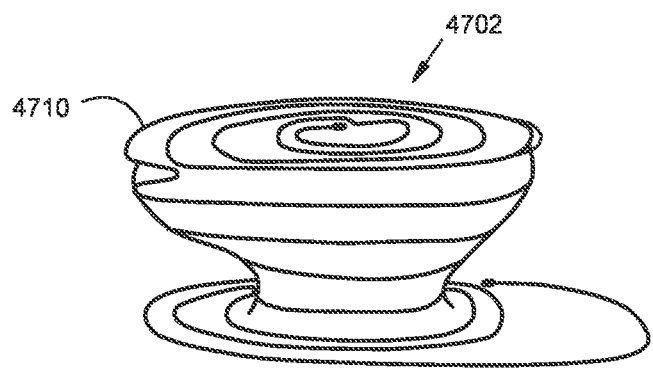
FIGS. 58A and 58B are a side perspective view and a top view, respectively, of a transcatheter prosthetic valve according to an embodiment.
Figure 58B:
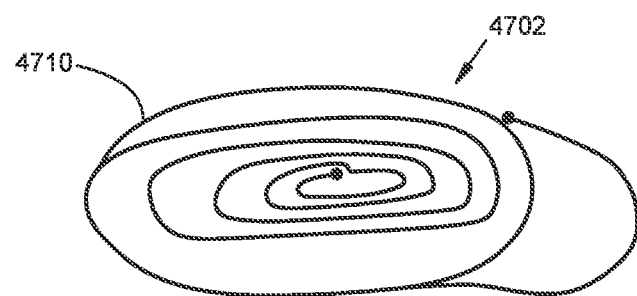

FIGS. 58A and 58B are illustrations of a side perspective view and a top view, respectively, of a valve 4702 having a wire frame 4710 that is formed from a single continuous wire, with an upper collar portion, a lower body portion having an hourglass shape, and a RVOT tab or distal lower tension arm extending away from the lower edge of the lower body portion of the frame 4710. The valve 4702 is shown in an expanded configuration.

Figure 59:
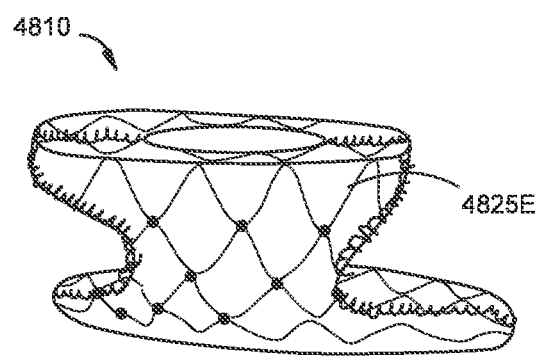
FIGS. 59 and 60 are side perspective views of a transcatheter prosthetic valve each according to a different embodiment.

FIG. 59 is an illustration of a side perspective view of a valve frame 4810 formed from a series of wave-shaped wires 4825E connected at connection points, with an upper collar portion, a lower body portion having an hourglass shape, and an RVOT tab or distal lower tension arm extending away from a lower edge of the lower body portion of the frame 4810. The valve frame 4810 is shown in an expanded configuration. Sewing features are shown along the joining edges.

Figure 60:
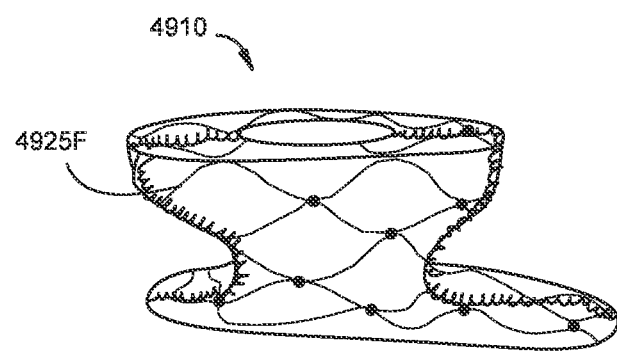

FIG. 60 is an illustration of a side perspective view of a valve frame 4910 formed from a series of horizontal wave-shaped wires 4925F connected at connection points, with an upper collar portion, a lower body portion having an hourglass shape, and an RVOT tab or distal lower tension arm extending away from a lower edge of the lower body portion of the frame 4910. The valve frame 4910 is shown in an expanded configuration. Sewing features are shown along the joining edges.

Figure 61:
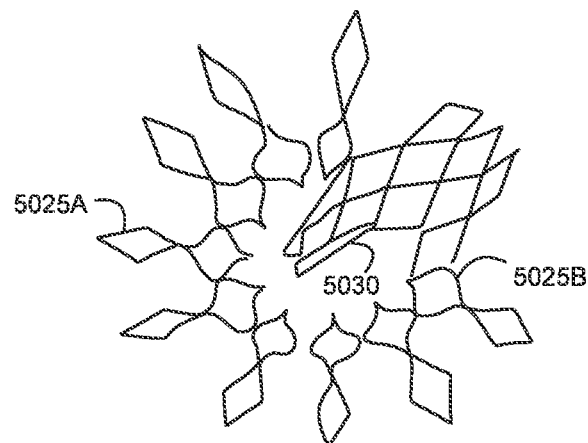
FIGS. 61-64 are various views of one or more portions of a wire frame of a transcatheter prosthetic valve according to embodiments.

FIG. 61 is an illustration of a top view of flat wire frame of metal or metal alloy having compressible wire cells configured in a strain minimizing orientation to facilitate orthogonal loading and delivery of a prosthetic tricuspid valve. FIG. 61 shows outer diamond cells 5025A used for a collar portion 5025B of a wire frame with inner wave cells 5025B used for a lower body portion of the wire frame, and diamond cells 5025A used for a subannular tab 5030 (e.g., a distal lower tension arm).

Figure 62:
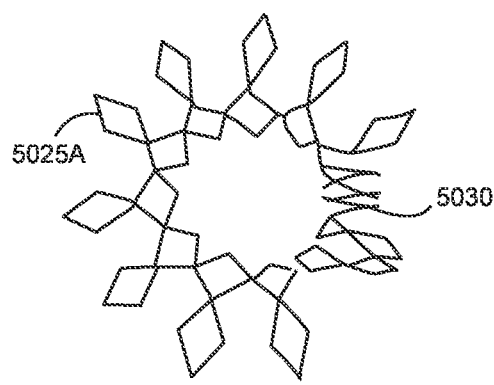

FIG. 62 is an illustration of a top view of a portion of a wire frame in a funnel configuration (heat set) showing compressible wire cells configured in a strain minimizing orientation to facilitate orthogonal loading and delivery of a prosthetic tricuspid valve. FIG. 62 shows outer diamond cells 5025A used for a collar portion of the wire frame and inner diamond cells 5025A used for a lower body portion of the wire frame and a subannular tab 5030 (e.g., a distal lower tension arm).

Figure 63:
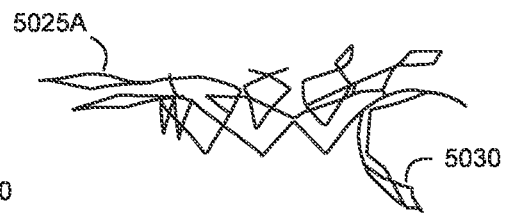

FIG. 63 is an illustration of a side view of a portion of a wire frame in a funnel configuration (heat set) showing compressible wire cells configured in a strain minimizing orientation to facilitate orthogonal loading and delivery of a prosthetic tricuspid valve. FIG. 63 shows outer diamond cells 5025A used for a collar portion of the wire frame and inner diamond cells 5025A used for a lower body portion of the wire frame and a subannular tab 5030 (e.g., a distal lower tension arm).

Figure 64:
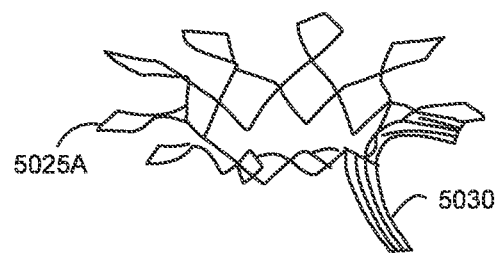

FIG. 64 is an illustration of a side perspective view of a portion of a wire frame in a funnel configuration (heat set) showing compressible wire cells configured in a strain minimizing orientation to facilitate orthogonal loading and delivery of a prosthetic tricuspid valve. FIG. 64 shows outer diamond cells 5025A used for a collar portion of the wire frame and inner diamond cells 5025A used for a lower body portion of the wire frame, and irregular shaped cells used for a subannular tab 5030 (e.g., a distal lower tension arm).

Figure 65A:
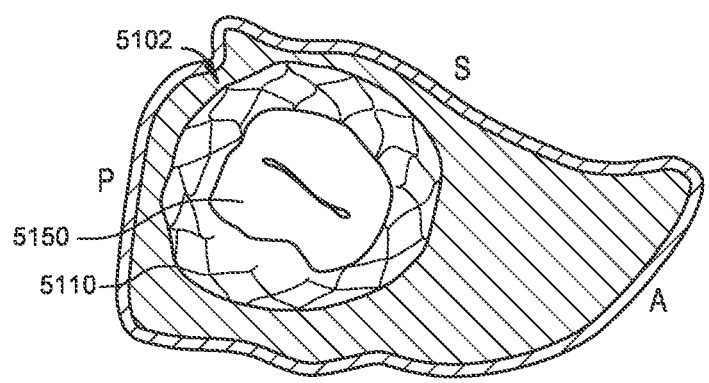
FIG. 65A is a top view of a transcatheter prosthetic valve shown within a cross-sectional view of an atrial floor and deployed within a native annulus.

FIG. 65A is an illustration of a top view of a prosthetic valve 5102 according to an embodiment having braid or laser-cut wire frame 5110 and shown mounted within a cross-sectional view of the atrial floor at the annulus of a native tricuspid valve.

Figure 65B:
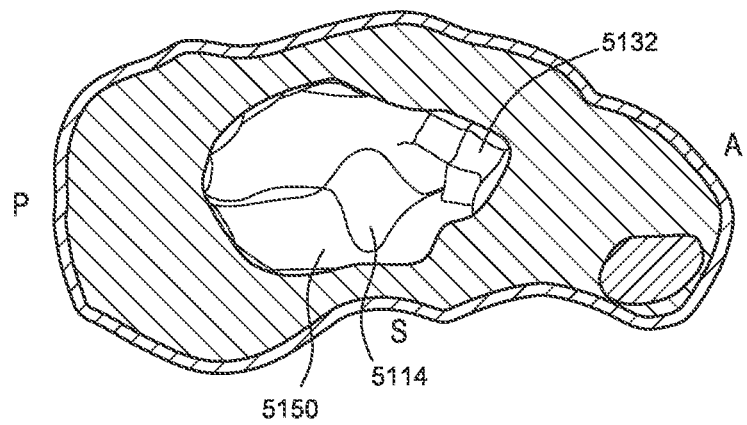
FIG. 65B is a bottom view of a transcatheter prosthetic valve shown within a cross-section view of a ventricular ceiling and deployed within a native annulus.

FIG. 65B is an illustration of a bottom view of the valve 5102 having the braid or laser-cut wire frame 5110 that includes and/or forms a distal lower tension arm 5132 and shown mounted within a cross-sectional view of the ventricular ceiling at the annulus of a native tricuspid valve. FIG. 65B shows a two-panel valve sleeve or flow control component 5150 in an open position and disposed within a central aperture 5114 of the frame 5110. The flow control component 5150 can be in the open position, for example, for atrial systole and ventricular diastole.

Figure 66:
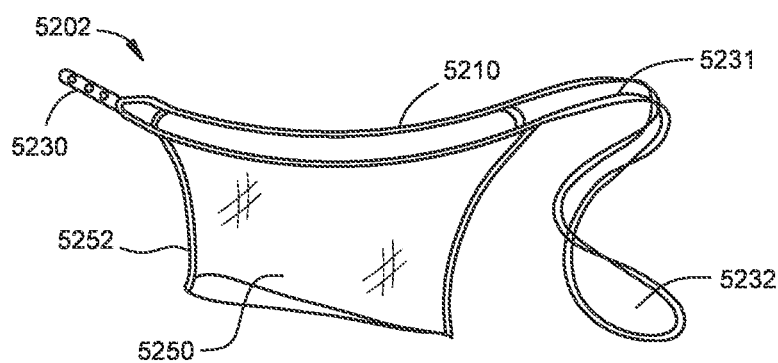
FIG. 66 is a side perspective view of a wire frame of a transcatheter prosthetic valve according to an embodiment.

FIG. 66 is an illustration of a prosthetic valve 5202 according to an embodiment, in an expanded configuration. The valve 5202 includes a frame 5210 that has and/or that forms a wire annulus support loop, with two vertical support posts 5252 extending down the edge on opposing sides of an inner sleeve or flow control component 5250. During compression into a delivery catheter, the posts 5252 are engineered to fold horizontally, and to elastically unfold during ejection to deploy the valve sleeve or flow control component 5252. FIG. 66 also shows the frame 5210 with a distal upper tension arm 5231 and a distal lower tension arm 5232 that can be formed as a unitary or integral part and covered with a biocompatible material. FIG. 66 also illustrates a proximal tab 5230 that can be, for example, a tension arm and/or an anchoring post or point.

Figure 67:
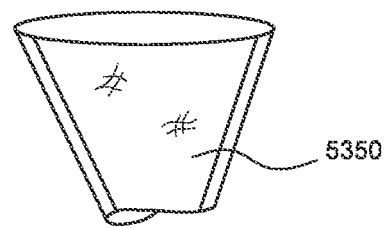
FIG. 67 is a side perspective view of a valve sleeve of a transcatheter prosthetic valve according to an embodiment.

FIG. 67 is an illustration of a two-panel embodiment of an inner valve sleeve or flow control component 5350. In some embodiments, the frame 5210 shown in FIG. 66 can be adapted to receive the flow control component 5350.

Figure 68A:
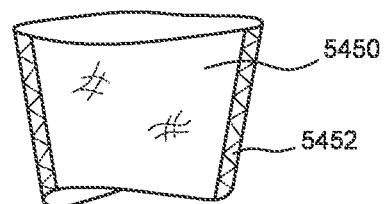
FIG. 68A is a side perspective view of a valve sleeve of a transcatheter prosthetic valve according to an embodiment.
Figure 68B:
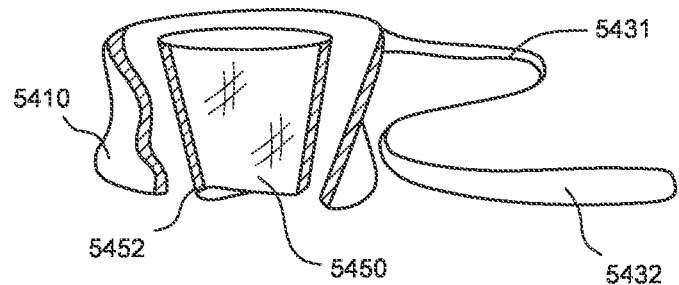
FIG. 68B is a cross-sectional view of the valve sleeve of FIG. 68A disposed within a frame of the transcatheter prosthetic valve.

FIGS. 68A and 68B are illustrations of a side perspective view and a cut away plan view, respectively, of a flow control component 5450 having two rigid support posts 5452. FIG. 68B shows the flow control component 5450 having the two rigid support posts 5452 mounted within the inner space or central aperture define by a tubular frame 5410, where the frame 5410 includes a distal upper tension arm 5431 and a distal lower tension arm 5432 extending away from the frame 5410.

Figure 69:
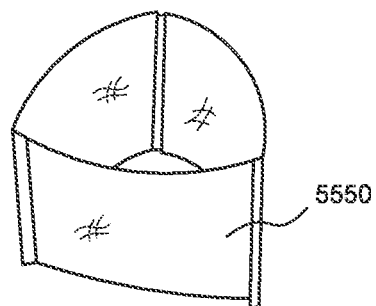
FIG. 69 is a side perspective view of a valve sleeve of a transcatheter prosthetic valve according to an embodiment.

FIG. 69 is an illustration of a three-panel embodiment of an inner valve sleeve of flow control component 5550 according to an embodiment.

Figure 70A:
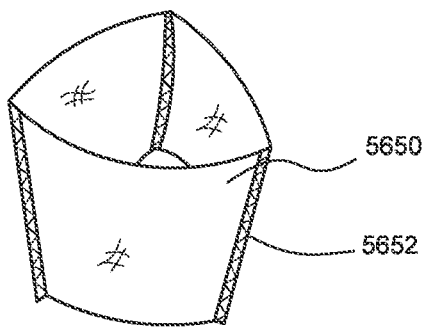
FIG. 70A is a side perspective view of a valve sleeve of a transcatheter prosthetic valve according to an embodiment.

FIG. 70A is an illustration of a three-panel embodiment of an inner valve sleeve or flow control component 5550 having three rigid support posts 5552 according to an embodiment.

Figure 70B:
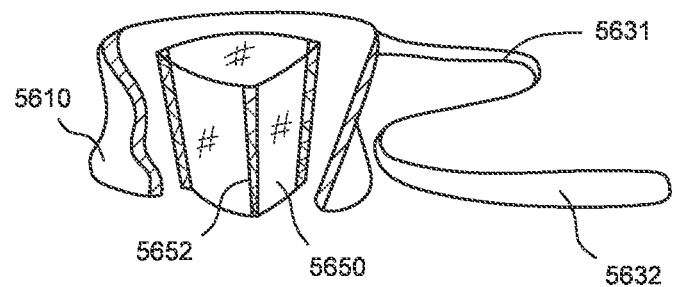
FIG. 70B is a cross-sectional view of the valve sleeve of FIG. 70A disposed within a frame of the transcatheter prosthetic valve.

FIG. 70B is an illustration of a cut away plan view of the three panel, three post valve sleeve or flow control component 5550 mounted within the inner space or central aperture defined by a tubular frame 5510, where the frame 5510 includes a distal upper tension arm 5531 and a distal lower tension arm 5532 extending away from the frame 5510.

Figure 71A:
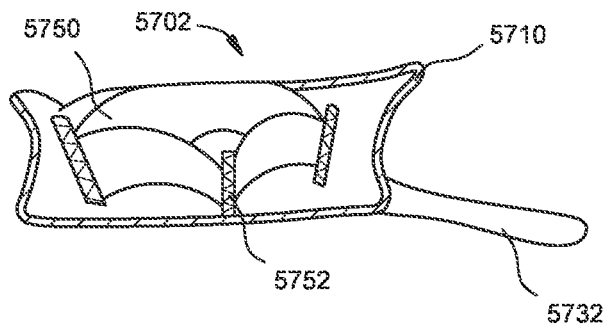
FIGS. 71A-71C are various views of a transcatheter prosthetic valve according to an embodiment.

FIG. 71A is an illustration of one embodiment of a partial cut-away interior view of a tri-leaflet embodiment of a low profile, e.g., 8-20 mm, side-loaded prosthetic valve 5702 having a frame 5710 and a flow control component 5750. The frame 5710 includes a distal lower tension arm 5732. The flow control component 5750 is a tri-leaflet flow control component with three rigid support posts 5752.

Figure 71B:
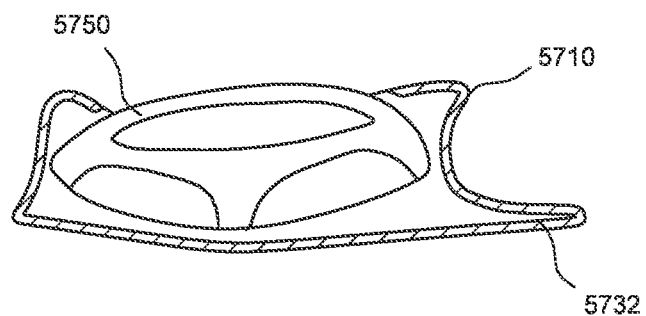

FIG. 71B is an illustration of another embodiment of a partial cut-away interior view of the tri-leaflet embodiment of the low profile, e.g., 8-20 mm, side-loaded prosthetic valve 5702 showing the flow control component 5750 in a non-cut-away view.

Figure 71C:
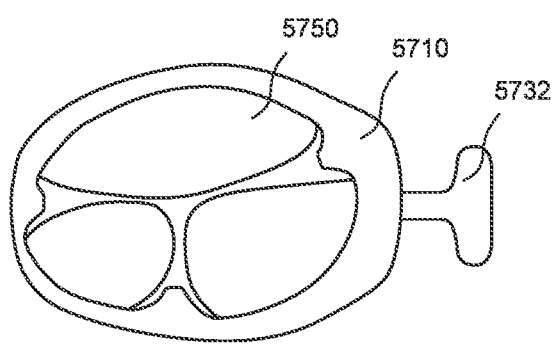

FIG. 71C is an illustration of a top view of the tri-leaflet embodiment of the low profile, e.g., 8-20 mm, side-loaded prosthetic valve 5702.

Figure 72A:
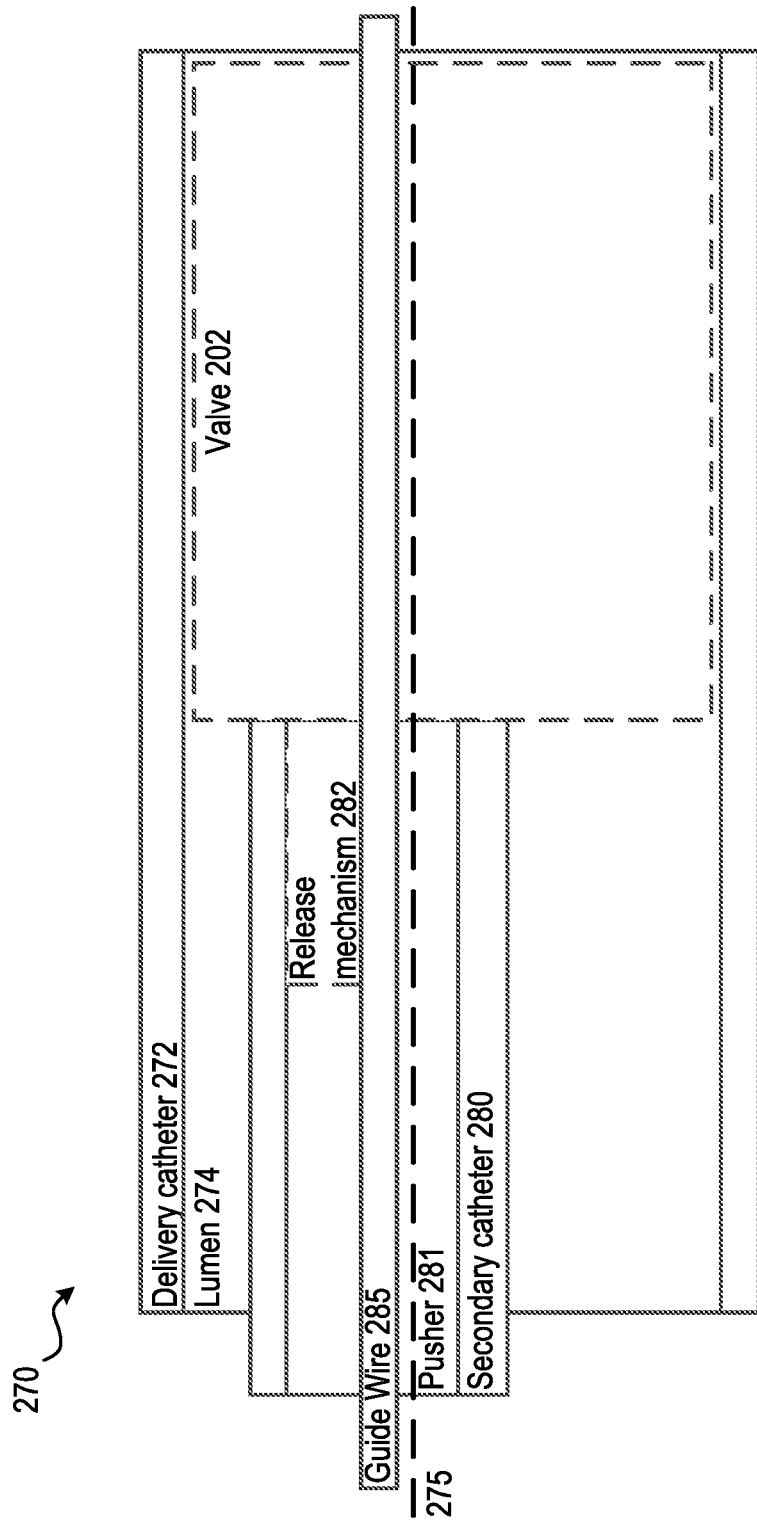
FIGS. 72A-72C are schematic illustrations of a delivery system for delivering a transcatheter prosthetic valve according to an embodiment.
Figure 72B:
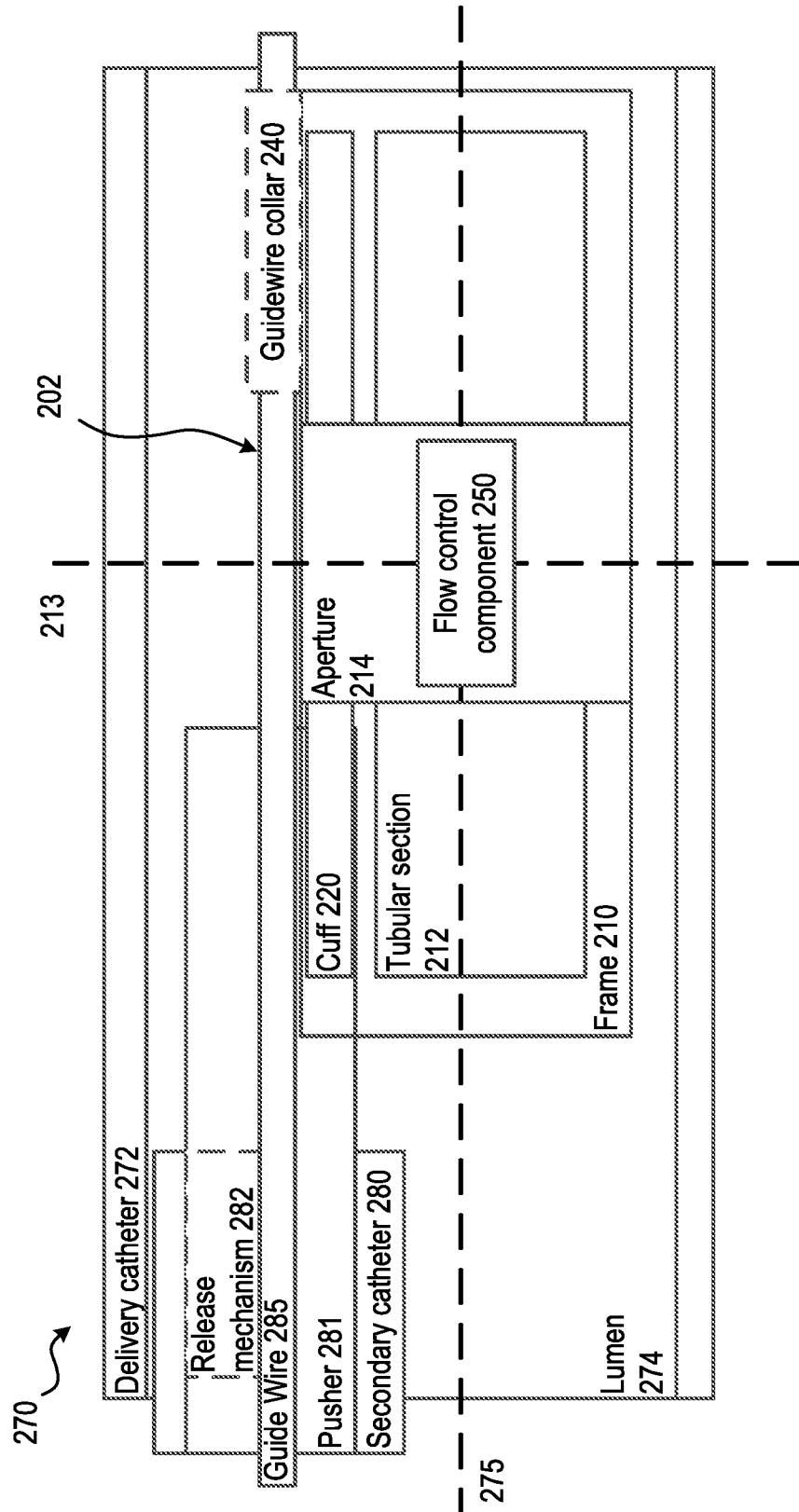
Figure 72C:
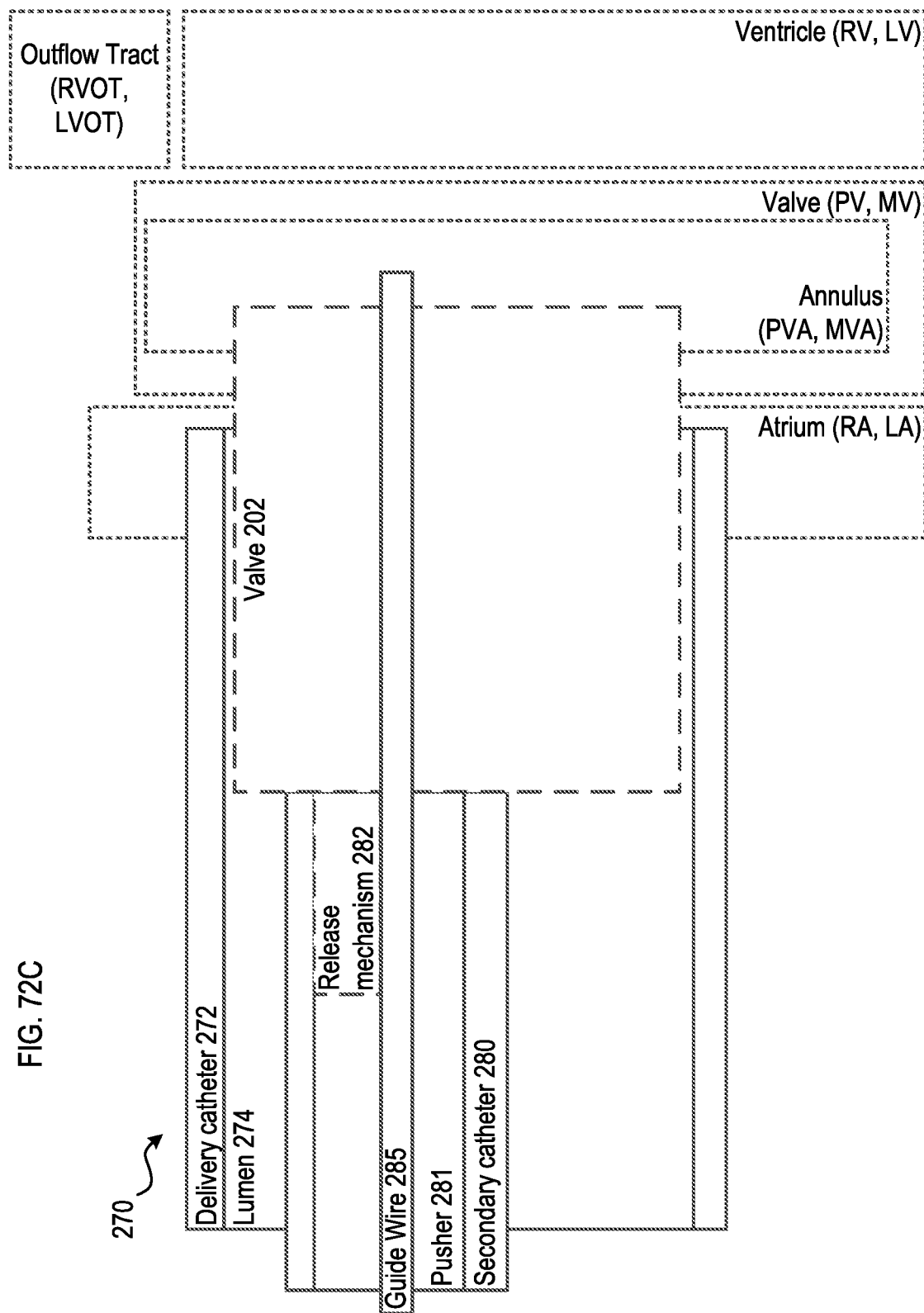

FIGS. 72A-72C are various schematic illustrations of a delivery system 270 for delivering a transcatheter prosthetic valve 202 according to an embodiment. The transcatheter prosthetic valve 202 is configured to deployed in a desired location within a body (e.g., of a human patient) and to permit blood flow in a first direction through an inflow end of the transcatheter prosthetic valve 202 and to block blood flow in a second direction, opposite the first direction, through an outflow end of the transcatheter prosthetic valve 202. For example, the transcatheter prosthetic valve 202 can be a transcatheter prosthetic heart valve configured to be deployed within the annulus of a native tricuspid valve or native mitral valve of a human heart to supplement and/or replace the functioning of the native valve.

The transcatheter prosthetic valve 202 is compressible and expandable in at least one direction perpendicular to a long-axis of the valve 202. The valve 202 is configured to compressible and expandable between an expanded configuration for implanting at a desired location in a body (e.g., a human heart) and a compressed configuration for introduction into the body via the delivery system 270.

In some embodiments, the prosthetic valve 202 can be similar to or substantially the same as the valve 102 described above with reference to FIGS. 1A-1F. For example, FIG. 72B shows that the valve 202 can include an annular support frame 210 and a flow control component 250. The annular support frame 210 can be similar to the frame 110 and can include a cuff or collar portion 220 and a tubular section (e.g., a lower tubular body portion) 212, and a guidewire collar 240. In addition, the annular support frame 210 defines an aperture 214 that extends along or in the direction of a central axis 213 of the frame 210. While not shown, the frame 210 and/or the valve 202 can also include one or more tension arms, anchoring tabs, and/or the like. The flow control component 250 can be similar to the flow control component 150 described above with reference to FIGS. 1A-1F. The valve 202 being substantially similar to the valve 102, is not described in further detail herein.

As shown in FIGS. 72A-72C, the delivery system 270 includes a delivery catheter 272, a secondary catheter 280, and a guidewire 285. The delivery system 270 can be configured to orthogonally deliver the compressed valve 202 and/or portions of the valve 202 (e.g., the compressed frame 210 or the compressed flow control component 250) to a desired location in the body such as, for example, the annulus of a native tricuspid valve and/or the annulus of a native mitral valve of the human heart. As described in detail above with reference to the valve 102, the delivery system 270 can orthogonally deliver the valve 202, which has been compressed to the compressed configuration by being compressed along the central axis 213 (FIG. 72B) or compressed in a lateral direction (e.g., orthogonal to the central axis 213 and a central lengthwise axis 275 of the delivery catheter 272). Such compression can result in elongation of the valve 202 along a longitudinal axis (not shown in FIGS. 72A-72C), which is substantially parallel to the central lengthwise axis 275 of the delivery catheter 272.

The delivery catheter 272 defines a lumen 274 that extends along or in the direction of the central lengthwise axis 275. The lumen 274 of the delivery catheter 272 can have a diameter sufficient to receive the compressed valve 202 therethrough. For example, the delivery catheter 272 can be 22-34 Fr, with any suitable corresponding internal lumen diameter and/or an internal lumen diameter sufficient to receive the prosthetic valve 202 in the compressed configuration.

The guidewire 285 extends or threads through the secondary catheter 280, the valve 202, and the delivery catheter 272. The guidewire 285 can be, for example, a sheathed guidewire at least partially sheathed by the secondary catheter 280. The guidewire 285 is configured to be advanced through the anatomy of the body and placed in a desired position relative to native tissue (e.g., a native valve). In some instances, the guidewire 285 can be advanced to provide a wire path (e.g., for the delivery catheter 272, the valve 202, etc.) to the RVOT. The guidewire 285 extends through the guidewire collar 240 of the valve 202 to provide a wire path along which the valve 202 is advanced.

The secondary catheter 280 can be a sheath, tube, annular rod or wire, and/or the like. In some embodiments, the secondary catheter 280 is a hypotube sheath disposed about a portion of the guidewire 285 (e.g., the secondary catheter 280 and the guidewire 285 collectively form a sheathed guidewire or sheathed guidewire assembly). The secondary catheter 280 can have a relatively small size allowing the secondary catheter 280 to be advanced through the delivery catheter 272 and/or at least partially disposed in or otherwise engaged with the guidewire collar 240. As shown in FIGS. 72A-72C, the secondary catheter 280 has a lumen with an internal diameter that is greater than the guidewire 285, allowing the guidewire 285 to pass therethrough.

The pusher 281 is disposed within the secondary catheter 280 and is configured to push on a portion of the valve 202 to advance the valve 202 through and/or out of the delivery catheter 272. In some implementations, the pusher 281 is configured to push against a portion of the guidewire collar 240 of the valve 202. For example, the guidewire collar 240 can allow the guidewire 285 to be advanced through the guidewire collar 240 and can block and/or substantially prevent the pusher 281 from being advanced beyond the guidewire collar 240 (or at least a portion thereof). While the pusher 281 is shown disposed in the secondary catheter 280, in some embodiments, the secondary catheter 280 can be used as the pusher 281. In such embodiments, the delivery system 270 need not include a separate pusher 281.

The guidewire collar 240 of the valve (FIG. 72B) can be any suitable element that selectively allows the guidewire 285 to be advanced therethrough while blocking or preventing the advancement of the secondary catheter 280 and/or the pusher 281 beyond the guidewire collar 240. In some embodiments, the guidewire collar 240 can be included in, formed by, and/or attached to the cuff 220 of the frame 210. In some embodiments, guidewire collar 240 can be included in, formed by, and/or attached to a tension arm such as, for example, a distal upper tension arm, a distal lower tension arm, and/or the like. In certain embodiments, the distal lower tension arm can form and/or can include a feature that forms the guidewire collar 240. It may be desirable to attach the guidewire collar 240 to the distal lower tension arm since both the guidewire 285 and the distal lower tension arm are inserted into or directed toward the RVOT.

In some embodiments, the guidewire collar 240 can be a ball or feature of a tension arm that defines an aperture or lumen that is sufficiently large to allow the guidewire 285 to pass through but is not sufficiently large to allow the secondary catheter 280 and/or the pusher 281 to be advanced therethrough. As such, the secondary catheter 280 and/or the pusher 281 can be stopped against the guidewire collar 240 by the larger circumference of the secondary catheter 280 and/or pusher 281 relative to the aperture or lumen of the guidewire collar 240. Such an arrangement allows the secondary catheter 280 and/or pusher 281 to push on the guidewire collar 240 and thus, the tension arm (e.g., the distal lower tension arm) to which it is attached. When the guidewire collar 240 is attached to a distal tension arm, the pushing on the guidewire collar 240 is operative to pull the valve 202 through and/or out of the delivery catheter 272. It is contemplated that the guidewire collar 240 can have any suitable configuration that allows the guidewire collar 240 to permit the advancement of the guidewire 285 while limiting, blocking, or preventing advancement of the secondary catheter 280 and/or the pusher 281. Moreover, the release mechanism 282 can be configured to release the guidewire 285, the secondary catheter 280 and/or the pusher 281 from the guidewire collar 240, for example, after deployment of the valve 202.

FIG. 72C shows the delivery system 270 delivering the valve 202 to a native valve such as a mitral valve or pulmonary valve (or tricuspid valve or aortic valve). The guidewire 285 is advanced to through the annulus of the native valve and disposed within the ventricle (e.g., within the RVOT). The delivery catheter 272 can be advanced over the guidewire 285 and delivered to the desired location at or near the annulus. Once the delivery catheter 272 is in the desired location, the valve 202 can be advanced over the guidewire 285 and within the delivery catheter 272 by pushing on the secondary catheter 280 and/or pusher 281. When the guidewire collar 240 is attached to a distal or anterior side of the valve 202 or frame 210, the pushing of the secondary catheter 280 and/or pusher 281 acts like a pulling force relative to, for example, the tubular section 212 of the valve frame 210 and/or the flow control component 250 of the valve 202. Moreover, the secondary catheter 280 and/or the pusher 281 can be used to eject the valve 202 from the delivery catheter 272. Once ejected from the delivery catheter 272, the valve 202 is allowed to expand to the expanded configuration and can be seated within the annulus of the native valve. In some embodiments, secondary catheter 280, the pusher 281, and/or the guidewire 285 can be released from the guidewire collar 240 to allow the secondary catheter 280, the pusher 281, and/or the guidewire 285 to be retracted and/or withdrawn. In some embodiments, the secondary catheter 280 and/or the pusher 281 can be used to push at least a proximal side of the valve 202 or valve frame 210 into the annulus, thereby completely seating and/or deploying the valve 202. Although not shown in FIGS. 72A-72C, in some embodiments the secondary catheter 280 and/or pusher 281 can be further used to deliver and/or anchor a tissue anchor to the proximal side of the valve 202 or valve frame 210. Thus, the delivery system 270 can deliver a traditionally compressed valve or orthogonally deliver vertically and/or laterally compressed valve 202.

FIG. 72D is a flowchart describing a method 300 for delivering a low profile, side-loaded prosthetic valve such as any of the valves disclosed herein, according to an embodiment. The method 300 includes disposing in an atrium of the heart, a distal portion of a delivery catheter containing a frame of a prosthetic valve in a compressed configuration, directed towards the annulus of a native valve of the heart, at 302. The valve can be any of the valves disclosed herein. For example, the valve can be similar in at least form and/or function to the valves 102 and/or 202 described above. In some embodiments, the valve can be a valve (i) where the valve has a tubular frame with a flow control component mounted within the tubular frame, (ii) where the valve or flow control component is configured to permit blood flow in a first direction through an inflow end of the valve and to block blood flow in a second direction, opposite the first direction, through an outflow end of the valve, (iii) where the valve is compressible and expandable and has a long-axis oriented at an intersecting angle of between 45-135 degrees to the first direction, and (iv) where the long-axis is parallel to a length-wise cylindrical axis of a delivery catheter used to deliver the valve.

A tension arm of the prosthetic valve frame is released from the delivery catheter, 304. The tension arm can be, for example, a distal lower tension arm of the valve frame. The arrangement of the valve within the delivery catheter can be such that the distal lower tension arm is distal to the valve body. In other words, the compressed valve is disposed within the delivery catheter such that a long-axis (a longitudinal axis) is substantially parallel to a long-axis or length-wise axis of the delivery catheter with the distal lower tension arm extending in a distal direction from the valve body. Thus, the distal lower tension arm is generally released from the delivery catheter prior to the valve body.

A distal portion of the tension arm is disposed on the ventricle side of the annulus of the native valve while the distal end of the delivery catheter remains on the atrium side of the annulus, at 306. The tension arm (e.g., the distal lower tension arm) can extend through the native annulus and at least partially disposed within the RVOT. In some instances, the tension arm can engage sub-annular tissue to at least partially secure the distal end portion of the valve to the native annular tissue while the remainder of the valve is maintained in a supra-annular position within the atrium side of the annulus.

The remainder of the prosthetic valve frame is released from the delivery catheter, at 308. As described in detail above with respect to specific embodiments, releasing the remainder of the prosthetic valve allows the prosthetic valve to expanded from the compressed configuration within the delivery catheter to the expanded configuration outside of the delivery catheter and suitable for deployment into the native annulus.

The method 300 optionally may include holding the prosthetic valve frame at an angle relative to the native valve annulus, at 310. The angle can be, for example, an oblique angle relative to the native valve annulus. In some embodiments, a delivery system or the like can include a secondary catheter or push/pull rod that can be used to (1) advance the valve through the delivery catheter and (2) temporarily hold the prosthetic valve at the angle relative to the native valve annulus. If the prosthetic valve is held at the angle, blood may be allowed to flow from the atrium to the ventricle partially through the native valve annulus around the prosthetic valve frame, and partially through the prosthetic valve, at 312. The blood flow may be used to optionally assess valve function, at 314. If the prosthetic valve does not appear to be functioning properly, the valve can be replaced without having to remove a fully deployed valve.

Dispose the tubular portion of the frame within the annulus of the native valve, at 316. For example, in some embodiments, the secondary catheter or push/pull rod can be used to push at least the proximal end portion of the valve into the native annulus. In some implementations, one or more walls of the valve and/or one or more proximal or distal tension arms can be used to seat the prosthetic valve within the native annulus. For example, the tension arms can exert opposing forces that can at least partially secure the prosthetic valve to the annular tissue. In some embodiments, the tension arms and/or any other portion of the frame can form a rotational or pressure lock against the annular tissue. With the tubular portion of the frame within the annulus of the native valve, the prosthetic valve can be fully deployed.

The method 300 optionally may include anchoring the proximal portion of the frame of the prosthetic valve to tissue surrounding the native valve, at 318. For example, the proximal portion of the frame can be anchored using any of the tissue anchors and/or anchoring methods described herein. In some implementations, the proximal portion of the frame can be anchored using a tissue anchor that engages a portion of the frame and inserted into the tissue surrounding the native valve.

The method 300 optionally may include delivering to an aperture of the prosthetic valve frame a flow control apparatus, at 320. For example, as described above with reference to the valve 102 shown in FIGS. 1A-1F, the valve can be deployed in the annulus of a native valve as a single integrated component—the valve including a valve frame and a flow control component disposed in the aperture of the valve frame. In other embodiments, however, the valve can be deployed in the annulus of a native valve in two or more independent or separate processes. In some instances, delivering the valve in two or more parts can allow the separately delivered components to be compressed into a smaller or tighter compressed configuration. In some such instances, the valve frame can be compressed and delivered to the annulus of the native valve as described in the method 300 above. After fully seating or deploying the valve frame in the annulus of the native valve, the flow control component can be compressed and delivered to the valve frame. The flow control component can be a self-expanding valve component or can be balloon-expanded once placed in a desired position within the valve frame.

Provided below is a discussion of certain aspects or embodiments of transcatheter prosthetic valves, delivery systems, and/or delivery methods. The transcatheter prosthetic valves (or aspects or portions thereof), the delivery systems, and/or the delivery methods described below with respect to specific embodiments can be substantially similar in at least form and/or function to the valve 202 and/or corresponding aspects of the valve 202, the delivery system 270, and/or the delivery method 300 described above with reference to FIGS. 72A-72D. Thus, certain aspects of the specific embodiments are not described in further detail herein.

Figure 73A:
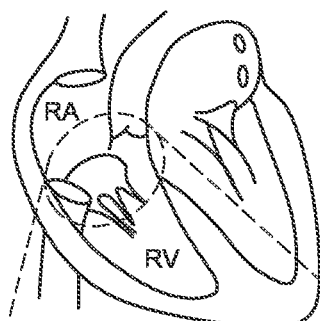
FIG. 73A is an illustration of the human heart anatomy and FIG. 73B is an enlarged illustration of a portion of the human heart anatomy of FIG. 73A.
Figure 73B:
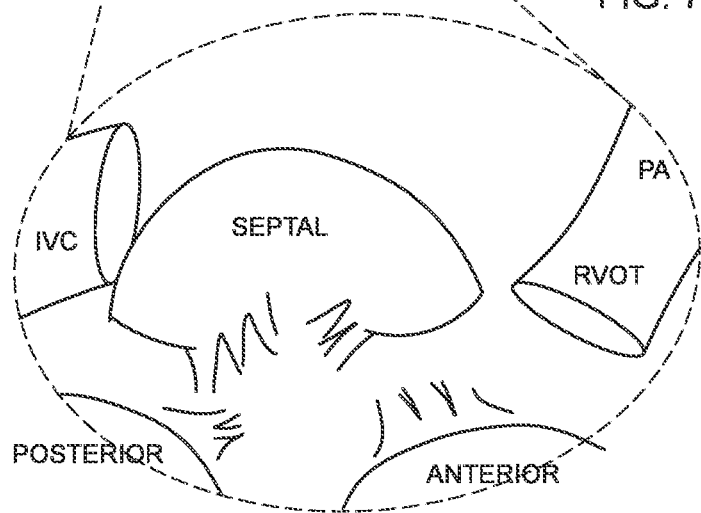

FIG. 73A is an illustration of a side view of human heart anatomy, and FIG. 73B is an enlarged illustration of a portion of the human heart anatomy of FIG. 73A showing the geometric relationship between the inferior vena cava (IVC), the three leaflet cusps of the tricuspid valve—anterior, posterior, septal—the RVOT, and the pulmonary artery (PA).

Figure 74:
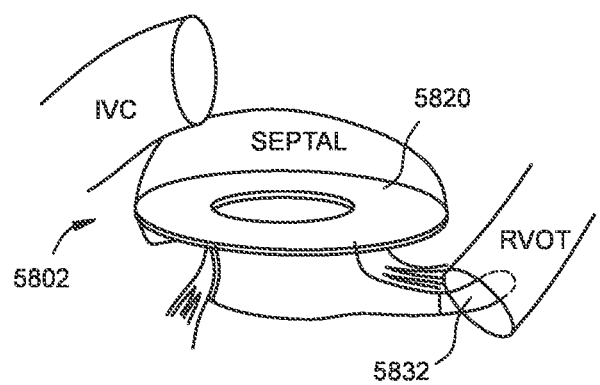
FIG. 74 is an illustration of a transcatheter prosthetic valve deployed within a native annulus of the human heart of FIGS. 73A and 73B according to an embodiment.

FIG. 74 is an illustration of a side perspective view of a side delivered valve 5802 seated with the native tricuspid annulus with collar portion 5820 of the valve 5802 (or valve frame) laying atrially above the tricuspid annulus and leaflets, lower body portion extending into and through the annulus to provide corrective hemodynamic flow from the flow control component. FIG. 74 also shows a RVOT footer tab or a distal lower tension arm 5832 disposed in the RVOT.

Figure 75A:
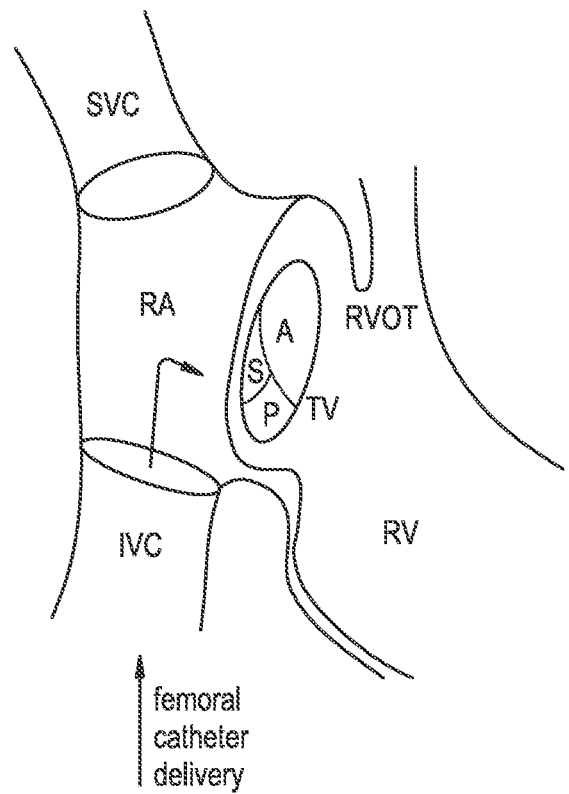
FIGS. 75A-75D, 76A-76C, 77A-77D, and 78A-78D illustrate a process of deploying a transcatheter prosthetic valve in a native annulus of the human heart each according to a different embodiment.

FIG. 75A is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet (S), the right ventricle (RV), and the right ventricular outflow tract (RVOT).

Figure 75B:
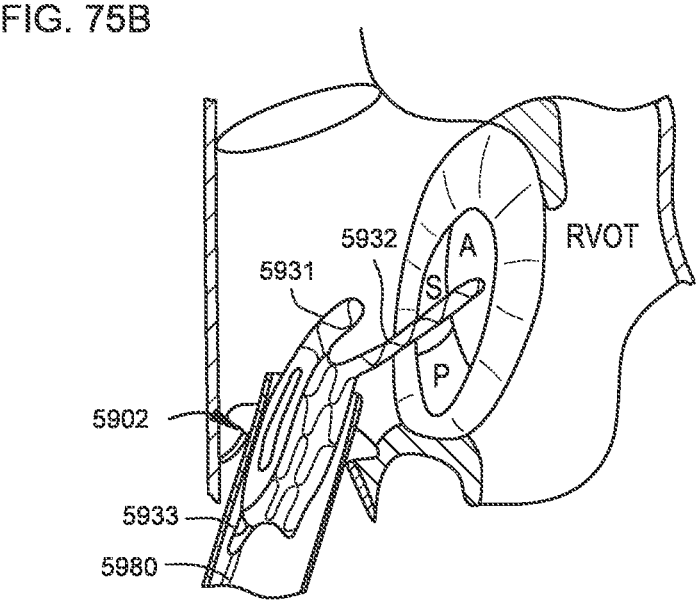

FIG. 75B is an illustration of a prosthetic valve 5902 according to an embodiment being delivered to the tricuspid valve annulus. FIG. 75B shows the valve 5902 having a braided/laser cut-frame 5910 with a distal lower tension arm 5932 that is being ejected from a delivery catheter 5972 and directed through the annulus and towards the right ventricular outflow tract.

Figure 75C:
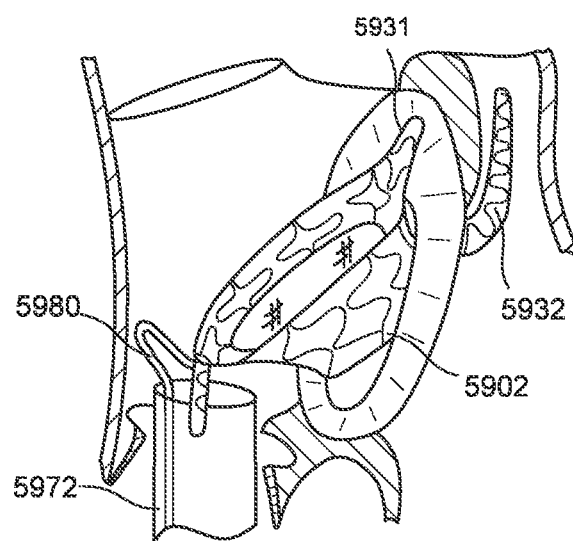

FIG. 75C is an illustration of the valve 5902 showing the braided/laser cut-frame 5910 with the distal lower tension arm 5932 and the distal upper tension arm 5931 ejected from the delivery catheter 5972 via a secondary catheter and/or pusher 5980, the distal lower tension arm 5932 being directed through the annulus and into the RVOT, and the distal upper tension arm 5931 staying in a supra-annular position, and causing a passive, structural anchoring of the distal side of the valve 5902 about the annulus.

Figure 75D:
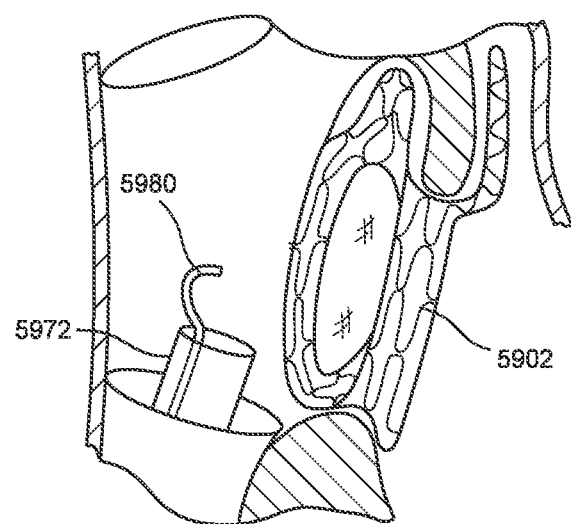

FIG. 75D is an illustration of the valve 5902 showing the entire braided/laser cut-frame 5910 ejected from the delivery catheter 5972, the distal lower tension arm 5932 being directed through the annulus and into the RVOT, the distal upper tension arm 5931 staying in a supra-annular position, and causing a passive, structural anchoring of the distal side of the valve about the annulus, and at least one tissue anchor (not shown) anchoring the proximal side of the prosthesis into the annulus tissue.

Figure 76A:
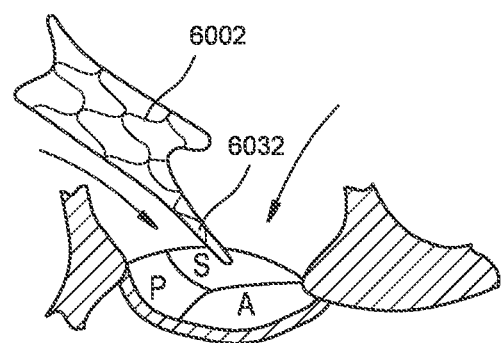

FIG. 76A is an illustration of a prosthetic valve 6002 according to an embodiment being delivered to tricuspid valve annulus. FIG. 76A shows a distal lower tension arm 6032 of the valve 6002 ejected from a delivery catheter and being directed through the annulus and towards the RVOT. In this example, delivery of the valve 6002 can include a valve assessment process.

Figure 76B:
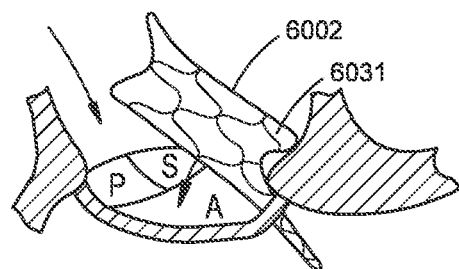

FIG. 76B shows distal lower tension arm 6032 and a distal upper tension arm 6031 ejected from the delivery catheter, the distal lower tension arm 6032 is directed through the annulus and into the RVOT, and the distal upper tension arm 6031 stays in a supra-annular position, and causing a passive, structural anchoring of the distal side of the valve 6002 about the annulus. FIG. 76B shows that the valve 6002 can be held (e.g., by a secondary catheter (not shown)) at an oblique angle in a pre-attachment position, so that the valve can be assessed, and once valve function and patient conditions are correct, the secondary catheter can push the proximal side of the valve 6002 from its oblique angle, down into the annulus. By allowing two pathways for blood flow, the first through the native valve near the posterior leaflet, and the second through the central aperture of the prosthetic valve 6002, a practitioner can determine if the heart is decompensating or if valve function is less than optimal. The secondary catheter can then install one or more anchoring elements or otherwise secure the valve 6002 in the native valve.

Figure 76C:
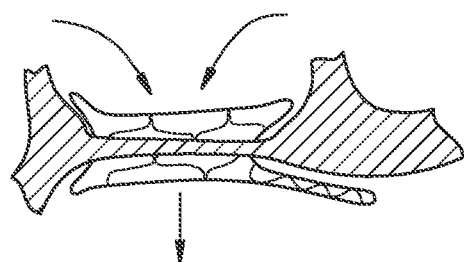

FIG. 76C is an illustration of the valve 6002 showing the entire braided/laser cut-frame valve 6002 ejected from the delivery catheter, the distal lower tension arm 6032 is directed through the annulus and into the RVOT, the distal upper tension arm 6031 stays in a supra-annular position, and causes a passive, structural anchoring of the distal side of the valve 6002 about the annulus, and optionally at least one tissue anchor (not shown) anchoring the proximal side of the valve 6002 into the annulus tissue.

Figure 77A:
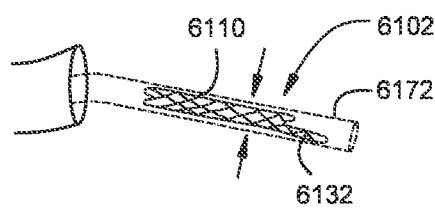

FIG. 77A is an illustration of a side perspective view of a valve 6102 that is vertically compressed without folding into a compressed configuration and loaded into a delivery catheter 6172. By using horizontal rather than traditional vertical diamond shaped cells, a frame 6110 of the valve 6102 can be compressed from top to bottom. This allows for orthogonal delivery of a much larger diameter valve than can be delivered using traditional axial compression. Additionally, the orthogonal delivery provides access from the IVC to the tricuspid annulus using a subannular distal-side anchoring tab or distal lower tensioning arm 6132. Normally, a delivery catheter would need to make a 90-120 degree right turn before expelling a traditional transcatheter axially compressed valve. In contrast, the vertically compressed valve 6102 (e.g., compressed in the direction of a central aperture or the direction of blood flow through the valve 6102) can be directly expelled into the distal side of the tricuspid annulus.

Figure 77B:
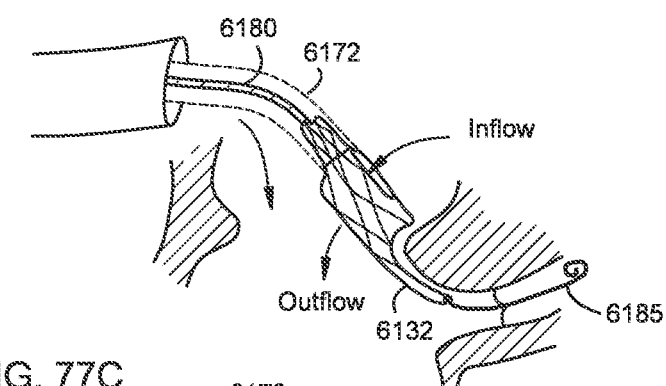

FIG. 77B is an illustration of a side perspective view of the valve 6102 being partially expelled or released from the delivery catheter 6172 that allows a transition from native blood flow through the native tricuspid valve and a partial flow around the prosthetic valve 6102 and into the native annulus to a partial flow through an inflow end (indicated in FIG. 77B by the arrow labeled "Inflow") and out of an outflow end (indicated in FIG. 77B by the arrow labeled "Outflow") of the prosthetic valve 6102 into the native annulus. A guide wire 6185 is shown pig-tailed into the pulmonary artery of the heart. A rigid pull rod/wire, pusher, and/or secondary catheter 6180 in some embodiments is engineered to ride over the guide wire 6185, thus allowing the valve 6102 to be delivered exactly where intended. The distal subannular tab or distal lower tension arm 6132 is directed into the RVOT and is configured to provide anchoring for the valve 6102 while it is positioned and assessed.

Figure 77C:
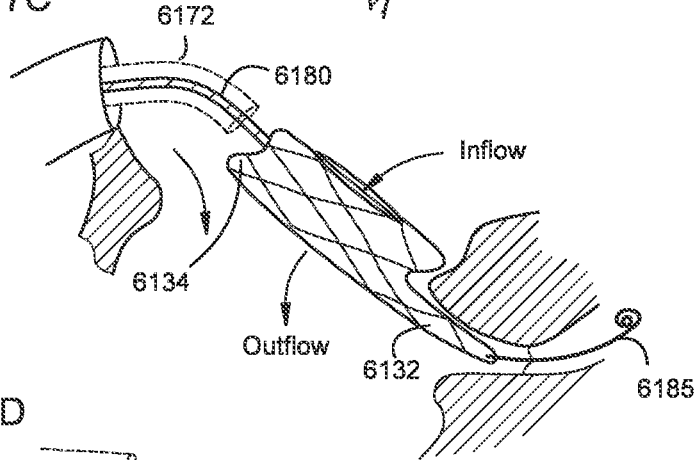

FIG. 77C is an illustration of a side perspective view of the valve 6102 being fully expelled or released from the delivery catheter 6172 into an expanded configuration. The valve 6102 is lodged using the distal tab or distal lower tension arm 6132 against the distal surface of the annulus and held using the rigid pull rod/wire or pusher 6180 at an elevated angle above the native annulus prior to complete deployment of the valve 6102. This allows a further transition from native blood flow through the native tricuspid valve with a partial flow around the prosthetic valve 6102 and into the native annulus, and an increasing partial flow through the inflow end and out of the outflow end of the prosthetic valve 6102 into the native annulus. FIG. 77C also shows the guide wire 6185 pig-tailed into the pulmonary artery of the heart (through the LVOT). FIG. 77C further shows a proximal subannular anchoring tab or proximal lower tension arm (proximal tab) 6134, which can facilitate the mounting or anchoring for the valve 6102 once entirely deployed in the native annulus.

Figure 77D:
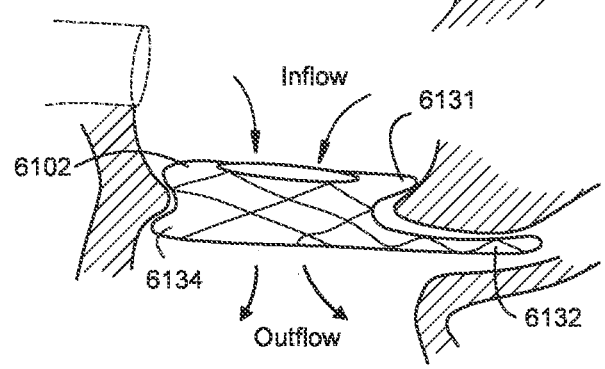

FIG. 77D is an illustration of a side perspective view of the valve 6102 being fully expelled or released from the delivery catheter 6172 and completely seated into the native annulus. The delivery of the valve 6102 just described allows a smooth transition from native blood flow to a full, complete flow through the prosthetic valve 6102 and thus, the native annulus. The valve 6102 is anchored using subannular distal tab (distal lower tension arm) 6132, the subannular proximal tab (proximal lower tension arm) 6134, and a supra-annular (atrial) upper tension arm (distal upper tension arm) 6131. Corrected replacement flow using the valve 6102 is shown by Inflow through the inflow end and Outflow through the outflow end of the prosthetic valve 6102 and thus, the native annulus.

Figure 78A:
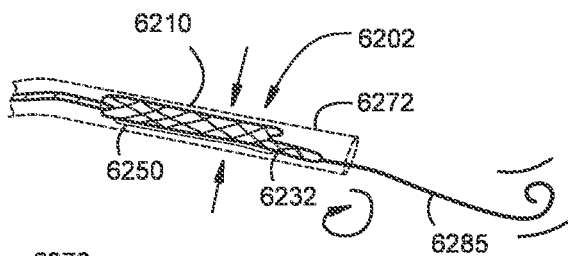

FIG. 78A is an illustration of a side perspective view of a valve 6202 that is vertically compressed without folding, into a compressed configuration and loaded into a delivery catheter 6272 and shows a flow control component 6250 in a rolled configuration. A guide wire 6285 and an RVOT tab or distal lower tension arm 6232 are shown extended into the pulmonary artery and allowing the valve 6202 to be precisely delivered.

Figure 78B:
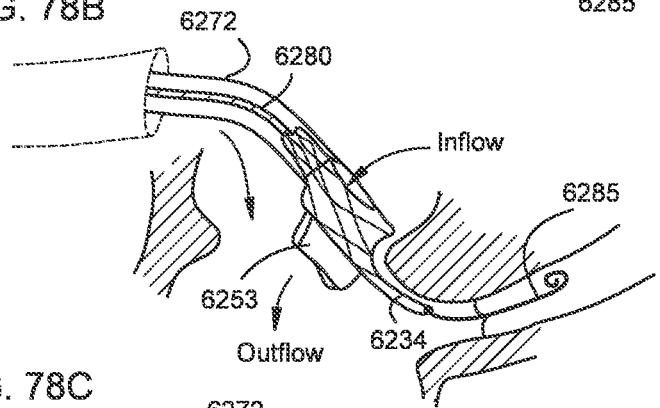

FIG. 78B is an illustration of a side perspective view of the valve 6202 being partially expelled or released from the delivery catheter 6272, with inner leaflets 6253 of the flow control component 6250 partially unfurled and extended. FIG. 78B shows a transition from native blood flow through the native tricuspid valve to a partial flow around the prosthetic valve 6202 and into the native annulus to a partial flow through an inflow end (indicated in FIG. 78B by the arrow labeled "Inflow") and out of an outflow end (indicated in FIG. 78B by the arrow labeled "Outflow") of the prosthetic valve 6202 into the native annulus. A rigid pull rod/wire, pusher, and/or secondary catheter 6280 in some embodiments is engineered to ride over the guide wire 6285. The RVOT tab or distal lower tension arm 6232 is directed into the RVOT and is configured to provide anchoring for the valve 6202 while it is positioned and assessed. The valve 6202 has a distal mid-wall arch above the RVOT tab or distal lower tension arm 6232 for engaging the native annulus.

Figure 78C:
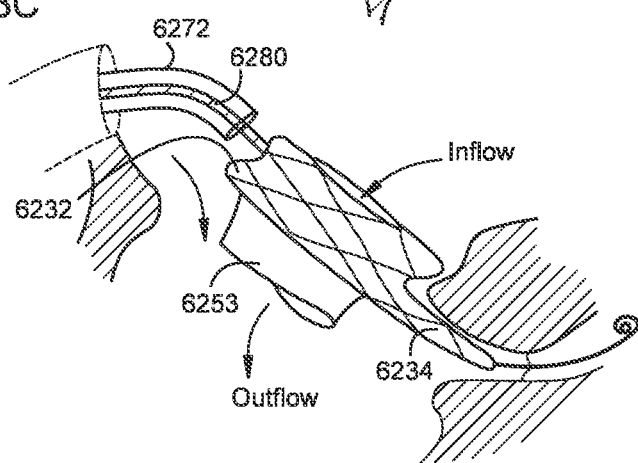

FIG. 78C is an illustration of a side perspective view of the valve 6202 being fully expelled or released from the delivery catheter 6272 into an expanded configuration, with the inner leaflets 6253 of the flow control component 6250 a fully unfurled and extended. The valve 6202 is lodged using the distal tab or distal lower tension arm 6232 against the distal surface of the annulus and held elevated using the rigid puller/pusher or secondary catheter 6280 at an angle above the native annulus prior to complete deployment. This allows a further transition from native blood flow through the native tricuspid valve with a partial flow around the prosthetic valve 6202 and into the native annulus, and an increasing partial flow through the inflow end and out of the outflow end of the prosthetic valve 6202 into or through the native annulus. FIG. 78C shows the distal mid-wall arch engaging the distal native annulus and shows a proximal mid-wall arch raised above the native annulus in preparation for a smooth transition to prosthetic flow when the valve 6202 is fully seated in the native annulus.

Figure 78D:
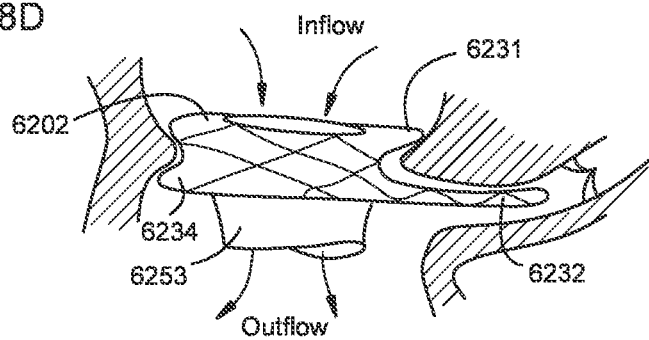

FIG. 78D is an illustration of a side perspective view of the valve 6202 being fully expelled or released from the delivery catheter 6272 and completely seated into the native annulus. The delivery of the valve 6202 just described allows a smooth transition from native blood flow to a full, complete flow through the prosthetic valve 6202 and thus, the native annulus. The valve 6202 is anchored using subannular distal tab or distal lower tension arm 6232, a subannular proximal tab or proximal lower tension arm 6234, and a supra-annular (atrial) tab or distal upper tension arm 6231. Corrected replacement flow through unfurled and extended leaflets 6253 is shown by Inflow through the inflow end and Outflow through the outflow end of the prosthetic valve 6202 and thus, the native annulus.

Figure 79A:
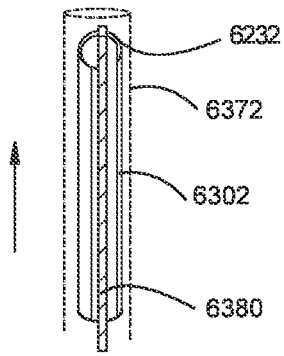
FIGS. 79A-79E illustrate a transcatheter prosthetic valve being transitioned from a compressed configuration (FIG. 79A) to an expanded configuration (FIGS. 79D and 79E) according to an embodiment.

FIG. 79A is an illustration of a side view of a valve 6302 in a compressed configuration within a delivery catheter 6372 according to an embodiment. FIG. 79A shows how a central tube/wire or secondary catheter 6380 can be distally attached to a distal edge, RVOT tab, or distal lower tension arm 6332 and by pushing on the rigid tube/wire or secondary catheter 6332, the compressed valve 6202 can be pulled from the proximal end of the catheter 6372 to the distal deployment end of the delivery catheter 6372. This pulling action avoids pushing the valve 6302 out of the delivery catheter 6302, which may cause additional radial expansion and radial forces that can damage the valve 6302 when it is compressed within the delivery catheter 6372.

Figure 79B:
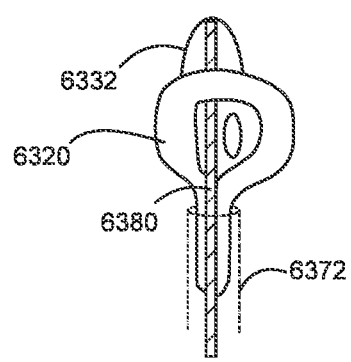

FIG. 79B is an illustration of a side view of the valve 6302 being partially compressed and partially released from the delivery catheter 6372 and shows how blood flow can begin to transition. The gradual, smooth transition from native flow to flow through the prosthetic valve 6302 by pulling on the valve 6302 using the rigid pusher or secondary catheter 6380 attached to the distal subannular anchoring tab or distal lower tension arm 6332 avoids the sphincter effect where the heart is cut off from the flow, resulting in a dry pump action, which can cause heart failure. When the valve 6302 is partially open (partially released) exposing only a part of a collar portion 6320 of a frame of the valve 6302 on a small fraction of right atrial blood flow going through the prosthetic valve 6302, the washing effect provides for a smooth transition to a larger volume going through the valve 6302.

Figure 79C:
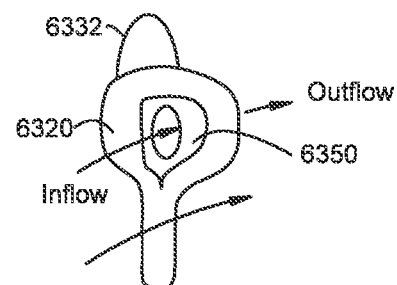

FIG. 79C is an illustration of a side view of the valve 6302 being partially compressed and partially released from the delivery catheter 6372 and shows how blood flow can begin its transition. The gradual, smooth transition from native flow to flow into the valve 6302 through an inflow end (indicated in FIG. 79C by the arrow labeled "Inflow") and out of an outflow end (indicated in FIG. 79C by the arrow labeled "Outflow") of the prosthetic valve 6302 by pulling from the distal subannular anchoring tab or distal lower tension arm 6332 avoids the sphincter effect where the heart is cut off from the flow, resulting in a dry pump action, and causing heart failure. When the valve is partially open exposing only a part of the collar portion 6320 on a small fraction of right atrial blood flow initially going through the prosthetic valve 6302, with an increasing amount transitioning from flow around the valve 6302 to flow going through the valve 6302, the washing effect provides for a smooth transition to a larger volume going through the valve 6302.

Figure 79D:
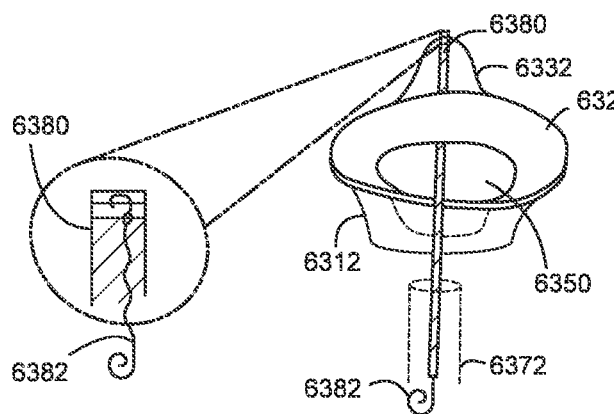

FIG. 79D is an illustration of a side view of valve 6302 being fully expanded or uncompressed into the expanded configuration and orthogonally released from the delivery catheter 6372, and still releasably attached to the distal pull wire/deployment control wire or hypotube (secondary catheter) 6380 via the distal tab/RVOT tab or distal lower tension arm 6332. The collar portion 6320 and lower body portion 6312 of the frame are fully expanded, permitting functioning of the flow control component 6350. FIG. 79D shows that the valve can be positioned or re-positioned by using the rigid pull wire 310. Since the blood flow is not blocked, an interventionist is allowed the opportunity and time to ensure correct orientation of the valve 6302, especially where the distal tab (mitral)/RVOT tab (tricuspid) or distal lower tension arm 6332 is used to assist in anchoring. Once proper orientation is achieved, the valve 6302 can be slowly seated into the native tricuspid annulus, providing a smooth blood flow transition from the native flow to the prosthetic flow. FIG. 79D also shows a release mechanism 6382 for releasing the rigid pull device or secondary catheter 6380 from the valve body or distal lower tension arm 6332 by pulling on a trigger wire that is attached to a release hook, lock, bead, or other release mechanism.

Figure 79E:
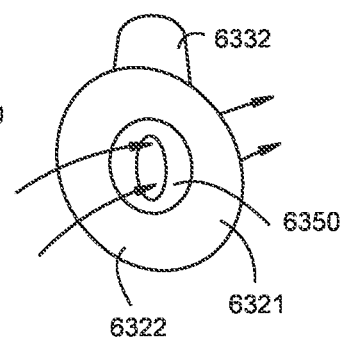

FIG. 79E is an illustration of a side view of the valve 6302 being fully expanded or uncompressed showing transition to all blood flow through the flow control component 6350 of the valve 6302 and no flow around the valve 6302 during or resulting from atrial sealing of an anterior collar portion 6321 and a posterior-septal collar portion 6322 against the atrial floor.

Figure 80A:
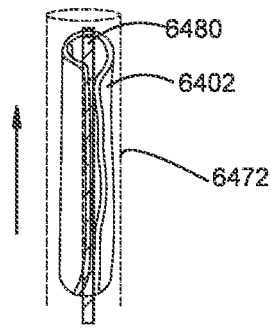
FIGS. 80A-80D illustrate a transcatheter prosthetic valve being transitioned from a compressed configuration (FIG. 80A) to an expanded configuration (FIG. 80D) according to an embodiment.

FIG. 80A is an illustration of a side view of a valve 6402 being rolled into a compressed configuration within a delivery catheter 6472 and being advanced by a distal rigid pull wire/draw-wire or secondary catheter 6480 (or far-side push-pull wire) attached to a leading edge of a collar 6420 of a valve frame 6410.

Figure 80B:
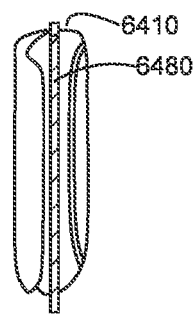

FIG. 80B is an illustration of a side view of valve 6402 being partially unrolled and deployed from the delivery catheter 6472 by action of the pushing rod or secondary catheter 6480 on the distal upper edge of the collar 6420.

Figure 80C:
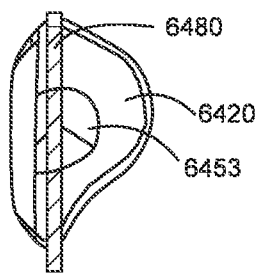

FIG. 80C is an illustration of a side view of the valve 6402 being partially unrolled and deployed from the delivery catheter 6472, and shows the pushing rod or secondary catheter 6480 maintaining connection to the valve 6401 while an anterior collar portion 6421 is unrolled and leaflets 6453 of a flow control component are uncovered.

Figure 80D:
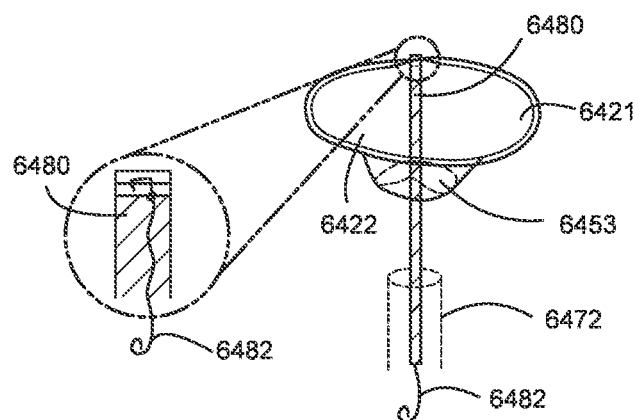

FIG. 80D is an illustration of a side view of valve 6402 being completely released and unrolled into the expanded configuration where the rigid pull device or secondary catheter 6480 is used to position the valve 6402 within the native annulus and obtain a good perivalvular seal via the anterior collar portion 6421 and a posterior-septal collar portion 6422 to transition to blood flow through the leaflets 6453. FIG. 80D also shows the release mechanism 6482 for releasing the rigid pull device or secondary catheter 6480 from the valve body or collar 6420 by pulling on a trigger wire that is attached to a release hook, lock, bead, or other release mechanism.

Figure 80E:
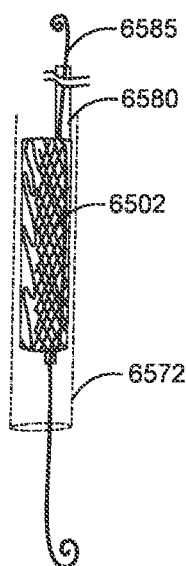
FIG. 80E is an illustration of a side view of a transcatheter prosthetic valve in a compressed configuration within a delivery catheter, and showing a secondary catheter configured to move the valve through the delivery catheter according to an embodiment.

FIG. 80E is an illustration of a side view of a valve 6502 according to an embodiment. FIG. 80E shows that the valve 6502 can have a combination wire cell frame construction as described above with reference to FIG. 34A and can be compressed into a compressed configuration within a delivery catheter 6572, and shows that a draw/pulling wire or secondary catheter 6580 can be attached to a forward end of the compressed valve 6502 and can be pushed to pull the valve 6502 through and/or out of the delivery catheter 6572. FIG. 80E also shows the valve 6502 and the draw/pulling wire or secondary catheter 6580 being positioned over a guidewire 6585.

Figure 81A:
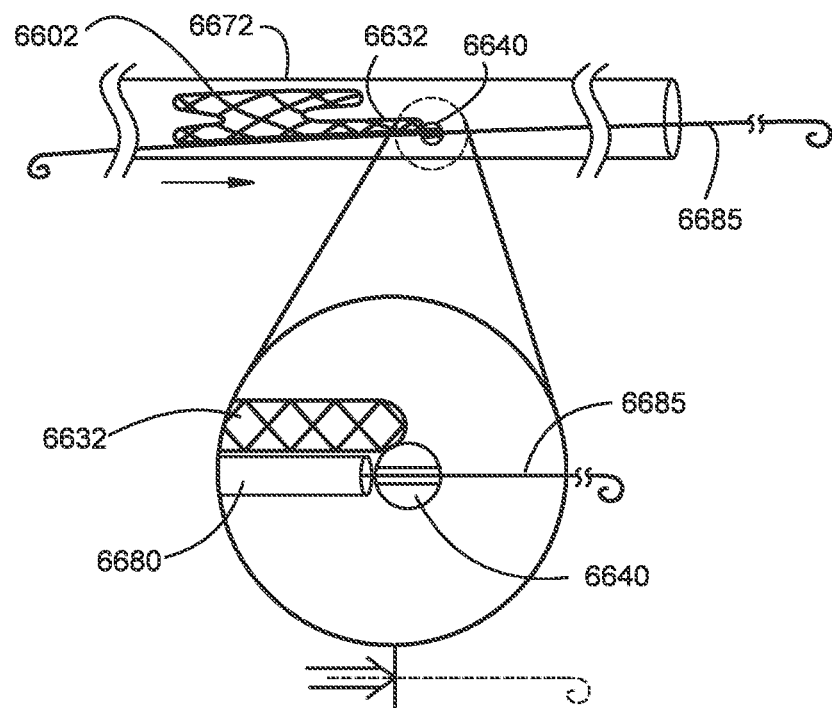
FIGS. 81A-81D are side views of a portion of a secondary catheter including a guidewire collar each according to a different embodiment.

FIG. 81A is an illustration of a side or plan transparent view of a delivery catheter 6672 loaded with a side-delivered (orthogonal) valve 6602 in a compressed configuration. The valve 6602 has a frame with a tension arm (e.g., a distal lower tension arm) 6632, a guidewire collar element 6640 attached to the tension arm 6632, and a guidewire 6685 extending through the guidewire collar element 6640 with a guidewire sheath or secondary catheter 6680 pushing against the guidewire collar element 6640. The enlarged inset shows a non-limiting example of the guidewire collar element 6640 attached to the tension arm 6632 with the guidewire 6685 extending through an aperture defined by the guidewire collar element 6640 and the hypotube sheath or secondary catheter 6680 stopped against the guidewire collar element 6640 by the larger circumference of the guidewire collar element 6640, permitting pushing on the tension arm (e.g., the distal lower tension arm) 6632 to pull the valve 6602 through and/or out of the delivery catheter 6672.

Figure 81B:
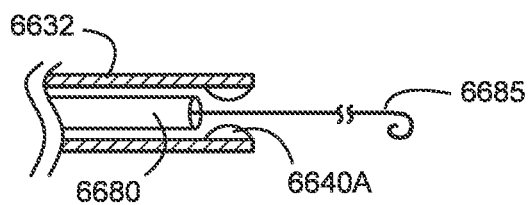

FIG. 81B is another non-limiting example of a guidewire collar element 6640A attached to the tension arm 6632 with the guidewire 6685 extending through the aperture of the guidewire collar element 6640A and the hypotube sheath or secondary catheter 6680 stopped by the larger circumference of the hypotube sheath or secondary catheter 6680 relative to the aperture defined by the guidewire collar element 6640A, permitting pushing on the tension arm (e.g., the distal lower tension arm) 6632 to pull the valve 6602 out of the delivery catheter 6672. FIG. 81B shows the tension arm 6632 being substantially hollow or annular, defining a lumen that extends therethrough. The guidewire collar element 6640A is shown as a structure (e.g., a rounded structure) that constricts the lumen that extends through the tension arm 6632, the hypotube sheath or secondary catheter 6680 having a circumference that is larger than the constriction permitting pushing on the tension arm (e.g., the distal lower tension arm) 6632 to pull the valve 6602 through and/or out of the delivery catheter 6672.

Figure 81C:
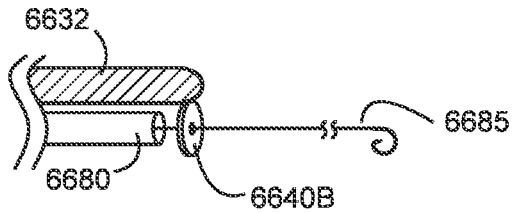

FIG. 81C is another non-limiting example of a guidewire collar element 6640B attached to the tension arm 6632 with the guidewire 6685 extending through the aperture of the guidewire collar element 6640B and the hypotube sheath or secondary catheter 6680 stopped by the guidewire collar element 6640B as it slides over the guidewire 6685—the guidewire is in the lumen of the hypotube sheath or secondary catheter 6680—by the larger circumference of the hypotube sheath or secondary catheter 6680 relative to the aperture defined by the guidewire collar element 6640B, permitting pushing on the tension arm (e.g., the distal lower tension arm) 6632 to pull the valve 6602 through and/or out of the delivery catheter 6672.

Figure 81D:
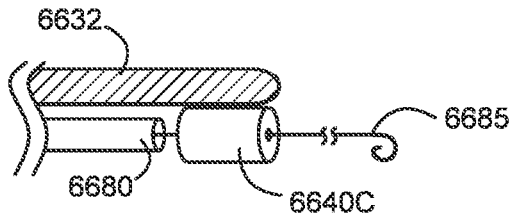

FIG. 81D is another non-limiting example of a guidewire collar element 6640C attached to the tension arm 6632 with the guidewire 6685 extending through the aperture of the guidewire collar element 6640C and the hypotube sheath or secondary catheter 6680 stopped by the larger circumference of the hypotube sheath or secondary catheter 6680 relative to the guidewire collar element 6640C, permitting pushing on the tension arm (e.g., the distal lower tension arm) 6632 to pull the valve 6602 through and/or out of the delivery catheter 6672.

Figure 82A:
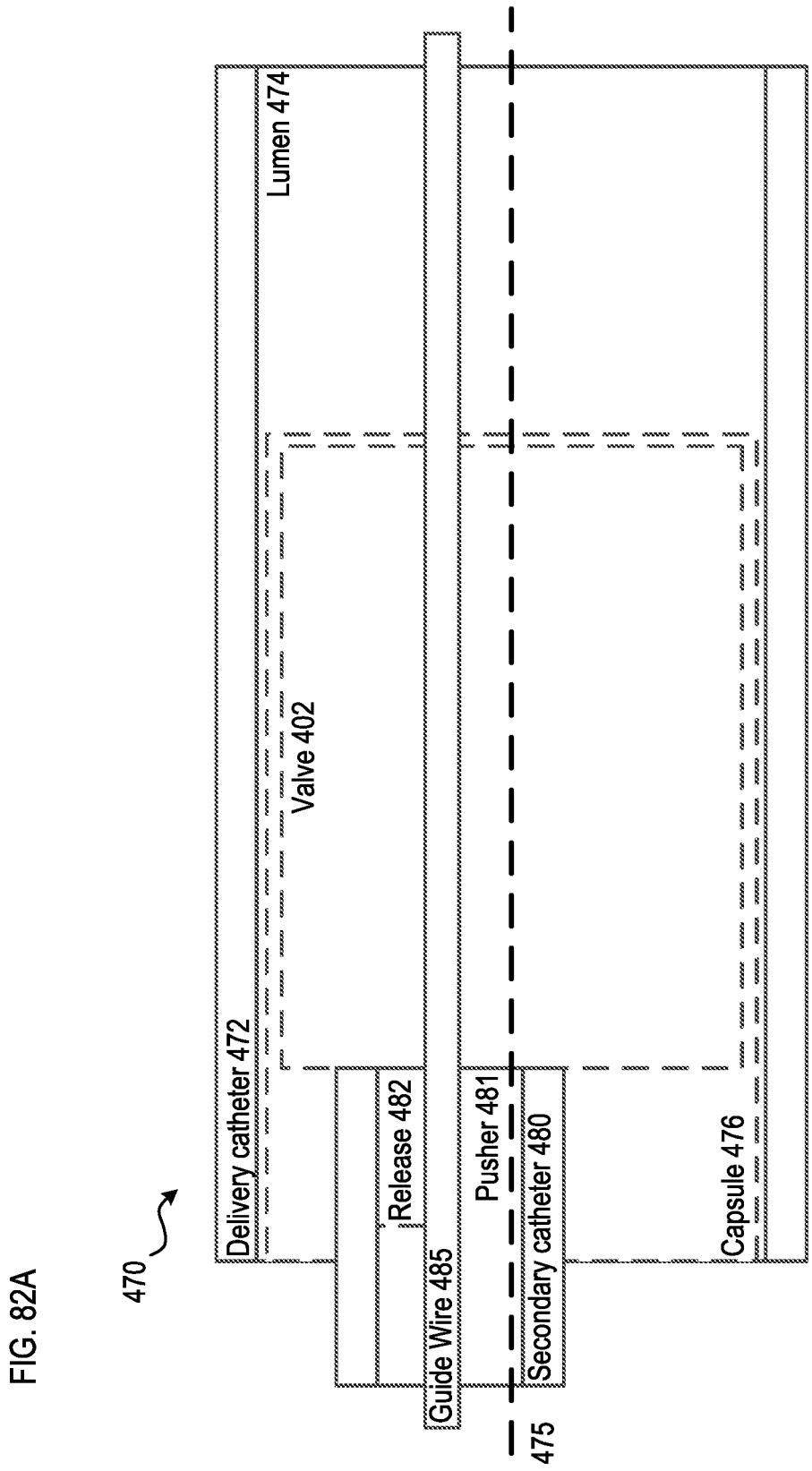
FIGS. 82A-82C are schematic illustrations of a delivery system for delivering a transcatheter prosthetic valve according to an embodiment.
Figure 82B:
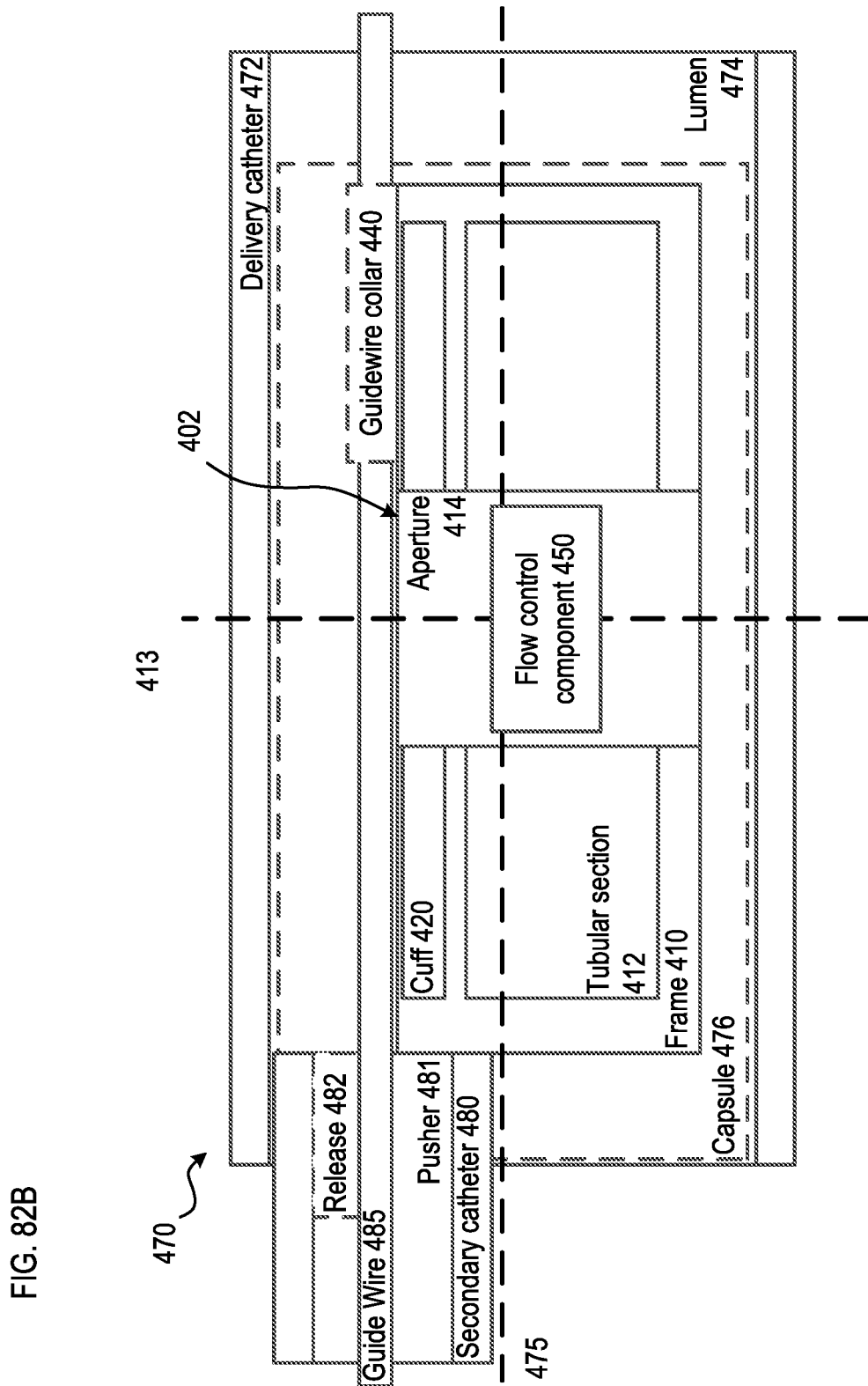
Figure 82C:
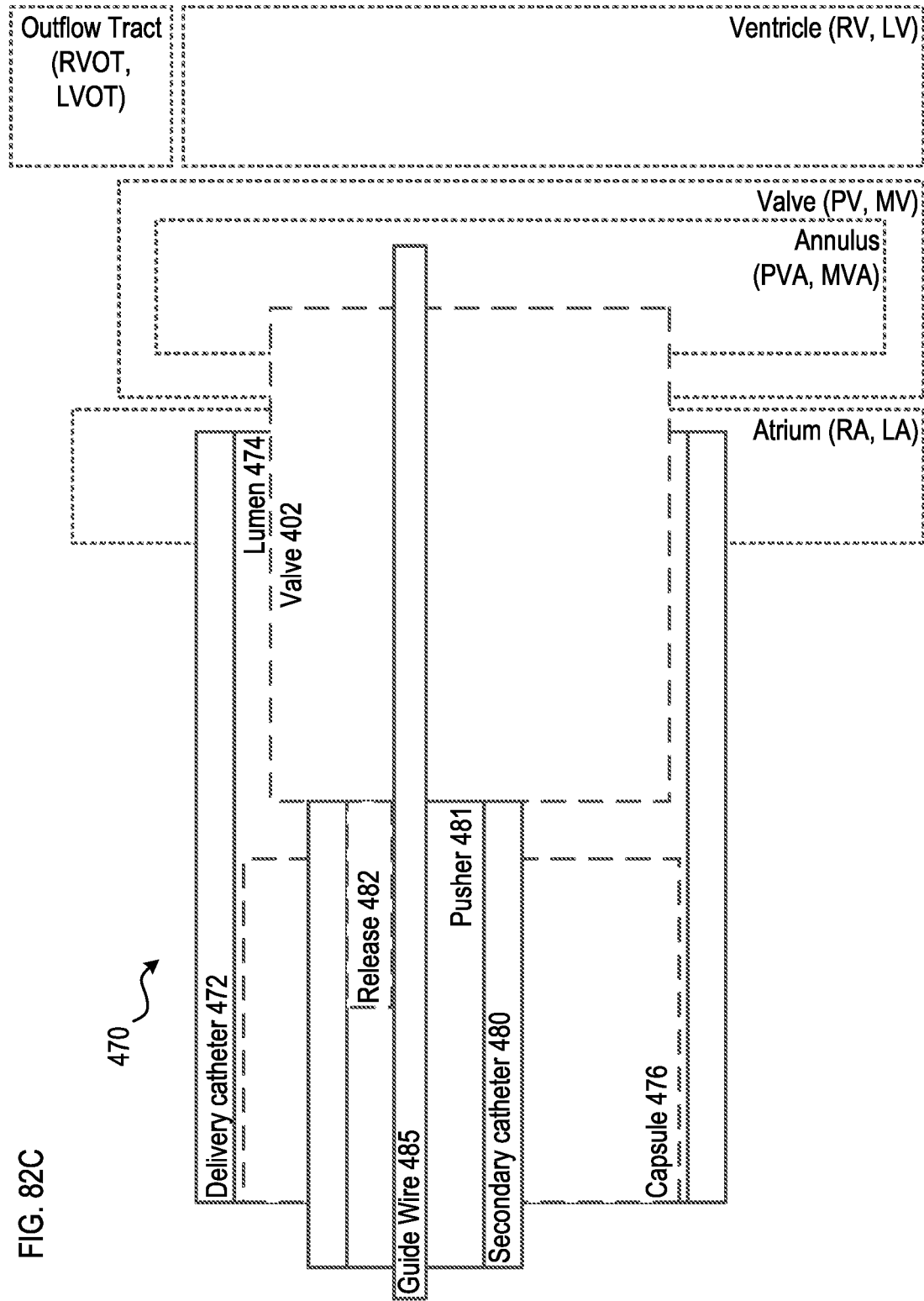

FIGS. 82A-82C are various schematic illustrations of a delivery system 470 for delivering a transcatheter prosthetic valve 402 according to an embodiment. The transcatheter prosthetic valve 402 is configured to deployed in a desired location within a body (e.g., of a human patient) and to permit blood flow in a first direction through an inflow end of the transcatheter prosthetic valve 402 and to block blood flow in a second direction, opposite the first direction, through an outflow end of the transcatheter prosthetic valve 402. For example, the transcatheter prosthetic valve 402 can be a transcatheter prosthetic heart valve configured to be deployed within the annulus of a native tricuspid valve or native mitral valve of a human heart to supplement and/or replace the functioning of the native valve.

The transcatheter prosthetic valve 402 is compressible and expandable in at least one direction perpendicular to a long-axis of the valve 402. The valve 402 is configured to compressible and expandable between an expanded configuration for implanting at a desired location in a body (e.g., a human heart) and a compressed configuration for introduction into the body via the delivery system 470.

In some embodiments, the prosthetic valve 402 can be similar to or substantially the same as the valve 102 described above with reference to FIGS. 1A-1F. For example, FIG. 82B shows that the valve 402 can include an annular support frame 410 and a flow control component 450. The annular support frame 410 can be similar to the frame 110 and can include a cuff or collar portion 420 and a tubular section (e.g., a lower tubular body portion) 412, and a guidewire collar 440. In addition, the annular support frame 410 (referred to herein as "frame") defines an aperture 414 that extends along or in the direction of a central axis 413 of the frame 410. While not shown, the frame 410 and/or the valve 402 can also include one or more tension arms, anchoring tabs, and/or the like. The flow control component 450 can be similar to the flow control component 150 described above with reference to FIGS. 1A-1F. The valve 402 being substantially similar to the valve 102, is not described in further detail herein.

As shown in FIGS. 82A-82C, the delivery system 470 includes a delivery catheter 472, a capsule 476, a secondary catheter 480, and a guidewire 485. The delivery system 470 can be configured to orthogonally deliver the compressed valve 402 and/or portions of the valve 402 (e.g., the compressed frame 410 or the compressed flow control component 450) to a desired location in the body such as, for example, the annulus of a native tricuspid valve and/or the annulus of a native mitral valve of the human heart. As described in detail above with reference to the valve 102, the delivery system 470 can orthogonally deliver the valve 402, which has been compressed to the compressed configuration by being compressed along the central axis 413 (FIG. 82B) or compressed in a lateral direction (e.g., orthogonal to the central axis 413 and a central lengthwise axis 475 of the delivery catheter 472). Such compression can result in elongation of the valve 402 along a longitudinal axis (not shown in FIGS. 82A-82C), which is substantially parallel to the central lengthwise axis 475 of the delivery catheter 472.

The delivery catheter 472 defines a lumen 474 that extends along or in the direction of the central lengthwise axis 475. The lumen 474 of the delivery catheter 472 can have a diameter sufficient to receive the compressed valve 402 therethrough. For example, the delivery catheter 472 can be 22-34 Fr.

The capsule 476 is configured to facilitate placement into the delivery catheter 472 of the valve 402 in the compressed configuration. FIG. 82A shows the valve 402 and at least a portion of the secondary catheter 480, the pusher 481, the release mechanism 482, and the guidewire 485 disposed within the capsule 476, which in turn, is positioned within or at the proximal end portion of the delivery catheter 472. As described in detail above, the valve 402 can be compressed from a configuration in which a circumference of the valve 402 in a plane orthogonal to the lengthwise axis 475 of the delivery catheter 472 is greater than the circumference or diameter of the lumen 474 of the delivery catheter 472. The capsule 476 can be configured to compress the valve 402 to the compressed configuration, or to receive the valve 402, which has already been compressed to the compressed configuration, such that the circumference of the compressed valve 402 within the capsule 476 is less than the circumference or diameter of the lumen 474 of the delivery catheter 472.

The capsule 476 can be any suitable capsule, catheter, compression member, and/or device configured to compress the valve 402 into the compressed configuration or to receive the valve 402, which has already been compressed to the compressed configuration. In some embodiments, the capsule 476 can be a compression catheter or sleeve configured to exert a compression force (e.g., squeeze) the valve 402. In some embodiments, the capsule 476 can be configured to maintain the valve 402 in a rolled or folded configuration (e.g., compressed configuration) prior to the valve 402 being delivered into the delivery catheter 472. In some embodiments, the delivery system 470 can include a tapering or funnel fixture that can compress the valve 402 to the compressed configuration, which can then be inserted into the capsule 476. In some embodiments, the capsule 476 can be configured to deliver the valve 402 to the proximal end of the delivery catheter 472 and once delivered, can be removed and/or the valve 402 can be ejected from the capsule 476 into the delivery catheter 472. In other embodiments, the valve 402 can remain within the capsule 476, which are advanced, collectively, through the delivery catheter 472.

The guidewire 485 extends or threads through the secondary catheter 480, the valve 402, and the delivery catheter 472. The guidewire 485 can be, for example, a sheathed guidewire at least partially sheathed by the secondary catheter 480. The guidewire 485 is configured to be advanced through the anatomy of the body and placed in a desired position relative to native tissue (e.g., a native valve). In some instances, the guidewire 485 can be advanced to provide a wire path (e.g., for the delivery catheter 472, the valve 402, etc.) to the RVOT. The guidewire 485 extends through the guidewire collar 440 of the valve 402 to provide a wire path along which the valve 402 is advanced.

The secondary catheter 480 can be a sheath, tube, annular rod or wire, and/or the like. In some embodiments, the secondary catheter 480 is a hypotube sheath disposed about a portion of the guidewire 485 (e.g., the secondary catheter 480 and the guidewire 485 collectively form a sheathed guidewire or sheathed guidewire assembly). The secondary catheter 480 can have a relatively small size allowing the secondary catheter 480 to be advanced through the delivery catheter 472 and/or at least partially disposed in or otherwise engaged with the guidewire collar 440. As shown in FIGS. 82A-82C, the secondary catheter 480 has a diameter that is greater than the guidewire 485, allowing the guidewire 485 to pass therethrough.

The pusher 481 is disposed within the secondary catheter 480 and is configured to push on a portion of the valve 402 to advance the valve 402 through and/or out of the delivery catheter 472. In some implementations, the pusher 481 is configured to push against a portion of the guidewire collar 440 of the valve 402. For example, the guidewire collar 440 can allow the guidewire 485 to be advanced through the guidewire collar 440 and can block and/or substantially prevent the pusher 481 from being advanced beyond the guidewire collar 440 (or at least a portion thereof). While the pusher 481 is shown disposed in the secondary catheter 480, in some embodiments, the secondary catheter 480 can be used as the pusher 481. In such embodiments, the delivery system 470 need not include a separate pusher 481.

The guidewire collar 440 of the valve (FIG. 82B) can be any suitable element that selectively allows the guidewire 485 to be advanced therethrough while blocking or preventing the advancement of the secondary catheter 480 and/or the pusher 481 beyond the guidewire collar 440. In some embodiments, the guidewire collar 440 can be included in, formed by, and/or attached to the cuff 420 of the frame 410. In some embodiments, guidewire collar 440 can be included in, formed by, and/or attached to a tension arm such as, for example, a distal upper tension arm, a distal lower tension arm, and/or the like. In certain embodiments, the distal lower tension arm can form and/or can include a feature that forms the guidewire collar 440. It may be desirable to attach the guidewire collar 440 to the distal lower tension arm since both the guidewire 485 and the distal lower tension arm are inserted into or directed toward the RVOT.

In some embodiments, the guidewire collar 440 can be a ball or feature of a tension arm that defines an aperture or lumen that is sufficiently large to allow the guidewire 485 to pass through but is not sufficiently large to allow the secondary catheter 480 and/or the pusher 481 to be advanced therethrough. As such, the secondary catheter 480 and/or the pusher 481 can be stopped against the guidewire collar 440 by the larger circumference of the secondary catheter 480 and/or pusher 481 relative to the aperture or lumen of the guidewire collar 440. Such an arrangement allows the secondary catheter 480 and/or pusher 481 to push on the guidewire collar 440 and thus, the tension arm (e.g., the distal lower tension arm) to which it is attached. When the guidewire collar 440 is attached to a distal tension arm, the pushing on the guidewire collar 440 is operative to pull the valve 402 through and/or out of the delivery catheter 472. It is contemplated that the guidewire collar 440 can have any suitable configuration that allows the guidewire collar 440 to permit the advancement of the guidewire 485 while limiting, blocking, or preventing advancement of the secondary catheter 480 and/or the pusher 481. Moreover, the release mechanism 482 can be configured to release the guidewire 485, the secondary catheter 480 and/or the pusher 481 from the guidewire collar 440, for example, after deployment of the valve 402.

FIG. 82C shows the delivery system 470 delivering the valve 402 to a native valve such as a mitral valve or pulmonary valve (or tricuspid valve or aortic valve). The guidewire 485 is advanced to through the annulus of the native valve and disposed within the ventricle (e.g., within the right ventricle outflow tract. The delivery catheter 472 can be advanced over the guidewire 485 and delivered to the desired location at or near the annulus. The valve 402 can be placed in the compressed configuration (e.g., by rolling, folding, and/or a combination thereof) and can be disposed within the capsule 476. Once the delivery catheter 472 is in the desired location and the compressed valve 402 is in the capsule 476, the capsule 476 can be used to deliver the compressed valve 402 into the lumen 474 of the delivery catheter 472.

FIG. 82A shows the capsule 476 delivering the compressed valve 402 into the proximal end of the delivery catheter 472. In some instances, once the valve 402 is in the lumen 474 of the delivery catheter 472, the capsule 476 can be removed and/or the valve 402 can be ejected from the capsule 476. In other embodiments, the valve 402 can remain in the capsule 476 as the valve 402 is advanced through the delivery catheter 472. The valve 402 can be advanced over the guidewire 485 and within the delivery catheter 472 by pushing on the secondary catheter 480 and/or pusher 481. When the guidewire collar 440 is attached to a distal or anterior side of the valve 402 or frame 410, the pushing of the secondary catheter 480 and/or pusher 481 acts like a pulling force relative to, for example, the tubular section 412 of the valve frame 410 and/or the flow control component 450 of the valve 402.

FIG. 82C shows the valve 402 partially ejected from the delivery catheter 472 and completely ejected from the capsule 476. The ejecting of the valve 402 from the capsule 476 and the delivery catheter 472 can be a single integrated process or step or can be performed in any number of independent processes and/or steps. Alternatively, the capsule 476 can be removed once the valve 402 is delivered into the lumen 474 of the delivery catheter 472.

The secondary catheter 480 and/or the pusher 481 can be used to eject the valve 402 from the delivery catheter 472. Once ejected from the delivery catheter 472, the valve 402 is allowed to expand to the expanded configuration and can be seated within the annulus of the native valve. In some embodiments, secondary catheter 480, the pusher 481, and/or the guidewire 485 can be released from the guidewire collar 440 to allow the secondary catheter 480, the pusher 481, and/or the guidewire 485 to be retracted and/or withdrawn. In some embodiments, the secondary catheter 480 and/or the pusher 481 can be used to push at least a proximal side of the valve 402 or valve frame 410 into the annulus, thereby completely seating and/or deploying the valve 402. Although not shown in FIGS. 82A-82C, in some embodiments the secondary catheter 480 and/or pusher 481 can be further used to deliver and/or anchor a tissue anchor to the proximal side of the valve 402 or valve frame 410. Thus, the delivery system 470 can deliver a traditionally compressed valve or orthogonally deliver a vertically and/or laterally compressed valve 402. Moreover, the delivery system 470 includes the capsule 476, which can maintain the valve 402 in the compressed configuration at least until the valve 402 is delivered into the delivery catheter 472.

Figure 82D:
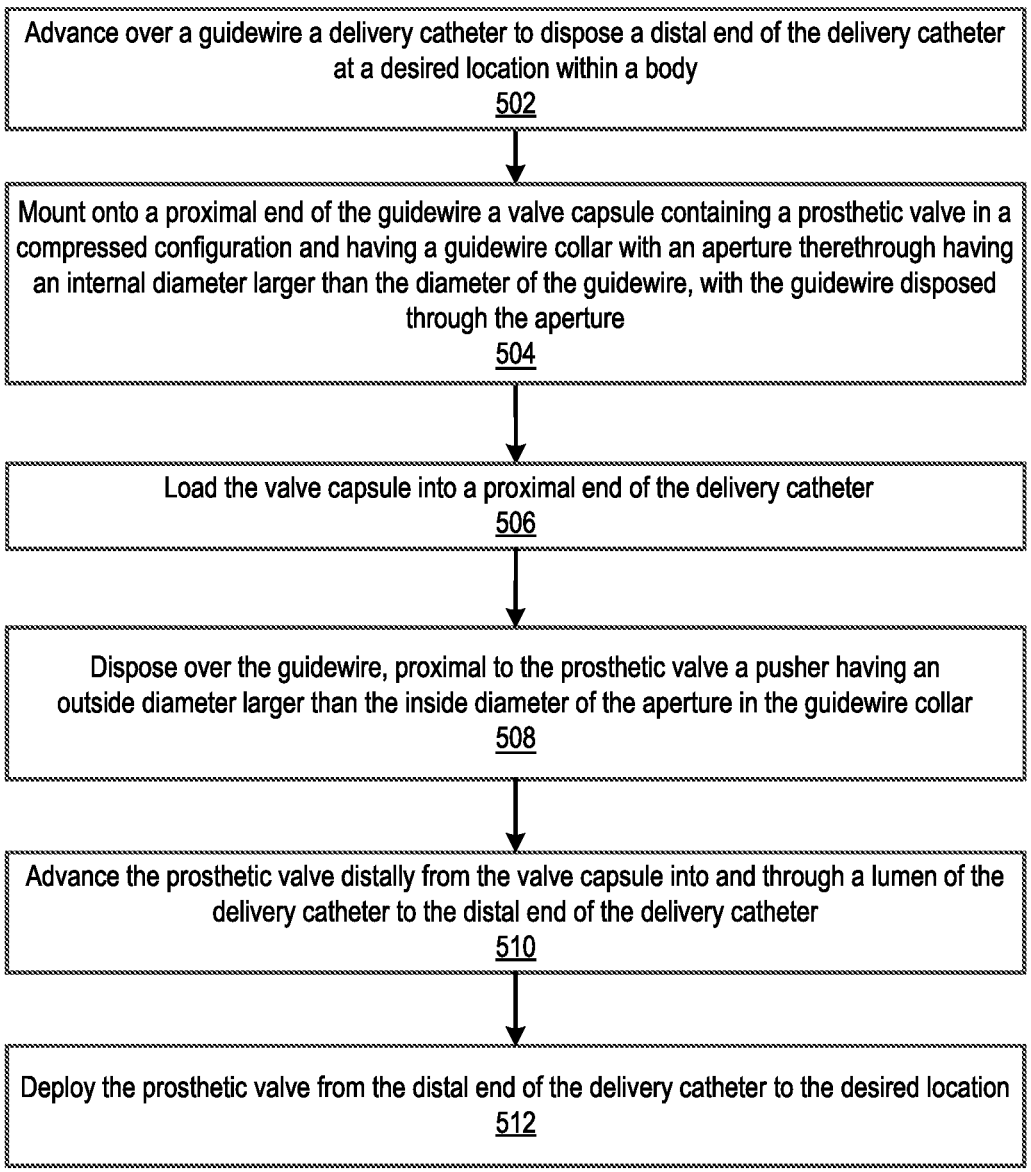
FIG. 82D is a flowchart describing a method for delivering a transcatheter prosthetic valve according to an embodiment.

FIG. 82D is a flowchart describing a method 500 for delivering a compressible prosthetic valve such as any of the prosthetic valves described herein, according to an embodiment. The method 500 includes advancing over a guidewire a delivery catheter to dispose a distal end of the delivery catheter at a desired location within a body, at 502. The desired location within the body can be, for example, an annulus of a native valve within the human heart. Prior to advancing the delivery catheter, the guidewire can be advanced into the desired location and placed, for example, within a right ventricle outflow tract or in another desired position relative to the annulus.

A valve capsule is mounted onto a proximal end of the guidewire, where the valve capsule contains a prosthetic valve in a compressed configuration and having a guidewire collar with an aperture therethrough having an internal diameter larger than the diameter of the guidewire, with the guidewire disposed through the aperture, at 504. The arrangement of the prosthetic valve, guidewire collar, guidewire, and capsule can be substantially similar to the arrangement described above with reference to the delivery system 470. In some embodiments, the valve capsule can be configured to place and/or to maintain the prosthetic valve in the compressed configuration prior to the prosthetic valve being delivered and/or loaded into the delivery catheter.

The valve capsule is loaded into a proximal end of the delivery catheter, at 506. The valve capsule can have an outer diameter or circumference that is smaller than the diameter or circumference of the lumen of the delivery catheter, thereby allowing the valve capsule to be disposed within the lumen. Moreover, the valve capsule can maintain the prosthetic valve in the compressed configuration and the loading of the valve capsule similarly loads the prosthetic valve into the proximal end of the delivery catheter.

Proximal to the prosthetic valve, a pusher is disposed over the guidewire, wherein the pusher has an outside diameter larger than the inside diameter of the aperture in the guidewire collar, at 508. The pusher can be similar to the pusher 481 described above with reference to FIGS. 82A-82C. In some embodiments, the pusher can be a secondary catheter or the like that can form a sheath of the guidewire. In other embodiments, the pusher can be inserted into or at least partially disposed within the secondary catheter.

The prosthetic valve is advanced distally from the valve capsule into and through the lumen of the delivery catheter to the distal end of the delivery catheter, at 510. In some embodiments, the loading and/or delivery of the valve capsule into the proximal end of the delivery catheter can begin to eject the prosthetic valve from the valve capsule as the valve capsule is moved relative to or within the delivery catheter. In other embodiments, the prosthetic valve can remain within the valve capsule until the prosthetic valve is at or near the distal end of the delivery catheter. In some embodiments, the valve capsule can be a compression catheter or sleeve that can be slid off or relative to the prosthetic valve to allow the prosthetic valve to move distally from the valve capsule. As described above with reference to the delivery system 470, the prosthetic valve can be advanced distally by pushing on the pusher and/or the second catheter, which in turn, can push or pull the prosthetic valve in the distal direction through the delivery catheter.

The prosthetic valve is deployed from the distal end of the delivery catheter to the desired location, at 512. As described above, the pusher or secondary catheter can be used to eject the prosthetic valve from the distal end of the delivery catheter. Moreover, the prosthetic valve can similarly be advanced relative to or ejected from the valve capsule. Thus, when the prosthetic valve is disposed outside of and distal to the delivery catheter (e.g., within the atrium of the heart), the prosthetic valve can be allowed to expand to an expanded configuration suitable for deployment into the annulus of the native valve. In some instances, the pusher and/or the secondary catheter can be used to push the prosthetic valve into the annulus of the native valve, and the prosthetic valve can form a seal with the native annular tissue when deployed therein.

Provided below is a discussion of certain aspects or embodiments of transcatheter prosthetic valves, delivery systems, and/or delivery methods. The transcatheter prosthetic valves (or aspects or portions thereof), the delivery systems, and/or the delivery methods described below with respect to specific embodiments can be substantially similar in at least form and/or function to the valve 402 and/or corresponding aspects of the valve 402, the delivery system 470, and/or the delivery method 500 described above with reference to FIGS. 82A-82D. Thus, certain aspects of the specific embodiments are not described in further detail herein.

Figure 83A:
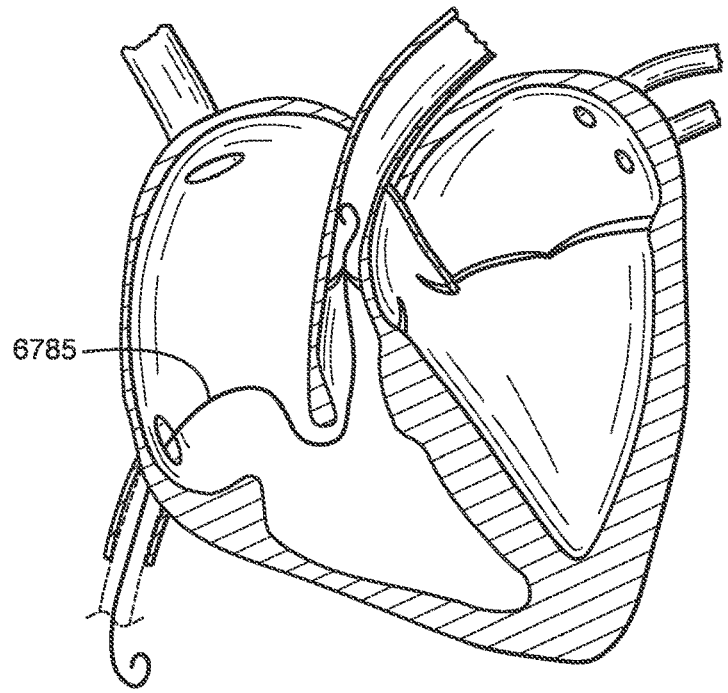
FIGS. 83A-83F illustrate a process of deploying a transcatheter prosthetic valve in a native annulus of the human heart according to an embodiment.

FIGS. 83A-83F illustrate a process for delivery of an orthogonal transcatheter prosthetic valve 6702 to the tricuspid annulus of the human heart. FIG. 83A is an illustration of a first step of the delivery process in which a guidewire 6785 with a hypotube sheath or secondary catheter 6780 is delivered to the RVOT. The guidewire 6785 has a diameter of about 0.035 in (or about 0.889 mm).

Figure 83B:
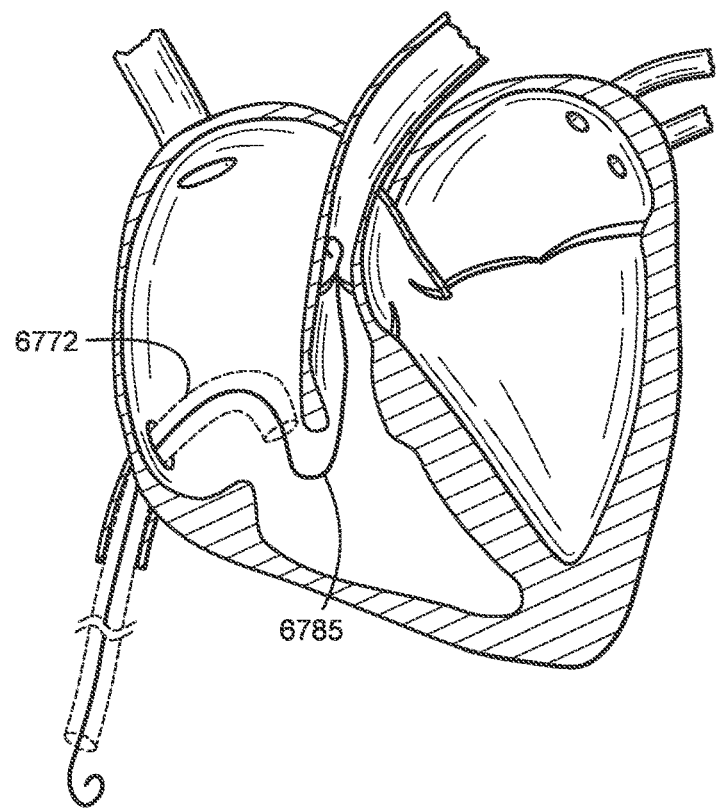

FIG. 83B shows a delivery catheter 6772 being advanced over the guidewire 6772 to and through the native tricuspid annulus to the right ventricle.

Figure 83C:
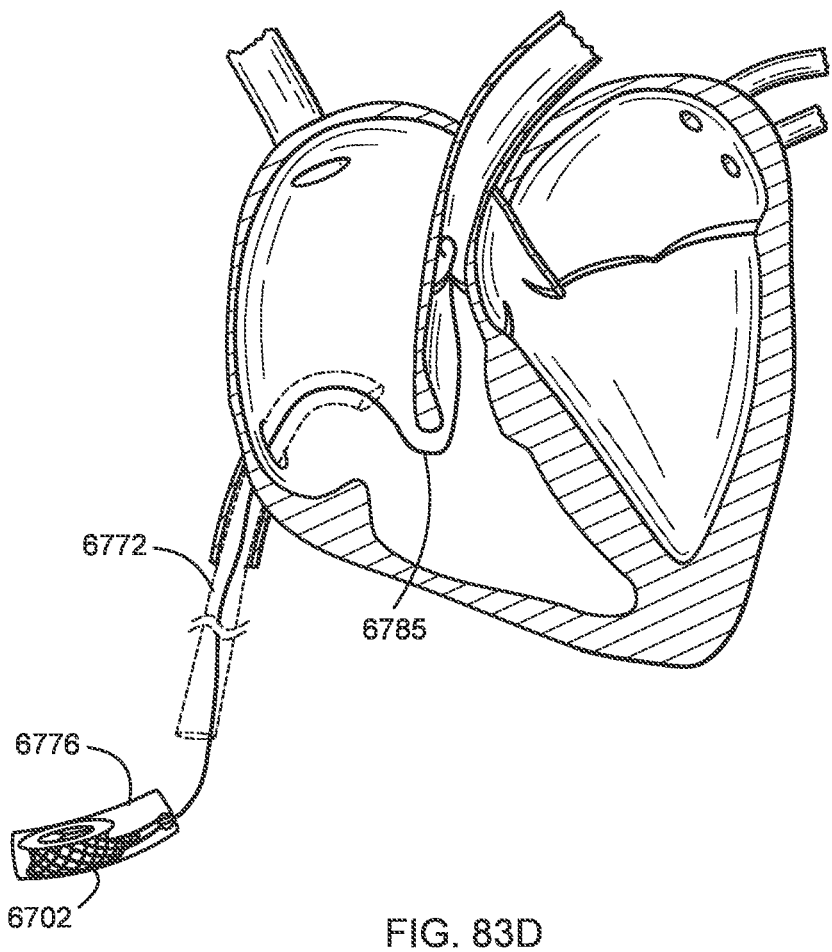

FIG. 83C shows the valve 6702 in a compressed configuration disposed within a capsule/compression catheter 6776. The capsule 6776 is loaded into a proximal end of the delivery catheter 6772 and the valve 6702 is withdrawn from the capsule 6776 into the delivery catheter 6772, with the sheathed guidewire 6785 threaded through the valve 6702 and providing a wire path to the RVOT, planned deployment location. In another embodiment, the capsule 6776 with the valve 6702 disposed therein can be advanced through at least part of the delivery catheter 6772. The guidewire 6785 can extend through a guidewire collar element 6740 of the valve 6702 while the larger circumference of the hypotube sheath or secondary catheter 6780 relative to an aperture of the guidewire collar element 6740 blocks passage of the hypotube sheath or secondary catheter 6780 through the guidewire collar element 6740.

Figure 83D:
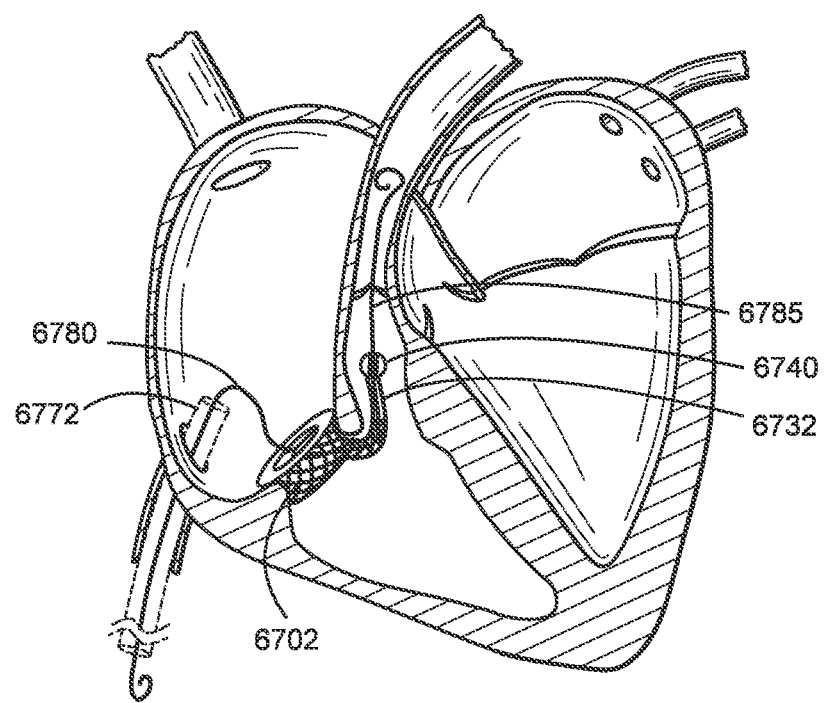

FIG. 83D shows the valve 6702 being expelled and/or released out of the delivery catheter 6772 into the expanded configuration and deployed into the native annulus by pushing on the hypotube sheath or secondary catheter 6780 against the guidewire collar element 6740 to pull the valve 6702 through the delivery catheter 6772 and into position in the native tricuspid annulus. The tension arm (e.g., the distal lower tension arm) 6732 is used to position the expanded valve 6702 in the native annulus.

Figure 83E:
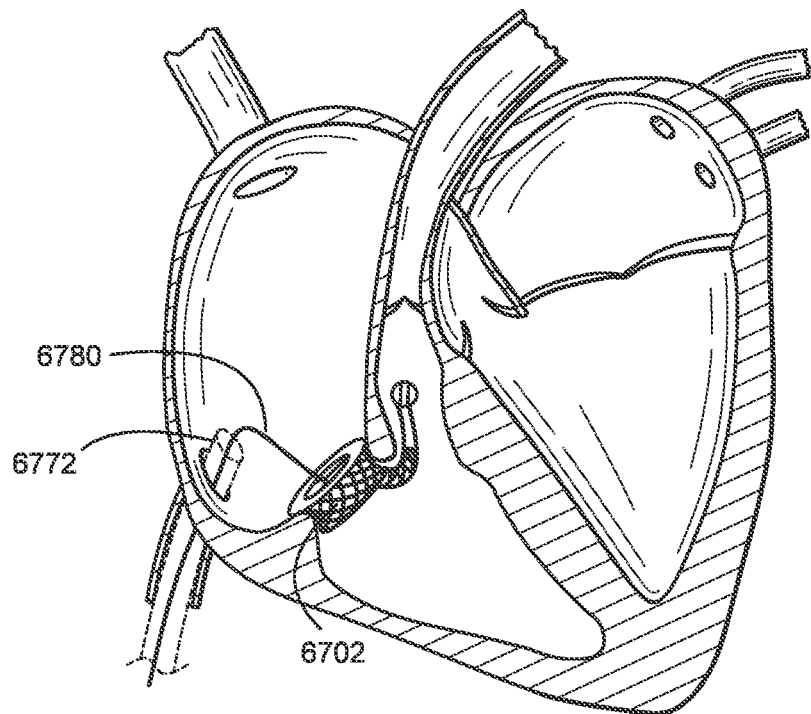

FIG. 83E shows the secondary catheter 6780, or steerable catheter, being used to push the proximal side of the valve 6702 into position within the native annulus.

Figure 83F:
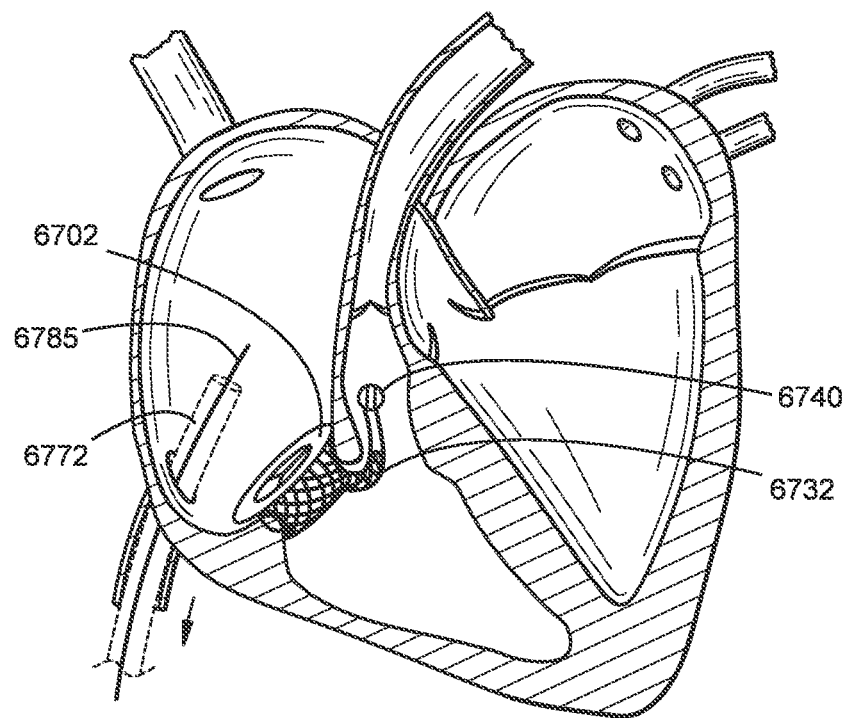

FIG. 83F shows withdrawal of the delivery system (e.g., the guidewire 6785 and the delivery catheter 6772) and anchoring of a proximal side (e.g., a posterior-septal side) of the valve 6702 to the annular tissue. FIG. 83F shows the expanded valve 6702 with an atrial sealing collar facing the atrium, a valve body (e.g., a lower tubular body portion) deployed within the native annulus and extending from atrium to ventricle, the anchoring tension arm or distal lower tension arm 6732 extending subannularly into the RVOT area, and the guidewire collar/ball 6740 at a distal end of the tension arm 6732. The guidewire 6785 and the delivery catheter 6772 are being withdrawn.

Figure 84A:
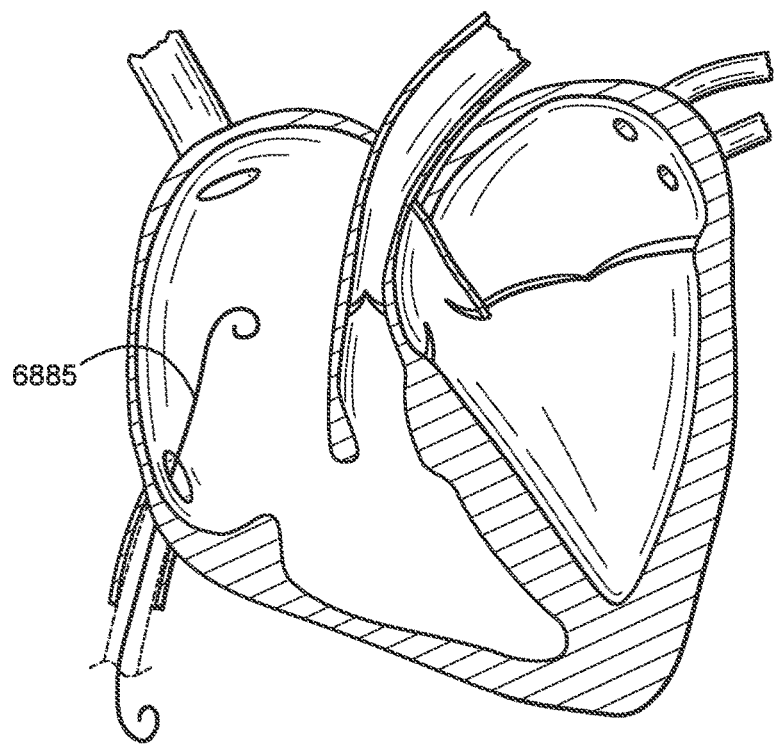
FIGS. 84A-84H illustrate a process of deploying a transcatheter prosthetic valve in a native annulus of the human heart according to an embodiment.

FIGS. 84A-84F illustrate a process for delivery of an orthogonal transcatheter prosthetic valve 6802 to the tricuspid annulus of the human heart. FIG. 84A is an illustration of a first step of the delivery process in which a guidewire 6885 is advanced from the femoral artery, through the inferior vena cava (IVC), to the right atrium. The guidewire 6885 is an 8 Fr guidewire (or about 2.667 mm in diameter).

Figure 84B:
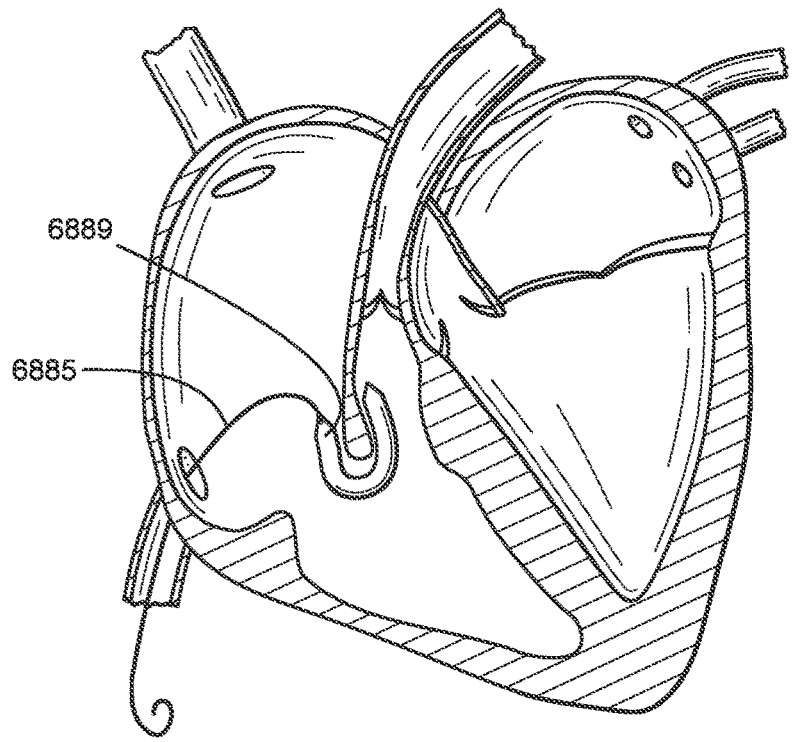

FIG. 84B shows a balloon catheter 6889 advanced over the guidewire 6885 through the native annulus and into the RVOT to expand and push aside native valve and leaflet tissue, chordae tendineae that might tangle the transcatheter delivery of the valve 6802.

Figure 84C:
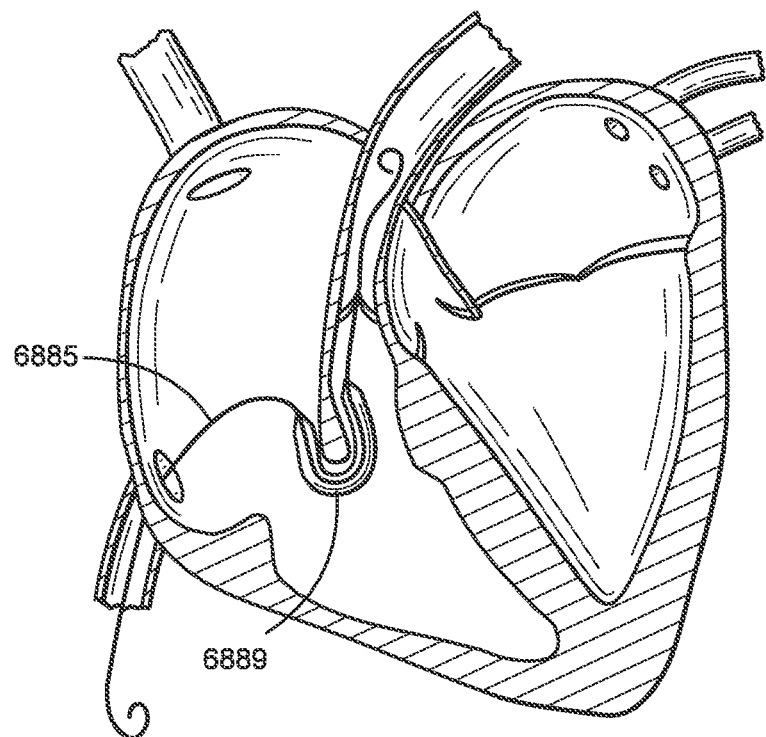

FIG. 84C shows a guidewire 6885 with a hypotube sheath or secondary catheter 6880 delivered to the RVOT. The guidewire 6885 has a diameter of about 0.035 in (or about 0.889 mm).

Figure 84D:
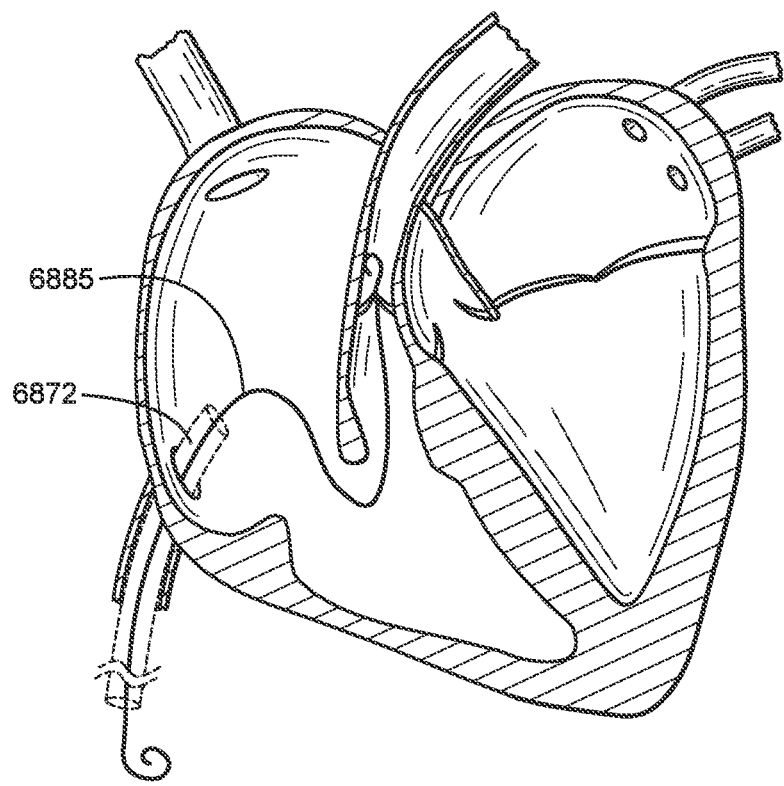

FIG. 84D shows a delivery catheter 6872 being advanced over the guidewire 6872 to and through the native tricuspid annulus to the right ventricle.

Figure 84E:
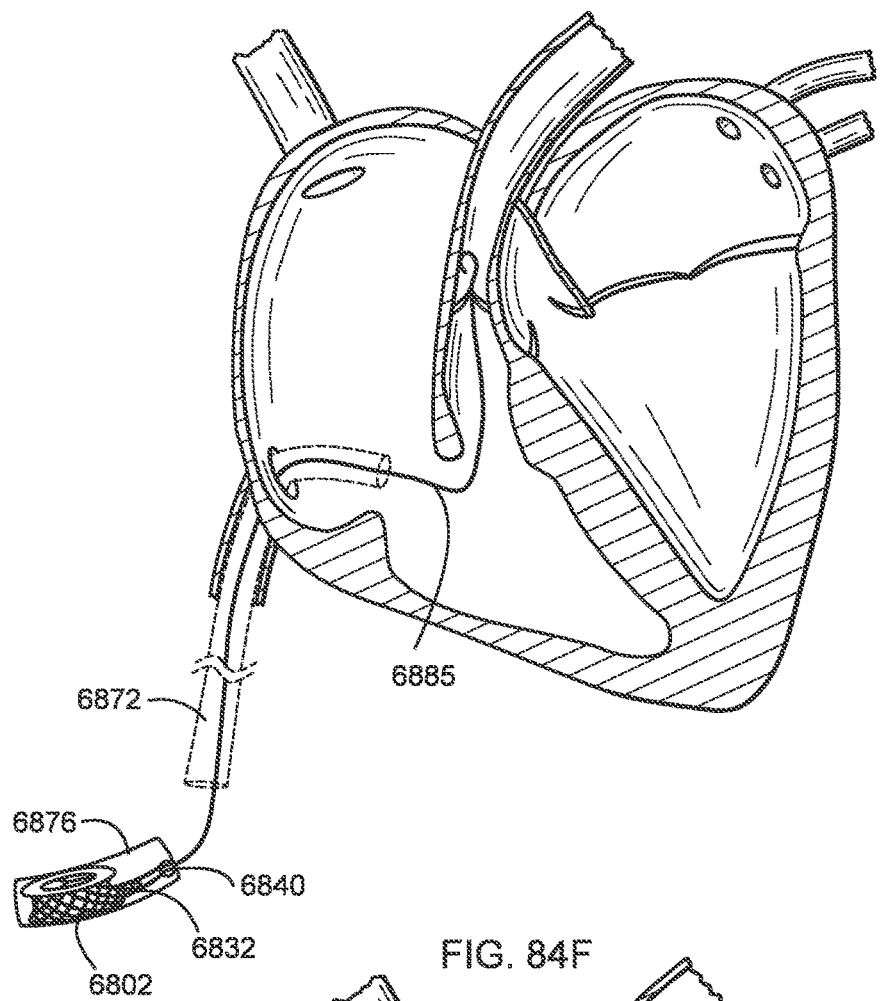

FIG. 84E shows the valve 6802 in a compressed configuration disposed within a capsule/compression catheter 6876. The capsule 6876 is loaded into a proximal end of the delivery catheter 6872 and the compressed valve 6802 is advanced through the delivery catheter 6872, with the sheathed guidewire 6885 threaded through the valve 6802 and providing a wire path to the RVOT, planned deployment location.

Figure 84F:
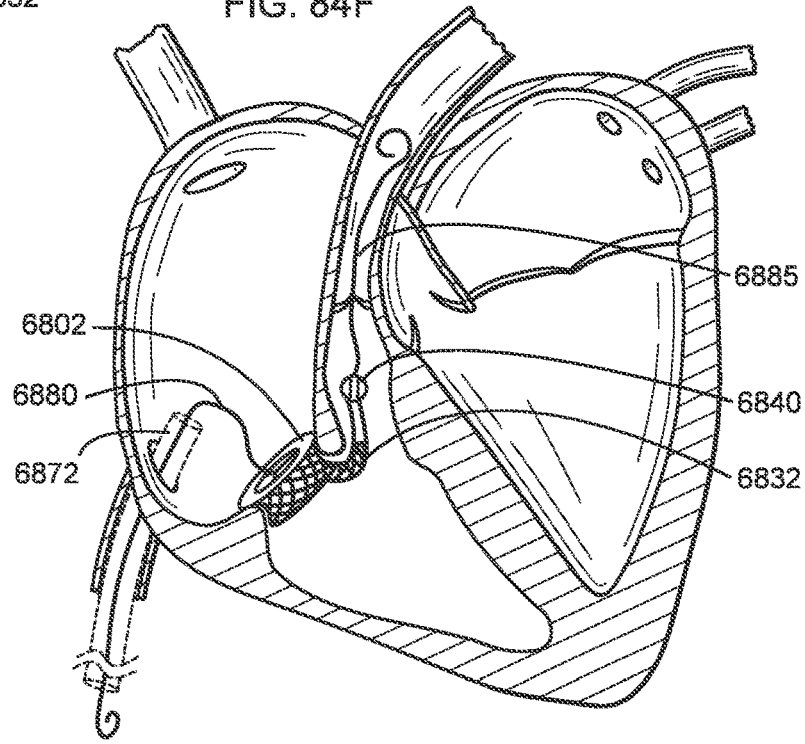

FIG. 84F shows the valve 6802 advanced though the delivery catheter 6872, expelled, expanded to the expanded configuration, and at least partially deployed into the native annulus by pushing on the outer sheath or secondary catheter 6880 of the guidewire 6885 to pull the valve 6802, pulling from a guidewire collar 6840 included in or coupled to a distal end of a tension arm (e.g., a distal lower tension arm) 6832, through the delivery catheter 6872 and into position in the native annulus. The tension arm 6832 is used to position the valve 6802.

Figure 84G:
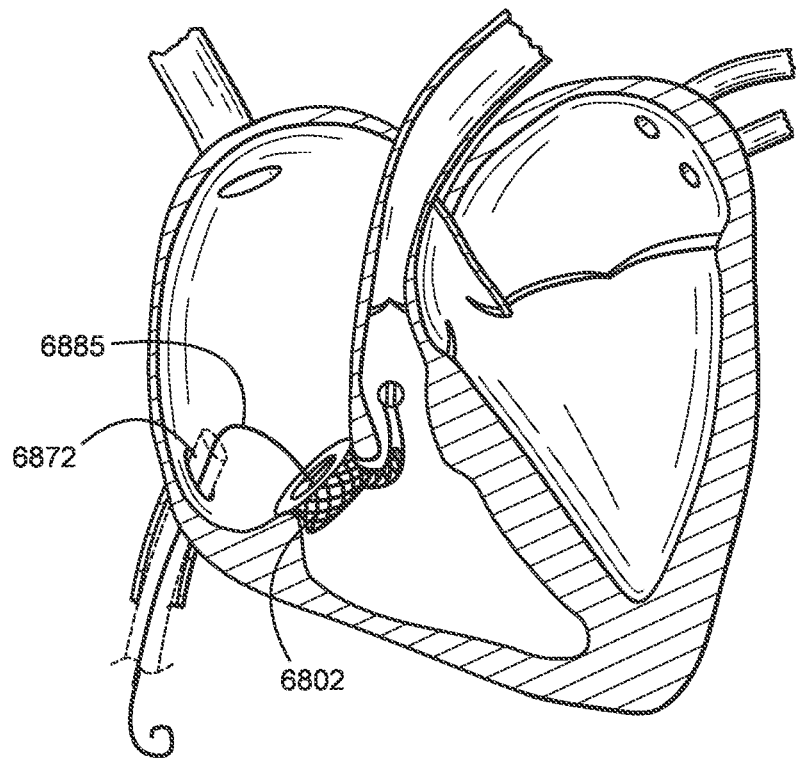

FIG. 84G shows the hypotube sheath or secondary catheter 6880, or steerable catheter, being used to push the proximal side of the valve 6802 nearest the IVC or access point into position within the tricuspid annulus.

Figure 84H:
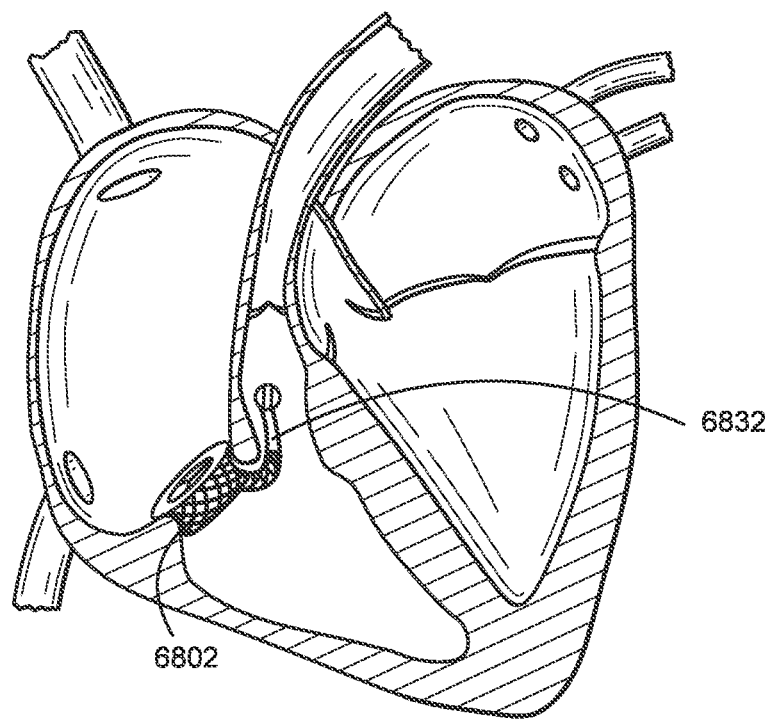

FIG. 84H shows withdrawal of the delivery system (e.g., the guidewire 6885 and the delivery catheter 6872) and anchoring of a proximal side (e.g., a posterior-septal side) of the valve 6802 to the annular tissue, and anchoring of the distal side of the valve 6802 using the distal subannular anchoring tension arm 6832. The guidewire 6885 and the delivery catheter 6872 are withdrawn.

Figure 85A:
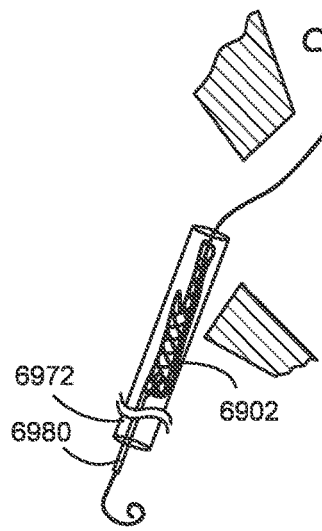
FIGS. 85A-85F illustrate a process of deploying a transcatheter prosthetic valve in a native annulus of the human heart according to an embodiment.

FIGS. 85A-85F illustrate a process for delivery of an orthogonal transcatheter prosthetic valve 6902 to the tricuspid annulus of the human heart. FIG. 85A is an illustration of a first step of the delivery process and shows the compressed side-deliverable valve 6902 disposed in a delivery catheter 6972 and advanced therethrough using a pushing sheath or rod or secondary catheter 6980. The delivery catheter 6972 is advanced over a guidewire 6985 to the native annulus by following the track of the guidewire 6985, which is at least partially disposed in a lumen of the pushing sheath or secondary catheter 6980.

Figure 85B:
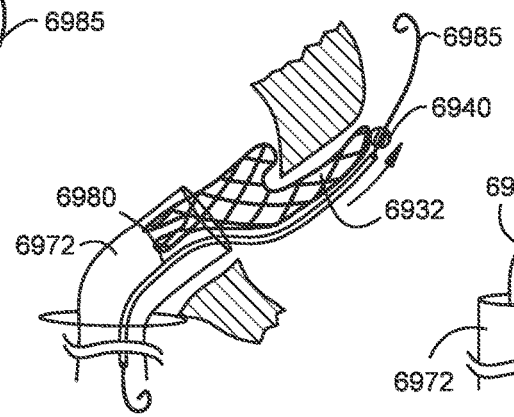

FIG. 85B shows pushing on the outer sheath or secondary catheter 6980 along with the guidewire 6985 threaded through a guidewire collar element 6940 included in and/or coupled to a tension arm (e.g., a distal lower tension arm) 6932 of the valve 6902 to pull the valve 6902 up the delivery catheter 6972 and into position, partially expelling the valve 6902 with the tension arm 6932 being placed into the RVOT and the distal side of the valve 6902 lodged against the native annular wall.

Figure 85C:
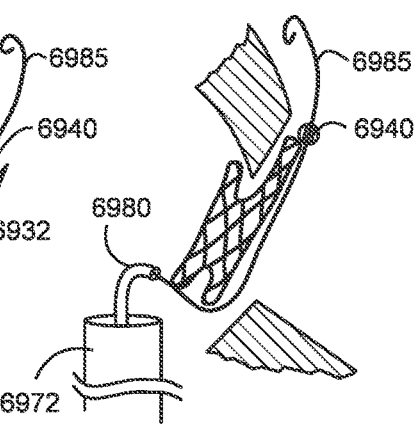

FIG. 85C shows the valve 6902 fully expelled from the delivery catheter 6972 into the expanded configuration and the pushing catheter or secondary catheter 6980 extending from the delivery catheter 6972 being used to push a proximal side of the valve 6902 into position within the native tricuspid annulus.

Figure 85D:
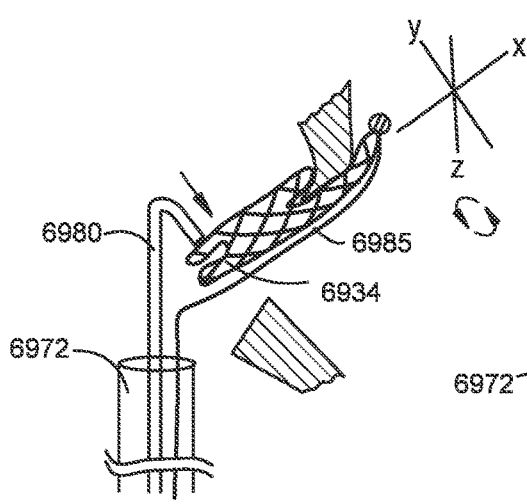

FIG. 85D shows how the tension arm (e.g., the distal lower tension arm) 6932 is used to position the valve 6902 while the pushing catheter or secondary catheter 6980 is used to push the proximal side of the valve 6902 into position within the native annulus to allow a proximal subannular anchoring tab (proximal tab) or proximal lower tension arm 6934 to engage and secure the valve 6902 against the native tissue.

Figure 85E:
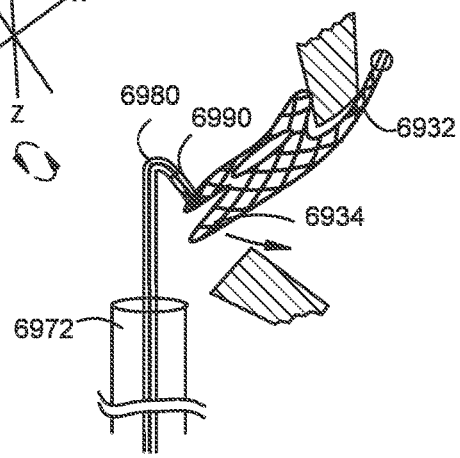

FIG. 85E shows how the pushing catheter and/or secondary catheter 6980 can be used to deliver a tissue anchor 6990 used to secure the proximal side of the valve 6902 to the native annular tissue.

Figure 85F:
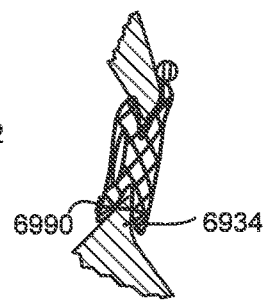

FIG. 85F shows withdrawal of the delivery system (e.g., the secondary catheter 6980, the guidewire 6985, and the delivery catheter 6972) and anchoring of the proximal side of the valve 6902 to the native annular tissue via the tissue anchor 6990. The secondary catheter 6980 can be used to push the tissue anchor 6990 into the native annular tissue to secure the tissue anchor 6990 to the native annular tissue.

Figure 86A:
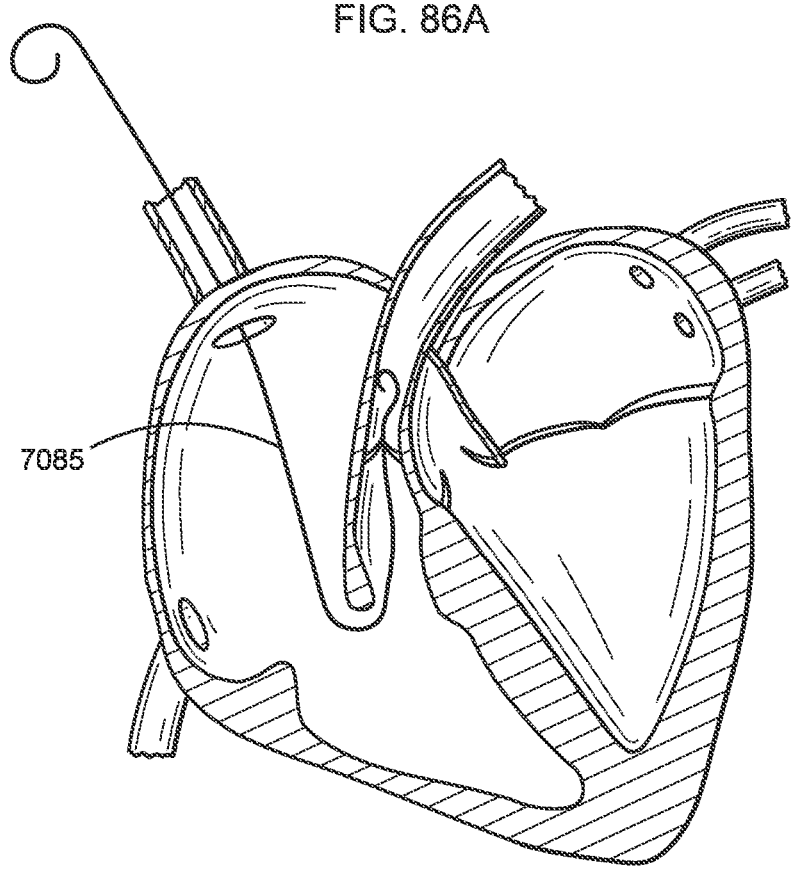
FIGS. 86A-86F illustrate a process of deploying a transcatheter prosthetic valve in a native annulus of the human heart according to an embodiment.

FIGS. 86A-86F illustrate a process for delivery of a transcatheter prosthetic valve 7002 to the tricuspid annulus of the human heart. FIG. 86A is an illustration of a first step of the delivery process in which a guidewire 7085 with a hypotube sheath or secondary catheter 7080 is delivered to the RVOT through the superior vena cava (SVC). The guidewire 7085 has a diameter of about 0.035 in (or about 0.889 mm).

Figure 86B:
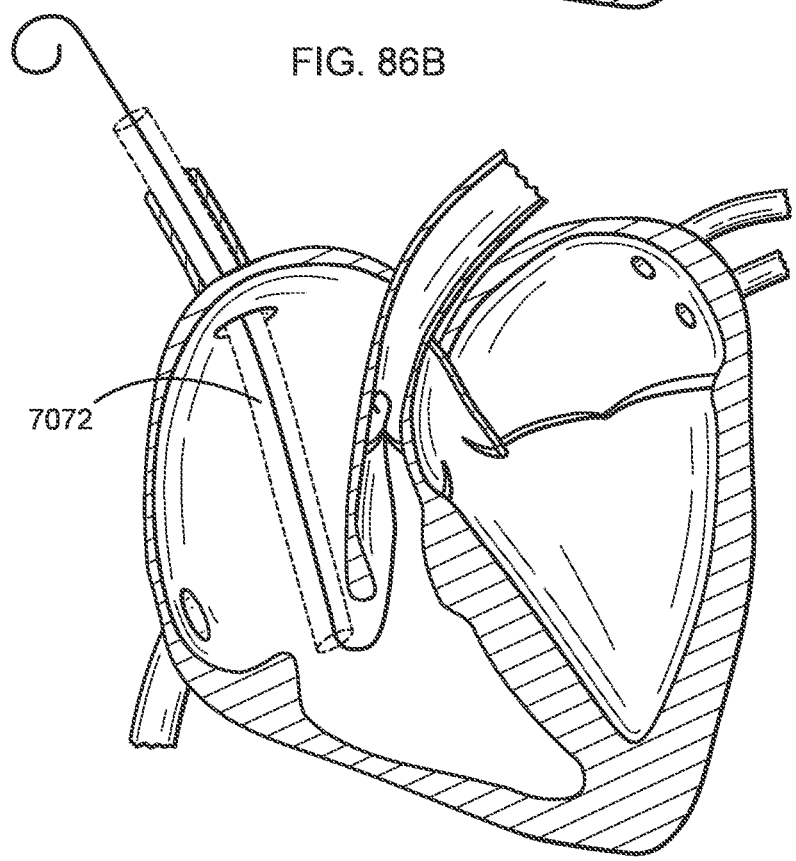

FIG. 86B shows a delivery catheter 7072 being advanced over the guidewire 7085 to and through the native tricuspid annulus to the right ventricle.

Figure 86C:
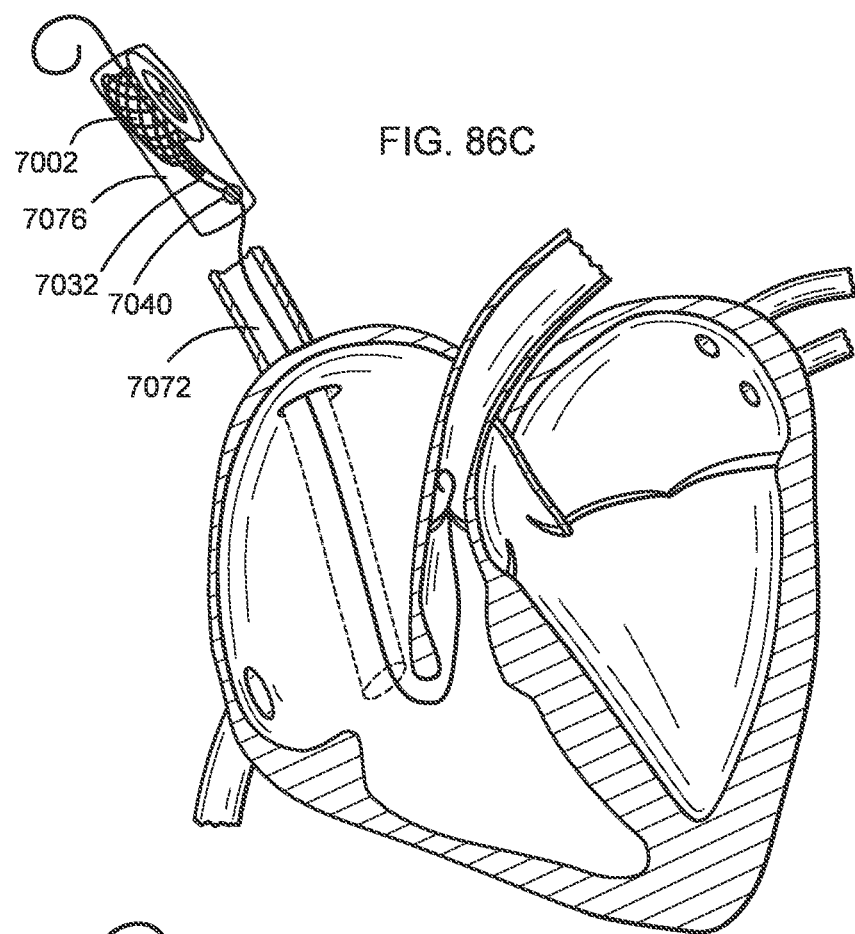

FIG. 86C shows the valve 7002 in a compressed configuration disposed within a capsule/compression catheter 7076. The capsule 7076 is loaded into a proximal end of the delivery catheter 7072 and the valve 7002 is withdrawn from the capsule 7076 into the delivery catheter 7072 for further advancement or the capsule 7076 is used to advance the valve 7002 within the delivery catheter 7072, with the sheathed guidewire 7085 threaded through the valve 7002 and providing a wire path to the RVOT, planned deployment location. The guidewire 7085 can extend through a guidewire collar element 7040 of the valve 7002 while the larger circumference of the hypotube sheath or secondary catheter 7080 relative to an aperture of the guidewire collar element 7040 blocks passage of the hypotube sheath or secondary catheter 7080 through the guidewire collar element 7040. The guidewire collar element 7040 can be coupled to a tension arm (e.g., a distal lower tension arm) 7032.

Figure 86D:
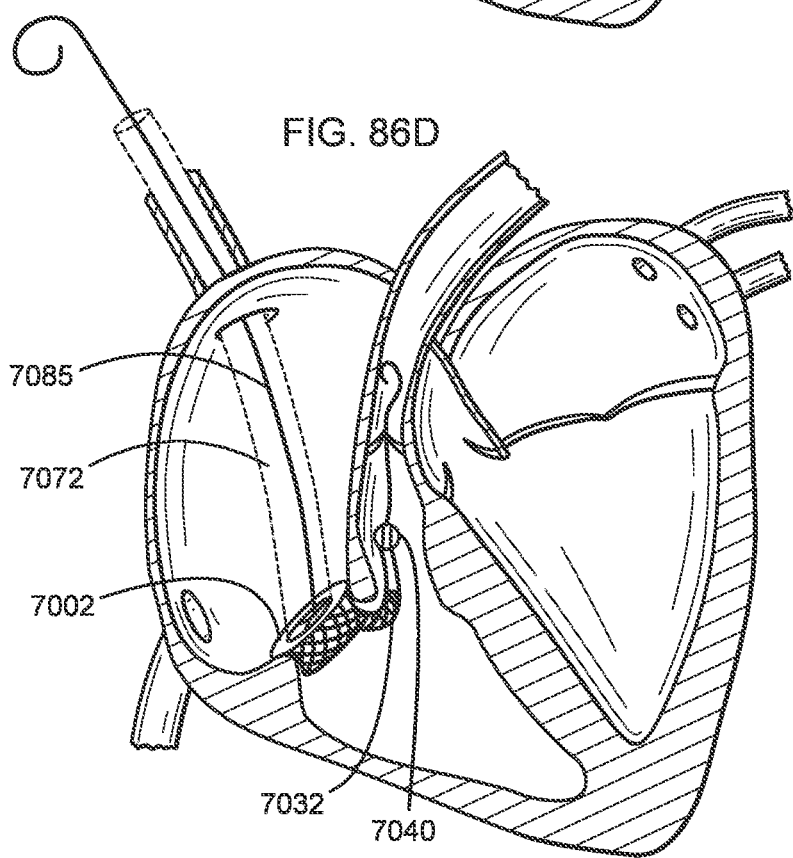

FIG. 86D shows the valve 7002 advanced up and expelled out of the delivery catheter 7072 into the expanded configuration and deployed into the native annulus by pushing on the outer sheath or secondary catheter 7080 to pull the valve 7002 by the guidewire collar element (ball) 7040 up the delivery catheter 7072 and into position. The tension arm or distal lower tension arm 7032 is used as a mount for the guidewire collar element (ball) 7040, to position the valve 7002 during deployment, and to provide subannular anchoring on the distal side.

Figure 86E:
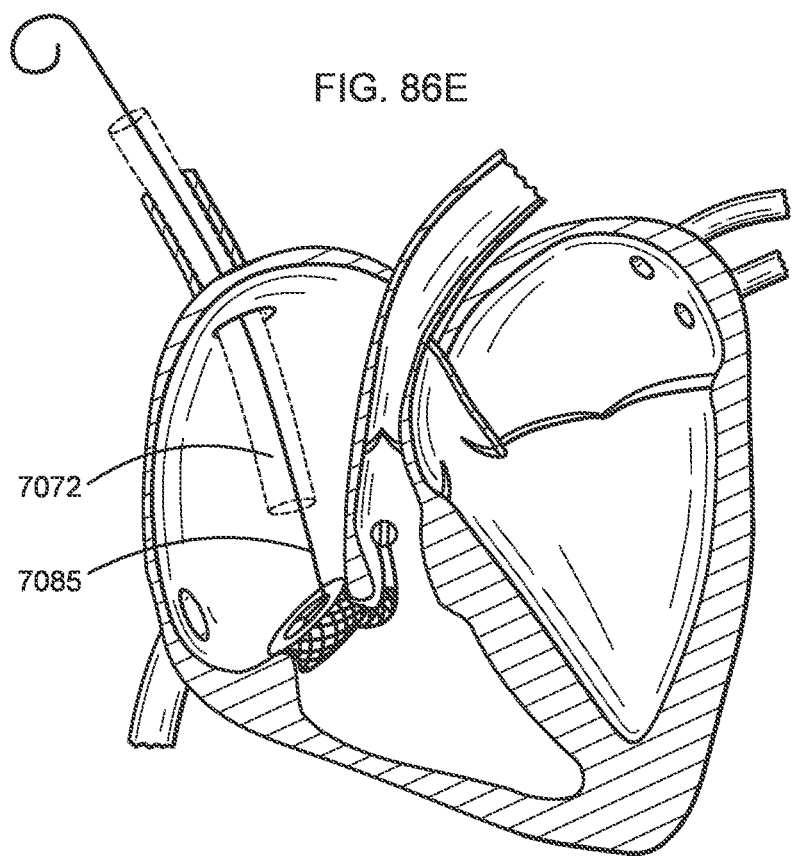

FIG. 86E shows the pushing catheter or secondary catheter 7080 extending from the delivery catheter 7072 and being used to push the proximal side of the valve 7002 into position within the native annulus.

Figure 86F:
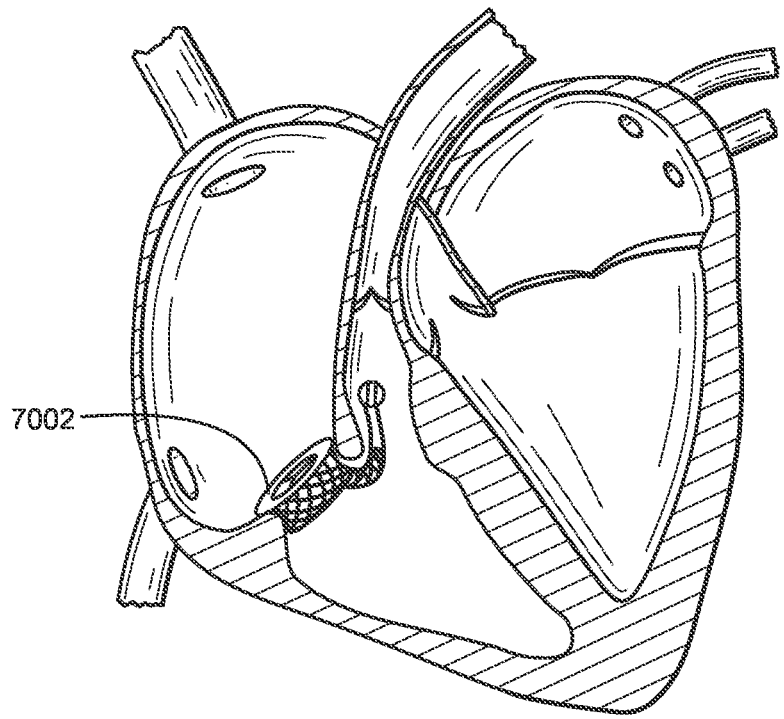

FIG. 86F shows withdrawal of the delivery system (e.g., the guidewire 7085 and the delivery catheter 7072) and anchoring of a proximal side of the expanded valve 7002 to the native annular tissue. FIG. 86F shows the expanded valve 7002 with an atrial sealing collar facing the atrium, a valve body (e.g., a lower tubular body portion) deployed within the native annulus and extending from atrium to ventricle, the anchoring tension arm or distal lower tension arm 7032 extending subannularly into the RVOT area, and the guidewire collar/ball 7040 at a distal end of the tension arm 7032. The guidewire 7085, the secondary catheter 7080, and the delivery catheter 7072 are withdrawn.

Figure 87A:
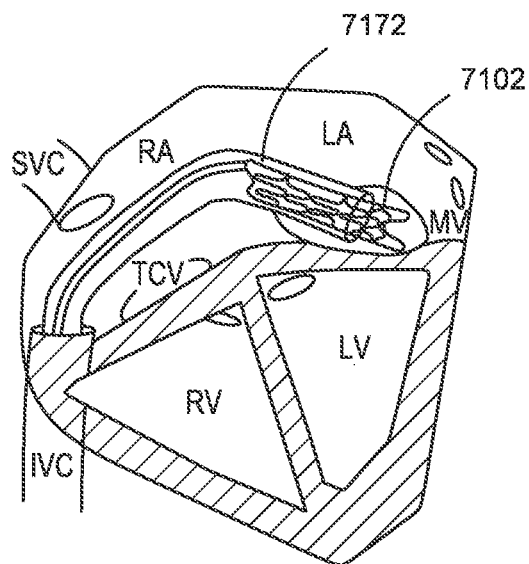
FIGS. 87A-87E illustrate a process of deploying a transcatheter prosthetic valve in a native annulus of the human heart according to an embodiment.

FIG. 87A is an illustration of a trans-septal (femoral-IVC) delivery of a low profile, e.g., 8-20 mm, side-loaded prosthetic mitral valve 7102 FIG. 87A shows the valve 7102 partially housed within a delivery catheter 7172, and partially ejected for deployment into the native mitral annulus.

Figure 87B:
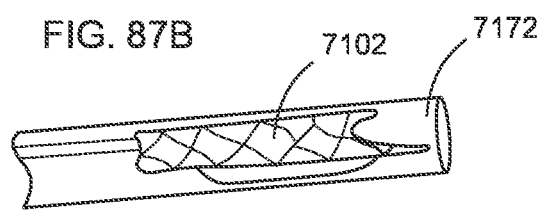

FIG. 87B is an illustration of the low profile, side-loaded, vertically compressed prosthetic mitral valve 7102 shown housed in a compressed configuration within the delivery catheter 7172.

Figure 87C:
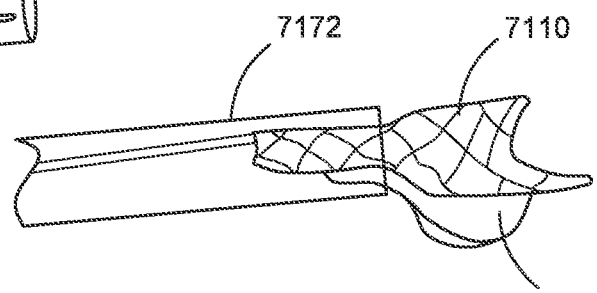

FIG. 87C is an illustration of the low profile, side-loaded prosthetic mitral valve 7102 shown partially housed within the delivery catheter 7172 and partially laterally ejected from the delivery catheter 7172 and positioned for deployment against the anterior side of the native mitral annulus. FIG. 87C shows the valve 7102 partially expanded, with a flow control component 7150 of the valve 7102 beginning to unfurl or expand.

Figure 87D:
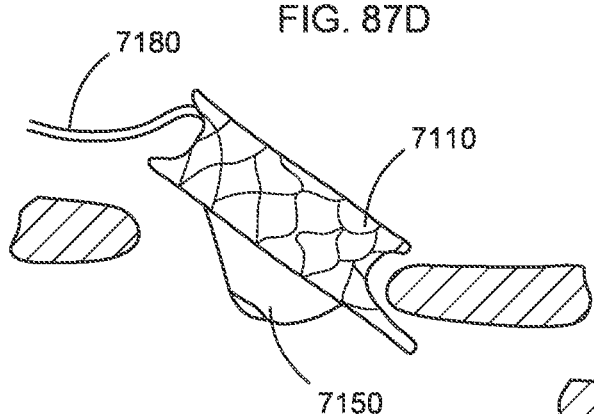

FIG. 87D is an illustration of the low profile, side-loaded prosthetic mitral valve 7102 shown ejected from the delivery catheter 7172 into the expanded configuration and positioned against the anterior side of the native mitral annulus. FIG. 87D shows a secondary catheter 7180 that can be pushed to pull the valve 7102 through the delivery catheter 7172 and to eject the valve 7102 from the delivery catheter 7172. FIG. 87D shows the valve 7102 in an expanded configuration, with the flow control component 7150 of the valve 7102 being unfurled and expanded.

Figure 87E:
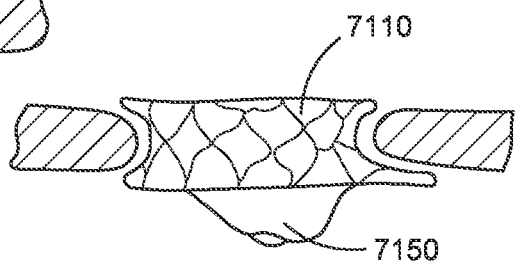

FIG. 87E is an illustration of a side or plan view of a low profile, side-loaded prosthetic valve 7102 shown deployed into the native mitral annulus. FIG. 87E shows the valve 7102 in the expanded configuration, with the flow control component 7150 of the valve 7102 being unfurled and expanded, and shows the delivery system (e.g., the delivery catheter 7172 and the secondary catheter 7180) withdrawn.

Figure 88A:
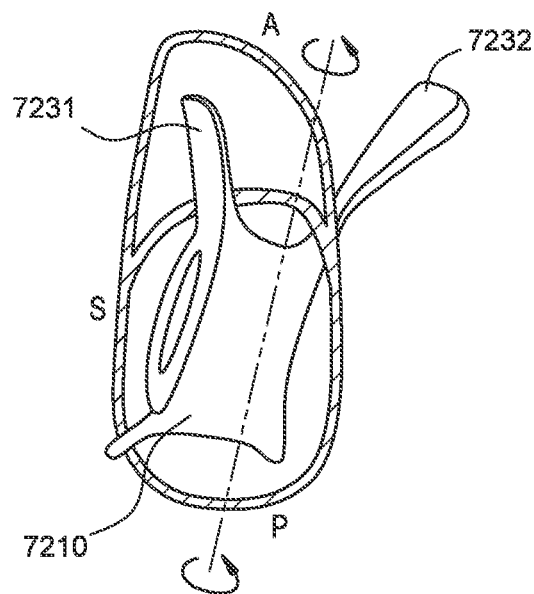
FIGS. 88A and 88B illustrate a process of deploying a transcatheter prosthetic valve in a native annulus of the human heart according to an embodiment.

FIG. 88A is an illustration of a side perspective view of a valve 7202 according to an embodiment, partially delivered to a native annulus. The valve 7202 is a rotational lock valve embodiment where the prosthetic valve 7202 is delivered to the native annulus with an off-set sub-annular tension arm/tab (e.g., a distal lower tension arm) 7232 positioned below the native annulus, and an off-set supra-annular tension arm/tab (e.g., a distal upper tension arm) 7231 positioned above the native annulus, while the valve 7202 (or at least a tubular valve frame 7210 thereof) is partially rolled off-set from the annular plane about a longitudinal axis.

Figure 88B:
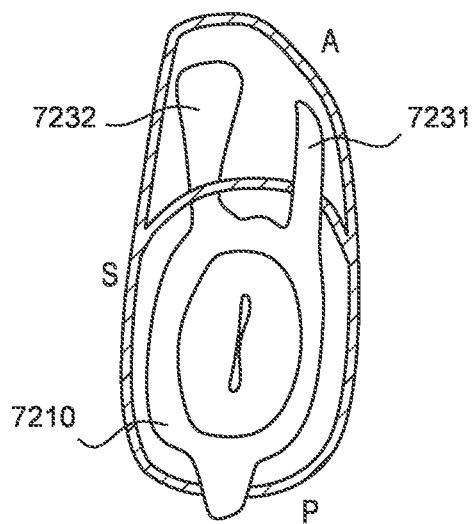
Figure 89A:
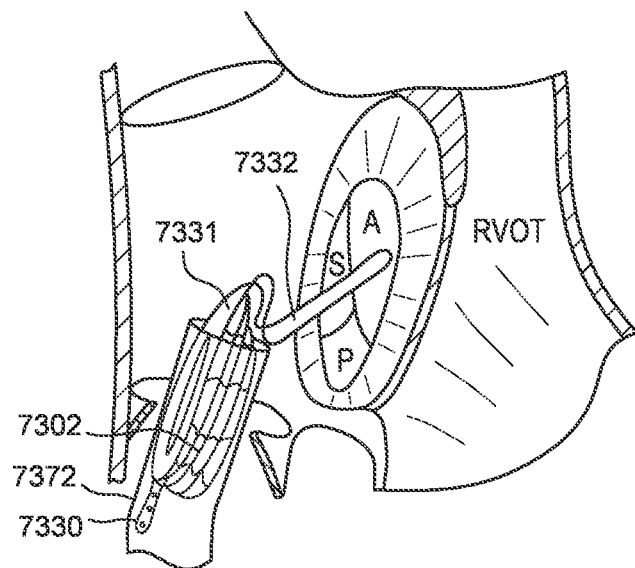
FIGS. 89A-89C illustrate a process of deploying a transcatheter prosthetic valve in a native annulus of the human heart according to an embodiment.

FIG. 88B is an illustration of a side perspective view of a valve 7202 showing the prosthetic valve 7202 delivered to the native annulus with the off-set sub-annular tension arm/tab (e.g., the distal lower tension arm) 7232 positioned below the native annulus, and the off-set supra-annular tension arm/tab (e.g., the distal upper tension arm) 7231 positioned above the native annulus, while the valve 7202 (or at least the tubular valve frame 7210) is partially rolled into a functional or fully deployed position parallel to the annular plane. Once the valve 7202 is rolled into position, and the tension arms 7231 and 7232 are locked against the supra-annular and subannular tissues, respectively. The valve 7210 can also be further anchored using traditional anchoring elements as disclosed herein. FIG. 88B also shows a flow control component FIG. 89A is an illustration of a prosthetic valve 7302 according to an embodiment being delivered to tricuspid valve annulus. FIG. 89A shows a wire-frame distal lower tension arm 7332 of the valve 7302 or valve frame being ejected from the delivery catheter 7372 and being directed through the annulus and towards the RVOT. FIG. 89A shows an embodiment of an accordion-compressed low profile valve 7302 and shows the distal lower tension arm 7332 directed towards the anterior leaflet for placement into the RVOT while the valve 7302 is in the compressed configuration within the delivery catheter 7372 or substantially within the delivery catheter 7372.

Figure 89B:
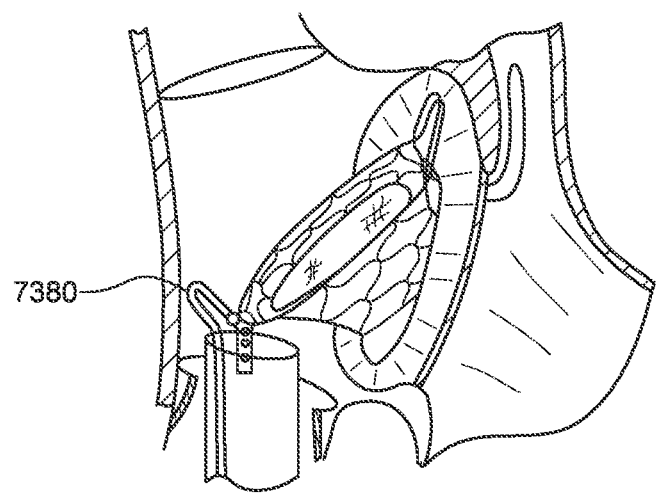

FIG. 89B shows the wire-frame distal lower tension arm 7332 and a distal upper tension arm 7331 ejected from the delivery catheter 7372, the distal lower tension arm 7332 is directed through the native annulus and into the RVOT, and the distal upper tension arm 7331 stays in a supra-annular position, causing a passive, structural anchoring of a distal side of the valve 7302 about the annulus. FIG. 89B also shows a steerable anchoring catheter or secondary catheter 7380 attached to a proximal anchoring tab 7330. While the valve 7302 is held in the expanded configuration in a pre-seating position, the valve 7302 can be assessed, and once valve function and patient conditions are correct, the steerable anchoring catheter 7380 can be used to push a proximal side of the valve 7302 from its oblique angle relative to a native annular plane, down into the annulus. The steerable anchoring catheter or secondary catheter 7380 can then be used to install one or more anchoring elements 7390.

Figure 89C:
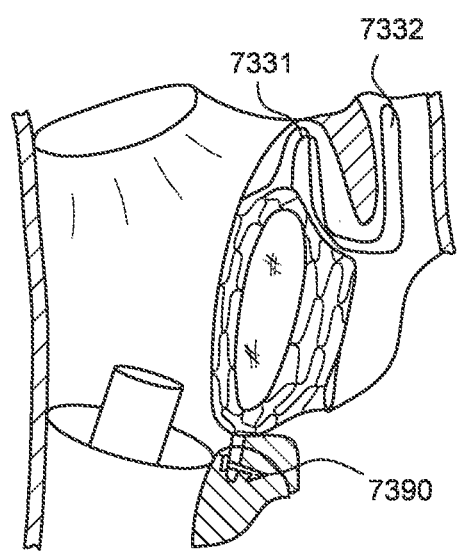

FIG. 89C shows the entire valve 7302 ejected from the delivery catheter 7372, the wire-frame distal lower tension arm 7332 directed through the annulus and into the RVOT, and the wire-frame distal upper tension arm 7331 staying in a supra-annular position, and causing a passive, structural anchoring of the distal side of the valve 7302 about the annulus, and at least one tissue anchor 7390 anchoring the proximal side of the valve 7302 into the annulus tissue.

Figure 90A:
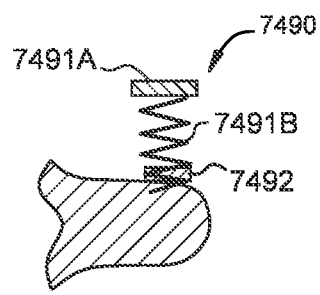
FIGS. 90A-90C illustrate a process of anchoring a transcatheter prosthetic valve to a target tissue via a tissue anchor according to an embodiment.
Figure 90B:
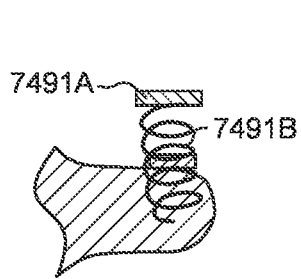
Figure 90C:
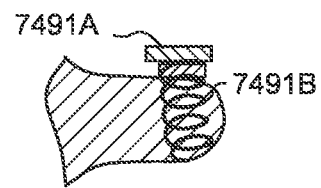

FIGS. 90A-90C show a plan view of a tissue anchor 7490 having a head 7491A and a screw 7491B that can be inserted and/or threaded into the native annular tissue. The tissue anchor 7490 includes a floating radio-opaque marker 7492 at a distal end of the tissue anchor 7490 (e.g., at an end of the screw 7491B) and in contact with the atrial surface of the annular tissue. FIG. 90B shows the screw 7491B of the tissue anchor 7490 being advanced into the annular tissue with the radio-opaque marker 7492 threaded onto the tissue anchor 7490 and maintaining position on the atrial surface of the annular tissue. FIG. 90C shows the tissue anchor 7490 completely advanced into the annular tissue such that the tissue anchor 740 and the threaded floating radio-opaque marker 7492 are now adjacent, indicating the desired depth, tension, and/or plication of the tissue anchor 7490 with respect to the annular tissue.

Figure 91A:
FIGS. 91A-91D are side views of a tissue anchor each according to a different embodiment.
Figure 91B:
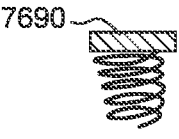
Figure 91C:
Figure 91D:

FIGS. 91A-91D illustrate a plan view of various tissue anchor configurations. FIG. 91A shows a tissue anchor 7590 according to an embodiment having a straight thread and a constant pitch. FIG. 91B shows a tissue anchor 7690 according to an embodiment having a straight thread and a variable pitch. FIG. 91C shows a tissue anchor 7790 according to an embodiment having a tapered thread and a constant pitch. FIG. 91D shows a tissue anchor 7890 according to an embodiment having a sunken taper thread and a variable pitch.

Figure 92A:
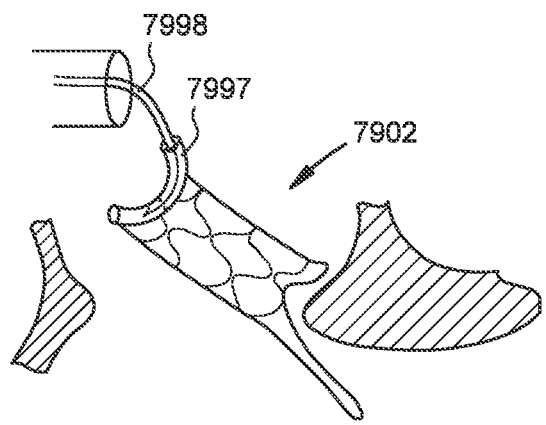
FIG. 92A-92D illustrate a process of deploying and anchoring a transcatheter prosthetic valve in a native annulus of a target tissue.

FIGS. 92A-92D illustrate a process for clipping and/or anchoring a lower profile prosthetic valve 7902 to annular tissue such as, for example, a proximal or anterior side of the native annulus. FIG. 92A shows the valve 7902 being inserted into the native valve annulus and the valve 7902 having an integral anchor delivery conduit or channel 7997 with a tissue anchor 7990 disposed in a lumen of anchor delivery conduit or channel 7997 and an anchor delivery catheter or pusher 7998 attached to the tissue anchor 7990.

Figure 92B:
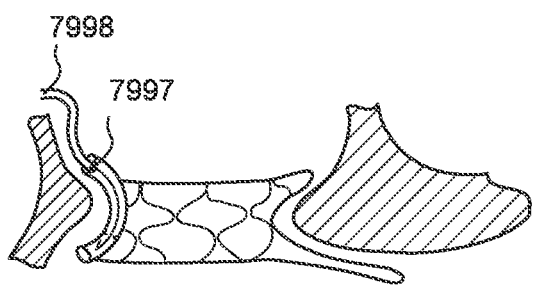

FIG. 92B shows the valve 7902 completely deployed within the native valve annulus and the integral anchor delivery conduit or channel 7997 with the anchor 7990 disposed in the lumen of the channel 7997 and the anchor delivery catheter or pusher 7998 attached to the anchor 7998.

Figure 92C:
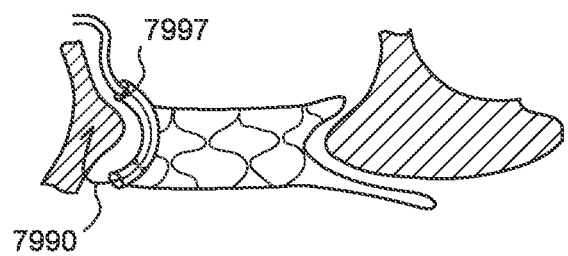

FIG. 92C shows the anchor 7990 being pushed out of the lumen of the anchor delivery conduit or channel 7997 and into the annular tissue. The anchor delivery catheter or pusher 7998 can be used to advance the anchor 7990 through the anchor delivery conduit or channel 7997.

Figure 92D:
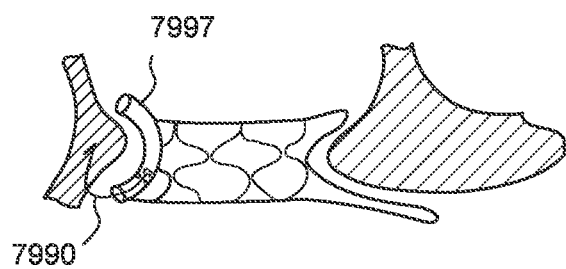

FIG. 92D shows the anchor 7990 in a locked position after being pushed out of the lumen of the delivery conduit or channel 7997 (e.g., via the anchor delivery catheter or pusher 7998) and into the annular tissue, thus anchoring the proximal side of the low profile valve 7902 to the proximal or anterior side of the native annular tissue.

Figure 93A:
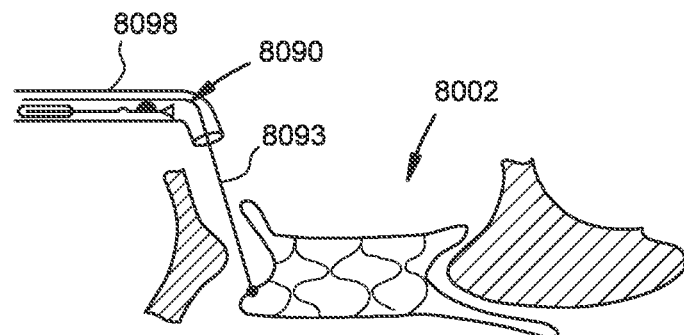
FIG. 93A-93E illustrate a process of deploying and anchoring a transcatheter prosthetic valve in a native annulus of a target tissue.

FIGS. 93A-93E illustrate a process for clipping and/or anchoring a lower profile prosthetic valve 8002 to annular tissue such as, for example, a proximal or anterior side of the native annulus. FIG. 93A shows the valve 8002 completely deployed within the native valve annulus. FIG. 93A also shows delivery of an attachment wire 8093 via an anchor delivery catheter or pusher 8098 with a clip or anchor 8090 housed within the lumen of the anchor delivery catheter 8098. The attachment wire 8093 is attached to a proximal or anterior side of the prosthetic valve 8002. The attachment wire 8093 is configured to engage or couple to the clip or anchor 8090 to couple the valve 8002 to the clip or anchor 8090.

Figure 93B:
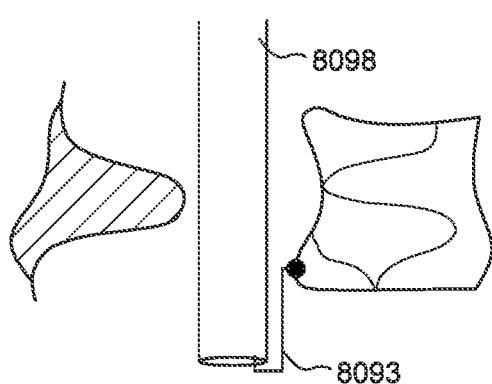

FIG. 93B shows the anchor delivery catheter 8098 inserted into an intra-annular space and shows the attachment wire 8093 attached to the proximal or anterior side of the valve 8002. The clip or anchor 8090 is housed within the lumen of the anchor delivery catheter 8098 and is not shown.

Figure 93C:
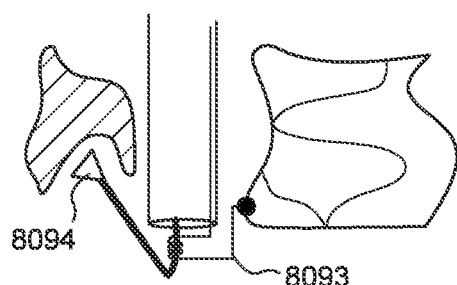

FIG. 93C shows a receiver element or portion 8094 of the clip or anchor 8090 ejected from the anchor delivery catheter 8098 and positioned behind tissue to be captured. The receiver element or portion 8094 is engaged with or connected to the attachment wire 8093.

Figure 93D:
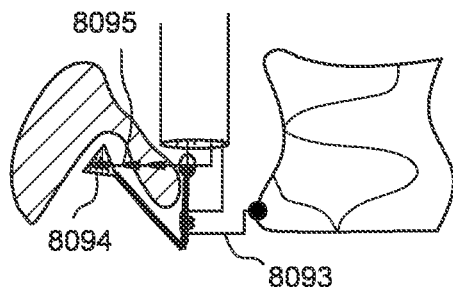

FIG. 93D shows an anchoring element or portion 8095 of the clip or anchor 8090 piercing the annular tissue behind which the receiver element or portion 8094 is positioned. The anchoring element or portion 8095 is inserted through the annular tissue and into the receiver element or portion 8094 of the clip or anchor 8090. The clip or anchor 8090 or at least the receiving element or portion 8094 of the clip or anchor 8090 are attached to the low profile valve 8002 via the attachment wire 8093.

Figure 93E:
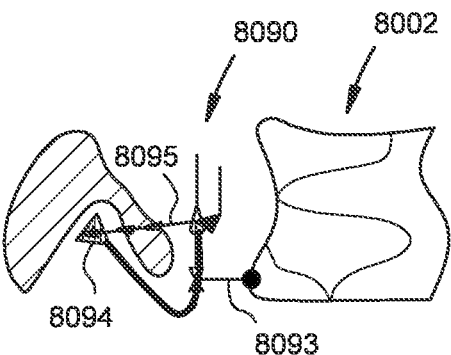

FIG. 93E shows the anchor element or portion 8095 of the clip or anchor 8090 extending through the annular tissue. The receiver element or portion 8094 of the clip or anchor 8090 and the anchor element or portion 8095 of the clip or anchor 8090 are connected to each other and to the annular tissue and connected by the attachment wire 8093 to the low profile valve 8002. The anchor delivery catheter 8098 is withdrawn and the clip or anchor 8090 remains.

FIG. 94 is a flowchart showing a method 8100 for orthogonal delivery of an implantable prosthetic valve to a desired location in the body according to an embodiment. The method 8100 includes providing a compressible and expandable prosthetic valve, at 8101. The compressible and expandable prosthetic valve can be any of the valves disclosed herein. For example, the compressible and expandable prosthetic valve can be a valve (i) where the valve has a tubular frame with a flow control component mounted within the tubular frame, (ii) where the valve or flow control component is configured to permit blood flow in a first direction through an inflow end of the valve and to block blood flow in a second direction, opposite the first direction, through an outflow end of the valve, (iii) where the valve is compressible and expandable and has a long-axis oriented at an intersecting angle of between 45-135 degrees to the first direction, and (iv) where the long-axis is parallel to a length-wise cylindrical axis of a delivery catheter used to deliver the valve. A delivery catheter is advanced to the desired location in the body, at 8102. The compressible and expandable prosthetic valve is delivered, at 8103, wherein the compressible and expandable prosthetic valve has a height of about 5-60 mm and a diameter of about 25-80 mm. The valve is compressible to a compressed configuration during introduction or delivery into the body using a delivery catheter. The compressible and expandable prosthetic valve is released from the delivery catheter, at 8104, wherein the valve is expandable to an expanded configuration after being released from the delivery catheter for implanting the valve in the desired location in the body.

FIG. 95 is a flowchart showing a method 8200 for orthogonally loading a compressible and expandable prosthetic valve into a delivery catheter according to an embodiment. The method 8200 includes providing a compressible and expandable prosthetic valve, at 8201. The compressible and expandable prosthetic valve can be any of the valves disclosed herein. For example, the compressible and expandable prosthetic valve can be a valve (i) where the valve has a tubular frame with a flow control component mounted within the tubular frame, (ii) where the valve or flow control component is configured to permit blood flow in a first direction through an inflow end of the valve and to block blood flow in a second direction, opposite the first direction, through an outflow end of the valve, (iii) where the valve is compressible and expandable and has a long-axis oriented at an intersecting angle of between 45-135 degrees to the first direction, (iv) where the long-axis is parallel to a length-wise cylindrical axis of a delivery catheter used to deliver the valve, and (v) where the valve has a height of about 5-60 mm and a diameter of about 25-80 mm. The compressible and expandable prosthetic valve is loaded into a tapering fixture or funnel attached to a delivery catheter, to compress the valve to a compressed configuration for introduction into the body using the delivery catheter for implanting at a desired location in the body, at 8202.

As described above with reference to FIGS. 1A and 1B, a transcatheter prosthetic valve can include a valve frame and a flow control component that are integral components or that are separate components coupled prior to delivery to the desired location in the body. Any of the prosthetic valves described herein, however, can include a valve frame and a flow control component that are separate components that are delivered separately and coupled or mounted within the desired location in the body. For example, a valve frame such as those described herein can be compressed and delivered to the desired location in the body via a delivery catheter. The frame can be released from the delivery catheter and deployed, for example, in the annulus of the native valve. The frame is in the expanded configuration once released from the delivery catheter, and thus, is deployed in the annulus of the native valve in the expanded configuration. A flow control component such as any of those described herein can then be delivered separately (e.g., via the delivery catheter or a separate or secondary delivery catheter) and mounted into the deployed frame. In some implementations, such an arrangement can allow for a commercially available flow control components, which are deployed within any of the frames described herein, which have been previously and/or separately deployed in the native annulus.

Provided below is a discussion of certain aspects or embodiments of transcatheter prosthetic valves, delivery systems, and/or delivery methods. The transcatheter prosthetic valves (or aspects or portions thereof), the delivery systems, and/or the delivery methods described below with respect to specific embodiments can be substantially similar in at least form and/or function to the valve 102 and/or corresponding aspects of the valve 102, the delivery system used to deliver the valve 102, and/or the delivery methods described above with reference to FIGS. 1A-1F. Thus, certain aspects of the specific embodiments are not described in further detail herein.

Figure 96A:
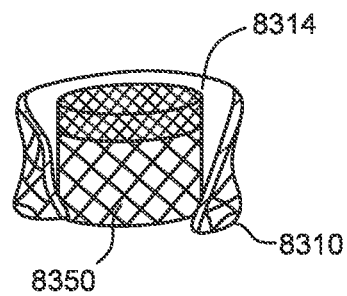
FIG. 96A is a cross-sectional view of a transcatheter prosthetic valve illustrating a valve sleeve disposed within a frame, according to an embodiment.

FIG. 96A is an illustration of an open cross-section view of a low profile, side-loaded prosthetic valve frame 8310 and shows an example of a commercially available valve or flow control component 8350 mounted within a central aperture 8314 defined by an inner surface of frame 8310.

Figure 96B:
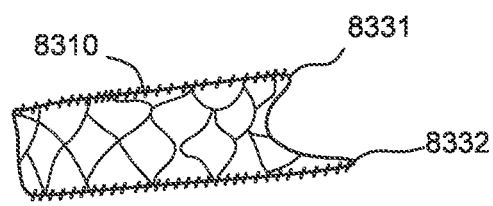
FIG. 96B is a side view of the transcatheter prosthetic valve of FIG. 96A in an expanded configuration.

FIG. 96B is an illustration of valve frame 8310 having a braid or laser-cut construction. FIG. 96B shows a longer distal lower tension arm 8332 for extending sub-annularly towards the RVOT (described in detail above), and a shorter distal upper tension arm 8331 for extending over the atrial floor (described in detail above). The tubular frame 8310 shown in FIG. 96B is about 10 mm in height and the commercially available valve sleeve or flow control component 8350 received by the frame 8310 can extend about 10 mm below the bottom of the tubular frame 8310 when received therein, resulting in a valve having a total height of 20 mm.

Figure 96C:
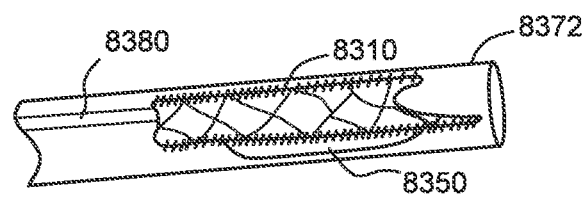
FIGS. 96C-96F illustrate a process of deploying the transcatheter prosthetic valve of FIG. 96A into a native annulus of a target tissue.

FIG. 96C is an illustration of the valve frame 8310 having the braid or laser-cut construction and the commercially available valve sleeve or flow control component 8350 in a compressed configuration within a delivery catheter 8372. FIG. 96C shows a secondary steerable catheter 8380 attached to the valve frame 8310 and used for ejecting, positioning, and anchoring the valve frame 8310 within the native annulus. The secondary catheter 8310 can also be used to retrieve a failed deployment of the valve frame 8310. The valve frame 8310 can be delivered to the native annulus with the valve sleeve or flow control component 8350 previously mounted therein such that the valve frame 8310 and flow control component 8350 are delivered together or can be delivered in separate processes.

Figure 96D:
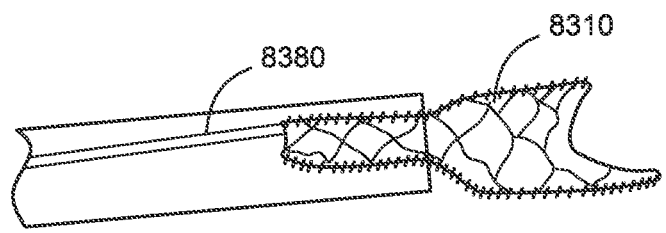

FIG. 96D is an illustration of the valve frame 8310 having a braid or laser-cut construction shown partially compressed within the delivery catheter 8372, and partially ejected from the delivery catheter 8372. FIG. 96D shows that while the valve frame 8372 is still compressed the distal lower tension arm 8332 can be manipulated through the leaflets and chordae tendineae to find a stable anterior-side lodgment for the distal side of the valve frame 8310. FIG. 96D also shows that the valve frame 8310 without the valve sleeve or flow control component 8350 showing that the frame 8310 can be delivered to the native annulus prior to and/or separate from the delivery of the flow control component 8350.

Figure 96E:
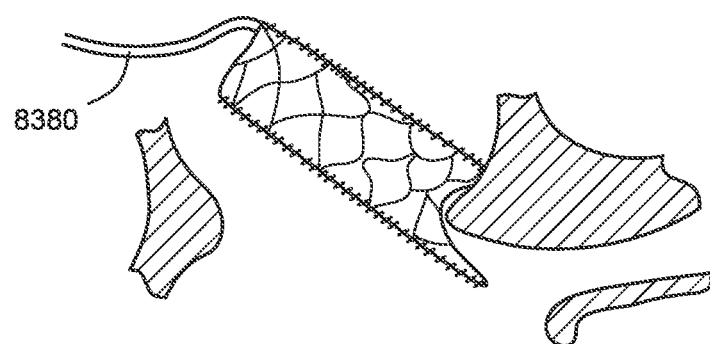

FIG. 96E is an illustration of the valve frame 8310 having the braid or laser-cut construction and engaging the tissue on the anterior side of the native annulus with the curved distal sidewall of the tubular frame 8310 sealing around the native annulus. FIG. 96E shows the valve frame 8310 held by the steerable secondary catheter 8380 at an oblique angle while valve frame 8310 function is assessed. FIG. 96E shows that the flow control component 8350 has not be delivered to the native annulus.

Figure 96F:
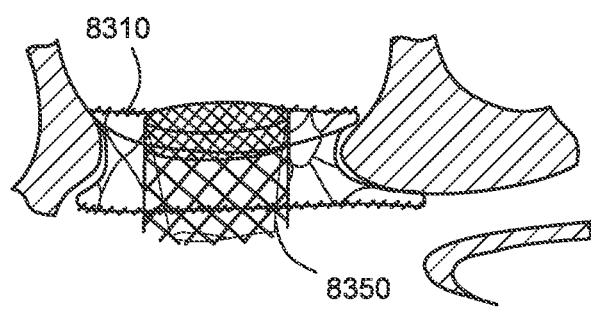

FIG. 96F is an illustration of a prosthetic valve having the braid or laser-cut tubular frame 8310 fully deployed into the tricuspid annulus. The distal side of the valve frame 8310 is shown engaging the tissue on the anterior side of the native annulus with the curved distal sidewall of the tubular frame 8310 sealing around the native annulus, and with the proximal sidewall tension-mounted into the posterior side of the native annulus. FIG. 96F shows the valve sleeve or flow control component 8350 delivered to the native annulus (after the delivery of the valve frame 8310) and mounted in the valve frame 8310. The valve sleeve or flow control component 8350 can be a commercially available flow control component.

Figure 97A:
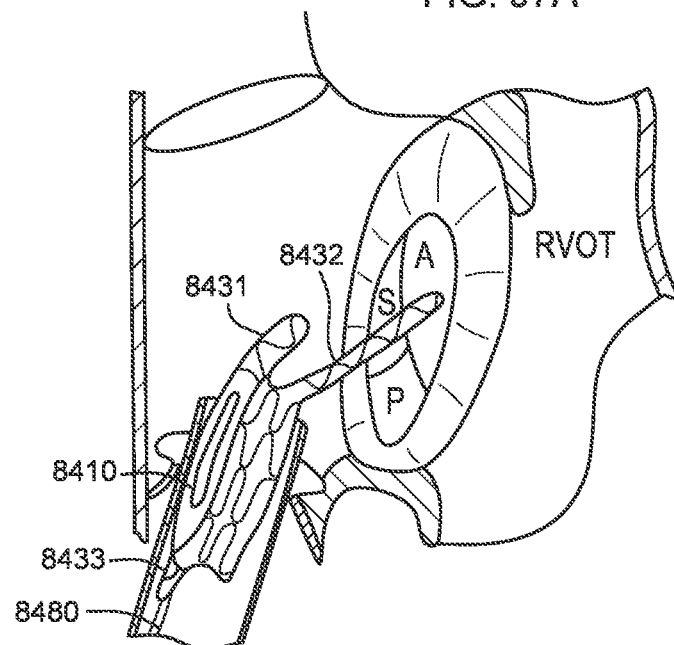
FIGS. 97A-97C illustrate a process of deploying a transcatheter prosthetic valve to a target tissue via a tissue anchor according to an embodiment.

FIG. 97A is an illustration of a valve frame 8410 according to an embodiment being delivered to tricuspid valve annulus. FIG. 97A shows the valve frame 8410 having the braided/laser cut-wire frame construction with a distal lower tension arm 8432 that is ejected from a delivery catheter 8410 and directed through the annulus and towards the RVOT.

Figure 97B:
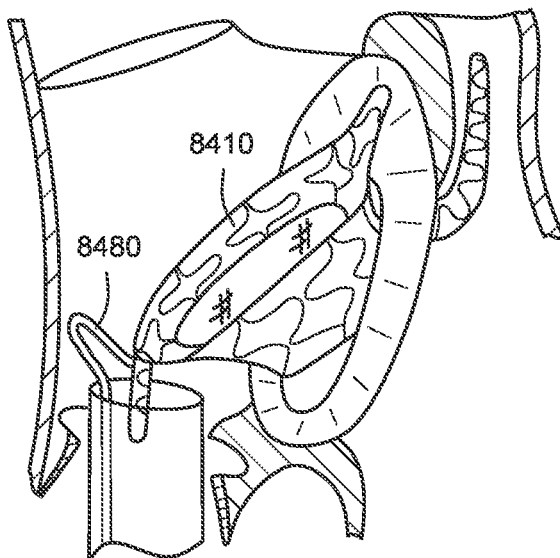

FIG. 97B shows the valve frame 8410 partially disposed within the delivery catheter 8472 with the distal lower tension arm 8432 and the distal upper tension arm 8431 ejected from the delivery catheter 8472. The distal lower tension arm 8432 is directed through the annulus and into the RVOT. The distal upper tension arm 8432 is shown staying in a supra-annular position, and causing a passive, structural anchoring of a distal side of the valve frame 8410 about the annulus. FIG. 97B shows that a steerable anchoring catheter or secondary catheter 8480 can hold the valve frame 8410 at an oblique angle in a pre-attachment position, so that the valve frame 8410 can be assessed, and once valve frame function and patient conditions are correct, the steerable anchoring catheter or secondary catheter 8480 can push the proximal side of the valve frame 8410 from its oblique angle, down into the native annulus. The steerable anchoring catheter or secondary catheter 8480 can then optionally install one or more anchoring elements.

Figure 97C:
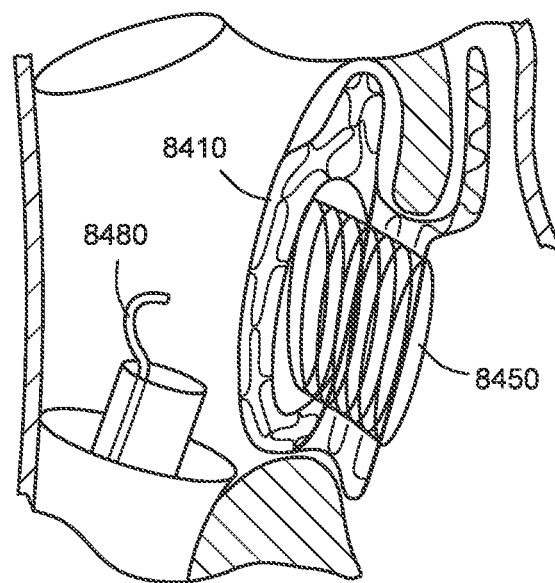

FIG. 97C is an illustration of a valve frame 8410 showing the entire braided/laser cut-frame 8410 ejected from the delivery catheter 8410. The distal lower tension arm 8432 is directed through the annulus and into the RVOT. The distal upper tension arm 8431 stays in a supra-annular position, and causes a passive, structural anchoring of the distal side of the valve frame 8410 about the annulus. At least one tissue anchor (not shown) can be used to anchor the proximal side of the valve frame 8410 into the annulus tissue. FIG. 97C shows how the opening or aperture of the frame 8410 can allow blood to flow through the aperture and can then have a commercial valve sleeve or flow control component 8450 secondarily delivered and deployed into the aperture and secured to valve frame 8410.

Figure 98A:
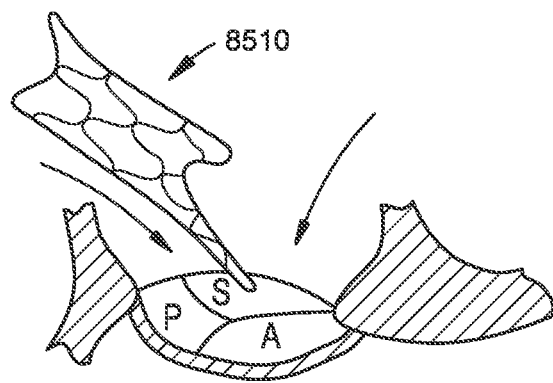
FIGS. 98A-98C illustrate a process of deploying a transcatheter prosthetic valve to a target tissue via a tissue anchor according to an embodiment.

FIG. 98A is an illustration of a valve frame 8510 according to an embodiment being delivered to tricuspid valve annulus. FIG. 98A shows the frame 8510 having a braided/laser cut-wire frame construction with a distal lower tension arm ejected from a delivery catheter (not shown) and being directed toward and/or through the native annulus and towards the RVOT. Delivery of the valve frame 8510 can also include a valve or valve frame assessment process.

Figure 98B:
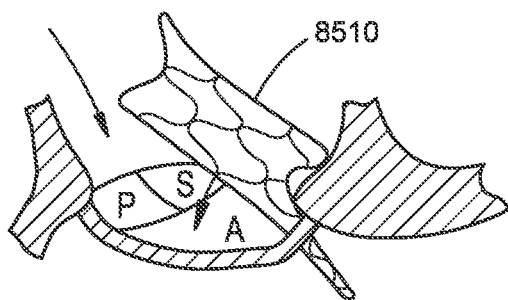

FIG. 98B shows the braided/laser cut-wire frame 8510 with the distal lower tension arm and a distal upper tension arm ejected from a delivery catheter. The distal lower tension arm is directed through the annulus and into the RVOT. The distal upper tension arm stays in a supra-annular position, and causes a passive, structural anchoring of the distal side of the valve frame 8510 about the annulus. The valve frame 8510 can be held at an oblique angle in a pre-attachment position (e.g., via a steerable anchoring catheter or secondary catheter, not shown), so that the valve frame 8510 can be assessed, and once valve frame function and patient conditions are correct, the proximal side of the valve frame 8510 can be pushed from its oblique angle, down into the native annulus.

Figure 98C:
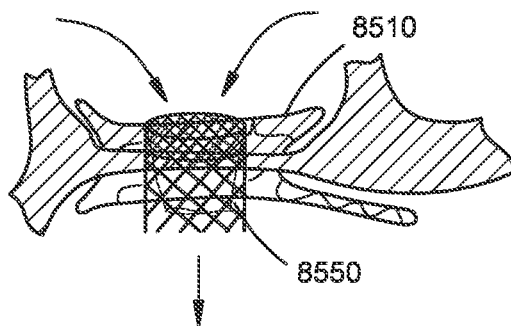

FIG. 98C shows the entire braided/laser cut-frame valve frame 8510 ejected from the delivery catheter, with the distal lower tension arm directed through the annulus and into the RVOT and the distal upper tension arm staying in a supra-annular position, and causing a passive, structural anchoring of the distal side of the valve frame 8510 about the annulus. Although not shown, at least one tissue anchor can be used to anchor the proximal side of the valve frame 8510 into the annulus tissue. FIG. 98C shows how a commercial valve sleeve or flow control component 8550 can be secondarily deployed into the opening or aperture of the frame 8510.

Figure 99A:
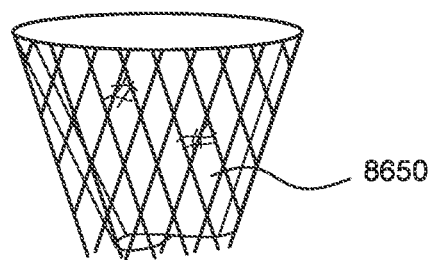
FIGS. 99A-99D illustrate at least a portion of a transcatheter prosthetic valve according to an embodiment.

FIG. 99A is an illustration of a commercial valve sleeve or flow control component 8650 that can be mounted within any of the frames disclosed herein.

Figure 99B:
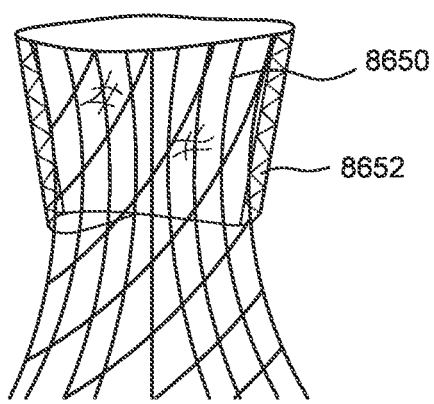

FIG. 99B is an illustration of the commercial valve sleeve or flow control component 8650 showing that the flow control component 8650 can be mounted within the any of the frames disclosed herein using and/or having two rigid support posts 8652.

Figure 99C:
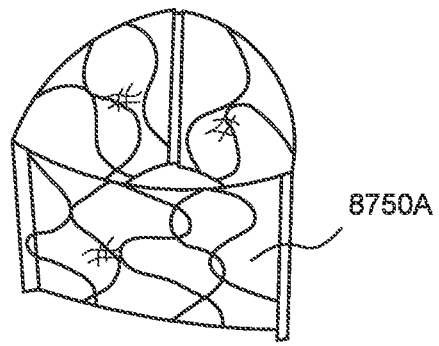

FIG. 99C is an illustration of a commercial valve sleeve or flow control component 8750A that can be mounted within any of the frames disclosed herein. The flow control component 8750A is shown as a three-panel embodiment.

Figure 99D:
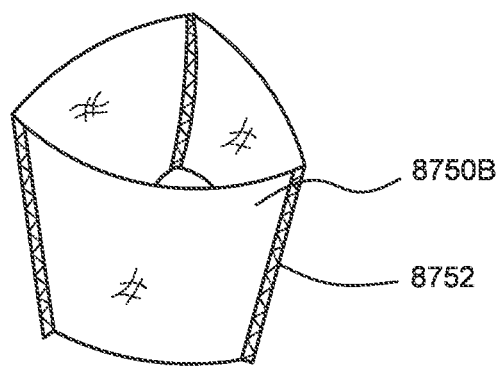

FIG. 99D is an illustration of the commercial valve sleeve or flow control component 8750B that can be mounted within any of the frames disclosed herein. The flow control component 8750B is shown as a three-panel embodiment having three rigid support posts 8752.

Figure 100:
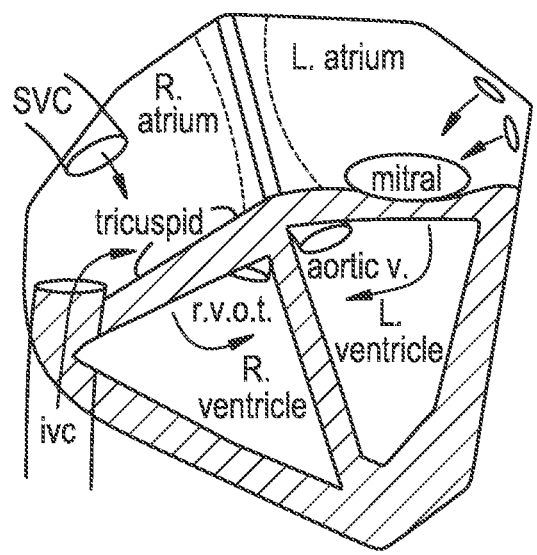
FIG. 100 is an illustration of the human heart, showing an approximate location of the valves, the atriums, the ventricles, and the pertinent blood vessels that enter and exit the chambers of the heart.

FIG. 100 is an illustration of the heart and shows an approximate location of the valves, the left and right atrium, the left and right ventricles, and the blood vessels that enter and exit the chambers of the heart.

Figure 101A:
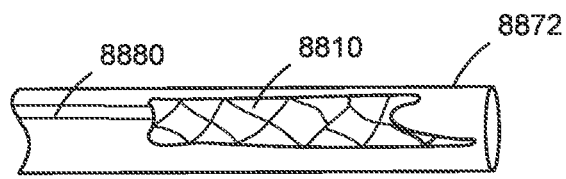
FIGS. 101A-101G illustrate a process of deploying a transcatheter prosthetic valve into a native annulus of a target tissue according to an embodiment.

FIG. 101A is an illustration of a low profile, e.g., 8-20 mm, side-loaded valve frame 8810 shown in a vertically compressed configuration and housed within a delivery catheter 8872.

Figure 101B:
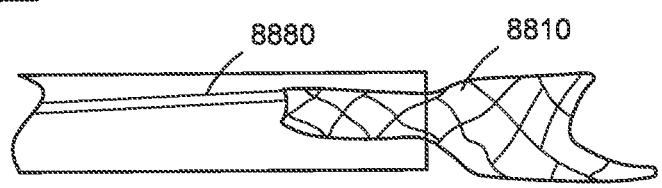

FIG. 101B shows the valve frame 8810 partially compressed and partially housed within a delivery catheter 8872, and partially laterally ejected from the delivery catheter 8872 and positioned for deployment against the anterior side of the annulus of a native valve, such as the tricuspid valve or mitral valve.

Figure 101C:
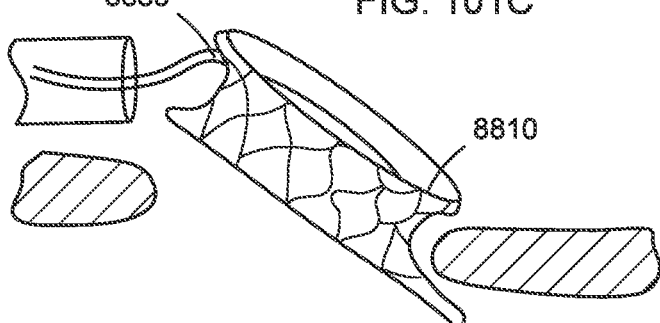

FIG. 101C shows the valve frame 8810 ejected from the delivery catheter 8872 and positioned against the anterior side of the native annulus. The valve frame 8510 can be held at an oblique angle in a pre-attachment position via a steerable anchoring catheter or secondary catheter 8880, so that the valve frame 8510 can be assessed, and once valve frame function and patient conditions are correct, the proximal side of the valve frame 8810 can be pushed from its oblique angle, down into the native annulus via the steerable anchoring catheter or secondary catheter 8880.

Figure 101D:
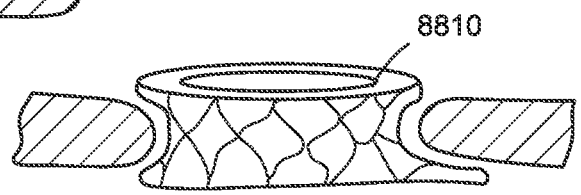

FIG. 101D shows the valve frame 8810 deployed into the native annulus of a heart valve.

Figure 101E:
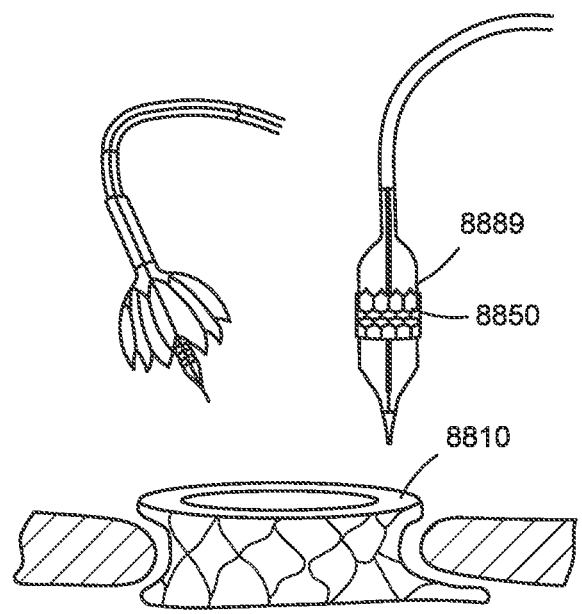
Figure 101F:
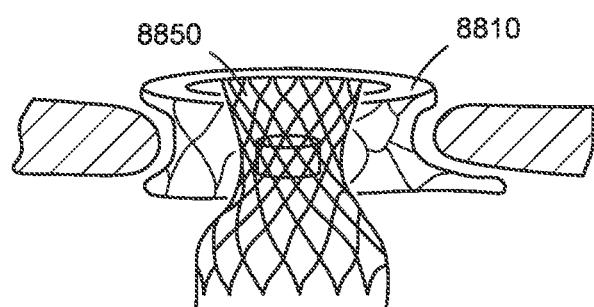
Figure 101G:
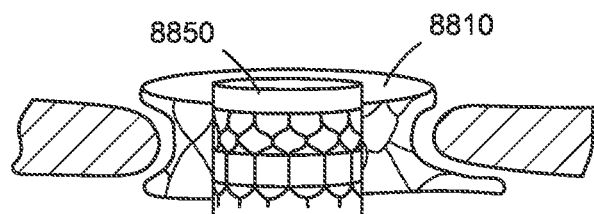

FIGS. 101E-101G illustrate side views of a valve or flow control component 8850 that can be inserted into the deployed frame 8810. FIG. 101E shows two alternate versions of flow control component 8850, secondarily deliverable by a suitable respective delivery catheter. In the embodiment on the left in FIG. 101E, the flow control component is self-expanding, and is delivered from the lumen of the delivery catheter and allowed to expand into the lumen or aperture of the valve frame 8810. In the embodiment on the right in FIG. 101E, the flow control component is a commercially-approved transcatheter balloon expandable flow control component 8850, that is delivered on a balloon catheter 8889, on which it can be expanded into the lumen or aperture of the valve frame 8810. FIG. 101F shows that the self-expanding embodiment of the valve or flow control component 8850 is deployed in the valve frame 8810 and allowed to expand to an expanded configuration within the lumen or aperture of the frame 8810. FIG. 101G shows that the balloon expandable valve or flow control component 8850 can be vertically deployed into the central lumen or aperture of the already (laterally, horizontally, orthogonally) deployed valve frame 8810.

Figure 102A:
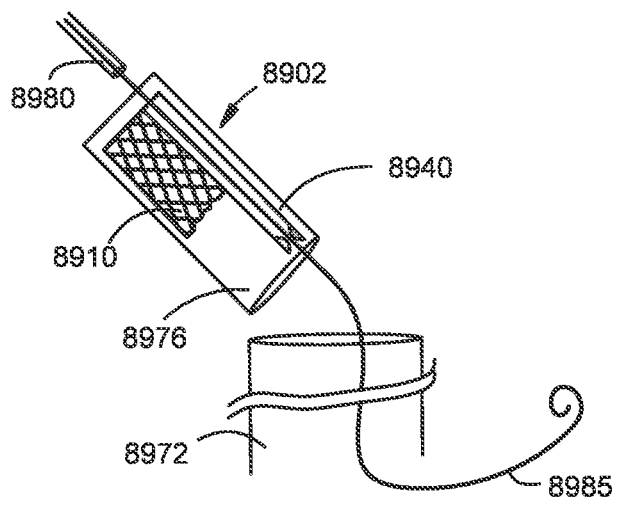
FIGS. 102A-102D illustrate a process of deploying a transcatheter prosthetic valve into a native annulus of a target tissue according to an embodiment.

FIGS. 102A-102D illustrate a process for delivering a co-axial transcatheter prosthetic valve 8902 to the annulus of a native valve of the human heart. FIG. 102A shows the valve 8902 in a co-axial compressed configuration being loaded using a compression capsule or compression catheter 8976 into a distal end of a delivery catheter 8972. FIG. 102A shows a hypotube or sheath (secondary catheter) 8980, a guidewire 8985 threaded through a guidewire collar 8940 coupled to, for example, a distal tension arm. The compression capsule or catheter 8976 is configured to compress the co-axial prosthetic valve to a size suitable for insertion into the delivery catheter 8972.

Figure 102B:
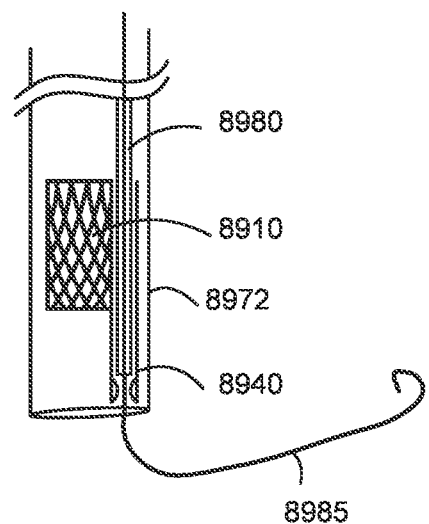

FIG. 102B shows the co-axial compressed valve 8902 being delivered to the distal end of the delivery catheter 8972, with the hypotube or secondary catheter 8980 and sheathed guidewire 8985 threaded through or disposed within a channel-type guidewire collar 8940 attached, for example, to a distal tension arm. The guidewire collar 8940 can include and/or form a constriction or other feature configured to permit advancement of the guidewire 8985 through the guidewire collar 8940 and to block advancement of the secondary catheter 8980, which can be used to advance the valve 8902 within the delivery catheter 8972.

Figure 102C:
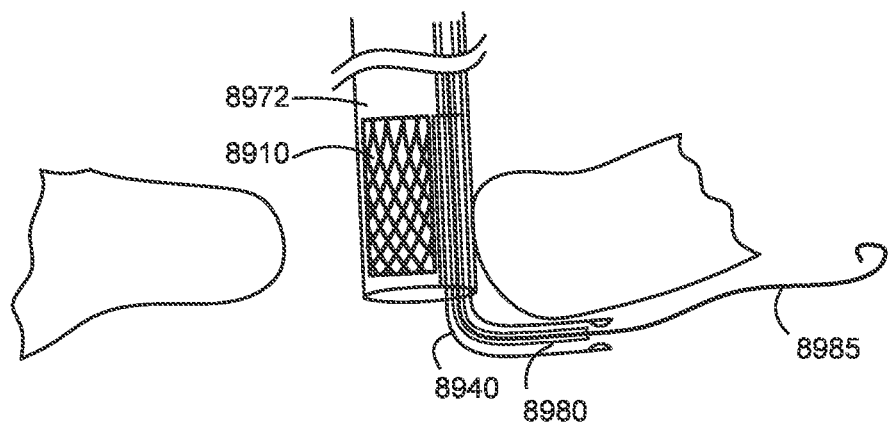

FIG. 102C shows the co-axial compressed valve 8902 partially expelled from the delivery catheter 8972, with a distal tension arm and/or the channel-type guidewire collar 8940 being positioned into the ventricular outflow tract of the native valve (e.g., the RVOT). The distal tension arm can form and/or define the channel-type guidewire collar 8940, thereby combining the functions or features.

Figure 102D:
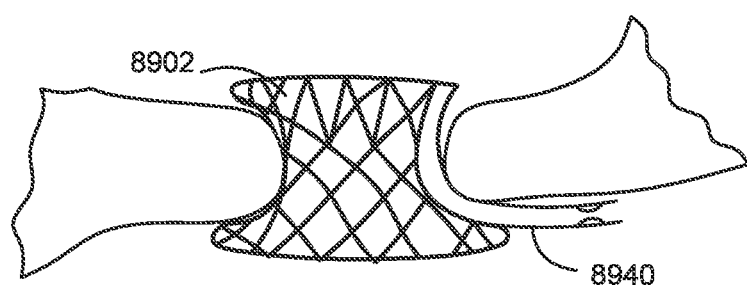

FIG. 102D shows that, once positioned, the self-expanding valve 8902 can be completely expelled from the delivery catheter 8972 and deployed as a prosthetic valve similar to any of those disclosed herein.

Figure 103A:
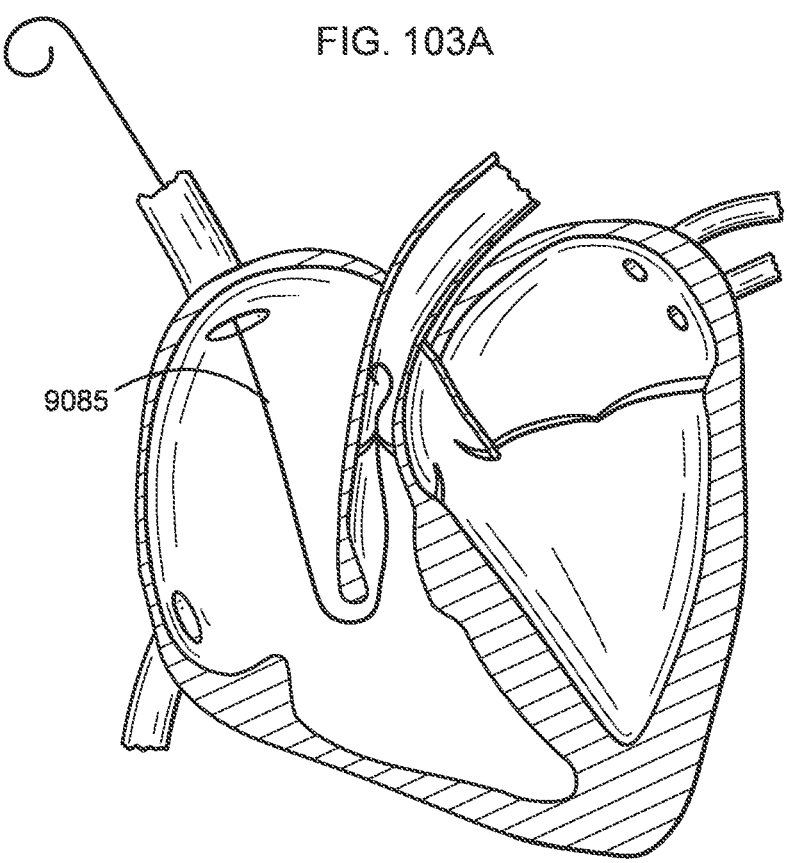

FIGS. 103A-103G illustrate a process for delivering a co-axial transcatheter prosthetic valve 9002 to the annulus of the tricuspid valve of the human heart. FIG. 103A is an illustration of a first step of the delivery process in which a guidewire 9085 with a hypotube sheath or secondary catheter 9080 is delivered to the RVOT through the superior vena cava (SVC). The guidewire 9085 has a diameter of about 0.035 in (or about 0.889 mm).

Figure 103B:
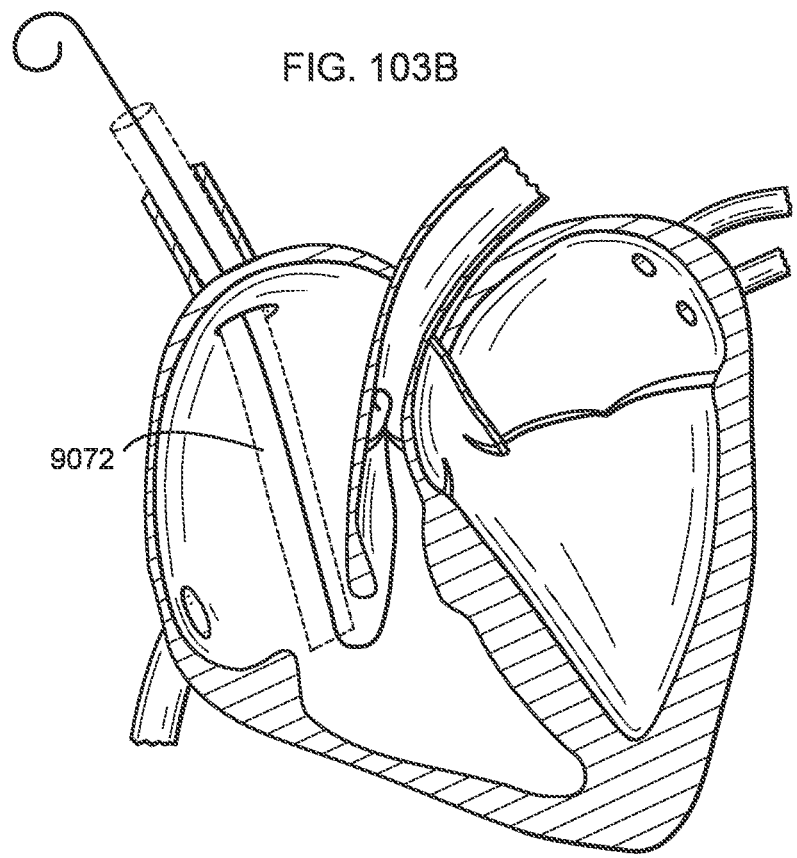

FIG. 103B shows a delivery catheter 9072 being advanced through the SVC over the guidewire 9085 to and through the native tricuspid annulus to the right ventricle.

Figure 103C:
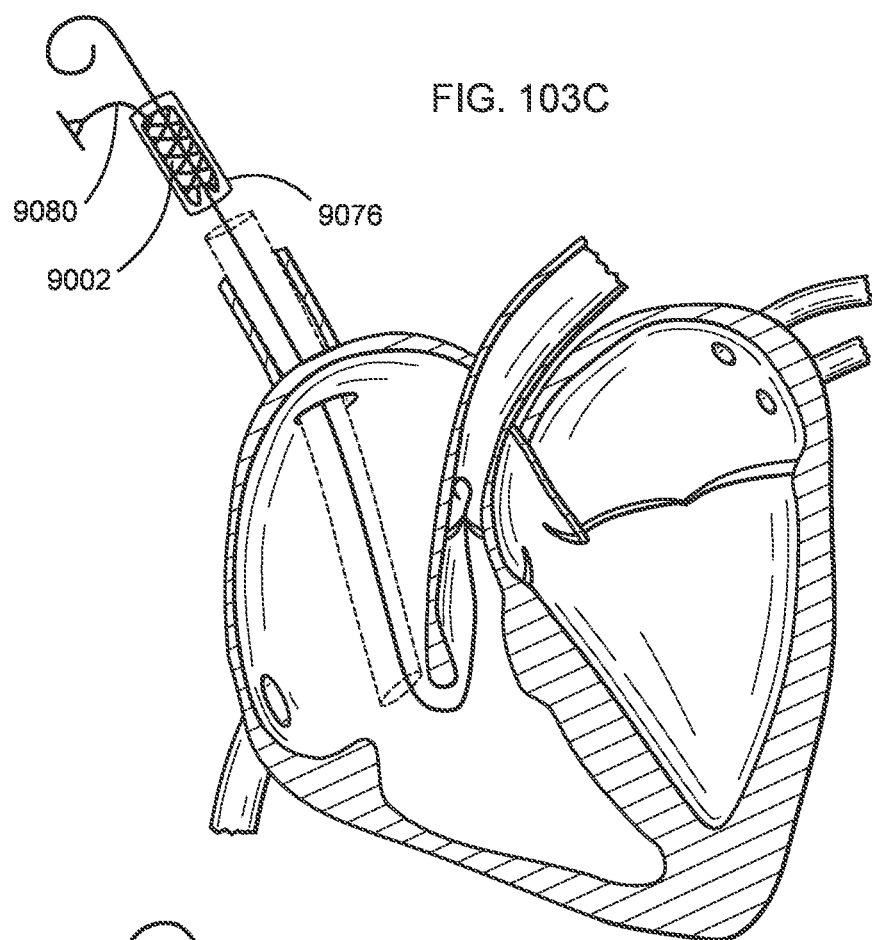

FIG. 103C shows the valve 9002 in a compressed configuration within a compression capsule 9076. The capsule 9076 can be used to compress the valve 9002 to an extent that the compressed valve 9002 fits within the delivery catheter 9072. FIG. 103C shows the capsule 9076 is loaded into the proximal end of the delivery catheter 9072 and the valve 9002 is withdrawn/delivered from the capsule 9076 into the delivery catheter 9072, with sheathed guidewire 9085 threaded through the valve 9002 and providing a wire path to the RVOT, planned deployment location.

Figure 103D:
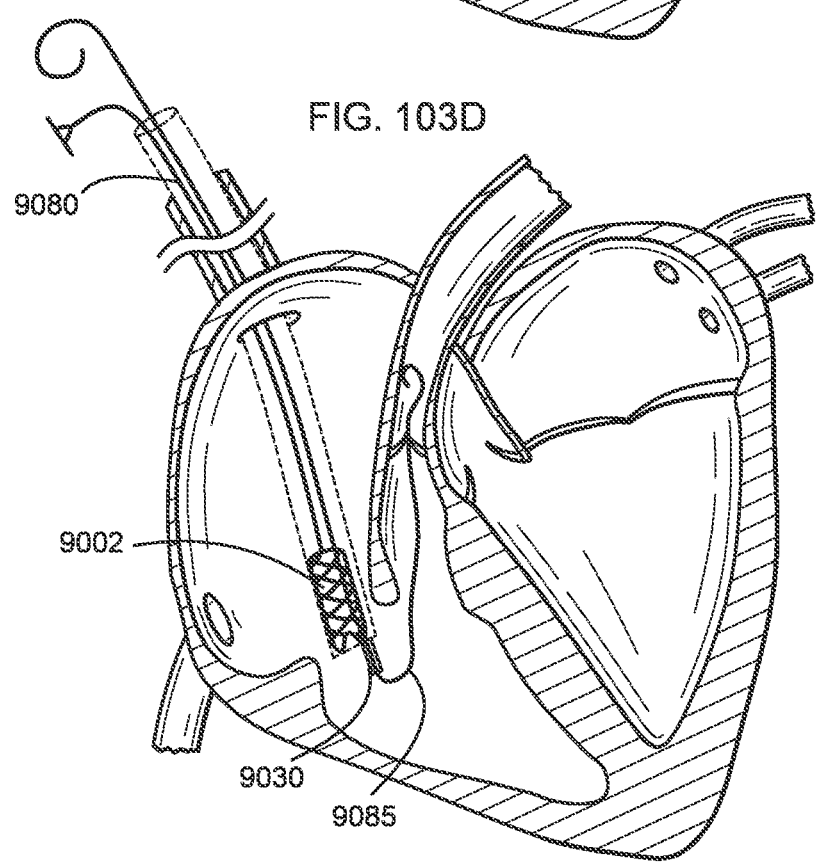

FIG. 103D shows the valve 9002 advanced up the delivery catheter 9072 and deployed into the native annulus by pushing on the outer hypotube sheath or secondary catheter 9080 to pull the valve 9002 up the delivery catheter 9072 and into position. FIG. 103D shows a tension arm 9030 of the valve 9002 is used to position the valve 9002 in the native annulus.

Figure 103E:
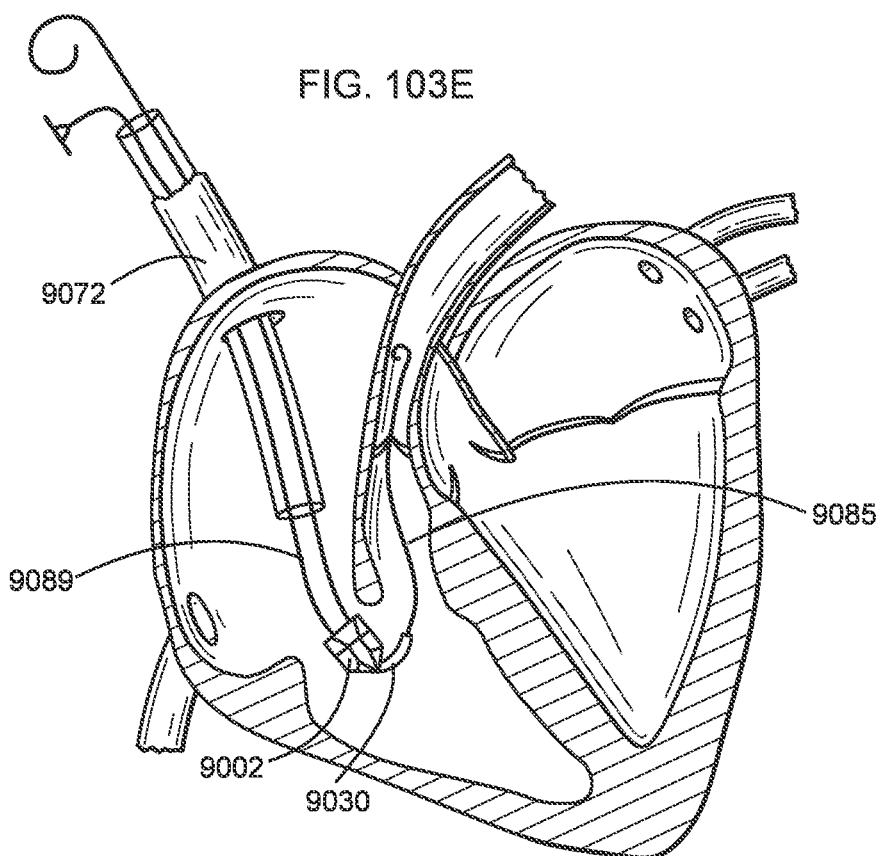

FIG. 103E shows a steerable balloon catheter 9089 being used to push the proximal side of the valve 9002 in the expanded configuration into position within the native annulus.

Figure 103F:
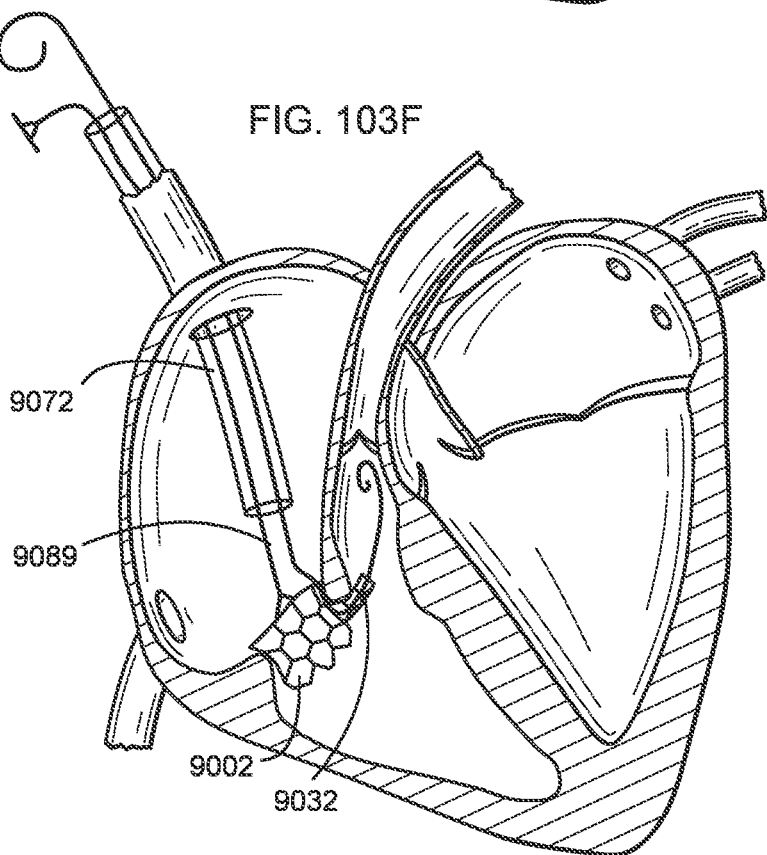

FIG. 103F shows balloon expansion of the co-axial valve 9002 in the native annulus. The proximal side of the valve 9002 can be anchored to the annular tissue.

FIG. 103G shows withdrawal of the delivery system (e.g., the delivery catheter 9072, the secondary catheter 9080, the guidewire 9085, etc.). The proximal side of the expanded valve 9002 is anchored to the annular tissue using any of the anchoring methods described herein.

FIGS. 104A-104F illustrate a process for delivering a co-axial balloon-expandable transcatheter prosthetic valve 9102 to the tricuspid annulus of the human heart. FIG. 104A shows a delivery catheter 9172 advanced over a guidewire 9185 to be deployed to the native annulus.

FIG. 104B shows the co-axial balloon-expandable valve 9102 in a compressed configuration within a compression capsule 9176. The capsule 9176 can be used to compress the valve 9102 to an extent that the compressed valve 9102 fits within the delivery catheter 9172. FIG. 104B shows the capsule 9176 is loaded into the proximal end of the delivery catheter 9172 and the valve 9102 is withdrawn/delivered from the capsule 9176 into the delivery catheter 9172, with the sheathed guidewire 9085 threaded through the valve 9102 and providing a wire path to the RVOT, planned deployment location. FIG. 104B shows the valve 9102 including a channel-type guidewire collar 9140 through which the guidewire 9185 is threaded.

FIG. 104C shows the co-axial valve 9102 being delivered to the proximal end of the delivery catheter 9172, with the sheathed guidewire 9180 threaded through the tension arm and/or guidewire collar 9140. The guidewire collar 9140 can couple to or can at least partially form a distal tension arm. The guidewire collar 9140 can include and/or form a constriction or other feature configured to permit advancement of the guidewire 9185 through the guidewire collar 9140 and to block advancement of a hypotube sheath or secondary catheter 9180, which can be used to advance the valve 9102 within the delivery catheter 9172.

FIG. 104D shows the co-axial valve 9102 partially expelled from the delivery catheter 9172 into the expanded configuration, with the distal tension arm and/or guidewire collar 9140 being positioned into the RVOT. FIG. 104D shows a balloon catheter 9189 connected to the valve 9102.

FIG. 104E shows that, once positioned and expanded by the balloon catheter 9189, the balloon-expanded co-axial valve 9102 can be completely deployed into the inner circumference of the native annulus to function as a prosthetic valve. FIG. 104F shows the deployed valve 9102 with the delivery system (e.g., the delivery catheter 9172, secondary catheter 9180, guidewire 9185, balloon catheter 9189, etc.) withdrawn.

FIG. 104F is an illustration of step 6 of a 6-step process for delivery of a co-axial prosthetic valve 143 to the tricuspid annulus. FIG. 104F shows the deployed valve.

Example. One embodiment of an orthogonally delivered transcatheter prosthetic valve has a tubular frame with a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm. Importantly, this heart valve substitute does not have a traditional valve configuration, can be delivered to the heart using the inferior vena cava (IVC/femoral transcatheter delivery pathway compressed within a catheter, and expelled from the catheter to be deployed without open-heart surgery.

Example. In another embodiment of a transcatheter valve, comprises: a cylindrical tubular frame having a height of about 5-60 mm and an outer diameter of about 25-80 mm, said tubular frame comprised of a braid, wire, or laser-cut wire frame having a substantially circular central aperture, said tubular frame partially covered with a biocompatible material; a collapsible flow control component disposed within the central aperture, said sleeve having a height of about 5-60 mm and comprised of at least two opposing leaflets that provide a reciprocating closable channel from a heart atrium to a heart ventricle; an upper tension arm attached to a distal upper edge of the tubular frame, the upper tension arm comprised of stent, segment of tubular frame, wire loop or wire frame extending from about 10-30 mm away from the tubular frame; a lower tension arm extending from a distal side of the tubular frame, the lower tension arm comprised of stent, segment of tubular frame, wire loop or wire frame extending from about 10-40 mm away from the tubular frame; and at least one tissue anchor to connect the tubular frame to native tissue.

Example. In another embodiment of a transcatheter valve, there is provided a feature wherein the sleeve is shaped as a conic cylinder, said top end having a diameter of 30-35 mm and said bottom end having a diameter of 8-20 mm.

Example. In another embodiment of a transcatheter valve, there is provided a feature wherein the cover is comprised of polyester, polyethylene terephthalate, decellularized pericardium, or a layered combination thereof.

Example. In an embodiment, there is also provided a method for orthogonal delivery of implantable prosthetic valve to a desired location in the body, wherein the method includes (i) advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

Example. In an embodiment, there is also provided a method for orthogonally loading an implantable prosthetic valve into a delivery catheter, where the method includes loading an implantable prosthetic valve sideways into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

Example. In an embodiment, there is also provided a method for orthogonally loading an implantable prosthetic valve into a delivery catheter, where the method includes (i) loading an implantable prosthetic valve into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

Example. The transcatheter prosthetic heart valve may be percutaneously delivered using a transcatheter process via the femoral through the IVC, carotid, sub-xiphoid, intercostal access across the chest wall, and trans-septal to the mitral annulus through the fossa ovalis. The device is delivered via catheter to the right or left atrium and is expanded from a compressed shape that fits with the internal diameter of the catheter lumen. The compressed valve is loaded external to the patient into the delivery catheter and is then pushed out of the catheter when the capsule arrives to the atrium. The cardiac treatment technician visualizes this delivery using available imaging techniques such as fluoroscopy or ultrasound, and in an embodiment, the valve self-expands upon release from the catheter since it is constructed in part from shape-memory material, such as Nitinol®, a nickel-titanium alloy used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated to ensure the device is secure, is located and oriented as planned, and is functioning as a substitute or successor to the native tricuspid valve.

Example—One embodiment of an orthogonally delivered transcatheter prosthetic valve frame has a tubular frame, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve is substantially parallel to a lengthwise cylindrical axis of the delivery catheter, wherein the valve has a height of about 5-60 mm and a diameter of about 25-80 mm. This heart valve frame can be delivered to the heart using the inferior vena cava (IVC/femoral transcatheter delivery pathway compressed within a catheter and expelled from the catheter to be deployed without open-heart surgery.

Example—In another embodiment of a transcatheter valve frame, a cylindrical tubular frame is provided having a height of about 5-60 mm and an outer diameter of about 25-80 mm, said tubular frame comprised of a braid, wire, or laser-cut wire frame having a substantially circular central aperture, said tubular frame partially covered with a biocompatible material; an upper tension arm attached to a distal upper edge of the tubular frame, the upper tension arm comprised of stent, segment of tubular frame, wire loop or wire frame extending from about 10-30 mm away from the tubular frame; a lower tension arm extending from a distal side of the tubular frame, the lower tension arm comprised of stent, segment of tubular frame, wire loop or wire frame extending from about 10-40 mm away from the tubular frame; and at least one tissue anchor to connect the tubular frame to native tissue.

Example—In an embodiment, there is also provided a method for orthogonal delivery of implantable prosthetic valve frame to a desired location in the body, where the method includes (i) advancing a delivery catheter to the desired location in the body and delivering an expandable prosthetic valve frame to the desired location in the body by releasing the valve frame from the delivery catheter, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve frame is substantially parallel to a lengthwise cylindrical axis of the delivery catheter, wherein the valve frame has a height of about 5-60 mm and a diameter of about 25-80 mm.

Example—In an embodiment, there is also provided a method for orthogonally loading an implantable prosthetic valve frame into a delivery catheter, where the method includes loading an implantable prosthetic valve frame sideways into a tapering fixture or funnel attached to a delivery catheter, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve frame is substantially parallel to a lengthwise cylindrical axis of the delivery catheter, wherein the valve frame has a height of about 5-60 mm and a diameter of about 25-80 mm.

Example—The transcatheter prosthetic heart valve may be percutaneously delivered using a transcatheter process via the femoral through the inferior vena cava (IVC), superior vena cava (SVC), jugular vein, brachial vein, sub-xiphoid, intercostal access across the chest wall, and trans-septal through the fossa ovalis. The device is delivered via catheter to the right or left atrium and is expanded from a compressed shape that fits with the internal diameter of the catheter lumen. The compressed valve is loaded external to the patient into the delivery catheter and is then pushed out of the catheter when the capsule arrives to the atrium. The cardiac treatment technician visualizes this delivery using available imaging techniques such as fluoroscopy or ultrasound, and in an embodiment the valve frame self-expands upon release from the catheter since it is constructed in part from shape-memory material, such as Nitinol®, a nickel-titanium alloy used in biomedical implants.

In another embodiment, the valve frame may be constructed for use with balloon-expansion after the capsule has been ejected from the catheter into the atrium. The atrial collar/frame is expanded to their functional diameter, and deployed into the native annulus, providing a radial tensioning force to secure the valve frame. Once the frame is deployed about the tricuspid annulus, fasteners secure the device about the native annulus. Additional fastening of the device to native structures may be performed, and the deployment is complete. Further adjustments using hemodynamic imaging techniques are contemplated in order to ensure the device is secure, is located and oriented as planned, and is functioning.

Example—Compression methods. In another embodiment, there is provided a method of compressing, wherein the implantable prosthetic heart valve is rolled or folded into a compressed configuration using at least one of (i) unilaterally rolling into a compressed configuration from one side of the annular support frame; (ii) bilaterally rolling into a compressed configuration from two opposing sides of the annular support frame; (iii) flattening the annular support frame into two parallel panels that are substantially parallel to the long-axis, and then rolling the flattened annular support frame into a compressed configuration; and (iv) flattening the annular support frame along a vertical axis to reduce a vertical dimension of the valve from top to bottom.

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A prosthetic valve, comprising:
a tubular frame having a sidewall and an atrial collar attached around a top edge of the sidewall;

a distal subannular anchoring tension arm extending from a lower distal edge of the side wall of the tubular frame, the distal subannular anchoring tension arm extending away from the distal side wall of the tubular frame; and a flow control component mounted within the tubular frame and configured to permit blood flow in a first direction through an inflow end of the prosthetic valve and block blood flow in a second direction, opposite the first direction, through an outflow end of the prosthetic valve, wherein the prosthetic valve is compressible to a compressed configuration for introduction into the body using a delivery catheter and expandable to an expanded configuration for implanting at a desired location in the body, the prosthetic valve having a long-axis oriented at an intersecting angle of between 45-135 degrees to the first direction when the prosthetic valve is in each of the compressed configuration and the expanded configuration, and wherein when the prosthetic valve in the compressed configuration is disposed in a lumen of the delivery catheter, the long-axis of the prosthetic valve is substantially parallel to a length-wise cylindrical axis of the lumen of the delivery catheter.

2. The prosthetic valve of claim 1, wherein the sidewall of the tubular frame is a trans-annular tubular segment of the tubular frame, the atrial collar includes a flared atrial cuff joined to the trans-annular tubular segment around a circumference of a top edge of the trans-annular tubular segment.

3. The prosthetic valve of claim 1, wherein the tubular frame is formed of one or more of a braid, wire, or laser-cut wire frame, an inner surface and an outer surface of the tubular frame being covered with a biocompatible material.

4. The prosthetic valve of claim 3, wherein the biocompatible material includes one or more of pericardial tissue and a woven synthetic polyester material.

5. The prosthetic valve of claim 1, wherein the tubular frame has a side profile forming an hourglass shape.

6. The prosthetic valve of claim 1, wherein the flow control component has a plurality of leaflets of pericardial material joined to form a rounded cylinder at an inflow end of the flow control component and having a flat closable aperture at an outflow end of the flow control component.

7. The prosthetic valve of claim 1, wherein the distal subannular anchoring tension arm is a wire loop or wire frame, an integrated frame section, or a stent.

8. The prosthetic valve of claim 1, wherein the distal subannular anchoring tension arm has a length of 10-40 mm.

9. The prosthetic valve of claim 1, further comprising:
a proximal subannular anchoring tension arm extending from a lower proximal edge of the side wall of the tubular frame; and
at least one tissue anchor connected to the tubular frame for engaging native tissue.

10. A frame for a prosthetic valve, the frame comprising:
a tubular frame defining a central lumen extending along a vertical axis of the tubular frame, the tubular frame having an outer circumferential surface engageable with native annular tissue; and
a subannular tension arm extending away from one side of a subannular portion of the tubular frame, the subannular tension arm being formed of wire loop or wire frame, integrated frame section, or stent,
wherein the tubular frame is compressible to a compressed configuration for introduction into the body using a delivery catheter and expandable to an expanded configuration for implanting at a desired location in the body, the prosthetic valve having a horizontal long-axis oriented at an intersecting angle between 45-135 degrees relative to the vertical axis of the of the tubular frame when the prosthetic valve is in each of the compressed configuration and the, and
wherein when the tubular frame in the compressed configuration is disposed in a lumen of the delivery catheter, the horizontal long-axis of the tubular frame is substantially parallel to a lengthwise cylindrical axis of the lumen of the delivery catheter.

11. The frame of claim 10, wherein the tubular frame includes a flared atrial cuff joined to a trans-annular tubular segment around a top edge of the trans-annular tubular segment, the outer circumferential surface being an outer circumferential surface of the trans-annular tubular segment.

12. The frame of claim 10, wherein said tubular frame is formed of a braid, wire, or laser-cut wire frame and is covered with a biocompatible material.

13. The frame of claim 10, wherein the tubular frame is coupleable to a flow control component along an inner circumferential surface of the tubular frame, the flow control component having a plurality of leaflets of pericardial material joined to form a rounded cylinder at an inflow end of the flow control component and having a closable aperture at an outflow end of the flow control component.

14. The frame of claim 10, further comprising:
an upper tension arm attached to and extending away from an upper edge of the tubular frame, the upper tension arm formed of wire loop or wire frame; and
a lower tension arm attached to and extending away from a lower edge of the tubular frame, the lower tension arm formed of wire loop or wire frame, integrated frame section, or stent.

15. A method for delivering a prosthetic valve to an annulus of a native valve between a ventricle and an atrium of a heart, the method comprising:
advancing to the atrium of the heart a delivery catheter containing the prosthetic valve in a compressed configuration, the prosthetic valve including a tubular frame and a flow control component mounted within the tubular frame and configured to permit blood flow in a first direction through the prosthetic valve and block blood flow in a second direction, opposite the first direction, the prosthetic valve having a long-axis oriented at an intersecting angle of between 45-135 degrees to the first direction, the long-axis of the prosthetic valve when in the compressed configuration being substantially parallel to a length-wise cylindrical axis of the delivery catheter;
releasing at least a distal subannular anchoring tension arm of the prosthetic valve from the delivery catheter by pushing the prosthetic valve in a distal direction relative to the delivery catheter using a pushing rod that is releasably connected to the prosthetic valve;
delivering the distal subannular anchoring tension arm to the ventricle side of the annulus of the native valve;
releasing a remainder of the prosthetic valve from the delivery catheter to allow the prosthetic valve to expand to an expanded configuration; and
seating the prosthetic valve so the tubular frame is disposed within the annulus of the native valve.

16. The method of claim 15, further comprising:
positioning the distal subannular anchoring tension arm of the prosthetic valve into the right ventricular outflow tract of the right ventricle; and positioning a distal upper tension arm of the prosthetic valve into a supra-annular position, the distal upper tension arm providing a supra-annular force in a direction of the ventricle and the distal subannular anchoring tension arm providing a sub-annular force in a direction of the atrium.

17. The method of claim 15, further comprising:
rotating the prosthetic valve using a steerable catheter along an axis parallel to a plane of the annulus of the native valve,
wherein a distal upper tension arm of the prosthetic valve is pressure locked against supra-annular tissue on an atrium side of the native valve, and
wherein the distal subannular anchoring tension arm of the prosthetic valve is pressure locked against sub-annular tissue on a ventricle side of the native valve.

18. The method of claim 15, wherein prior to the seating the prosthetic valve, the method further comprising:
allowing blood to flow from the atrium to the ventricle through both of the native valve and the prosthetic valve.

19. The method of claim 15, wherein prior to the advancing to the atrium of the heart the delivery catheter containing the prosthetic valve in the compressed configuration, the method further comprising:
transitioning the prosthetic valve to the compressed configuration by compressing the prosthetic valve laterally in a direction perpendicular to the first direction and compressing the prosthetic valve axially in a direction parallel to the first direction; and
loading the prosthetic valve in the compressed configuration into the lumen of the delivery catheter such that the long-axis of the prosthetic valve is substantially parallel to the length-wise cylindrical axis of the delivery catheter.

* * * * *